United States Patent
Seko et al.

(10) Patent No.: US 7,402,580 B2
(45) Date of Patent: Jul. 22, 2008

(54) FUSED PYRIDAZINE DERIVATIVE COMPOUNDS AND DRUGS CONTAINING THESE COMPOUNDS AS THE ACTIVE INGREDIENT

(75) Inventors: Takuya Seko, Osaka (JP); Jun Takeuchi, Mishima-gun (JP); Shinya Takahashi, Mishima-gun (JP); Yoshihisa Kamanaka, Mishima-gun (JP); Wataru Kamoshima, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 275 days.

(21) Appl. No.: 10/505,012

(22) PCT Filed: Feb. 18, 2003

(86) PCT No.: PCT/JP03/01694

§ 371 (c)(1),
(2), (4) Date: Aug. 18, 2004

(87) PCT Pub. No.: WO03/070707

PCT Pub. Date: Aug. 28, 2003

(65) Prior Publication Data

US 2005/0085476 A1    Apr. 21, 2005

(30) Foreign Application Priority Data

Feb. 19, 2002 (JP) ............................. 2002-042259
Jul. 9, 2002 (JP) ............................. 2002-199673

(51) Int. Cl.
*C07D 403/12* (2006.01)
*C07D 405/12* (2006.01)
*C07D 237/32* (2006.01)
*A61K 31/502* (2006.01)

(52) U.S. Cl. .................... 514/233.8; 544/237; 544/116; 514/248

(58) Field of Classification Search ................ 544/237, 544/116; 514/233.8, 248
See application file for complete search history.

(56) References Cited

U.S. PATENT DOCUMENTS

2005/0080096 A1    4/2005    Ishida et al.

FOREIGN PATENT DOCUMENTS

EP    1148053 A    1/2000
WO    WO 00/44726 A    1/2000

OTHER PUBLICATIONS

Szabo et al. Montashefte fur Chemie, 133, 241-248 (2002).*
Migliara, Onofrio; Petruso, et al., Hydrazinolysis of 4-Acyl and 4-Ethoxycarbonyl-3H-imidazo[1,5-b] pyridazine-5,7-(6H)diones: 8-Oxo-7, 8-dioxo-1,4,5,6,7,8-Hexahydropyridazino[4,5-c]pyridazine Derivatives, J. Heterocyclic Chem., May 1980, vol. 17, pp. 529-531.
Chem.abstr., vol. 65 (1966), the abstract No. 13692g, W.E.Hahn, et al., Reactions of dimercaptomaleic acid derivatives. IV. Synthesis of some bicyclic systems containing 1,4-dithiin ring, Lodz. Towarz. Nauk, Wydzial III, Acta. Chim. (1965), 10, 31-8.

* cited by examiner

*Primary Examiner*—Kahsay T Habte
(74) *Attorney, Agent, or Firm*—Sughrue Mion, PLLC

(57) ABSTRACT

Fused pyridazine derivatives represented by formula (I) or pharmaceutically acceptable salts thereof (wherein each symbol has the meaning as defined in the specification.).

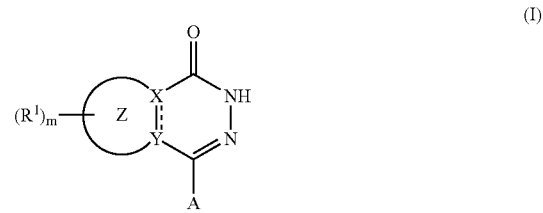

(I)

Because of inhibiting poly(ADP-ribose)polymerase, the compounds represented by formula (I) are useful as preventives and/or remedies for various ischemic diseases (in brain, cord, heart, digestive tract, skeletal muscle, retina, etc.), inflammatory diseases (inflammatory bowel disease, multiple cerebrosclerosis, arthritis, etc.), neurodegenerative diseases (extrapyramidal disorder, Alzheimer's disease, muscular dystrophy, lumbar spinal canal stenosis, etc.), diabetes, shock, head trauma, renal failure, hyperalgesia, etc. Moreover, these compounds are useful as agents against retroviruses (HIV etc.), sensitizers in treating cancer and immunosuppressants.

12 Claims, No Drawings

FUSED PYRIDAZINE DERIVATIVE COMPOUNDS AND DRUGS CONTAINING THESE COMPOUNDS AS THE ACTIVE INGREDIENT

TECHNICAL FIELD

The present invention relates to fused pyridazine derivative compounds.

More particularly, the present invention relates to
(1) pyridazine derivative compounds represented by formula (I)

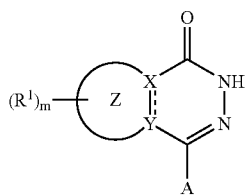

(wherein all symbols have the same meanings as described below), or pharmaceutically acceptable salts thereof,
(2) a process for preparing thereof, and
(3) an agent comprising the same as an active ingredient.

BACKGROUND ART

Poly(ADP-ribose)polymerase (abbreviated as PARP hereinafter), which is a nuclear enzyme activated by DNA strand breaks, plays a role in the transfer reaction of ADP-ribose moiety from nicotinamide adenine dinucleotide (abbreviated as $NAD^+$ hereinafter) to various proteins such as histones, DNA-polymerases and DNA-topoisomerases, etc.

DNA strand breaks caused by Peroxynitrite ($ONOO^-$) and oxygen radicals lead to overactivation of PARP (PARP is activated up to 100 times when Zn finger domain of PARP binds to DNA with nicks.). It is thought that overactivation of PARP causes depletion of $NAD^+$, which is essential for electron transport system, and consequently depletion of ATP, leading to energy failure, ultimately resulting in cell death. (The suicide hypothesis of PARP activation: *Free Radic. Biol. Med.*, 21, 855 (1996); *TIPS.*, 19, 287 (1998)). Therefore, it is considered that PARP inhibitor is useful as inhibitor of cell death.

Since caspase-3, which is one of interleukin-1β-converting enzyme family, specifically cleaves PARP as the substrate (*Cell.*, 81, 801 (1995)), it is suggested PARP is associated with apoptosis.

It is reported that 3-aminobenzamide and nicotinamide generally known as inhibitors of PARP are useful for inhibition of cell death and improvement of diseases on various models of ischemic diseases (cerebral, myocardial, intestinal, skeletal muscular or retinal ischemia etc.), inflammatory diseases (arthritis, inflammatory bowel disease or multiple sclerosis etc.), diabetes, shock, extrapyramidal disease (*TIPS.*, 19, 287 (1998); *Eur. J. Pharmacol.*, 350, 1 (1998)) and hyperalgesia (*Pain*, 72, 355 (1997)) in vitro, in vivo and in PARP knockout mouse. And it is reported that PARP inhibitor is useful as an antiretroviral drug such as an anti HIV drug (*Biochem. Biophys. Res. Commun.*, 180, 504 (1991)), a sensitizer of anticancer therapy (*Radiat. Res.*, 126, 367 (1991); *Br. J. Cancer.*, 72, 849 (1995)) or an immunosuppressant (*Int. J. Immunopharmac.*, 17, 265 (1995)).

PARP inhibitor is useful for prevention and/or treatment of various diseases, for example, ischemic diseases (cerebral infarction, myocardial infarction, reperfusion injury or postoperative injury etc.), inflammatory diseases (inflammatory bowel disease, multiple sclerosis, arthritis or lung injury etc.), neurodegenerative disorders (extrapyramidal disease, Parkinson's disease, Alzheimer's disease, muscular dystrophy or lumbar spinal canal stenosis etc.), glaucoma, diabetes, diabetic complication, shock, head trauma, spinal cord injury, renal failure, hyperalgesia or blood flow obstruction etc. And it is useful as an antiretroviral drug such as an anti HIV drug, a sensitizer of anticancer therapy or an immunosuppressant.

As PARP inhibitor, for example, in the specification of WO00/44726, it is described that 2H-phthalazin-1-one derivatives represented by formula (A)

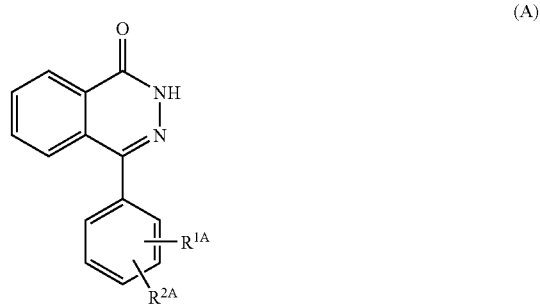

(wherein $R^{1A}$ is
(i) C1-4 alkyl substituted by hydroxy or amino, or
(ii) $-A^{1A}-A^{2A}-A^{3A}$, in which $A^{1A}$ is $-NR^{3A}C(O)-$ etc. wherein $R^{3A}$ is hydrogen or C1-4 alkyl etc., $A^{2A}$ is C1-8 alkylene etc., $A^{3A}$ is (i) hydrogen, (ii) $-NR^{17A}R^{18A}$ or (iii) $Cyc^{2A}$ etc. wherein $R^{17A}$ is (i) hydrogen, (ii) C1-8 alkyl etc., and $R^{18A}$ is (i) hydrogen or (ii) C1-8 alkyl etc., $Cyc^{2A}$ is 3-10 membered mono- or bi-heterocyclic ring containing 1-4 of nitrogen atoms, 1-2 of oxygen atoms and/or one sulfur atom, $R^{2A}$ is hydrogen or halogen etc. Necessary parts were extracted from the description of groups.) have PARP inhibitory activity.

In the specification of DE3302021, it is described that compounds represented by formula (B)

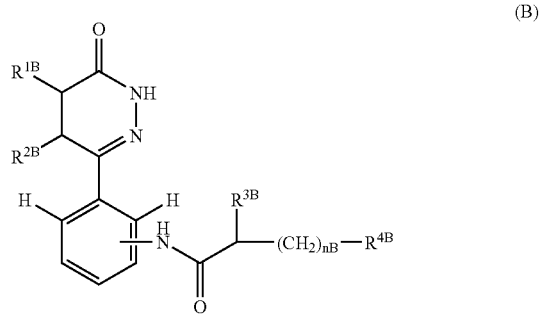

(wherein $R^{1B}$ is hydrogen or C1-3 alkyl, $R^{2B}$ is hydrogen, $R^{1B}$ and $R^{2B}$, taken together, are C1-4 alkylene, $R^{3B}$ is hydrogen or methyl, nB is 0-3, $R^{4B}$ is 1-pyrrolyl. Necessary parts were extracted from the description of groups.) have inhibitory activity of platelet aggregation.

In the specification of WO98/31674, it is described that compounds represented by formula (C)

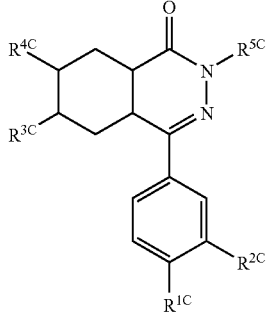

(wherein $R^{1C}$ is C1-4 alkoxy etc., $R^{2C}$ is C1-8 alkoxy etc., $R^{3C}$ and $R^{4C}$ is hydrogen or $R^{3C}$ and $R^{4C}$, taken together, are bond, $R^{5C}$ is hydrogen etc. Necessary parts were extracted from the description of groups.) have phosphodiesterase inhibitory activity.

In *Journal of Medicinal Chemistry.*, 44(16), 2511-2522 and 2523-2535 (2001), it is described that 4-(3-chloro-4-methoxyphenyl)-4a,5,8,8a-tetrahydrophthalazin-1(2H)-one (CAS Registry No. 244077-36-9) and 4-(3,4-dimethoxyphenyl)-5,6,7,8-tetrahydrophthalazin-1(2H)-one (CAS Registry No. 358368-98-6) have phosphodiesterase inhibitory activity.

In *Tetrahedron.*, 39(20), 3419-27 (1983), 4-phenyl-6,7,8,8a-tetrahydropyrrolo[1,2-d][1,2,4]triazin-1(2H)-one (CAS Registry No. 89311-30-8) is described as synthetic intermediate.

In *Synthesis.*, 240-242 (1995), 4-phenyl-5,6,7,8-tetrahydrophthalazin-1(2H)-one (CAS Registry No. 154810-22-7), 4-(4-methylphenyl)-5,6,7,8-tetrahydrophthalazin-1(2H)-one (CAS Registry No. 154810-23-8), 4-(4-fluorophenyl)-5,6,7,8-tetrahydrophthalazin-1(2H)-one (CAS Registry No. 154810-24-9), 4-(4-chlorophenyl)-5,6,7,8-tetrahydrophthalazin-1(2H)-one (CAS Registry No. 154810-25-0), and 4-(4-bromophenyl)-5,6,7,8-tetrahydrophthalazin-1(2H)-one (CAS Registry No. 154810-26-1) are described as synthetic intermediate.

In *Bioorganic and Medicinal Chemistry.*, 6, 349-454 (1998), 7-hydroxy-4-phenyl-6,7,8,8a-tetrahydropyrrolo[1,2-d][1,2,4]triazin-1(2H)-one (CAS Registry No. 206126-90-1) and 4-phenyl-8,8a-dihydro[1,3]thiazolo[3,4-d][1,2,4]triazin-1(2H)-one (CAS Registry No. 206126-96-7) are described as synthetic intermediate.

In *Journal of Medicinal Chemistry.*, 43(12), 2310-2323 (2000), 4-(pyridin-4-ylmethyl)-5,6,7,8-tetrahydrophthalazin-1(2H)-one (CAS Registry No. 212142-89-7) is described as synthetic intermediate.

In the specification of FR2647676, 4-t-butoxycarbonylmethyl-5,6,7,8-tetrahydrophthalazin-1(2H)-one (CAS Registry No. 134972-12-6) and 4-ethoxycarbonylmethyl-5,6,7,8-tetrahydrophthalazin-1(2H)-one (CAS Registry No. 134973-24-3) are described as synthetic intermediate.

DISCLOSURE OF THE INVENTION

In order to find a compound having poly(ADP-ribose) polymerase activity, the present inventors have conducted intensive studies and found, as a result, that the objects can be accomplished by the pyridazine derivative represented by formula (I), and thus the present invention has been accomplished.

The present invention relates to (1) a fused pyridazine derivative compound represented by formula (I)

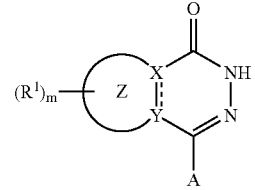

wherein $R^1$ is
(1) a hydrogen atom, (2) C1-8 alkyl, (3) C1-8 alkoxy, (4) hydroxy, (5) halogen atom, (6) nitro, (7) $NR^2R^3$, (8) C2-8 acyl, (9) C1-8 alkoxy substituted by phenyl or (10) C2-8 acyl substituted by $NR^2R^3$, $R^2$ and $R^3$ are each independently
(1) a hydrogen atom or (2) C1-8 alkyl, X and Y are each independently
(1) C, (2) CH or (3) N,

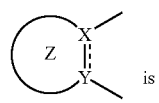

is
(1) a single bond or (2) a double bond,

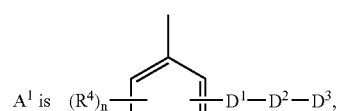

is (1) partially or fully saturated C3-10 mono-carbocyclic aryl or (2) partially or fully saturated 3-10 membered mono-hetero aryl containing 1 to 4 hetero atom(s) selected from oxygen, nitrogen and sulfur atoms, A is (1) $A^1$, (2) $A^2$, (3) $A^3$, (4) $A^4$ or (5) $A^5$,

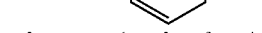

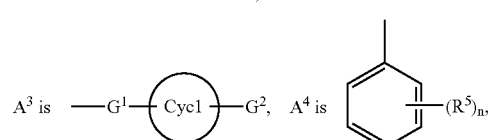

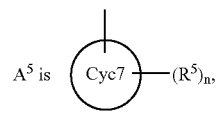

$D^1$ is (1) —NR$^6$C(O)—, (2) —NR$^6$C(S)—, (3) —NR$^6$SO$_2$—, (4) —CH$_2$—NR$^6$—, (5) —CH$_2$—O—, (6) —OC(O)—, (7) —CH$_2$—NR$^6$C(O)—, (8) —NR$^6$C(O)NR$^7$—, (9) —NR$^6$C(O)O—, (10) —NR$^6$C(S)NR$^7$—, (11) —NR$^6$— or (12) —NR$^6$C(=NR$^7$)—, $R^6$ and $R^7$ are each independently (1) a hydrogen atom, (2) C1-8 alkyl, (3) phenyl or (4) C1-8 alkyl substituted by phenyl, $D^2$ is (1) C1-8 alkylene, (2) C2-8 alkenylene, (3) Cyc2, (4) —(C1-4 alkylene)-O—(C1-4 alkylene)-, (5) —(C1-4 alkylene)-S—(C1-4 alkylene)-, (6) —(C1-4 alkylene)-NR$^8$—(C1-4 alkylene)-, (7)-(Cyc2)-(C1-8 alkylene)-, (8) —(C1-8 alkylene)-(Cyc2)- or (9) —(C1-4 alkylene)-(Cyc2)-(C1-4 alkylene)-, $R^8$ is (1) a hydrogen atom, (2) C1-8 alkyl, (3) C1-8 alkoxycarbonyl, (4) phenyl or (5) C1-8 alkyl substituted by phenyl, $D^3$ is (1) a hydrogen atom, (2) —NR$^9$R$^{10}$, (3) Cyc3, (4) —OR$^{11}$, (5) COOR$^{12}$, (6) CONR$^{13}$R$^{14}$, (7) cyano, (8) a halogen atom, (9) —C(=CR$^{15}$)NR$^{16}$R$^{17}$ or (10) —NR$^{18}$C(=NR$^{19}$)NR$^{20}$R$^{21}$, $R^9$ and $R^{13}$ are each independently (1) a hydrogen atom, (2) C1-8 alkyl, (3) C2-8 alkenyl, (4) C2-8 alkynyl, (5) Cyc3, (6) C1-8 alkoxy, (7) C2-8 alkenyloxy, (8) C2-8 alkynyloxy or (9) C1-8 alkyl substituted by Cyc3, C1-8 alkoxy, C1-8 alkylthio, cyano, hydroxy or 1 to 3 halogen atom(s), $R^{10}$ and $R^{14}$ are each independently (1) a hydrogen atom, (2) C1-8 alkyl, (3) C2-8 alkenyl, (4) C2-8 alkynyl, (5) C1-8 alkoxycarbonyl, (6) C2-8 acyl, (7) C3-8 cycloalkyl, (8) C1-8 alkoxycarbonyl substituted by Cyc4 or 1 to 3 halogen atom(s), or (9) C1-8 alkyl substituted by C1-8 alkoxy, $R^{11}$ and $R^{12}$ are each independently (1) a hydrogen atom or (2) C1-8 alkyl, $R^{15}$, $R^{16}$, $R^{17}$, $R^{18}$, $R^{19}$, $R^{20}$ and $R^{21}$ are each independently (1) a hydrogen atom, (2) C1-8 alkyl, (3) C1-8 alkoxycarbonyl, (4) phenyl or (5) C1-8 alkyl substituted by phenyl, $R^4$ is (1) a hydrogen atom, (2) C1-8 alkyl, (3) C1-8 alkoxy, (4) hydroxy, (5) halogen atom, (6) nitro or (7) NR$^{22}$R$^{23}$, $R^{22}$ and $R^{23}$ are each independently (1) a hydrogen atom or (2) C1-8 alkyl, $E^1$ is C1-4 alkylene, $E^2$ is (1) —C(O)NR$^{24}$—, (2) —NR$^{24}$C(O)—, (3) —NR$^{24}$—, (4) —C(O)O— or (5) —S—, $R^{24}$ is (1) a hydrogen atom, (2) C1-8 alkyl or (3) C1-8 alkyl substituted by phenyl, $E^3$ is (1) a bond or (2) C1-8 alkylene, $E^4$ is (1) C1-8 alkyl, (2) C2-8 alkenyl, (3) C2-8 alkynyl, (4) Cyc5, (5) NR$^{25}$R$^{26}$, (6) OR$^{27}$, (7) SR$^{27}$, (8) COOR$^{27}$, (9) C1-8 alkyl substituted by two of OR$^{25}$, (10) C1-8 alkyl substituted by 1 to 3 halogen atom(s), (11) cyano or (12) C2-8 acyl, $R^{25}$ is (1) a hydrogen atom, (2) C1-8 alkyl, (3) C2-8 alkenyl, (4) C2-8 alkynyl, (5) Cyc5 or (6) C1-8 alkyl substituted by Cyc5 or OR$^{28}$, $R^{26}$ is (1) a hydrogen atom, (2) C1-8 alkyl, (3) C1-8 alkoxycarbonyl, (4) phenyl or (5) C1-8 alkyl substituted by phenyl, $R^{27}$ is (1) a hydrogen atom, (2) C1-8 alkyl, (3) Cyc5 or (4) C1-8 alkyl substituted by Cyc5, $R^{28}$ is (1) a hydrogen atom or (2) C1-8 alkyl, $G^1$ is C1-8 alkylene, Cyc1 is (1) partially or fully saturated C3-10 mono- or bi-carbocyclic aryl, or (2) partially or fully saturated 3-10 membered mono- or bi-hetero aryl containing 1 to 4 hetero atom(s) selected from oxygen, nitrogen and sulfur atoms, $G^2$ is (1) a hydrogen atom, (2) C1-8 alkyl, (3) C1-8 alkoxycarbonyl, (4) C2-8 acyl, (5) Cyc6, (6) C1-8 alkyl or C2-8 alkenyl substituted by 1 to 2 substituent(s) selected from Cyc6, hydroxy and C1-8 alkoxy, (7) C1-8 alkoxycarbonyl substituted by Cyc6, (8) —C(O)-Cyc6, (9) nitro, (10) NR$^{41}$R$^{42}$, (11) C1-8 alkoxy or (12) C1-8 alkyl substituted by NR$^{41}$R$^{42}$, $R^{41}$ and $R^{42}$ are each dependently (1) a hydrogen atom or (2) C1-8 alkyl, $R^5$ is (1) a hydrogen atom, (2) C1-8 alkyl, (3) C1-8 alkoxy, (4) hydroxy, (5) nitro, (6) NR$^{29}$R$^{30}$, (7) C1-8 alkyl substituted by NR$^{29}$R$^{30}$, (8) NHSO$_2$OH, (9) amidino, (10) cyano, (11) a halogen atom, (12) Cyc8 or (13) C1-8 alkyl substituted by Cyc8, $R^{29}$ and $R^{30}$ are each independently (1) a hydrogen atom or (2) C1-8 alkyl, Cyc2, Cyc3, Cyc4, Cyc5, Cyc6 and Cyc8 are each independently (1) partially or fully saturated C3-10 mono- or bi-carbocyclic aryl, or (2) partially or fully saturated 3-10 membered mono- or bi-hetero aryl containing 1 to 4 hetero atom(s) selected from oxygen, nitrogen and sulfur atoms, Cyc7 is (1) partially or fully saturated C3-10 mono- or bi-carbocyclic aryl, or (2) partially or fully saturated 3-10 membered mono- or bi-hetero aryl containing 1 to 4 hetero atom(s) selected from oxygen, nitrogen and sulfur atoms, with proviso that Cyc7 is not benzene, Cyc2, Cyc3, Cyc4, Cyc5, Cyc6 and Cyc8 are optionally substituted by 1 to 3 substituent(s) selected from (1) C1-8 alkyl, (2) C2-8 alkenyl, (3) C1-8 alkoxy, (4) halogen atom, (5) trihalomethyl, (6) trihalomethoxy, (7) C1-8 alkoxycarbonyl, (8) oxo, (9) C1-8 alkyl substituted by C1-8 alkoxy or phenyl, (10) hydroxy and (11) NR$^{29}$R$^{30}$;

m and n are each independently 1 or 2, wherein (i) when A is $A^1$ or $A^2$, then

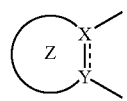

is not

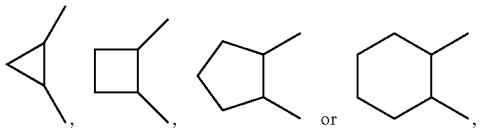

(ii) when A is $A^4$ and

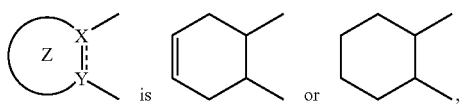 is then
$R^5$ is not hydroxy or C1-8 alkoxy,
(iii) when A is $A^5$, then

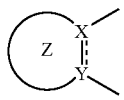

is not

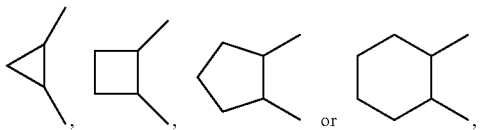

and
(iv) following compounds of (1) to (13) are excepted;
(1) 4-(3-chloro-4-methoxyphenyl)-4a,5,8,8a-tetrahydrophthalazin-1(2H)-one,
(2) 4-(3,4-dimethoxyphenyl)-5,6,7,8-tetrahydrophthalazin-1(2H)-one,
(3) 4-phenyl-6,7,8,8a-tetrahydropyrrolo[1,2-d][1,2,4]triazin-1(2H)-one,
(4) 4-phenyl-5,6,7,8-tetrahydrophthalazin-1(2H)-one,
(5) 4-(4-methylphenyl)-5,6,7,8-tetrahydrophthalazin-1(2H)-one,
(6) 4-(4-fluorophenyl)-5,6,7,8-tetrahydrophthalazin-1(2H)-one,
(7) 4-(4-chlorophenyl)-5,6,7,8-tetrahydrophthalazin-1(2H)-one,
(8) 4-(4-bromophenyl)-5,6,7,8-tetrahydrophthalazin-1(2H)-one,
(9) 7-hydroxy-4-phenyl-6,7,8,8a-tetrahydropyrrolo[1,2-d][1,2,4]triazin-1(2H)-one,
(10) 4-phenyl-8,8a-dihydro[1,3]thiazolo[3,4-d][1,2,4]triazin-1(2H)-one,
(11) 4-(pyridin-4-ylmethyl)-5,6,7,8-tetrahydrophthalazin-1(2H)-one,
(12) 4-t-butoxycarbonylmethyl-5,6,7,8-tetrahydrophthalazin-1(2H)-one,
(13) 4-ethoxycarbonylmethyl-5,6,7,8-tetrahydrophthalazin-1(2H)-one, or
a pharmaceutically acceptable salt thereof, (2) a process for preparing thereof, and
(3) an agent comprising the same as an active ingredient.

In the specification, C1-8 alkyl means methyl, ethyl, propyl, butyl, pentyl, hexyl, heptyl, octyl or isomeric groups thereof.

In the specification, C2-8 alkenyl means ethenyl, propenyl, butenyl, pentenyl, hexenyl, heptenyl, octenyl or isomeric groups thereof.

In the specification, C2-8 alkynyl means ethynyl, propynyl, butynyl, pentynyl, hexynyl, heptynyl, octynyl or isomeric groups thereof.

In the specification, C1-8 alkoxy means methoxy, ethoxy, propoxy, butoxy, pentyloxy, hexyloxy, heptyloxy, octyloxy or isomeric groups thereof.

In the specification, C2-8 alkenyloxy means ethenyloxy, propenyloxy, butenyloxy, pentenyloxy, hexenyloxy, heptenyloxy, octenyloxy or isomeric groups thereof.

In the specification, C2-8 alkynyloxy means ethynyloxy, propynyloxy, butynyloxy, pentynyloxy, hexynyloxy, heptynyloxy, octynyloxy or isomeric groups thereof.

In the specification, C1-8 alkylthio means methylthio, ethylthio, propylthio, butylthio, pentylthio, hexylthio, heptylthio, octylthio or isomeric groups thereof.

In the specification, C1-4 alkylene means methylene, ethylene, trimethylene, tetramethylene or isomeric groups thereof.

In the specification, C1-8 alkylene means methylene, ethylene, trimethylene, tetramethylene, pentamethylene, hexamethylene, heptamethylene, octamethylene or isomeric groups thereof.

In the specification, C2-8 alkenylene means ethenylene, propenylene, butenylene, pentenylene, hexenylene, heptenylene, octenylene or isomeric groups thereof.

In the specification, C1-8 alkoxycarbonyl means methoxycarbonyl, ethoxycarbonyl, propoxycarbonyl, butoxycarbonyl, pentyloxycarbonyl, hexyloxycarbonyl, heptyloxycarbonyl, octyloxycarbonyl or isomeric groups thereof.

In the specification, trihalomethyl is methyl substituted by three halogen atoms.

In the specification, trihalomethoxyl is methoxyl substituted by three halogen atoms.

In the specification, C2-8 acyl means ethanoyl (acethyl), propanoyl (propionyl), butanoyl (butyryl), pentanoyl (valeryl), hexanoyl, heptanoyl, octanoyl or isomeric groups thereof.

In the specification, C3-8 cycloalkyl means cyclopropyl, cyclobutyl, cyclopentyl, cyclohexyl, cycloheptyl, cyclooctyl.

In the specification, halogen means chlorine, bromine, fluorine or iodine.

In the specification, partially or fully saturated C3-10 mono-carbocyclic aryl represented by

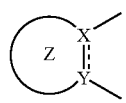

is cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclohexadiene, cycloheptadiene, cyclooctadiene etc.

In the specification, partially or fully saturated 3-10 membered mono-hetero aryl containing 1 to 4 hetero atom(s) selected from oxygen, nitrogen and sulfur atoms represented by

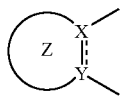

means aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine (dihydrothiopyran), tetrahydrothiaine (tetrahydrothiopyran), dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane etc.

In the specification, among partially or fully saturated 3-10 membered mono- or bi-hetero aryl containing 1 to 4 hetero atoms selected from oxygen, nitrogen or sulfur atom represented by Cyc1, Cyc2, Cyc3, Cyc4, Cyc5, Cyc6, Cyc7 and Cyc8, 3-10 membered mono- or bi-hetero aryl containing 1 to 4 hetero atoms selected from oxygen, nitrogen or sulfur atom means, for example, pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole etc.

Also, partially or fully saturated 3-10 membered mono- or bi-hetero aryl containing 1-4 hetero atoms selected from oxygen, nitrogen or sulfur atom, means aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine (dihydrothiopyran), tetrahydrothiaine (tetrahydrothiopyran), dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane, benzodithiane etc.

The above hetero ring includes N-oxide which is the compound where nitrogen is oxidized.

In the specification, partially or fully saturated C3-10 mono- or bi-carbocyclic aryl represented by Cyc1, Cyc2, Cyc3, Cyc4, Cyc5, Cyc6, Cyc7 and Cyc8 is cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, benzene, pentalene, azulene, perhydroazulene, perhydropentalene, indene, perhydroindene, indan, naphthalene, teterahydronaphthalene or perhydronaphthalene etc.

Unless otherwise specified, all isomers are included in the present invention. For example, alkyl, alkenyl, alkynyl, alkylene and alkoxy group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

According to the present invention, unless otherwise indicated and as is apparent for those skilled in the art, symbol

..........

indicates that it is bound to the opposite side of the sheet (namely α-configuration), symbol

▲ indicates that it is bound to the front side of the sheet (namely β-configuration), symbol

∿ indicates that it is α-, β- or a mixture thereof, and symbol

/ indicates that it is a mixture of α-configuration and β-configuration.

The compound of the present invention can be converted into a pharmaceutically acceptable salt by known methods.

The pharmaceutically acceptable salt is preferably water-soluble.

The pharmaceutically acceptable salt means, for example, salts of alkali metals (potassium, sodium, lithium, etc.), salts of alkaline earth metals (calcium, magnesium, etc.), ammonium salts (tetramethylammonium, tetrabutylammonium, etc.), salts of organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid-addition salts (inorganic acid salts (hydrochloride, hydrobromate, hydroiodate, sulfate, phosphate, nitrate, etc.), organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.), etc.

Furthermore, solvates or solvates of the above alkai (earth) metals, ammonium, organic amines and acid-addition salts of the compound of the present invention are included in the pharmaceutically acceptable salt of the present invention.

The solvate is preferably nontoxic and water-soluble. Appropriate solvate means, for example, solvates such as water, an alcohol solvent (ethanol etc.), etc.

In the specification,

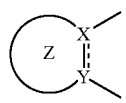

is preferably partially or fully saturated C3-7 mono-carbocyclic aryl, or partially or fully saturated 3-7 membered mono-hetero aryl containing 1 to 2 hetero atom(s) selected from oxygen, nitrogen and sulfur atom. Moreover, partially or fully saturated C3-7 mono-carbocyclic aryl, or partially or fully saturated 3-7 membered mono-hetero aryl is preferably following compounds;

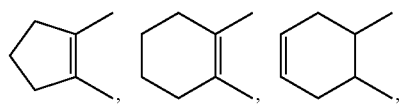

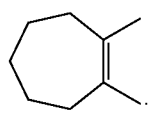

Partially or fully saturated 3-7 membered mono-hetero aryl containing 1 to 2 hetero atom(s) selected from oxygen, nitrogen and sulfur atoms is preferably following compounds;

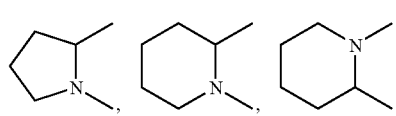

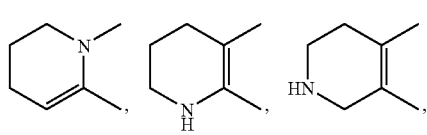

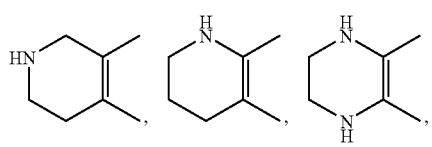

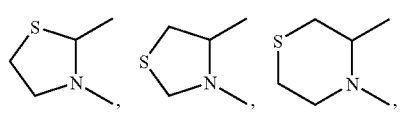

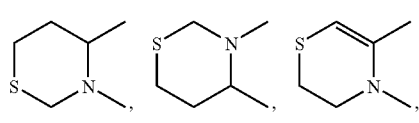

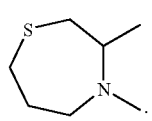

In the specification, A is preferably $A^1$, $A^2$ or $A^3$.

In the specification, $D^1$ is preferably —$NR^6C(O)$—, —$NR^6C(S)$—, —$NR^6SO_2$— or —$CH_2$—$NR^6$—, and more preferably —$NR^6C(O)$—.

In the specification, $D^2$ is preferably C1-8 alkylene, C2-8 alkenylene, —(C1-4 alkylene)-O—(C1-4 alkylene)-, —(C1-4 alkylene)-S—(C1-4 alkylene)-, —(C1-4 alkylene)-NR$^8$—(C1-4 alkylene)- or —(C1-8 alkylene)-(Cyc2)-, and more preferably C1-8 alkylene.

In the specification, $D^3$ is preferably —NR$^9$R$^{10}$ or Cyc3.

In the specification, $E^1$ is preferably C1-4 alkylene.

In the specification, $E^2$ is preferably —C(O)NR$^{24}$, —NR$^{24}$C(O)—, NR$^{24}$ or —S—

In the specification, $E^3$ is preferably bond or C1-8 alkylene.

In the specification, $E^4$ is preferably Cyc5 or NR$^{25}$R$^{26}$.

In the specification, Cyc1 is preferably partially or fully saturated 3-10 membered mono-hetero aryl containing 1 to 2 hetero atom(s) selected from oxygen, nitrogen and sulfur atom.

In the specification, when A is $A^3$ or $A^4$, at least one of X and Y is preferably N.

In the specification, when A is $A^3$ or $A^4$,

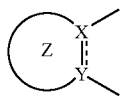

is preferably

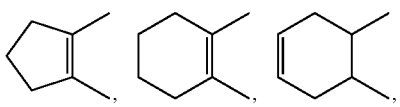

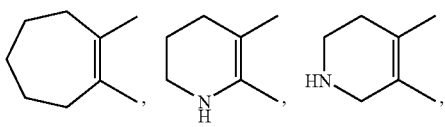

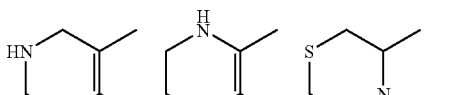

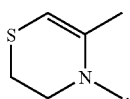

Among the compounds of the present invention represented by formula (I), preferred compounds are compounds represented by formula (I-A-1)

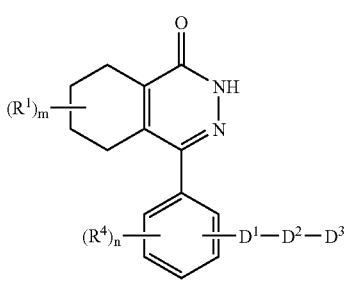

(I-A-1)

(wherein all symbols have the same meanings as described above.), compounds represented by formula (I-A-2)

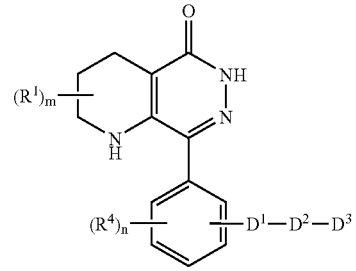

(I-A-2)

(wherein all symbols have the same meanings as described above.), compounds represented by formula (I-B-1)

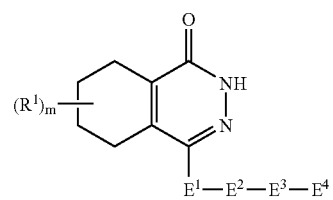

(I-B-1)

(wherein all symbols have the same meanings as described above.), compounds represented by formula (I-B-2)

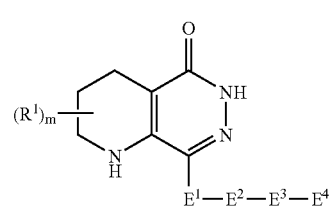

(I-B-2)

(wherein all symbols have the same meanings as described above.), compounds represented by formula (I-C-1)

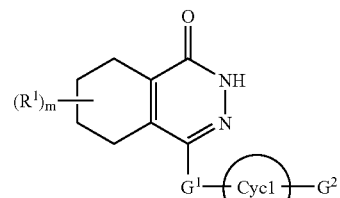

(I-C-1)

(wherein all symbols have the same meanings as described above.), and compounds represented by formula (I-C-2)

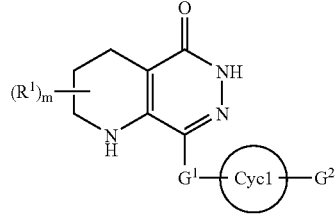
(I-C-2)

(wherein all symbols have the same meanings as described above.).

Concrete compounds of the present invention include compounds shown in Tables 1 to 90, compounds described in Examples, and pharmaceutically acceptable salts thereof.

In each Table, Me represents methyl group, Et represents ethyl group, Pr represents propyl group, i-Pr represents isopropyl group, Bu represents butyl group, c-Pr represents cyclopropyl group, c-Bu represents cyclobutyl group, c-Pen represents cyclopentyl group, c-Hex represents cyclohexyl group, Ph represents phenyl group, Bn represents benzyl group, and other symbols have the same meanings as described above.

TABLE 1

(I-A-1-1)

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | (amidine structure: butyl-C(=NH)NH₂) |
| 10 | (guanidine structure: propyl-NH-C(=NH)NH₂) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |

TABLE 1-continued (I-A-1-1)

| No | —D²—D³ |
|---|---|
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | Et-NH-CH₂-C≡CH |
| 22 | pentyl-NH-CH₂-C≡CH |
| 23 | butyl-NH-CH₂-C≡CH |
| 24 | pentyl-N(Me)-CH₂-C≡CH |
| 25 | butyl-N(Me)-CH₂-C≡CH |
| 26 | Me₂C(Me)-CH₂-CH₂-N(Me)-CH₂-C≡CH |
| 27 | Me₂C(Me)-CH₂-CH₂-CH₂-N(Me)-CH₂-C≡CH |
| 28 | pentyl-NH-CH₂-CH=C(Me)₂ |
| 29 | butyl-NH-CH₂-CH=C(Me)₂ |
| 30 | Me₂C(Me)-CH₂-CH₂-CH₂-NH-CH₂-CH=C(Me)₂ |

TABLE 2

(I-A-1-1)

| No | —D²—D³ |
|----|--------|
| 31 | (3,3-dimethylbutyl)NH-CH₂-CH=C(Me)Me |
| 32 | butyl-NH-CH₂-C(=CH₂)-Me |
| 33 | butyl-NH-C(Me)=CH₂ (with Me) |
| 34 | (3,3-dimethylbutyl)NH-CH₂-C(=CH₂)Me |
| 35 | (3,3-dimethylbutyl)NH-C(Me)=CH₂ |
| 36 | ethyl-O-CH₂CH₂-NH₂ |
| 37 | ethyl-O-CH₂CH₂-NH-CH₂-C(=CH₂)Me |
| 38 | ethyl-O-CH₂CH₂-NH-CH₂-CH=C(Me)Me |
| 39 | ethyl-O-CH₂CH₂-N(Me)-CH₂-C≡CH |
| 40 | ethyl-S-CH₂CH₂-NH₂ |
| 41 | ethyl-S-CH₂CH₂-NH-CH₂-C(=CH₂)Me |
| 42 | ethyl-S-CH₂CH₂-NH-CH₂-CH=C(Me)Me |

TABLE 2-continued (I-A-1-1)

| No | —D²—D³ |
|----|--------|
| 43 | ethyl-S-CH₂CH₂-N(Me)-CH₂-C≡CH |
| 44 | ethyl-NH-CH₂CH₂-NH₂ |
| 45 | 3-methylazetidine (NH) |
| 46 | 4-methylcyclohexyl-NH₂ |
| 47 | 3-methylbenzyl-NH₂ |
| 48 | 4-ethylpyridine |
| 49 | 3-ethylaniline-NH₂ |
| 50 | 3-propylpyridine |
| 51 | butyl-pyrrolidine |
| 52 | pentyl-pyrrolidine |
| 53 | butyl-(3-methoxypyrrolidine) |
| 54 | pentyl-(3-methoxypyrrolidine) |

TABLE 2-continued
(I-A-1-1)
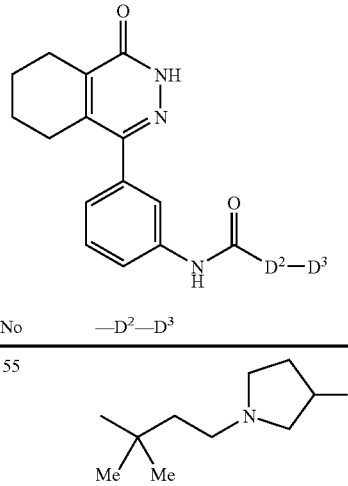
| No | —D²—D³ |
|---|---|
| 55 | 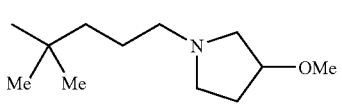 |
| 56 | 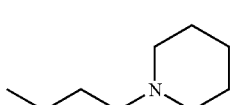 |
| 57 | 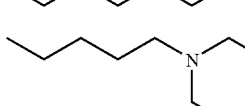 |
| 58 | 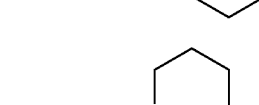 |
| 59 | 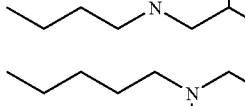 |
| 60 | 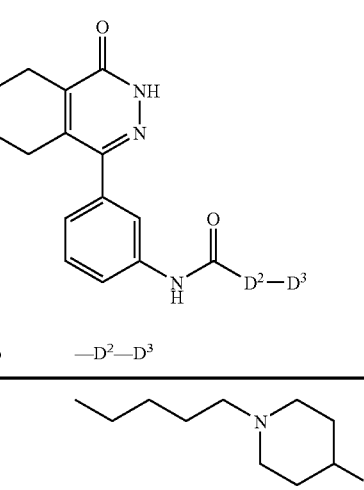 |
TABLE 3
(I-A-1-1)
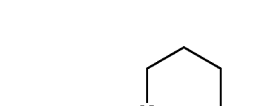
| No | —D²—D³ |
|---|---|
| 61 | 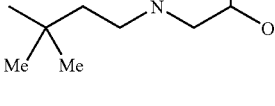 |
TABLE 3-continued
(I-A-1-1)
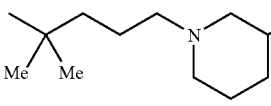
| No | —D²—D³ |
|---|---|
| 62 | 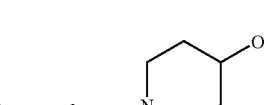 |
| 63 |  |
| 64 |  |
| 65 | 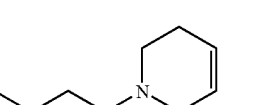 |
| 66 | 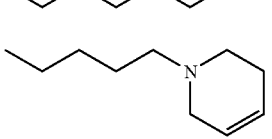 |
| 67 | 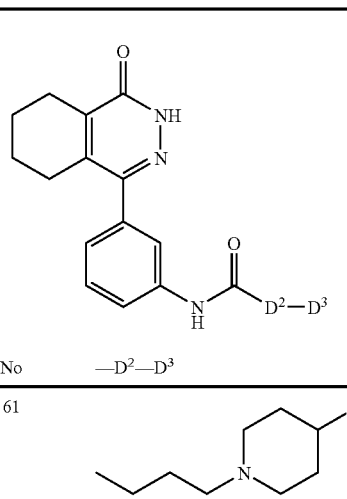 |
| 68 | |
| 69 | |
| 70 | |

TABLE 3-continued (I-A-1-1)

| No | —D²—D³ |
|---|---|
| 71 | propyl-morpholine |
| 72 | butyl-morpholine |
| 73 | pentyl-morpholine |
| 74 | 3,3-dimethylbutyl-morpholine (Me, Me) |
| 75 | 4,4-dimethylpentyl-morpholine (Me, Me) |
| 76 | ethoxyethyl-azetidine |
| 77 | ethoxyethyl-pyrrolidine |
| 78 | ethoxyethyl-piperidine |
| 79 | ethoxyethyl-3-methoxypyrrolidine |
| 80 | ethoxyethyl-3-methoxypiperidine |

TABLE 3-continued (I-A-1-1)

| No | —D²—D³ |
|---|---|
| 81 | ethoxyethyl-4-methoxypiperidine |
| 82 | ethoxyethyl-tetrahydropyridine |
| 83 | ethoxyethyl-morpholine |
| 84 | ethylthioethyl-3-methoxypyrrolidine |
| 85 | ethylthioethyl-3-methoxypiperidine |
| 86 | ethylthioethyl-4-methoxypiperidine |
| 87 | ethylthioethyl-tetrahydropyridine |
| 88 | ethylthioethyl-morpholine |

TABLE 4
(I-A-1-2)
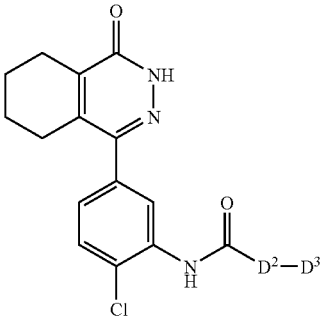
| No | —D²—D³ |
|----|--------|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | 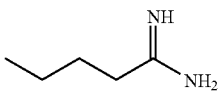 |
| 10 | 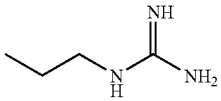 |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | 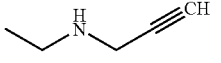 |
| 22 |  |
| 23 | 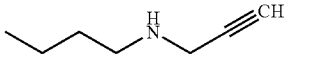 |
| 24 | 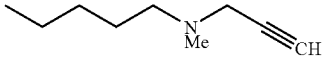 |
| 25 | 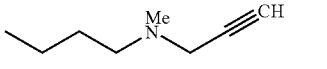 |
| 26 | 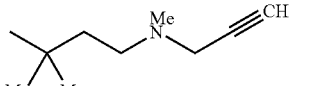 |
| 27 | 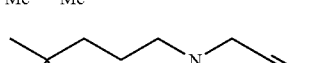 |
TABLE 4-continued
(I-A-1-2)
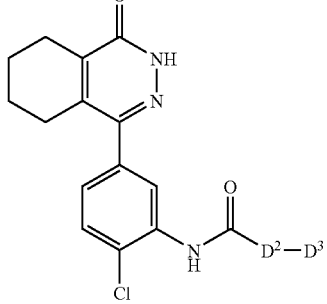
| No | —D²—D³ |
|----|--------|
| 28 | 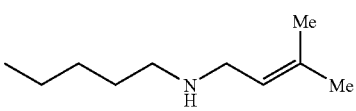 |
| 29 | 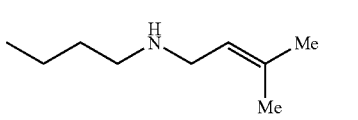 |
| 30 |  |
TABLE 5
(I-A-1-2)
| No | —D²—D³ |
|----|--------|
| 31 |  |
| 32 |  |
| 33 | 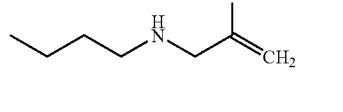 |

TABLE 5-continued
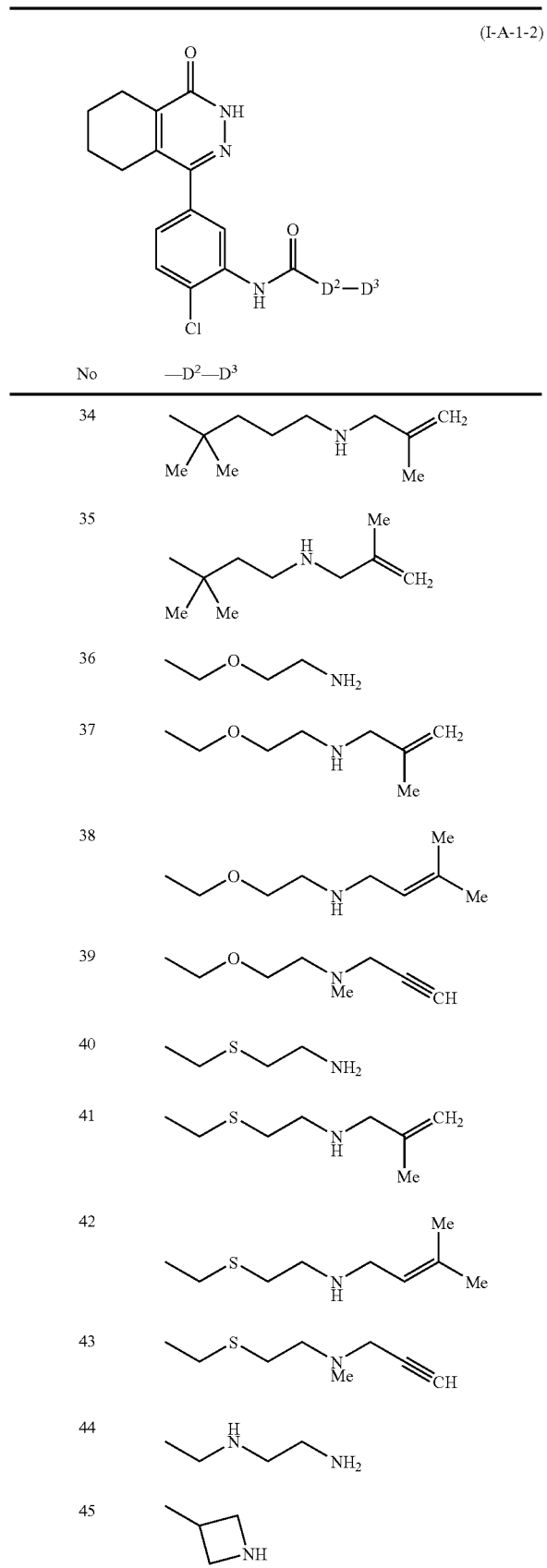
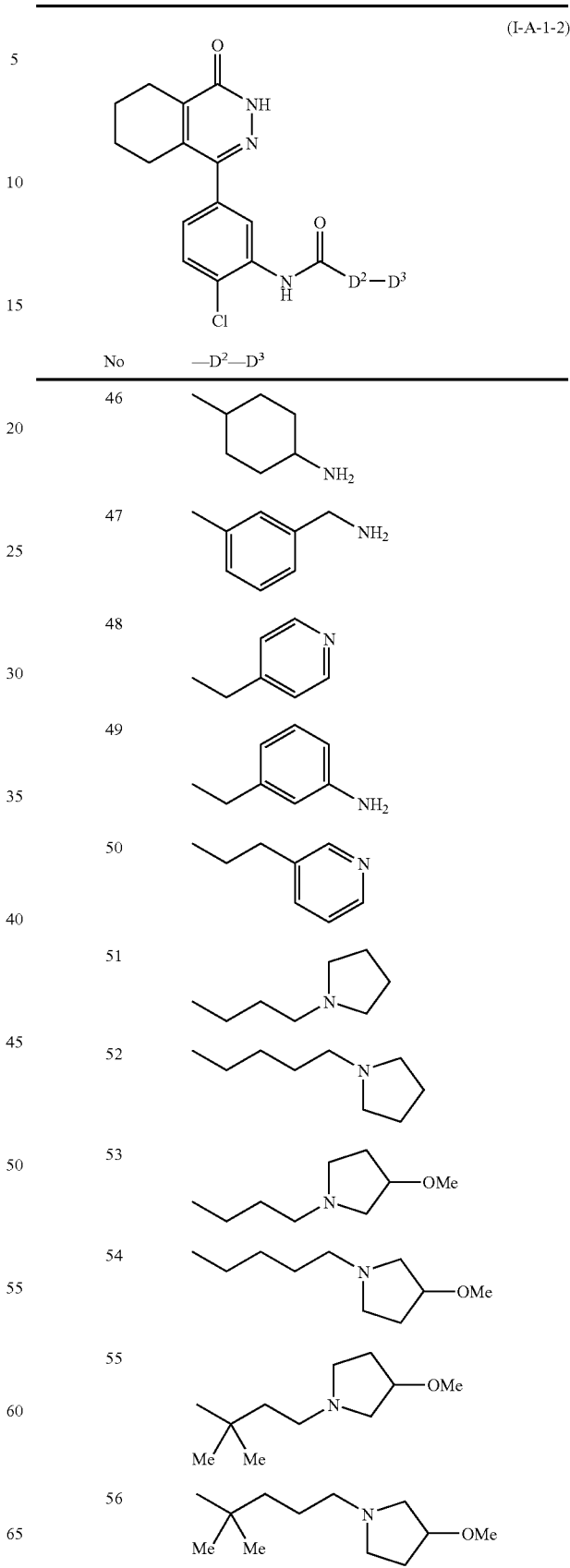

TABLE 5-continued (I-A-1-2)

| No | —D²—D³ |
|---|---|
| 57 | butyl-piperidine |
| 58 | pentyl-piperidine |
| 59 | butyl-3-methoxypiperidine |
| 60 | pentyl-3-methoxypiperidine |

TABLE 6

(I-A-1-2)

| No | —D²—D³ |
|---|---|
| 61 | butyl-4-methoxypiperidine |
| 62 | pentyl-4-methoxypiperidine |

TABLE 6-continued (I-A-1-2)

| No | —D²—D³ |
|---|---|
| 63 | 3,3-dimethylbutyl-3-methoxypiperidine |
| 64 | 4,4-dimethylpentyl-3-methoxypiperidine |
| 65 | 3,3-dimethylbutyl-4-methoxypiperidine |
| 66 | 4,4-dimethylpentyl-4-methoxypiperidine |
| 67 | butyl-tetrahydropyridine |
| 68 | pentyl-tetrahydropyridine |
| 69 | 3,3-dimethylbutyl-tetrahydropyridine |
| 70 | 4,4-dimethylpentyl-tetrahydropyridine |
| 71 | propyl-morpholine |

TABLE 6-continued (I-A-1-2)

| No | —D²—D³ |
|---|---|
| 72 | butyl-morpholine |
| 73 | pentyl-morpholine |
| 74 | 3,3-dimethylbutyl-morpholine |
| 75 | 4,4-dimethylpentyl-morpholine |
| 76 | ethoxyethyl-azetidine |
| 77 | ethoxyethyl-pyrrolidine |
| 78 | ethoxyethyl-piperidine |
| 79 | ethoxyethyl-3-methoxypyrrolidine |
| 80 | ethoxyethyl-3-methoxypiperidine |

TABLE 6-continued (I-A-1-2)

| No | —D²—D³ |
|---|---|
| 81 | ethoxyethyl-4-methoxypiperidine |
| 82 | ethoxyethyl-tetrahydropyridine |
| 83 | ethoxyethyl-morpholine |
| 84 | ethylthioethyl-3-methoxypyrrolidine |
| 85 | ethylthioethyl-3-methoxypiperidine |
| 86 | ethylthioethyl-4-methoxypiperidine |
| 87 | ethylthioethyl-tetrahydropyridine |
| 88 | ethylthioethyl-morpholine |

TABLE 7

(I-A-1-3)

[Structure: 5,6,7,8-tetrahydrophthalazin-1(2H)-one substituted at 4-position with phenyl bearing CF₃ and NHC(O)-D²-D³]

| No | —D²—D³ |
|----|--------|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | pentanimidamide (butyl-C(=NH)NH₂) |
| 10 | propyl-NH-C(=NH)NH₂ (guanidine) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | ethyl-NH-CH₂-C≡CH |
| 22 | pentyl-NH-CH₂-C≡CH |
| 23 | butyl-NH-CH₂-C≡CH |
| 24 | pentyl-N(Me)-CH₂-C≡CH |
| 25 | butyl-N(Me)-CH₂-C≡CH |
| 26 | Me₂C(Me)CH₂CH₂-N(Me)-CH₂-C≡CH |
| 27 | Me₂C(Me)CH₂CH₂CH₂-N(Me)-CH₂-C≡CH |

TABLE 7-continued (I-A-1-3)

[Same structure as above]

| No | —D²—D³ |
|----|--------|
| 28 | pentyl-NH-CH₂-CH=C(Me)Me |
| 29 | butyl-NH-CH₂-CH=C(Me)Me |
| 30 | Me₃C-CH₂CH₂CH₂-NH-CH₂-CH=C(Me)Me |

TABLE 8

(I-A-1-3)

[Same structure as above]

| No | —D²—D³ |
|----|--------|
| 31 | Me₃C-CH₂CH₂-NH-CH₂-CH=C(Me)Me |
| 32 | pentyl-NH-CH₂-C(Me)=CH₂ |
| 33 | butyl-NH-CH₂-C(Me)=CH₂ |

TABLE 8-continued (I-A-1-3)

| No | —D²—D³ |
|---|---|
| 34 | (CH₂)₃ chain: CMe₂-CH₂-CH₂-CH₂-NH-CH₂-C(=CH₂)Me |
| 35 | CMe₂-CH₂-CH₂-NH-CH₂-C(=CH₂)Me |
| 36 | Et-O-CH₂-CH₂-NH₂ |
| 37 | Et-O-CH₂-CH₂-NH-CH₂-C(=CH₂)Me |
| 38 | Et-O-CH₂-CH₂-NH-CH₂-CH=CMe₂ |
| 39 | Et-O-CH₂-CH₂-N(Me)-CH₂-C≡CH |
| 40 | Et-S-CH₂-CH₂-NH₂ |
| 41 | Et-S-CH₂-CH₂-NH-CH₂-C(=CH₂)Me |
| 42 | Et-S-CH₂-CH₂-NH-CH₂-CH=CMe₂ |
| 43 | Et-S-CH₂-CH₂-N(Me)-CH₂-C≡CH |
| 44 | Et-NH-CH₂-CH₂-NH₂ |
| 45 | 3-methyl-azetidine |
| 46 | 4-methylcyclohexylamine |
| 47 | 3-methylbenzylamine |
| 48 | 4-ethylpyridine |
| 49 | 3-ethylaniline |
| 50 | 3-propylpyridine |
| 51 | 1-butylpyrrolidine |
| 52 | 1-pentylpyrrolidine |
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |

TABLE 8-continued
(I-A-1-3)
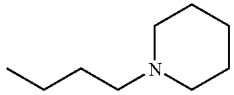
| No | —D²—D³ |
|---|---|
| 57 | 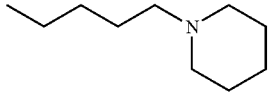 |
| 58 |  |
| 59 | 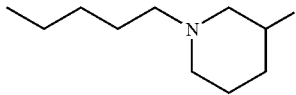 |
| 60 | 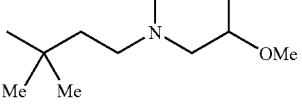 |
TABLE 9
(I-A-1-3)
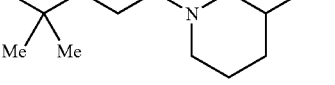
| No | —D²—D³ |
|---|---|
| 61 | 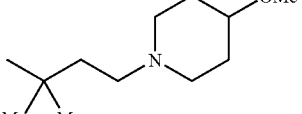 |
| 62 | 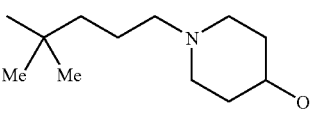 |
TABLE 9-continued
(I-A-1-3)
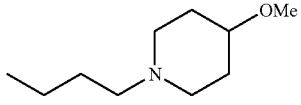
| No | —D²—D³ |
|---|---|
| 63 | |
| 64 | |
| 65 | |
| 66 | |
| 67 | |
| 68 | |
| 69 | |
| 70 | |
| 71 | 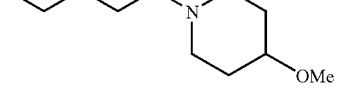 |

TABLE 9-continued (I-A-1-3)

| No | —D²—D³ |
|---|---|
| 72 | butyl-morpholine |
| 73 | pentyl-morpholine |
| 74 | 3,3-dimethylbutyl-morpholine |
| 75 | 4,4-dimethylpentyl-morpholine |
| 76 | ethoxyethyl-azetidine |
| 77 | ethoxyethyl-pyrrolidine |
| 78 | ethoxyethyl-piperidine |
| 79 | ethoxyethyl-3-methoxypyrrolidine |
| 80 | ethoxyethyl-3-methoxypiperidine |
| 81 | ethoxyethyl-4-methoxypiperidine |
| 82 | ethoxyethyl-tetrahydropyridine |
| 83 | ethoxyethyl-morpholine |
| 84 | ethylthioethyl-3-methoxypyrrolidine |
| 85 | ethylthioethyl-3-methoxypiperidine |
| 86 | ethylthioethyl-4-methoxypiperidine |
| 87 | ethylthioethyl-tetrahydropyridine |
| 88 | ethylthioethyl-morpholine |

TABLE 10

(I-A-1-4)

[Structure: 5,6,7,8-tetrahydrophthalazin-1(2H)-one with 4-(3-(NH-D²-D³)phenyl) substituent]

| No | —D²—D³ |
|----|--------|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | butyl-C(=NH)NH₂ (pentanimidamide chain) |
| 10 | propyl-NH-C(=NH)NH₂ (guanidine) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | Et-NH-CH₂-C≡CH |
| 22 | pentyl-NH-CH₂-C≡CH |
| 23 | butyl-NH-CH₂-C≡CH |
| 24 | pentyl-N(Me)-CH₂-C≡CH |
| 25 | butyl-N(Me)-CH₂-C≡CH |
| 26 | (3,3-dimethylbutyl)-N(Me)-CH₂-C≡CH |
| 27 | (4,4-dimethylpentyl)-N(Me)-CH₂-C≡CH |

TABLE 10-continued (I-A-1-4)

[Same structure as above]

| No | —D²—D³ |
|----|--------|
| 28 | pentyl-NH-CH₂-CH=C(Me)₂ |
| 29 | butyl-NH-CH₂-CH=C(Me)₂ |
| 30 | (4,4-dimethylpentyl)-NH-CH₂-CH=C(Me)₂ |

TABLE 11

(I-A-1-4)

[Same structure as above]

| No | —D²—D³ |
|----|--------|
| 31 | (3,3-dimethylbutyl)-NH-CH₂-CH=C(Me)₂ |
| 32 | pentyl-NH-CH₂-C(Me)=CH₂ |
| 33 | butyl-NH-CH₂-C(Me)=CH₂ |
| 34 | (4,4-dimethylpentyl)-NH-CH₂-C(Me)=CH₂ |

TABLE 11-continued (I-A-1-4)

| No | —D²—D³ |
|---|---|
| 35 | Me-C(Me)(Me)-CH2CH2-NH-CH2-C(Me)=CH2 |
| 36 | EtO-CH2CH2-NH2 |
| 37 | EtO-CH2CH2-NH-CH2-C(Me)=CH2 |
| 38 | EtO-CH2CH2-NH-CH2-CH=C(Me)Me |
| 39 | EtO-CH2CH2-N(Me)-CH2-C≡CH |
| 40 | EtS-CH2CH2-NH2 |
| 41 | EtS-CH2CH2-NH-CH2-C(Me)=CH2 |
| 42 | EtS-CH2CH2-NH-CH2-CH=C(Me)Me |
| 43 | EtS-CH2CH2-N(Me)-CH2-C≡CH |
| 44 | Et-NH-CH2CH2-NH2 |
| 45 | 3-methylazetidine |
| 46 | 4-methylcyclohexylamine |

TABLE 11-continued (I-A-1-4)

| No | —D²—D³ |
|---|---|
| 47 | 3-methylbenzylamine |
| 48 | 4-ethylpyridine |
| 49 | 3-ethylaniline |
| 50 | 3-propylpyridine |
| 51 | 1-butylpyrrolidine |
| 52 | 1-pentylpyrrolidine |
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |
| 57 | 1-butylpiperidine |

TABLE 11-continued (I-A-1-4)

| No | —D²—D³ |
|---|---|
| 58 | pentyl-piperidine |
| 59 | butyl-(3-methoxy)piperidine |
| 60 | pentyl-(3-methoxy)piperidine |

TABLE 12

(I-A-1-4)

| No | —D²—D³ |
|---|---|
| 61 | butyl-(4-methoxy)piperidine |
| 62 | pentyl-(4-methoxy)piperidine |
| 63 | 3,3-dimethylbutyl-(3-methoxy)piperidine |
| 64 | 4,4-dimethylpentyl-(3-methoxy)piperidine |
| 65 | 3,3-dimethylbutyl-(4-methoxy)piperidine |
| 66 | 4,4-dimethylpentyl-(4-methoxy)piperidine |
| 67 | butyl-tetrahydropyridine |
| 68 | pentyl-tetrahydropyridine |
| 69 | 3,3-dimethylbutyl-tetrahydropyridine |
| 70 | 4,4-dimethylpentyl-tetrahydropyridine |
| 71 | propyl-morpholine |
| 72 | butyl-morpholine |
| 73 | pentyl-morpholine |

TABLE 12-continued (I-A-1-4)

| No | —D²—D³ |
|----|--------|
| 74 | (3,3-dimethylbutyl)morpholine |
| 75 | (4,4-dimethylpentyl)morpholine |
| 76 | 2-ethoxyethyl-azetidine |
| 77 | 2-ethoxyethyl-pyrrolidine |
| 78 | 2-ethoxyethyl-piperidine |
| 79 | 2-ethoxyethyl-3-methoxypyrrolidine |
| 80 | 2-ethoxyethyl-3-methoxypiperidine |
| 81 | 2-ethoxyethyl-4-methoxypiperidine |
| 82 | 2-ethoxyethyl-tetrahydropyridine |
| 83 | 2-ethoxyethyl-morpholine |

TABLE 12-continued (I-A-1-4)

| No | —D²—D³ |
|----|--------|
| 84 | 2-(ethylthio)ethyl-3-methoxypyrrolidine |
| 85 | 2-(ethylthio)ethyl-3-methoxypiperidine |
| 86 | 2-(ethylthio)ethyl-4-methoxypiperidine |
| 87 | 2-(ethylthio)ethyl-tetrahydropyridine |
| 88 | 2-(ethylthio)ethyl-morpholine |

TABLE 13

(I-A-1-5)

| No | —D²—D³ |
|----|--------|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |

TABLE 13-continued (I-A-1-5)

[Structure: 4-(4-chloro-3-(NH-D²-D³)phenyl)-5,6,7,8-tetrahydrophthalazin-1(2H)-one]

| No | —D²—D³ |
|----|--------|
| 9 | pentanimidamide: —C(=NH)NH₂ group with butyl chain (pentanamidine) |
| 10 | N-propylguanidine: —NH—C(=NH)—NH₂ with propyl |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | Et-NH-CH₂-C≡CH |
| 22 | n-Pentyl-NH-CH₂-C≡CH |
| 23 | n-Butyl-NH-CH₂-C≡CH |
| 24 | n-Pentyl-N(Me)-CH₂-C≡CH |
| 25 | n-Butyl-N(Me)-CH₂-C≡CH |
| 26 | Me₂C(Me)-CH₂CH₂-N(Me)-CH₂-C≡CH (3,3-dimethylbutyl) |
| 27 | Me₃C-CH₂CH₂CH₂-N(Me)-CH₂-C≡CH |
| 28 | n-Pentyl-NH-CH₂-CH=C(Me)₂ |

TABLE 13-continued (I-A-1-5)

[Same core structure]

| No | —D²—D³ |
|----|--------|
| 29 | n-Butyl-NH-CH₂-CH=C(Me)Me |
| 30 | Me₃C-CH₂CH₂CH₂-NH-CH₂-CH=C(Me)Me |

TABLE 14

(I-A-1-5)

[Same core structure]

| No | —D²—D³ |
|----|--------|
| 31 | Me₂C(Me)-CH₂CH₂-NH-CH₂-CH=C(Me)Me |
| 32 | n-Pentyl-NH-CH₂-C(Me)=CH₂ |
| 33 | n-Butyl-NH-CH₂-C(Me)=CH₂ |
| 34 | Me₃C-CH₂CH₂CH₂-NH-CH₂-C(Me)=CH₂ |

TABLE 14-continued (I-A-1-5)

| No | —D²—D³ |
|---|---|
| 35 | (Me)(Me)(Me)C-CH₂CH₂-NH-CH₂-C(Me)=CH₂ |
| 36 | EtO-CH₂CH₂-NH₂ |
| 37 | EtO-CH₂CH₂-NH-CH₂-C(Me)=CH₂ |
| 38 | EtO-CH₂CH₂-NH-CH₂-CH=C(Me)Me |
| 39 | EtO-CH₂CH₂-N(Me)-CH₂-C≡CH |
| 40 | EtS-CH₂CH₂-NH₂ |
| 41 | EtS-CH₂CH₂-NH-CH₂-C(Me)=CH₂ |
| 42 | EtS-CH₂CH₂-NH-CH₂-CH=C(Me)Me |
| 43 | EtS-CH₂CH₂-N(Me)-CH₂-C≡CH |
| 44 | Et-NH-CH₂CH₂-NH₂ |
| 45 | 3-azetidinyl (NH) |
| 46 | 4-methylcyclohexyl-NH₂ |
| 47 | 3-methylbenzyl-NH₂ |
| 48 | 4-ethylpyridyl |
| 49 | 3-ethylphenyl-NH₂ |
| 50 | 3-propylpyridyl |
| 51 | 1-butylpyrrolidinyl |
| 52 | 1-pentylpyrrolidinyl |
| 53 | 1-butyl-3-methoxypyrrolidinyl |
| 54 | 1-pentyl-3-methoxypyrrolidinyl |
| 55 | (Me)₂C(Me)-CH₂CH₂-(3-methoxypyrrolidin-1-yl) |
| 56 | (Me)₂C(Me)-CH₂CH₂CH₂-(3-methoxypyrrolidin-1-yl) |
| 57 | 1-butylpiperidinyl |

TABLE 14-continued (I-A-1-5)

| No | —D²—D³ |
|---|---|
| 58 | n-pentyl-piperidine |
| 59 | n-butyl-3-methoxypiperidine |
| 60 | n-pentyl-3-methoxypiperidine |

TABLE 15

(I-A-1-5)

| No | —D²—D³ |
|---|---|
| 61 | n-butyl-4-methoxypiperidine |
| 62 | n-pentyl-4-methoxypiperidine |
| 63 | 3,3-dimethylbutyl-3-methoxypiperidine |

TABLE 15-continued (I-A-1-5)

| No | —D²—D³ |
|---|---|
| 64 | 3,3-dimethylbutyl-3-methoxypiperidine |
| 65 | 3,3-dimethylbutyl-4-methoxypiperidine |
| 66 | 3,3-dimethylpentyl-4-methoxypiperidine |
| 67 | n-butyl-1,2,3,6-tetrahydropyridine |
| 68 | n-pentyl-1,2,3,6-tetrahydropyridine |
| 69 | 3,3-dimethylbutyl-1,2,3,6-tetrahydropyridine |
| 70 | 3,3-dimethylpentyl-1,2,3,6-tetrahydropyridine |
| 71 | n-propyl-morpholine |
| 72 | n-butyl-morpholine |
| 73 | n-pentyl-morpholine |

TABLE 15-continued (I-A-1-5)

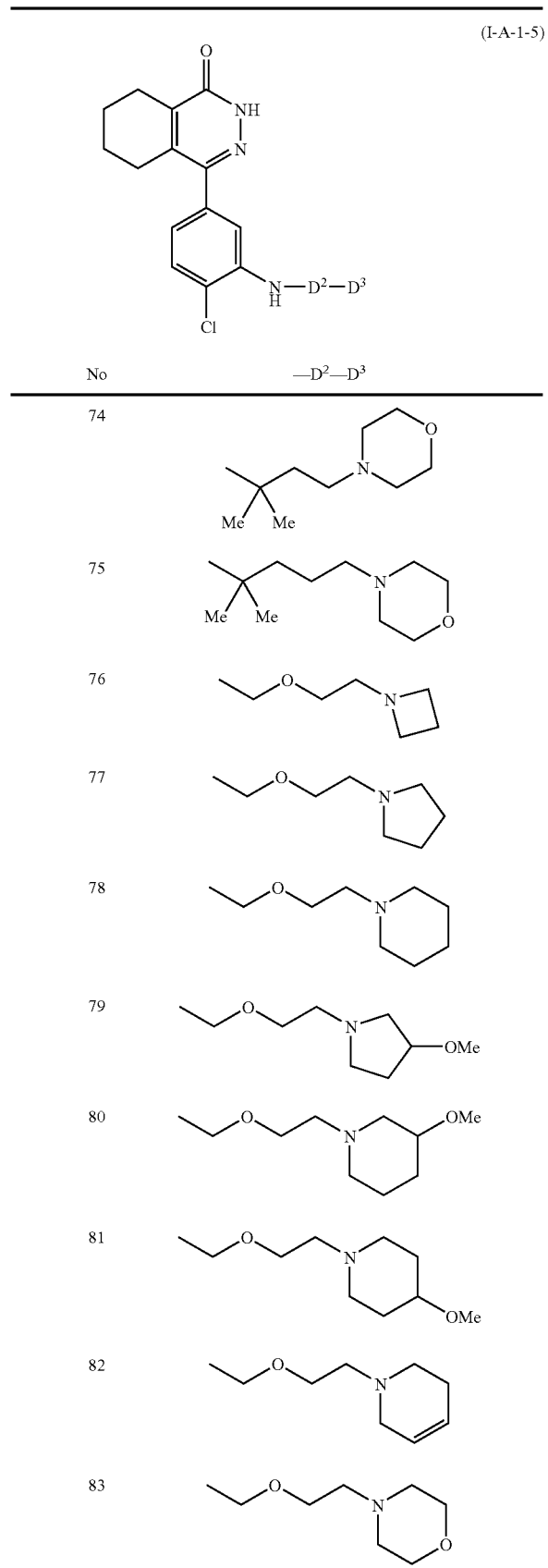

| No | —D²—D³ |
|---|---|
| 74 | (morpholine-CH₂CH₂-C(Me)₂-) |
| 75 | (morpholine-CH₂CH₂CH₂-C(Me)₂-) |
| 76 | (azetidine-CH₂CH₂-O-CH₂CH₃) |
| 77 | (pyrrolidine-CH₂CH₂-O-CH₂CH₃) |
| 78 | (piperidine-CH₂CH₂-O-CH₂CH₃) |
| 79 | (3-OMe-pyrrolidine-CH₂CH₂-O-CH₂CH₃) |
| 80 | (3-OMe-piperidine-CH₂CH₂-O-CH₂CH₃) |
| 81 | (4-OMe-piperidine-CH₂CH₂-O-CH₂CH₃) |
| 82 | (tetrahydropyridine-CH₂CH₂-O-CH₂CH₃) |
| 83 | (morpholine-CH₂CH₂-O-CH₂CH₃) |

TABLE 15-continued (I-A-1-5)

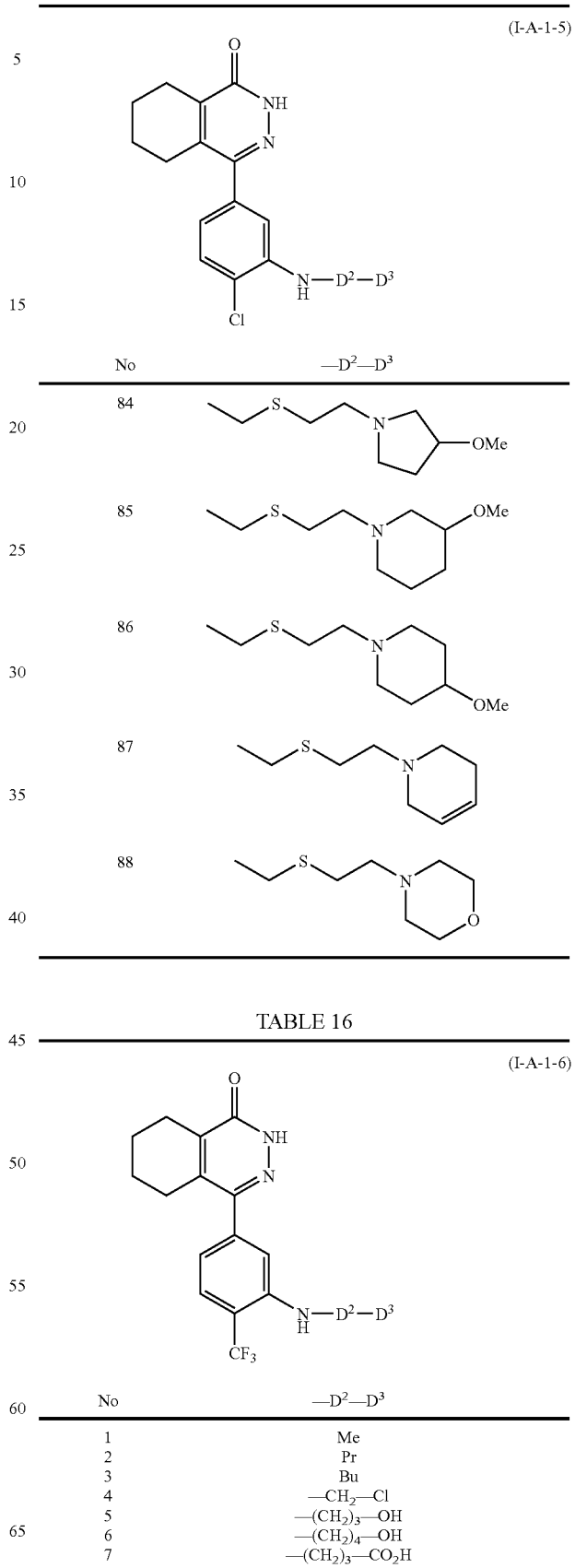

| No | —D²—D³ |
|---|---|
| 84 | (3-OMe-pyrrolidine-CH₂CH₂-S-Et) |
| 85 | (3-OMe-piperidine-CH₂CH₂-S-Et) |
| 86 | (4-OMe-piperidine-CH₂CH₂-S-Et) |
| 87 | (tetrahydropyridine-CH₂CH₂-S-Et) |
| 88 | (morpholine-CH₂CH₂-S-Et) |

TABLE 16

(I-A-1-6)

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |

TABLE 16-continued (I-A-1-6)

| No | —D²—D³ |
|---|---|
| 8 | —(CH₂)₃—CO₂Me |
| 9 | pentanimidamide (butyl-C(=NH)-NH₂) |
| 10 | N-propylguanidine |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | Et-NH-CH₂-C≡CH |
| 22 | pentyl-NH-CH₂-C≡CH |
| 23 | butyl-NH-CH₂-C≡CH |
| 24 | pentyl-N(Me)-CH₂-C≡CH |
| 25 | butyl-N(Me)-CH₂-C≡CH |
| 26 | Me₂C(Me)-CH₂-N(Me)-CH₂-C≡CH |
| 27 | Me₃C-CH₂CH₂CH₂-N(Me)-CH₂-C≡CH |
| 28 | pentyl-NH-CH₂-CH=CMe₂ |

TABLE 16-continued (I-A-1-6)

| No | —D²—D³ |
|---|---|
| 29 | butyl-NH-CH₂-CH=CMe₂ |
| 30 | Me₃C-CH₂CH₂CH₂-NH-CH₂-CH=CMe₂ |

TABLE 17

(I-A-1-6)

| No | —D²—D³ |
|---|---|
| 31 | Me₂C(Me)-CH₂CH₂-NH-CH₂-CH=CMe₂ |
| 32 | pentyl-NH-CH₂-C(Me)=CH₂ |
| 33 | butyl-NH-CH₂-C(Me)=CH₂ |
| 34 | Me₃C-CH₂CH₂CH₂-NH-CH₂-C(Me)=CH₂ |

TABLE 17-continued (I-A-1-6)

| No | —D²—D³ |
|---|---|
| 35 | Me₂C(Me)CH₂CH₂-NH-CH₂-C(Me)=CH₂ |
| 36 | EtO-CH₂CH₂-NH₂ |
| 37 | EtO-CH₂CH₂-NH-CH₂-C(Me)=CH₂ |
| 38 | EtO-CH₂CH₂-NH-CH₂-CH=C(Me)Me |
| 39 | EtO-CH₂CH₂-N(Me)-CH₂-C≡CH |
| 40 | EtS-CH₂CH₂-NH₂ |
| 41 | EtS-CH₂CH₂-NH-CH₂-C(Me)=CH₂ |
| 42 | EtS-CH₂CH₂-NH-CH₂-CH=C(Me)Me |
| 43 | EtS-CH₂CH₂-N(Me)-CH₂-C≡CH |
| 44 | Et-NH-CH₂CH₂-NH₂ |
| 45 | 3-methyl-azetidine (NH) |
| 46 | 4-methyl-cyclohexyl-NH₂ |
| 47 | 3-methyl-benzyl-NH₂ |
| 48 | 4-ethyl-pyridine |
| 49 | 3-ethyl-aniline-NH₂ |
| 50 | 3-propyl-pyridine |
| 51 | butyl-pyrrolidine |
| 52 | pentyl-pyrrolidine |
| 53 | butyl-3-methoxy-pyrrolidine |
| 54 | pentyl-3-methoxy-pyrrolidine |
| 55 | Me₂C(Me)CH₂CH₂-(3-methoxy-pyrrolidine) |
| 56 | Me₂C(Me)CH₂CH₂CH₂-(3-methoxy-pyrrolidine) |
| 57 | butyl-piperidine |

TABLE 17-continued
(I-A-1-6)
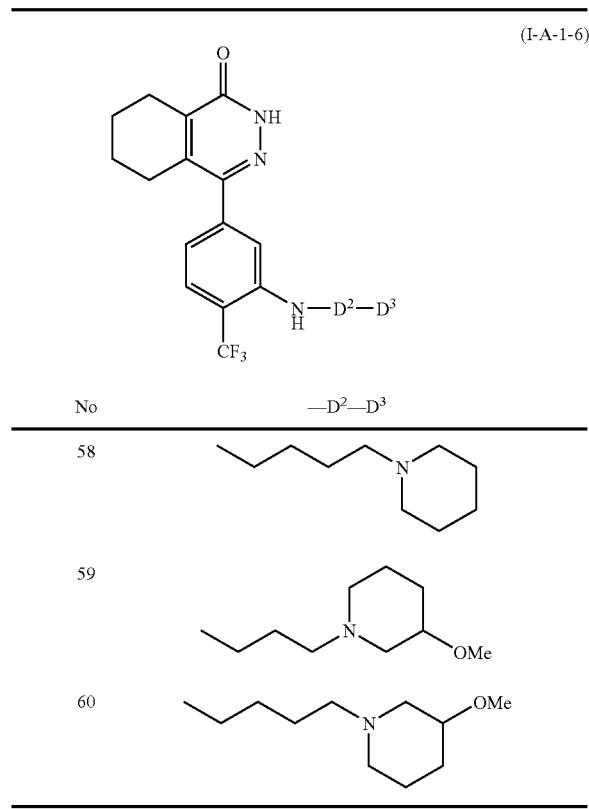
| No | —D²—D³ |
|----|--------|
| 58 | |
| 59 | |
| 60 | |
TABLE 18
(I-A-1-6)
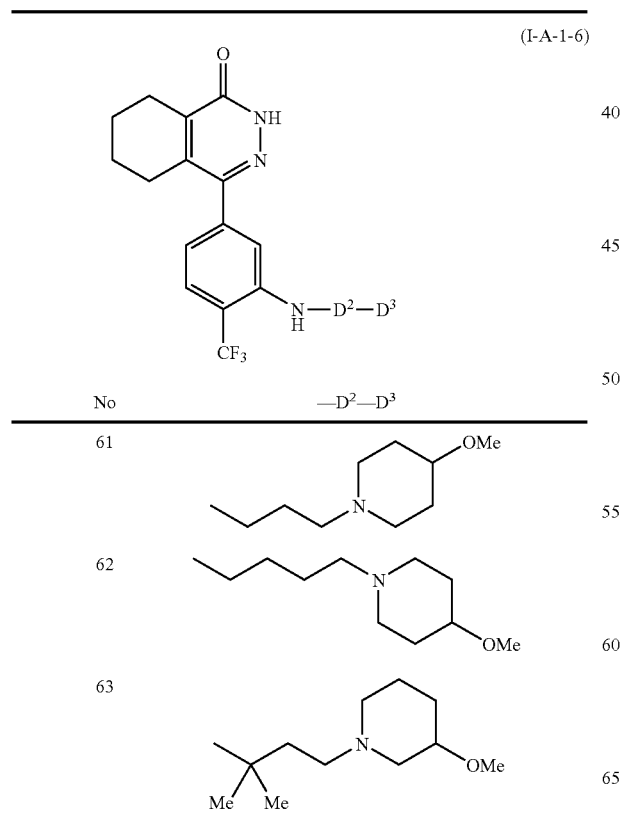
| No | —D²—D³ |
|----|--------|
| 61 | |
| 62 | |
| 63 | |
TABLE 18-continued
(I-A-1-6)
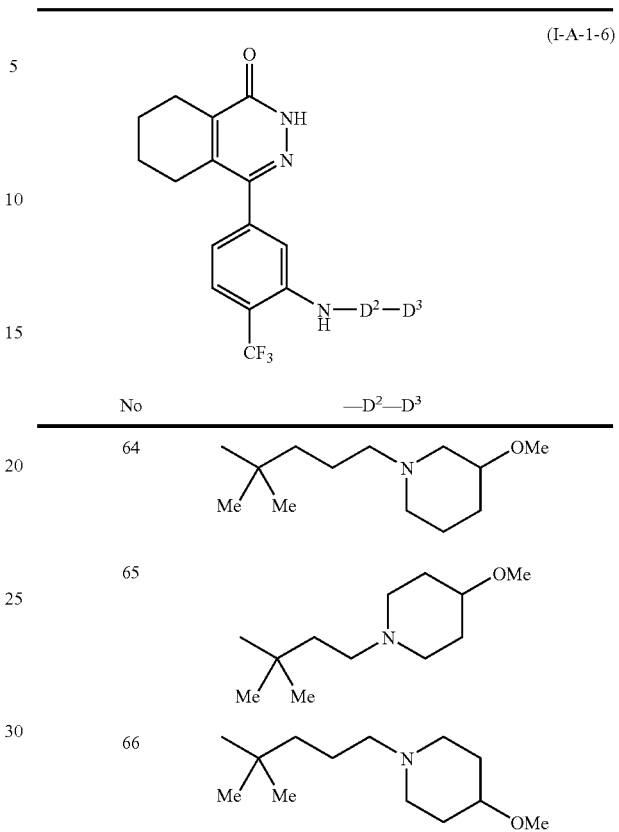
| No | —D²—D³ |
|----|--------|
| 64 | |
| 65 | |
| 66 | |
| 67 | |
| 68 | |
| 69 | |
| 70 | |
| 71 | |
| 72 | |
| 73 | |

TABLE 18-continued (I-A-1-6)

[Structure: 4-(2-(trifluoromethyl)-5-substituted-aminophenyl)-5,6,7,8-tetrahydrophthalazin-1(2H)-one with -NH-D²-D³ substituent]

| No | —D²—D³ |
|---|---|
| 74 | 3,3-dimethyl-propyl-morpholine |
| 75 | 3,3-dimethyl-butyl-morpholine |
| 76 | 2-ethoxyethyl-azetidine |
| 77 | 2-ethoxyethyl-pyrrolidine |
| 78 | 2-ethoxyethyl-piperidine |
| 79 | 2-ethoxyethyl-3-methoxypyrrolidine |
| 80 | 2-ethoxyethyl-3-methoxypiperidine |
| 81 | 2-ethoxyethyl-4-methoxypiperidine |
| 82 | 2-ethoxyethyl-1,2,3,6-tetrahydropyridine |
| 83 | 2-ethoxyethyl-morpholine |

TABLE 18-continued (I-A-1-6)

[Same core structure]

| No | —D²—D³ |
|---|---|
| 84 | 2-(ethylthio)ethyl-3-methoxypyrrolidine |
| 85 | 2-(ethylthio)ethyl-3-methoxypiperidine |
| 86 | 2-(ethylthio)ethyl-4-methoxypiperidine |
| 87 | 2-(ethylthio)ethyl-1,2,3,6-tetrahydropyridine |
| 88 | 2-(ethylthio)ethyl-morpholine |

TABLE 19

(I-A-1-7)

[Structure: 4-(3-((substituted-amino)methyl)phenyl)-5,6,7,8-tetrahydrophthalazin-1(2H)-one]

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |

TABLE 19-continued
(I-A-1-7)
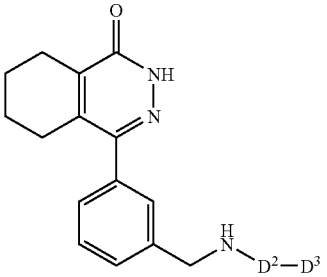
| No | —D²—D³ |
|----|--------|
| 9  | 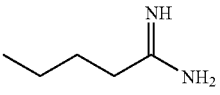 |
| 10 | 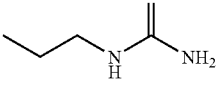 |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | 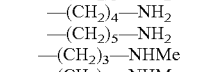 |
| 22 | 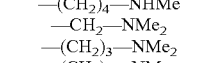 |
| 23 | 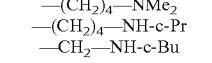 |
| 24 | 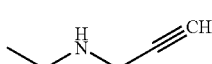 |
| 25 | 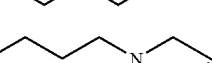 |
| 26 |  |
| 27 | 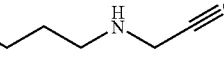 |
| 28 | 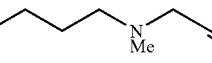 |
| 29 | 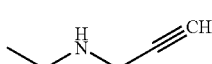 |
TABLE 19-continued
(I-A-1-7)
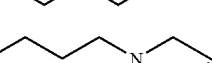
| No | —D²—D³ |
|----|--------|
| 30 |  |
TABLE 20
(I-A-1-7)
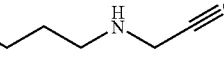
| No | —D²—D³ |
|----|--------|
| 31 | 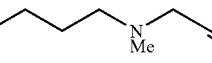 |
| 32 | 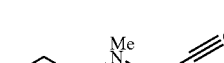 |
| 33 | 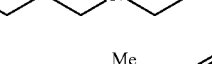 |
| 34 | 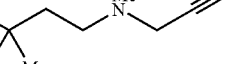 |
| 35 | 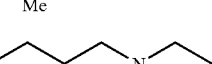 |
| 36 | 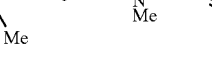 |

TABLE 20-continued
(I-A-1-7)
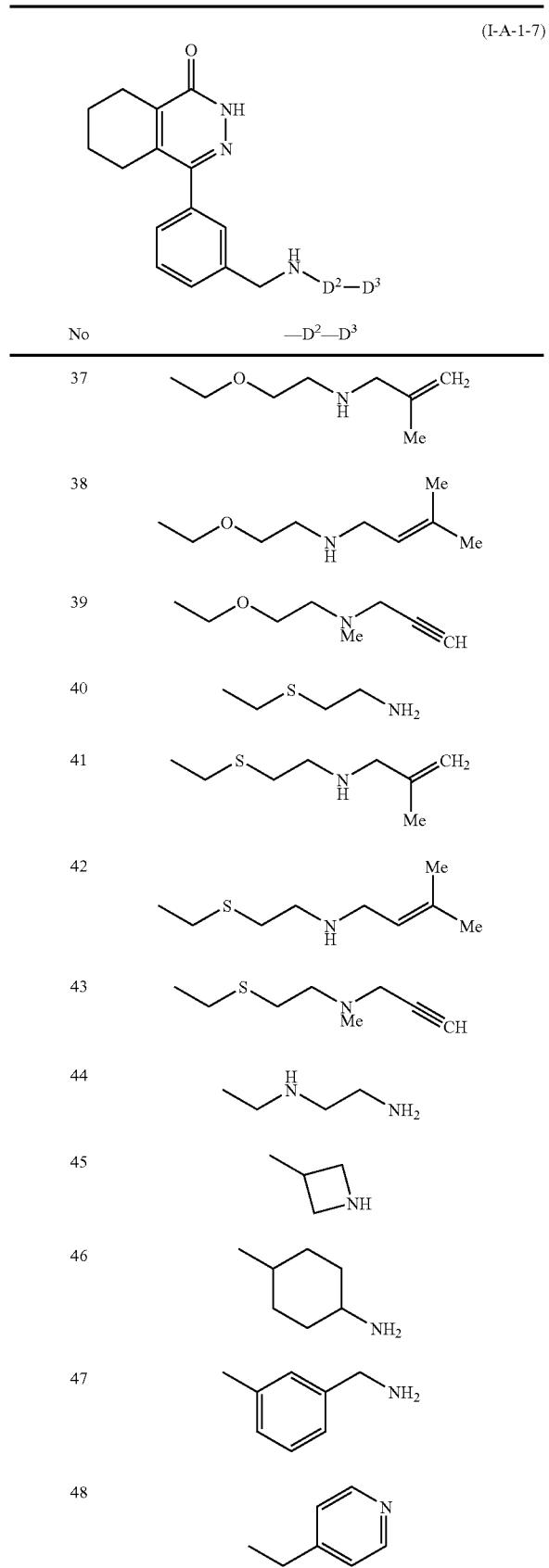
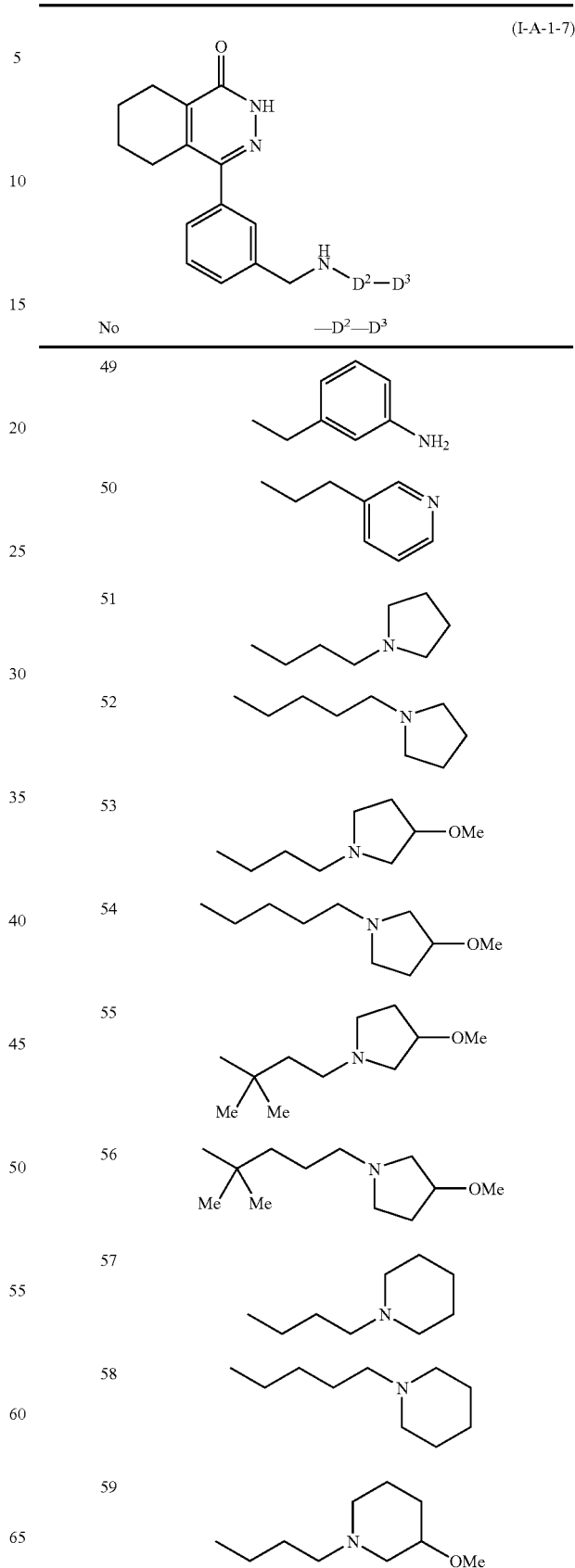

TABLE 20-continued (I-A-1-7)

| No | —D²—D³ |
|---|---|
| 60 | pentyl-N(piperidine-3-OMe) |

TABLE 21

(I-A-1-7)

| No | —D²—D³ |
|---|---|
| 61 | butyl-N(piperidine-4-OMe) |
| 62 | pentyl-N(piperidine-4-OMe) |
| 63 | (3,3-dimethylbutyl)-N(piperidine-3-OMe) |
| 64 | (4,4-dimethylpentyl)-N(piperidine-3-OMe) |
| 65 | (3,3-dimethylbutyl)-N(piperidine-4-OMe) |

TABLE 21-continued (I-A-1-7)

| No | —D²—D³ |
|---|---|
| 66 | (4,4-dimethylpentyl)-N(piperidine-4-OMe) |
| 67 | butyl-N(tetrahydropyridine) |
| 68 | pentyl-N(tetrahydropyridine) |
| 69 | (3,3-dimethylbutyl)-N(tetrahydropyridine) |
| 70 | (4,4-dimethylpentyl)-N(tetrahydropyridine) |
| 71 | propyl-N(morpholine) |
| 72 | butyl-N(morpholine) |
| 73 | pentyl-N(morpholine) |
| 74 | (3,3-dimethylbutyl)-N(morpholine) |
| 75 | (4,4-dimethylpentyl)-N(morpholine) |

TABLE 21-continued (I-A-1-7)

[Structure: 5,6,7,8-tetrahydrophthalazin-1(2H)-one with 4-(3-(CH₂-NH-D²-D³)phenyl) substituent]

| No | —D²—D³ |
|---|---|
| 76 | -O-CH₂CH₂-N(azetidine) |
| 77 | -O-CH₂CH₂-N(pyrrolidine) |
| 78 | -O-CH₂CH₂-N(piperidine) |
| 79 | -O-CH₂CH₂-N(3-methoxypyrrolidine) |
| 80 | -O-CH₂CH₂-N(3-methoxypiperidine) |
| 81 | -O-CH₂CH₂-N(4-methoxypiperidine) |
| 82 | -O-CH₂CH₂-N(1,2,3,6-tetrahydropyridine) |
| 83 | -O-CH₂CH₂-N(morpholine) |
| 84 | -S-CH₂CH₂-N(3-methoxypyrrolidine) |
| 85 | -S-CH₂CH₂-N(3-methoxypiperidine) |
| 86 | -S-CH₂CH₂-N(4-methoxypiperidine) |

TABLE 21-continued (I-A-1-7)

[Structure: 5,6,7,8-tetrahydrophthalazin-1(2H)-one with 4-(3-(CH₂-NH-D²-D³)phenyl) substituent]

| No | —D²—D³ |
|---|---|
| 87 | -S-CH₂CH₂-N(1,2,3,6-tetrahydropyridine) |
| 88 | -S-CH₂CH₂-N(morpholine) |

TABLE 22

(I-A-1-8)

[Structure: 5,6,7,8-tetrahydrophthalazin-1(2H)-one with 4-(4-chloro-3-(CH₂-NH-D²-D³)phenyl) substituent]

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | butyl-C(=NH)-NH₂ (pentanimidamide) |
| 10 | propyl-NH-C(=NH)-NH₂ (propylguanidine) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |

TABLE 22-continued (I-A-1-8)

| No | —D²—D³ |
|---|---|
| 18 | —(CH₂)₄—NMe₂ |
| 19 | —(CH₂)₄—NH-c-Pr |
| 20 | —CH₂—NH-c-Bu |
| 21 | Et—NH—CH₂—C≡CH |
| 22 | n-Pentyl—NH—CH₂—C≡CH |
| 23 | n-Butyl—NH—CH₂—C≡CH |
| 24 | n-Pentyl—N(Me)—CH₂—C≡CH |
| 25 | n-Butyl—N(Me)—CH₂—C≡CH |
| 26 | Me₂C(Me)CH₂CH₂—N(Me)—CH₂—C≡CH |
| 27 | Me₂C(Me)CH₂CH₂CH₂—N(Me)—CH₂—C≡CH |
| 28 | n-Pentyl—NH—CH₂—CH=C(Me)₂ |
| 29 | n-Butyl—NH—CH₂—CH=C(Me)₂ |
| 30 | Me₂C(Me)CH₂CH₂CH₂—NH—CH₂—CH=C(Me)₂ |

TABLE 23

(I-A-1-8)

| No | —D²—D³ |
|---|---|
| 31 | Me₃C-CH₂CH₂—NH—CH₂—CH=C(Me)₂ |
| 32 | n-Pentyl—NH—CH₂—C(Me)=CH₂ |
| 33 | n-Butyl—NH—CH₂—C(Me)=CH₂ |
| 34 | Me₃C-CH₂CH₂—NH—CH₂—C(Me)=CH₂ |
| 35 | Me₃C-CH₂CH₂CH₂—NH—CH₂—C(Me)=CH₂ |
| 36 | EtO-CH₂CH₂—NH₂ |
| 37 | EtO-CH₂CH₂—NH—CH₂—C(Me)=CH₂ |
| 38 | EtO-CH₂CH₂—NH—CH₂—CH=C(Me)₂ |
| 39 | EtO-CH₂CH₂—N(Me)—CH₂—C≡CH |
| 40 | EtS-CH₂CH₂—NH₂ |
| 41 | EtS-CH₂CH₂—NH—CH₂—C(Me)=CH₂ |
| 42 | EtS-CH₂CH₂—NH—CH₂—CH=C(Me)₂ |

TABLE 23-continued (I-A-1-8)

| No | —D²—D³ |
|---|---|
| 43 | ethyl-S-CH₂CH₂-N(Me)-CH₂-C≡CH |
| 44 | EtNH-CH₂CH₂-NH₂ |
| 45 | 3-azetidinyl (NH) |
| 46 | 4-aminocyclohexyl |
| 47 | 3-(aminomethyl)phenyl |
| 48 | 4-ethylpyridine |
| 49 | 3-ethylaniline |
| 50 | 3-propylpyridine |
| 51 | 1-butylpyrrolidine |
| 52 | 1-pentylpyrrolidine |

TABLE 23-continued (I-A-1-8)

| No | —D²—D³ |
|---|---|
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |
| 57 | 1-butylpiperidine |
| 58 | 1-pentylpiperidine |
| 59 | 1-butyl-3-methoxypiperidine |
| 60 | 1-pentyl-3-methoxypiperidine |

TABLE 24

(I-A-1-8)

| No | —D²—D³ |
|---|---|
| 61 | 4-methoxypiperidine with butyl |
| 62 | 4-methoxypiperidine with pentyl |
| 63 | 3-methoxypiperidine with 3,3-dimethylbutyl |
| 64 | 3-methoxypiperidine with 4,4-dimethylpentyl |
| 65 | 4-methoxypiperidine with 3,3-dimethylbutyl |
| 66 | 4-methoxypiperidine with 4,4-dimethylpentyl |
| 67 | 1,2,3,6-tetrahydropyridine with butyl |
| 68 | 1,2,3,6-tetrahydropyridine with pentyl |
| 69 | 1,2,3,6-tetrahydropyridine with 3,3-dimethylbutyl |

TABLE 24-continued (I-A-1-8)

| No | —D²—D³ |
|---|---|
| 70 | 1,2,3,6-tetrahydropyridine with 4,4-dimethylpentyl |
| 71 | morpholine with propyl |
| 72 | morpholine with butyl |
| 73 | morpholine with pentyl |
| 74 | morpholine with 3,3-dimethylbutyl |
| 75 | morpholine with 4,4-dimethylpentyl |
| 76 | azetidine with 2-ethoxyethyl |
| 77 | pyrrolidine with 2-ethoxyethyl |
| 78 | piperidine with 2-ethoxyethyl |
| 79 | 3-methoxypyrrolidine with 2-ethoxyethyl |

TABLE 24-continued
(I-A-1-8)
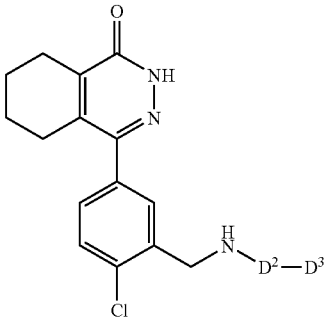
| No | —D²—D³ |
|---|---|
| 80 |  |
| 81 |  |
| 82 |  |
| 83 |  |
| 84 |  |
| 85 |  |
| 86 |  |
| 87 |  |
| 88 |  |
TABLE 25
(I-A-1-9)
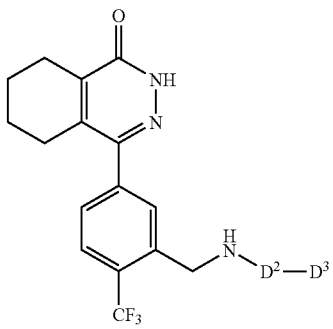
| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | 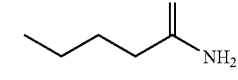 |
| 10 | 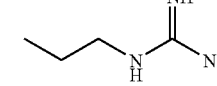 |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | 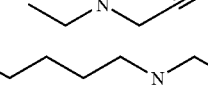 |
| 22 | 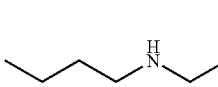 |
| 23 | 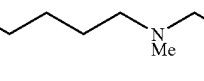 |
| 24 | 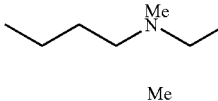 |
| 25 | 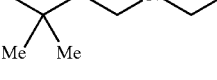 |
| 26 | 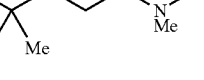 |
| 27 |  |

TABLE 25-continued (I-A-1-9)

| No | —D²—D³ |
|----|--------|
| 28 | pentyl-NH-CH₂-CH=C(Me)Me |
| 29 | butyl-NH-CH₂-CH=C(Me)Me |
| 30 | Me₂C(Me)-CH₂CH₂CH₂-NH-CH₂-CH=C(Me)Me |

TABLE 26

(I-A-1-9)

| No | —D²—D³ |
|----|--------|
| 31 | Me₂C(Me)-CH₂CH₂-NH-CH₂-CH=C(Me)Me |
| 32 | pentyl-NH-CH₂-C(Me)=CH₂ |
| 33 | butyl-NH-CH₂-C(Me)=CH₂ |
| 34 | Me₂C(Me)-CH₂CH₂CH₂-NH-CH₂-C(Me)=CH₂ |
| 35 | Me₃C-CH₂CH₂-NH-CH₂-C(Me)=CH₂ |
| 36 | EtO-CH₂CH₂-NH₂ |
| 37 | EtO-CH₂CH₂-N(Me)-CH₂-C(Me)=CH₂ |
| 38 | EtO-CH₂CH₂-NH-CH₂-CH=C(Me)Me |
| 39 | EtO-CH₂CH₂-N(Me)-CH₂-C≡CH |
| 40 | EtS-CH₂CH₂-NH₂ |
| 41 | EtS-CH₂CH₂-NH-CH₂-C(Me)=CH₂ |
| 42 | EtS-CH₂CH₂-NH-CH₂-CH=C(Me)Me |
| 43 | EtS-CH₂CH₂-N(Me)-CH₂-C≡CH |
| 44 | Et-NH-CH₂CH₂-NH₂ |
| 45 | 2-methylazetidine |

TABLE 26-continued
(I-A-1-9)
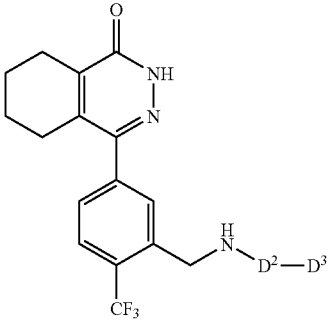
| No | —D²—D³ |
|---|---|
| 46 | 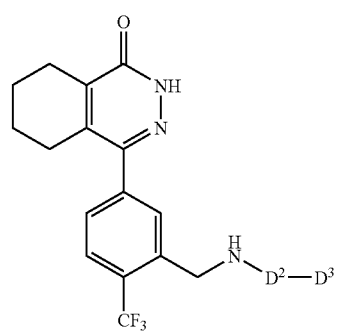 |
| 47 | 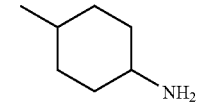 |
| 48 | 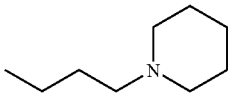 |
| 49 | 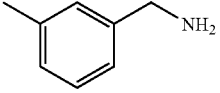 |
| 50 | 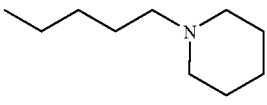 |
| 51 | 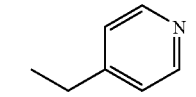 |
| 52 | 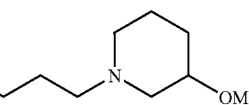 |
| 53 | 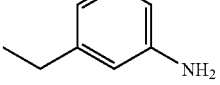 |
| 54 | 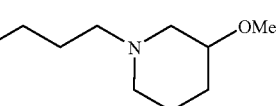 |
| 55 | 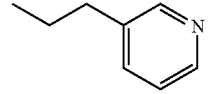 |
| 56 | 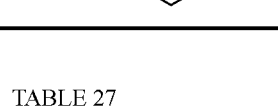 |
TABLE 26-continued
(I-A-1-9)
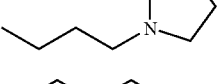
| No | —D²—D³ |
|---|---|
| 57 | 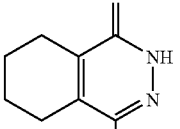 |
| 58 |  |
| 59 | 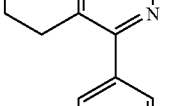 |
| 60 | 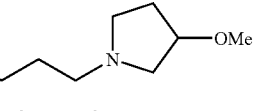 |
TABLE 27
(I-A-1-9)
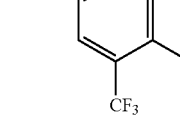
| No | —D²—D³ |
|---|---|
| 61 | 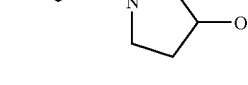 |
| 62 |  |

TABLE 27-continued
(I-A-1-9)
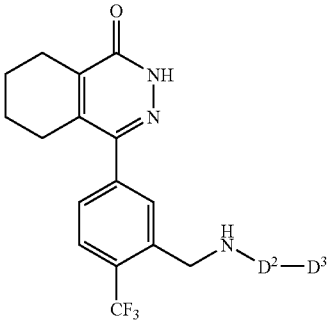
| No | —D²—D³ |
|----|--------|
| 63 | 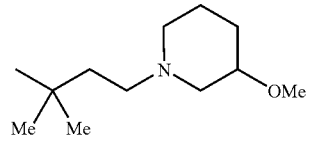 |
| 64 | 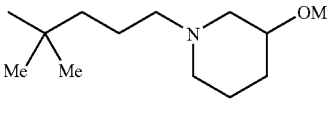 |
| 65 | 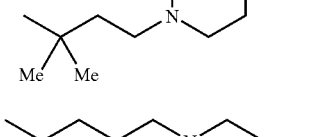 |
| 66 | 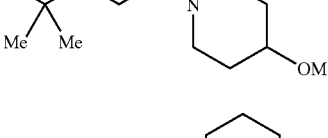 |
| 67 | 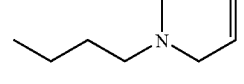 |
| 68 | 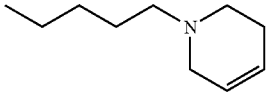 |
| 69 | 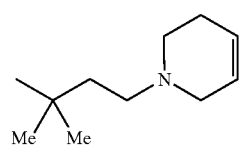 |
| 70 | 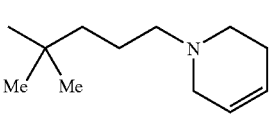 |
| 71 | 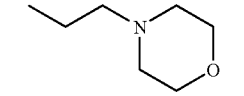 |
TABLE 27-continued
(I-A-1-9)
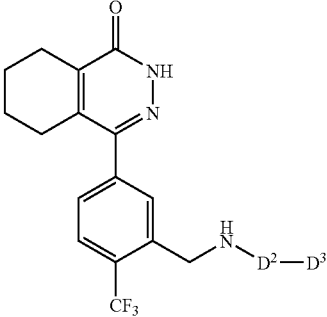
| No | —D²—D³ |
|----|--------|
| 72 | 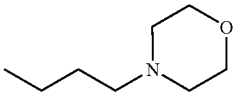 |
| 73 | 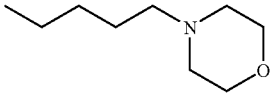 |
| 74 | 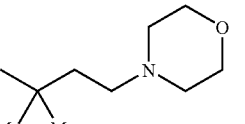 |
| 75 | 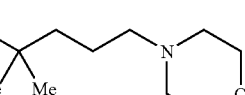 |
| 76 | 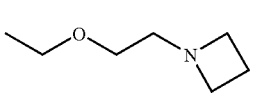 |
| 77 | 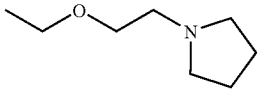 |
| 78 | 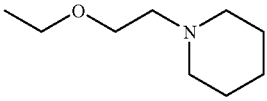 |
| 79 | 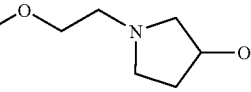 |
| 80 | 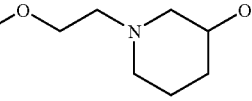 |
| 81 | 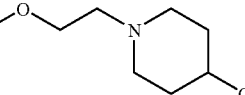 |

TABLE 27-continued (I-A-1-9)

[Structure: 5,6,7,8-tetrahydrophthalazin-1(2H)-one with phenyl substituent bearing CH2-NH-D²-D³ and CF3 groups]

| No | —D²—D³ |
|---|---|
| 82 | [2-ethoxyethyl-3,6-dihydro-2H-pyridin-1-yl] |
| 83 | [2-ethoxyethyl-morpholin-4-yl] |
| 84 | [2-(ethylthio)ethyl-3-methoxypyrrolidin-1-yl] |
| 85 | [2-(ethylthio)ethyl-3-methoxypiperidin-1-yl] |
| 86 | [2-(ethylthio)ethyl-4-methoxypiperidin-1-yl] |
| 87 | [2-(ethylthio)ethyl-3,6-dihydro-2H-pyridin-1-yl] |
| 88 | [2-(ethylthio)ethyl-morpholin-4-yl] |

TABLE 28

(I-A-2-1)

[Structure: 5,6,7,8-tetrahydropyrido[2,3-d]pyridazin-4(3H)-one with phenyl substituent bearing NH-C(=O)-D²-D³]

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | [pentanimidamide] |
| 10 | [propylguanidine] |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | [ethyl(prop-2-yn-1-yl)amino] |
| 22 | [pentyl(prop-2-yn-1-yl)amino] |
| 23 | [butyl(prop-2-yn-1-yl)amino] |
| 24 | [pentyl(methyl)(prop-2-yn-1-yl)amino] |
| 25 | [butyl(methyl)(prop-2-yn-1-yl)amino] |
| 26 | [3,3-dimethylbutyl(methyl)(prop-2-yn-1-yl)amino] |
| 27 | [4,4-dimethylpentyl(methyl)(prop-2-yn-1-yl)amino] |

TABLE 28-continued (I-A-2-1)

| No | —D²—D³ |
|---|---|
| 28 | pentyl-NH-CH₂-CH=C(Me)Me |
| 29 | butyl-NH-CH₂-CH=C(Me)Me |
| 30 | Me₂C(Me)-CH₂CH₂-NH-CH₂-CH=C(Me)Me |

TABLE 29

(I-A-2-1)

| No | —D²—D³ |
|---|---|
| 31 | Me₂C(Me)-CH₂CH₂-NH-CH₂-CH=C(Me)Me |
| 32 | pentyl-NH-CH₂-C(Me)=CH₂ |
| 33 | butyl-NH-CH₂-C(Me)=CH₂ |
| 34 | Me₂C(Me)-CH₂CH₂CH₂-NH-CH₂-C(Me)=CH₂ |
| 35 | Me₂C(Me)-CH₂CH₂-NH-CH₂-C(Me)=CH₂ |
| 36 | Et-O-CH₂CH₂-NH₂ |
| 37 | Et-O-CH₂CH₂-NH-CH₂-C(Me)=CH₂ |
| 38 | Et-O-CH₂CH₂-NH-CH₂-CH=C(Me)Me |
| 39 | Et-O-CH₂CH₂-N(Me)-CH₂-C≡CH |
| 40 | Et-S-CH₂CH₂-NH₂ |
| 41 | Et-S-CH₂CH₂-NH-CH₂-C(Me)=CH₂ |
| 42 | Et-S-CH₂CH₂-NH-CH₂-CH=C(Me)Me |
| 43 | Et-S-CH₂CH₂-N(Me)-CH₂-C≡CH |
| 44 | Et-NH-CH₂CH₂-NH₂ |
| 45 | 2-methylazetidine |

TABLE 29-continued (I-A-2-1)

| No | —D²—D³ |
|---|---|
| 46 | 4-aminocyclohexyl (methyl-substituted, NH₂) |
| 47 | (3-methylphenyl)methanamine |
| 48 | 4-ethylpyridine |
| 49 | 3-ethylaniline |
| 50 | 3-propylpyridine |
| 51 | 1-butylpyrrolidine |
| 52 | 1-pentylpyrrolidine |
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |

TABLE 29-continued (I-A-2-1)

| No | —D²—D³ |
|---|---|
| 57 | 1-butylpiperidine |
| 58 | 1-pentylpiperidine |
| 59 | 1-butyl-3-methoxypiperidine |
| 60 | 1-pentyl-3-methoxypiperidine |

TABLE 30

(I-A-2-1)

| No | —D²—D³ |
|---|---|
| 61 | 1-butyl-4-methoxypiperidine |
| 62 | 1-pentyl-4-methoxypiperidine |

TABLE 30-continued (I-A-2-1)

| No | —D²—D³ |
|---|---|
| 63 | 3-methoxypiperidine connected via neopentyl (CMe₂) linker |
| 64 | 3-methoxypiperidine connected via 4,4-dimethylbutyl linker |
| 65 | 4-methoxypiperidine connected via neopentyl (CMe₂) linker |
| 66 | 4-methoxypiperidine connected via 4,4-dimethylbutyl linker |
| 67 | 1,2,3,6-tetrahydropyridine connected via propyl linker |
| 68 | 1,2,3,6-tetrahydropyridine connected via butyl linker |
| 69 | 1,2,3,6-tetrahydropyridine connected via neopentyl (CMe₂) linker |
| 70 | 1,2,3,6-tetrahydropyridine connected via 4,4-dimethylbutyl linker |
| 71 | morpholine connected via propyl linker |
| 72 | morpholine connected via butyl linker |

TABLE 30-continued (I-A-2-1)

| No | —D²—D³ |
|---|---|
| 73 | morpholine connected via pentyl linker |
| 74 | morpholine connected via neopentyl (CMe₂) linker |
| 75 | morpholine connected via 4,4-dimethylbutyl linker |
| 76 | azetidine connected via 2-ethoxyethyl linker |
| 77 | pyrrolidine connected via 2-ethoxyethyl linker |
| 78 | piperidine connected via 2-ethoxyethyl linker |
| 79 | 3-methoxypyrrolidine connected via 2-ethoxyethyl linker |
| 80 | 3-methoxypiperidine connected via 2-ethoxyethyl linker |
| 81 | 4-methoxypiperidine connected via 2-ethoxyethyl linker |
| 82 | 1,2,3,6-tetrahydropyridine connected via 2-ethoxyethyl linker |

TABLE 30-continued (I-A-2-1)

| No | —D²—D³ |
|---|---|
| 83 | ethoxyethyl-morpholine |
| 84 | ethylthio-ethyl-(3-methoxy)pyrrolidine |
| 85 | ethylthio-ethyl-(3-methoxy)piperidine |
| 86 | ethylthio-ethyl-(4-methoxy)piperidine |
| 87 | ethylthio-ethyl-tetrahydropyridine |
| 88 | ethylthio-ethyl-morpholine |

TABLE 31

(I-A-2-2)

| No | —D²—D³ |
|---|---|
| 1 | Me |
| 2 | Pr |
| 3 | Bu |

TABLE 31-continued (I-A-2-2)

| No | —D²—D³ |
|---|---|
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | pentanimidamide |
| 10 | propyl guanidine |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | ethyl-NH-propargyl |
| 22 | pentyl-NH-propargyl |
| 23 | butyl-NH-propargyl |
| 24 | pentyl-NMe-propargyl |
| 25 | butyl-NMe-propargyl |
| 26 | neopentyl-NMe-propargyl |
| 27 | (3,3-dimethylbutyl)-NMe-propargyl |

TABLE 31-continued
(I-A-2-2)
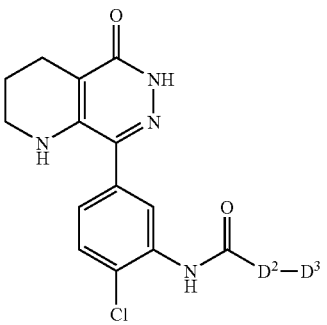
| No | —D²—D³ |
|---|---|
| 28 | 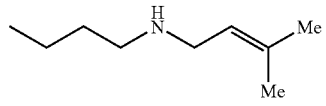 |
| 29 | 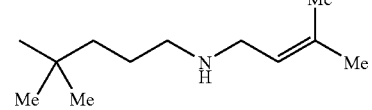 |
| 30 | 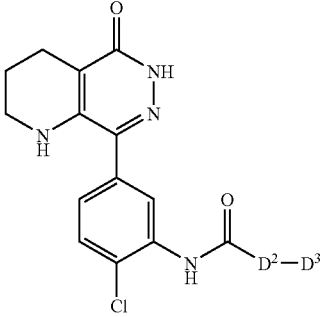 |
TABLE 32
(I-A-2-2)
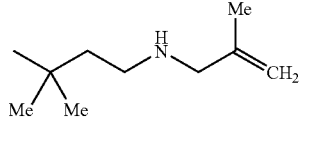
| No | —D²—D³ |
|---|---|
| 31 | 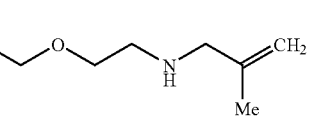 |
| 32 | 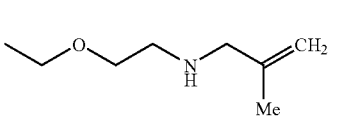 |
| 33 | 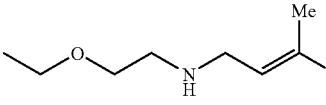 |
TABLE 32-continued
(I-A-2-2)
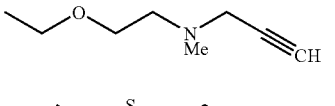
| No | —D²—D³ |
|---|---|
| 34 | 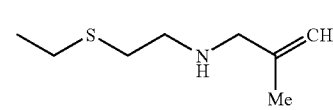 |
| 35 | 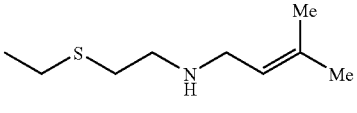 |
| 36 | 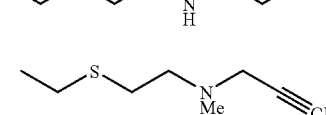 |
| 37 | 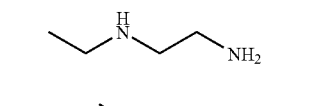 |
| 38 |  |
| 39 | 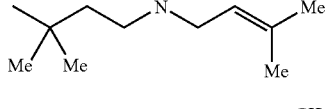 |
| 40 | 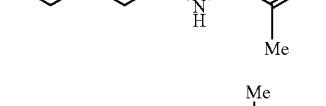 |
| 41 | 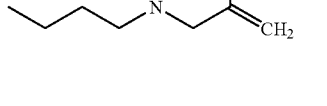 |
| 42 |  |
| 43 |  |
| 44 |  |
| 45 |  |

TABLE 32-continued (I-A-2-2)

[Structure: tetrahydropyrido-pyridazinone linked to 4-chloro-3-(NHC(=O)–D²–D³)phenyl]

| No | —D²—D³ |
|---|---|
| 46 | 4-methylcyclohexylamine |
| 47 | 3-methylbenzylamine |
| 48 | 4-ethylpyridine |
| 49 | 3-ethylaniline |
| 50 | 3-propylpyridine |
| 51 | butyl-pyrrolidine |
| 52 | pentyl-pyrrolidine |
| 53 | butyl-(3-methoxy)pyrrolidine |
| 54 | pentyl-(3-methoxy)pyrrolidine |
| 55 | 3,3-dimethylbutyl-(3-methoxy)pyrrolidine |
| 56 | 4,4-dimethylpentyl-(3-methoxy)pyrrolidine |

TABLE 32-continued (I-A-2-2)

[Structure: tetrahydropyrido-pyridazinone linked to 4-chloro-3-(NHC(=O)–D²–D³)phenyl]

| No | —D²—D³ |
|---|---|
| 57 | butyl-piperidine |
| 58 | pentyl-piperidine |
| 59 | butyl-(3-methoxy)piperidine |
| 60 | pentyl-(3-methoxy)piperidine |

TABLE 33

(I-A-2-2)

[Structure: tetrahydropyrido-pyridazinone linked to 4-chloro-3-(NHC(=O)–D²–D³)phenyl]

| No | —D²—D³ |
|---|---|
| 61 | butyl-(4-methoxy)piperidine |
| 62 | pentyl-(4-methoxy)piperidine |

TABLE 33-continued (I-A-2-2)

| No | —D²—D³ |
|---|---|
| 63 | piperidine with 3,3-dimethylbutyl on N and 3-OMe |
| 64 | piperidine with 4,4-dimethylpentyl on N and 3-OMe |
| 65 | piperidine with 3,3-dimethylbutyl on N and 4-OMe |
| 66 | piperidine with 4,4-dimethylpentyl on N and 4-OMe |
| 67 | 1,2,3,6-tetrahydropyridine with butyl on N |
| 68 | 1,2,3,6-tetrahydropyridine with pentyl on N |
| 69 | 1,2,3,6-tetrahydropyridine with 3,3-dimethylbutyl on N |
| 70 | 1,2,3,6-tetrahydropyridine with 4,4-dimethylpentyl on N |
| 71 | morpholine with propyl on N |
| 72 | morpholine with butyl on N |

TABLE 33-continued (I-A-2-2)

| No | —D²—D³ |
|---|---|
| 73 | morpholine with pentyl on N |
| 74 | morpholine with 3,3-dimethylbutyl on N |
| 75 | morpholine with 4,4-dimethylpentyl on N |
| 76 | azetidine with 2-ethoxyethyl on N |
| 77 | pyrrolidine with 2-ethoxyethyl on N |
| 78 | piperidine with 2-ethoxyethyl on N |
| 79 | pyrrolidine with 2-ethoxyethyl on N and 3-OMe |
| 80 | piperidine with 2-ethoxyethyl on N and 3-OMe |
| 81 | piperidine with 2-ethoxyethyl on N and 4-OMe |

TABLE 33-continued (I-A-2-2)

| No | —D²—D³ |
|---|---|
| 82 | ethoxyethyl-tetrahydropyridine |
| 83 | ethoxyethyl-morpholine |
| 84 | ethylthio-ethyl-3-methoxypyrrolidine |
| 85 | ethylthio-ethyl-3-methoxypiperidine |
| 86 | ethylthio-ethyl-4-methoxypiperidine |
| 87 | ethylthio-ethyl-tetrahydropyridine |
| 88 | ethylthio-ethyl-morpholine |

TABLE 34

(I-A-2-3)

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | butyl-amidine |
| 10 | propyl-guanidine |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | ethyl-NH-propargyl |
| 22 | pentyl-NH-propargyl |
| 23 | butyl-NH-propargyl |
| 24 | pentyl-N(Me)-propargyl |
| 25 | butyl-N(Me)-propargyl |

TABLE 34-continued (I-A-2-3)

| No | —D²—D³ |
|---|---|
| 26 | Me₃C-CH₂CH₂-N(Me)-CH₂-C≡CH |
| 27 | Me₃C-CH₂CH₂CH₂-N(Me)-CH₂-C≡CH |
| 28 | n-C₅H₁₁-NH-CH₂-CH=C(Me)Me |
| 29 | n-C₄H₉-NH-CH₂-CH=C(Me)Me |
| 30 | Me₃C-CH₂CH₂CH₂-NH-CH₂-CH=C(Me)Me |

TABLE 35

(I-A-2-3)

| No | —D²—D³ |
|---|---|
| 31 | Me₃C-CH₂CH₂-NH-CH₂-CH=C(Me)Me |
| 32 | n-C₅H₁₁-NH-CH₂-C(Me)=CH₂ |
| 33 | n-C₄H₉-NH-CH₂-C(Me)=CH₂ |
| 34 | Me₃C-CH₂CH₂CH₂-NH-CH₂-C(Me)=CH₂ |
| 35 | Me₃C-CH₂CH₂-NH-CH₂-C(Me)=CH₂ |
| 36 | EtO-CH₂CH₂-NH₂ |
| 37 | EtO-CH₂CH₂-NH-CH₂-C(Me)=CH₂ |
| 38 | EtO-CH₂CH₂-NH-CH₂-CH=C(Me)Me |
| 39 | EtO-CH₂CH₂-N(Me)-CH₂-C≡CH |
| 40 | EtS-CH₂CH₂-NH₂ |
| 41 | EtS-CH₂CH₂-NH-CH₂-C(Me)=CH₂ |
| 42 | EtS-CH₂CH₂-NH-CH₂-CH=C(Me)Me |
| 43 | EtS-CH₂CH₂-N(Me)-CH₂-C≡CH |

TABLE 35-continued (I-A-2-3)

| No | —D²—D³ |
|---|---|
| 44 | ethylenediamine with N-ethyl (H-N-CH2CH2-NH2 with ethyl) |
| 45 | 3-azetidinyl (azetidine NH) |
| 46 | 4-methylcyclohexylamine |
| 47 | 3-methylbenzylamine |
| 48 | 2-(pyridin-4-yl)ethyl |
| 49 | 3-ethylaniline |
| 50 | 3-(pyridin-3-yl)propyl |
| 51 | 4-(pyrrolidin-1-yl)butyl |
| 52 | 5-(pyrrolidin-1-yl)pentyl |

TABLE 35-continued (I-A-2-3)

| No | —D²—D³ |
|---|---|
| 53 | 4-(3-methoxypyrrolidin-1-yl)butyl |
| 54 | 5-(3-methoxypyrrolidin-1-yl)pentyl |
| 55 | 3,3-dimethyl-4-(3-methoxypyrrolidin-1-yl)butyl |
| 56 | 4,4-dimethyl-5-(3-methoxypyrrolidin-1-yl)pentyl |
| 57 | 4-(piperidin-1-yl)butyl |
| 58 | 5-(piperidin-1-yl)pentyl |
| 59 | 4-(3-methoxypiperidin-1-yl)butyl |
| 60 | 5-(3-methoxypiperidin-1-yl)pentyl |

TABLE 36

(I-A-2-3)

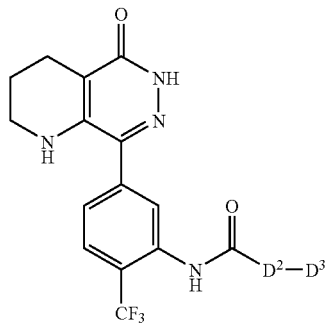

| No | —D²—D³ |
|---|---|
| 61 | 4-methoxypiperidine with butyl |
| 62 | 4-methoxypiperidine with pentyl |
| 63 | 3-methoxypiperidine with 3,3-dimethylbutyl |
| 64 | 3-methoxypiperidine with 4,4-dimethylpentyl |
| 65 | 4-methoxypiperidine with 3,3-dimethylbutyl |
| 66 | 4-methoxypiperidine with 4,4-dimethylpentyl |
| 67 | 1,2,3,6-tetrahydropyridine with butyl |
| 68 | 1,2,3,6-tetrahydropyridine with pentyl |
| 69 | 1,2,3,6-tetrahydropyridine with 3,3-dimethylbutyl |

TABLE 36-continued (I-A-2-3)

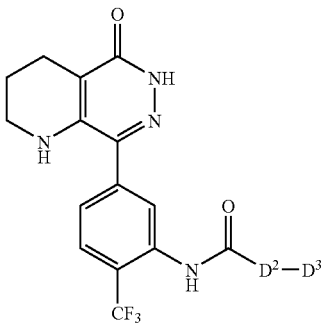

| No | —D²—D³ |
|---|---|
| 70 | 1,2,3,6-tetrahydropyridine with 4,4-dimethylpentyl |
| 71 | morpholine with propyl |
| 72 | morpholine with butyl |
| 73 | morpholine with pentyl |
| 74 | morpholine with 3,3-dimethylbutyl |
| 75 | morpholine with 4,4-dimethylpentyl |
| 76 | azetidine with 2-ethoxyethyl |
| 77 | pyrrolidine with 2-ethoxyethyl |
| 78 | piperidine with 2-ethoxyethyl |
| 79 | 3-methoxypyrrolidine with 2-ethoxyethyl |

TABLE 36-continued (I-A-2-3)

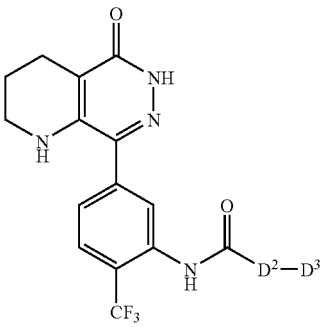

| No | —D²—D³ |
|---|---|
| 80 | ethoxyethyl-3-methoxypiperidine |
| 81 | ethoxyethyl-4-methoxypiperidine |
| 82 | ethoxyethyl-tetrahydropyridine |
| 83 | ethoxyethyl-morpholine |
| 84 | ethylthioethyl-3-methoxypyrrolidine |
| 85 | ethylthioethyl-3-methoxypiperidine |
| 86 | ethylthioethyl-4-methoxypiperidine |
| 87 | ethylthioethyl-tetrahydropyridine |
| 88 | ethylthioethyl-morpholine |

TABLE 37

(I-A-2-4)

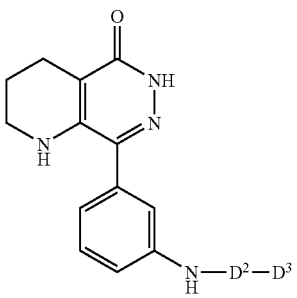

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | pentanimidamide |
| 10 | propylguanidine |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | ethyl-N-propargyl |
| 22 | pentyl-N-propargyl |
| 23 | butyl-N-propargyl |
| 24 | pentyl-N-Me-propargyl |
| 25 | butyl-N-Me-propargyl |
| 26 | neopentyl-N-Me-propargyl |
| 27 | (3,3-dimethylbutyl)-N-Me-propargyl |

TABLE 37-continued
(I-A-2-4)
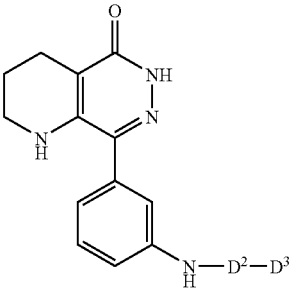
| No | —D²—D³ |
|---|---|
| 28 | 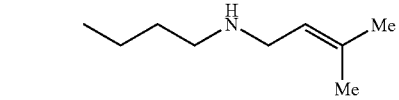 |
| 29 |  |
| 30 | 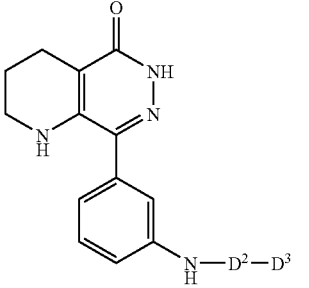 |
TABLE 38
(I-A-2-4)
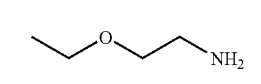
| No | —D²—D³ |
|---|---|
| 31 |  |
| 32 | 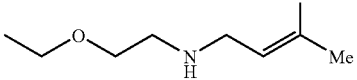 |
| 33 | 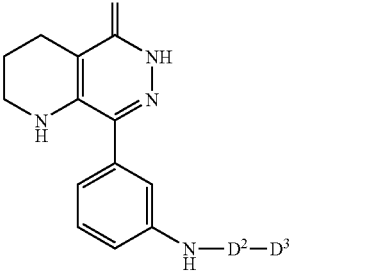 |
| 34 | 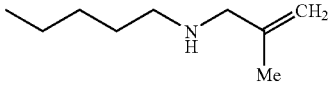 |
TABLE 38-continued
(I-A-2-4)
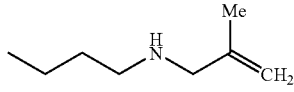
| No | —D²—D³ |
|---|---|
| 35 | 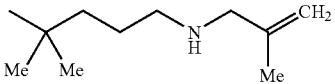 |
| 36 | |
| 37 | |
| 38 | |
| 39 | |
| 40 | |
| 41 | |
| 42 | |
| 43 | |
| 44 | |
| 45 | |
| 46 | 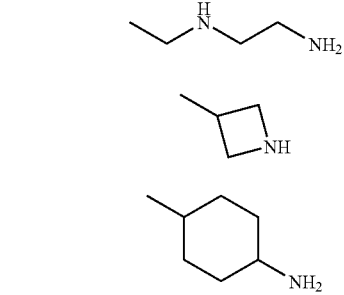 |

TABLE 38-continued (I-A-2-4)

| No | —D²—D³ |
|----|--------|
| 47 | 3-(aminomethyl)toluene |
| 48 | 4-ethylpyridine |
| 49 | 3-ethylaniline |
| 50 | 3-propylpyridine |
| 51 | 1-butylpyrrolidine |
| 52 | 1-pentylpyrrolidine |
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |
| 57 | 1-butylpiperidine |
| 58 | 1-pentylpiperidine |
| 59 | 1-butyl-3-methoxypiperidine |
| 60 | 1-pentyl-3-methoxypiperidine |

TABLE 39

(I-A-2-4)

| No | —D²—D³ |
|----|--------|
| 61 | 1-butyl-4-methoxypiperidine |
| 62 | 1-pentyl-4-methoxypiperidine |
| 63 | 1-(3,3-dimethylbutyl)-3-methoxypiperidine |

TABLE 39-continued (I-A-2-4)

| No | —D²—D³ |
|---|---|
| 64 | 3-methoxypiperidine with 4,4-dimethylbutyl linker |
| 65 | 4-methoxypiperidine with 3,3-dimethylpropyl linker |
| 66 | 4-methoxypiperidine with 4,4-dimethylbutyl linker (OMe down) |
| 67 | 1,2,3,6-tetrahydropyridine with butyl linker |
| 68 | 1,2,3,6-tetrahydropyridine with pentyl linker |
| 69 | 1,2,3,6-tetrahydropyridine with 3,3-dimethylpropyl linker |
| 70 | 1,2,3,6-tetrahydropyridine with 4,4-dimethylbutyl linker |
| 71 | morpholine with propyl linker |
| 72 | morpholine with butyl linker |
| 73 | morpholine with pentyl linker |

TABLE 39-continued (I-A-2-4)

| No | —D²—D³ |
|---|---|
| 74 | morpholine with 3,3-dimethylpropyl linker |
| 75 | morpholine with 4,4-dimethylbutyl linker |
| 76 | azetidine with ethoxyethyl linker |
| 77 | pyrrolidine with ethoxyethyl linker |
| 78 | piperidine with ethoxyethyl linker |
| 79 | 3-methoxypyrrolidine with ethoxyethyl linker |
| 80 | 3-methoxypiperidine with ethoxyethyl linker |
| 81 | 4-methoxypiperidine with ethoxyethyl linker |
| 82 | 1,2,3,6-tetrahydropyridine with ethoxyethyl linker |
| 83 | morpholine with ethoxyethyl linker |

TABLE 39-continued (I-A-2-4)

| No | —D²—D³ |
|---|---|
| 84 | [structure: ethylthio-ethyl-N-pyrrolidinyl-OMe] |
| 85 | [structure: ethylthio-ethyl-N-piperidinyl-3-OMe] |
| 86 | [structure: ethylthio-ethyl-N-piperidinyl-4-OMe] |
| 87 | [structure: ethylthio-ethyl-N-tetrahydropyridinyl] |
| 88 | [structure: ethylthio-ethyl-morpholinyl] |

TABLE 40

(I-A-2-5)

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |

TABLE 40-continued (I-A-2-5)

| No | —D²—D³ |
|---|---|
| 9 | [structure: pentanimidamide] |
| 10 | [structure: propyl guanidine] |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | [structure: ethyl-NH-propargyl] |
| 22 | [structure: pentyl-NH-propargyl] |
| 23 | [structure: butyl-NH-propargyl] |
| 24 | [structure: pentyl-NMe-propargyl] |
| 25 | [structure: butyl-NMe-propargyl] |
| 26 | [structure: neopentyl-NMe-propargyl] |
| 27 | [structure: 3,3-dimethylbutyl-NMe-propargyl] |
| 28 | [structure: pentyl-NH-3-methyl-2-butenyl] |

TABLE 40-continued
(I-A-2-5)
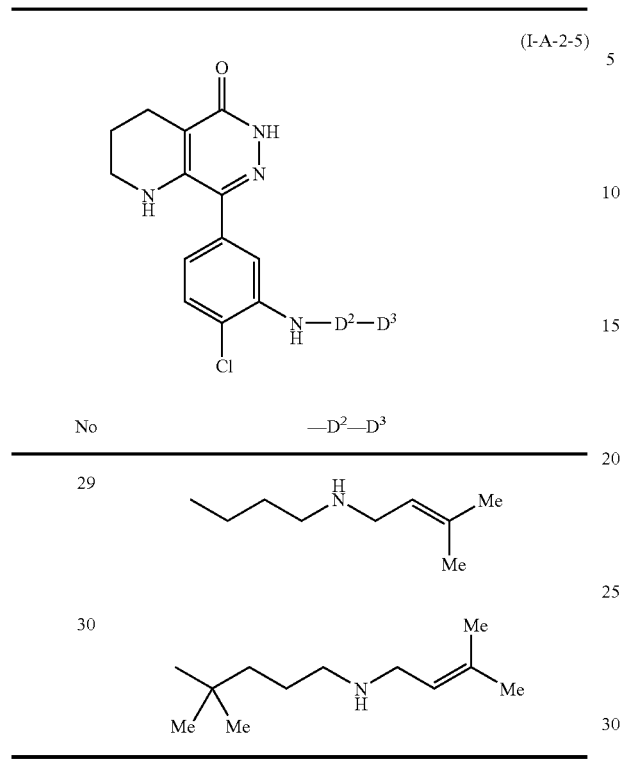
| No | —D²—D³ |
|----|--------|
| 29 | |
| 30 | |
TABLE 41
(I-A-2-5)
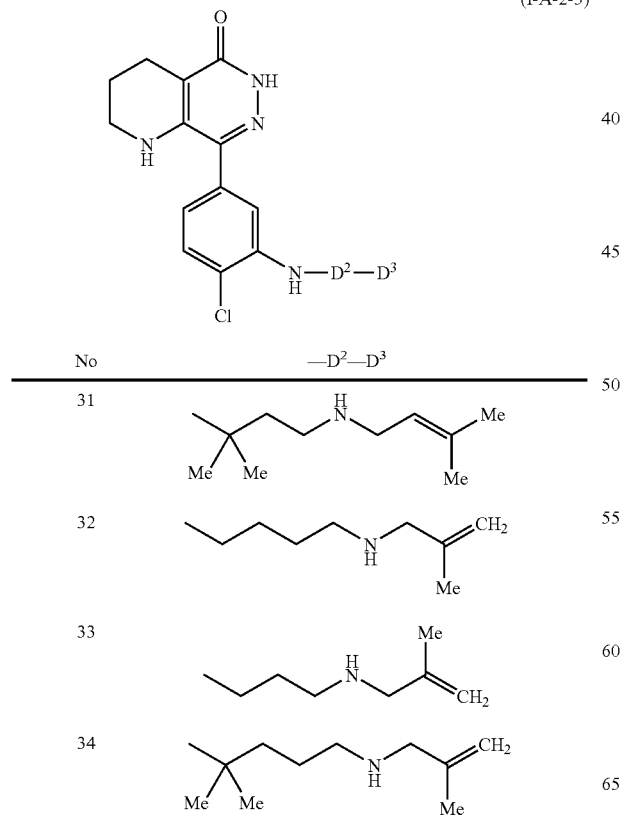
| No | —D²—D³ |
|----|--------|
| 31 | |
| 32 | |
| 33 | |
| 34 | |
TABLE 41-continued
(I-A-2-5)
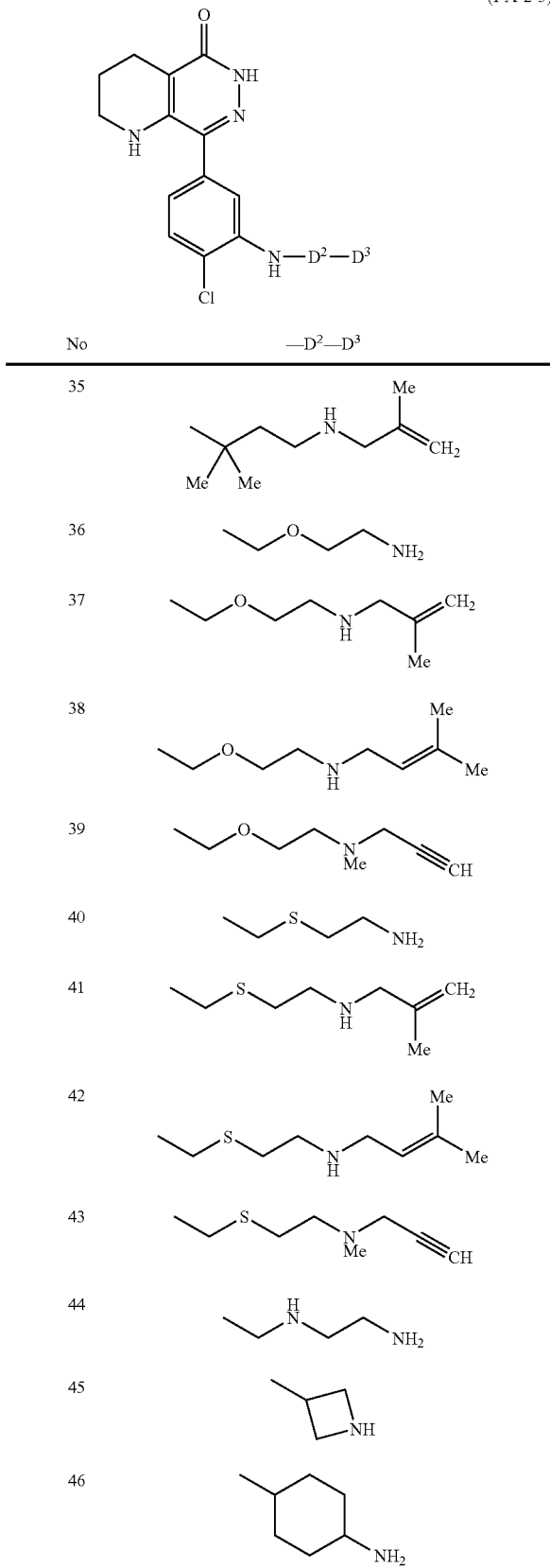
| No | —D²—D³ |
|----|--------|
| 35 | |
| 36 | |
| 37 | |
| 38 | |
| 39 | |
| 40 | |
| 41 | |
| 42 | |
| 43 | |
| 44 | |
| 45 | |
| 46 | |

TABLE 41-continued (I-A-2-5)

| No | —D²—D³ |
|---|---|
| 47 | 3-(aminomethyl)toluene group |
| 48 | 4-ethylpyridine group |
| 49 | 3-ethylaniline group |
| 50 | 3-propylpyridine group |
| 51 | 4-(pyrrolidin-1-yl)butyl |
| 52 | 5-(pyrrolidin-1-yl)pentyl |
| 53 | 4-(3-methoxypyrrolidin-1-yl)butyl |
| 54 | 5-(3-methoxypyrrolidin-1-yl)pentyl |
| 55 | 3,3-dimethyl-4-(3-methoxypyrrolidin-1-yl)butyl |
| 56 | 5,5-dimethyl-6-(3-methoxypyrrolidin-1-yl)hexyl (with dimethyl) |
| 57 | 4-(piperidin-1-yl)butyl |

TABLE 41-continued (I-A-2-5)

| No | —D²—D³ |
|---|---|
| 58 | 5-(piperidin-1-yl)pentyl |
| 59 | 4-(3-methoxypiperidin-1-yl)butyl |
| 60 | 5-(3-methoxypiperidin-1-yl)pentyl |

TABLE 42

(I-A-2-5)

| No | —D²—D³ |
|---|---|
| 61 | 4-(4-methoxypiperidin-1-yl)butyl |
| 62 | 5-(4-methoxypiperidin-1-yl)pentyl |
| 63 | 3,3-dimethyl-4-(3-methoxypiperidin-1-yl)butyl |

TABLE 42-continued (I-A-2-5)

| No | —D²—D³ |
|---|---|
| 64 | 3-methoxypiperidine with neopentyl-propyl linker (Me, Me gem-dimethyl) |
| 65 | 4-methoxypiperidine with neopentyl-ethyl linker |
| 66 | 4-methoxypiperidine with neopentyl-propyl linker |
| 67 | 1,2,3,6-tetrahydropyridine with butyl linker |
| 68 | 1,2,3,6-tetrahydropyridine with pentyl linker |
| 69 | 1,2,3,6-tetrahydropyridine with neopentyl-ethyl linker |
| 70 | 1,2,3,6-tetrahydropyridine with neopentyl-propyl linker |
| 71 | morpholine with propyl linker |
| 72 | morpholine with butyl linker |
| 73 | morpholine with pentyl linker |

TABLE 42-continued (I-A-2-5)

| No | —D²—D³ |
|---|---|
| 74 | morpholine with neopentyl-ethyl linker |
| 75 | morpholine with neopentyl-propyl linker |
| 76 | azetidine with ethoxyethyl linker |
| 77 | pyrrolidine with ethoxyethyl linker |
| 78 | piperidine with ethoxyethyl linker |
| 79 | 3-methoxypyrrolidine with ethoxyethyl linker |
| 80 | 3-methoxypiperidine with ethoxyethyl linker |
| 81 | 4-methoxypiperidine with ethoxyethyl linker |
| 82 | 1,2,3,6-tetrahydropyridine with ethoxyethyl linker |
| 83 | morpholine with ethoxyethyl linker |

TABLE 42-continued
(I-A-2-5)
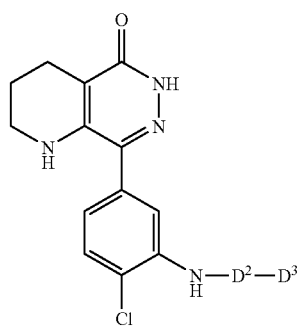
| No | —D²—D³ |
|---|---|
| 84 | 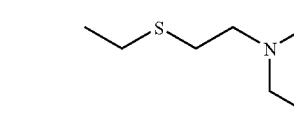 |
| 85 | 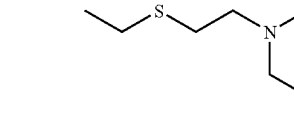 |
| 86 | 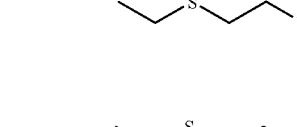 |
| 87 | 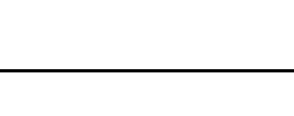 |
| 88 | 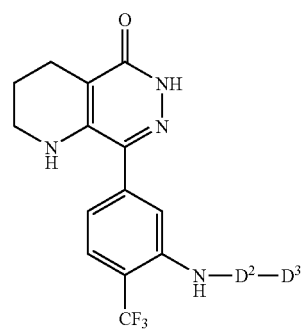 |
TABLE 43
(I-A-2-6)
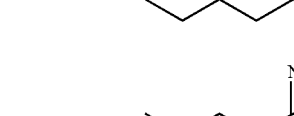
| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
TABLE 43-continued
(I-A-2-6)
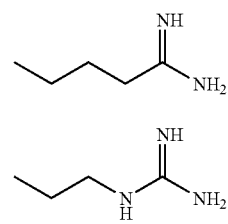
| No | —D²—D³ |
|---|---|
| 8 | —(CH₂)₃—CO₂Me |
| 9 | 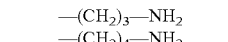 |
| 10 | 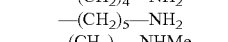 |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | 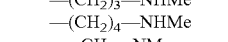 |
| 22 | 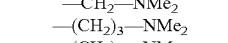 |
| 23 | 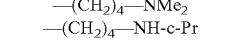 |
| 24 | 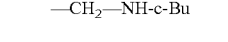 |
| 25 |  |
| 26 | 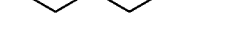 |
| 27 | 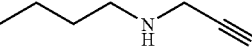 |
| 28 |  |

TABLE 43-continued (I-A-2-6)

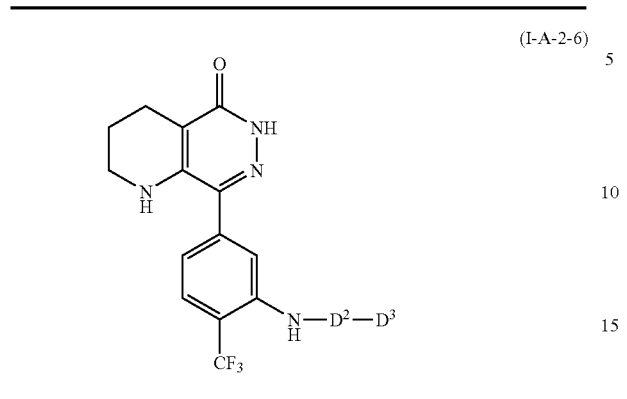

| No | —D²—D³ |
|----|--------|
| 29 | (butyl-NH-CH₂-CH=C(Me)Me, prenyl) |
| 30 | (Me₃C-CH₂-CH₂-CH₂-NH-CH₂-CH=C(Me)Me) |

TABLE 44

(I-A-2-6)

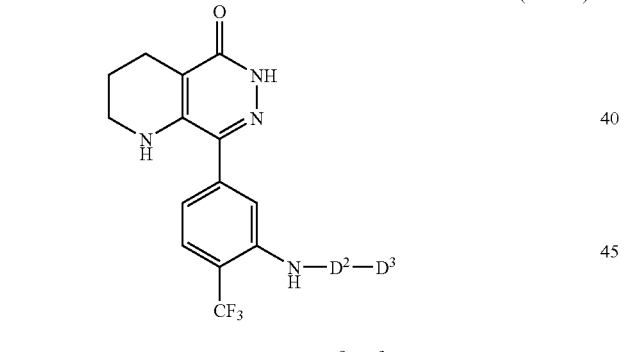

| No | —D²—D³ |
|----|--------|
| 31 | (Me₃C-CH₂-CH₂-NH-CH₂-CH=C(Me)Me) |
| 32 | (pentyl-NH-CH₂-C(Me)=CH₂) |
| 33 | (butyl-NH-CH₂-C(Me)=CH₂) |
| 34 | (Me₃C-CH₂-CH₂-CH₂-NH-CH₂-C(Me)=CH₂) |

TABLE 44-continued (I-A-2-6)

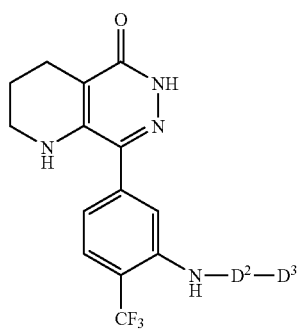

| No | —D²—D³ |
|----|--------|
| 35 | (Me₂C(Me)-CH₂-CH₂-NH-CH₂-C(Me)=CH₂) |
| 36 | (Et-O-CH₂-CH₂-NH₂) |
| 37 | (Et-O-CH₂-CH₂-NH-CH₂-C(Me)=CH₂) |
| 38 | (Et-O-CH₂-CH₂-NH-CH₂-CH=C(Me)Me) |
| 39 | (Et-O-CH₂-CH₂-N(Me)-CH₂-C≡CH) |
| 40 | (Et-S-CH₂-CH₂-NH₂) |
| 41 | (Et-S-CH₂-CH₂-NH-CH₂-C(Me)=CH₂) |
| 42 | (Et-S-CH₂-CH₂-NH-CH₂-CH=C(Me)Me) |
| 43 | (Et-S-CH₂-CH₂-N(Me)-CH₂-C≡CH) |
| 44 | (Et-NH-CH₂-CH₂-NH₂) |
| 45 | (2-methylazetidine) |
| 46 | (4-methylcyclohexylamine) |

TABLE 44-continued (I-A-2-6)

| No | —D²—D³ |
|---|---|
| 47 | 3-(aminomethyl)toluene (benzyl with m-methyl, CH₂NH₂) |
| 48 | 4-ethylpyridine |
| 49 | 3-ethylaniline (NH₂) |
| 50 | 3-propylpyridine |
| 51 | butyl-pyrrolidine |
| 52 | pentyl-pyrrolidine |
| 53 | butyl-(3-methoxy)pyrrolidine |
| 54 | pentyl-(3-methoxy)pyrrolidine |
| 55 | 3,3-dimethylbutyl-(3-methoxy)pyrrolidine |
| 56 | 4,4-dimethylpentyl-(3-methoxy)pyrrolidine |
| 57 | butyl-piperidine |

TABLE 44-continued (I-A-2-6)

| No | —D²—D³ |
|---|---|
| 58 | pentyl-piperidine |
| 59 | butyl-(3-methoxy)piperidine |
| 60 | pentyl-(3-methoxy)piperidine |

TABLE 45

(I-A-2-6)

| No | —D²—D³ |
|---|---|
| 61 | butyl-(4-methoxy)piperidine |
| 62 | pentyl-(4-methoxy)piperidine |
| 63 | 3,3-dimethylbutyl-(3-methoxy)piperidine |

TABLE 45-continued (I-A-2-6)

| No | —D²—D³ |
|---|---|
| 64 | 3-methoxypiperidine with neopentyl-propyl linker |
| 65 | 4-methoxypiperidine with neopentyl-ethyl linker |
| 66 | 4-methoxypiperidine with neopentyl-propyl linker |
| 67 | 1,2,3,6-tetrahydropyridine with propyl linker |
| 68 | 1,2,3,6-tetrahydropyridine with butyl linker |
| 69 | 1,2,3,6-tetrahydropyridine with neopentyl-ethyl linker |
| 70 | 1,2,3,6-tetrahydropyridine with neopentyl-propyl linker |
| 71 | morpholine with ethyl linker |
| 72 | morpholine with propyl linker |
| 73 | morpholine with butyl linker |

TABLE 45-continued (I-A-2-6)

| No | —D²—D³ |
|---|---|
| 74 | morpholine with neopentyl-ethyl linker |
| 75 | morpholine with neopentyl-propyl linker |
| 76 | azetidine with ethoxyethyl linker |
| 77 | pyrrolidine with ethoxyethyl linker |
| 78 | piperidine with ethoxyethyl linker |
| 79 | 3-methoxypyrrolidine with ethoxyethyl linker |
| 80 | 3-methoxypiperidine with ethoxyethyl linker |
| 81 | 4-methoxypiperidine with ethoxyethyl linker |
| 82 | 1,2,3,6-tetrahydropyridine with ethoxyethyl linker |
| 83 | morpholine with ethoxyethyl linker |

TABLE 45-continued
(I-A-2-6)
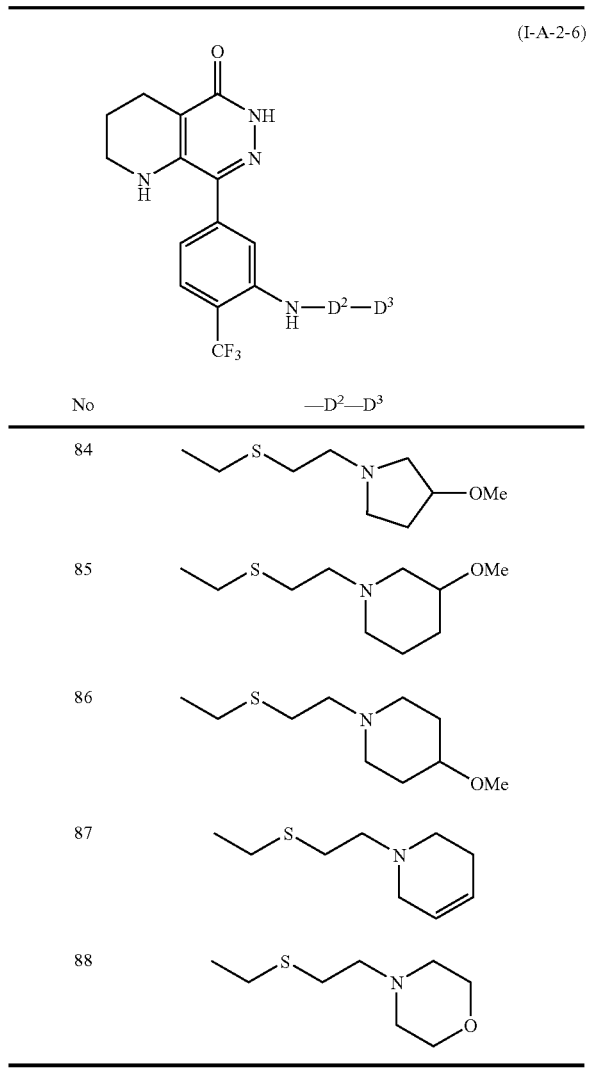
| No | —D²—D³ |
|---|---|
| 84 | |
| 85 | |
| 86 | |
| 87 | |
| 88 | |
TABLE 46
(I-A-2-7)
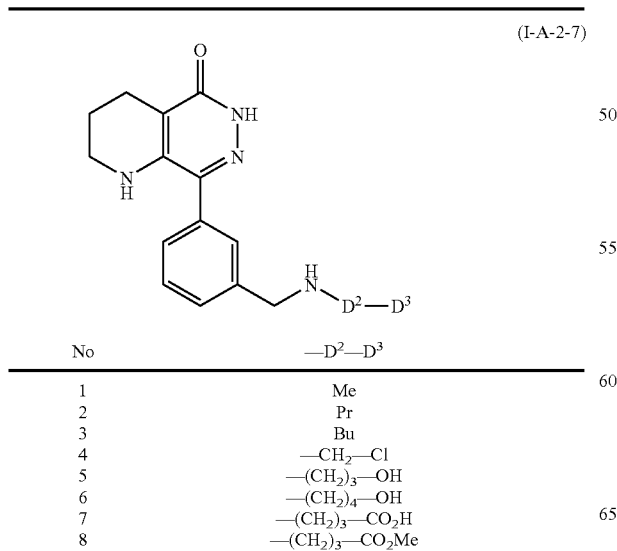
| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
TABLE 46-continued
(I-A-2-7)
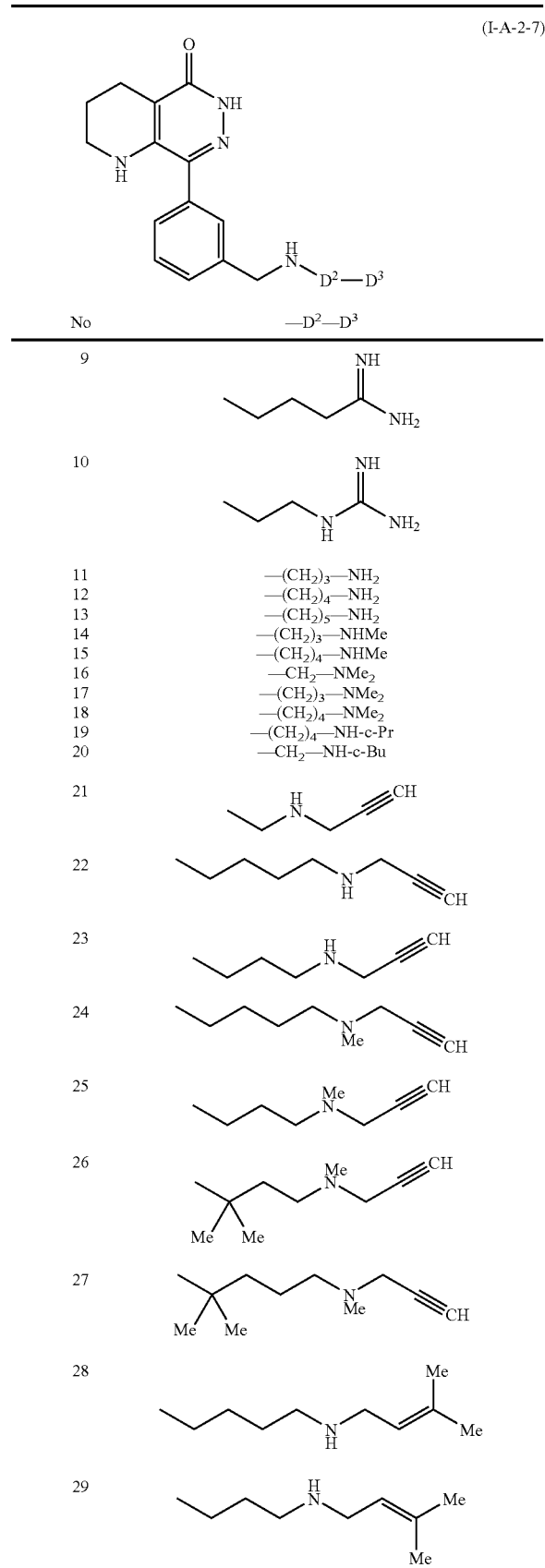
| No | —D²—D³ |
|---|---|
| 9 | |
| 10 | |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | |
| 22 | |
| 23 | |
| 24 | |
| 25 | |
| 26 | |
| 27 | |
| 28 | |
| 29 | |

TABLE 46-continued
(I-A-2-7)
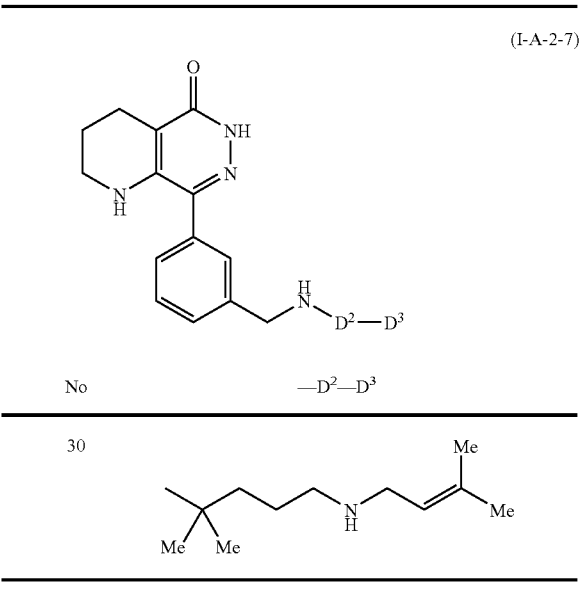
| No | —D²—D³ |
|---|---|
| 30 | 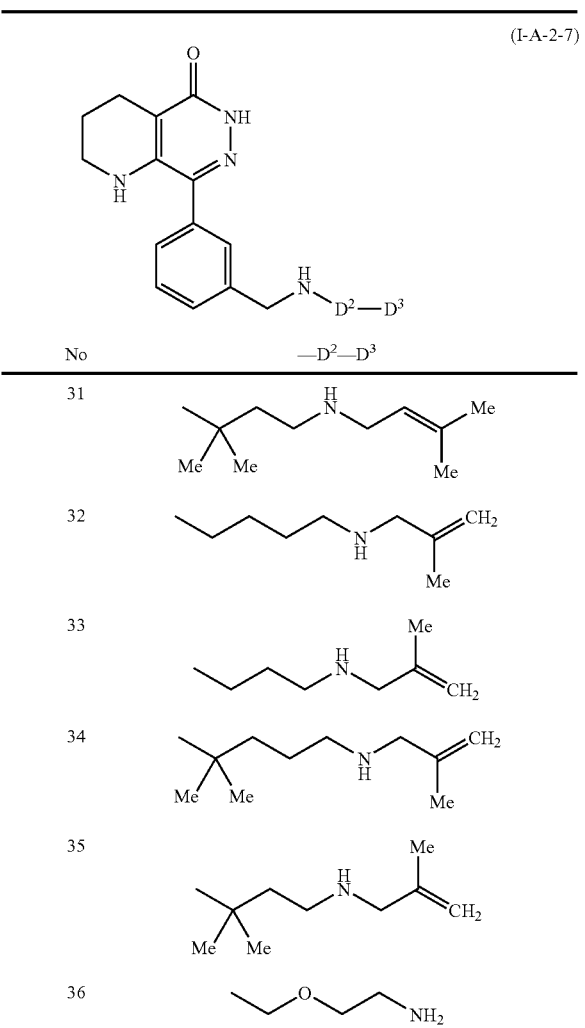 |
TABLE 47
(I-A-2-7)
| No | —D²—D³ |
|---|---|
| 31 | |
| 32 | |
| 33 | |
| 34 | |
| 35 | |
| 36 | |
TABLE 47-continued
(I-A-2-7)
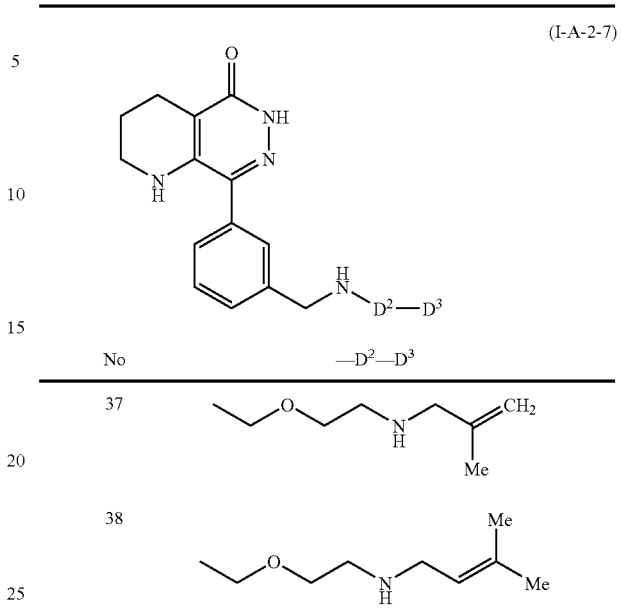
| No | —D²—D³ |
|---|---|
| 37 | |
| 38 | |
| 39 | |
| 40 | |
| 41 | |
| 42 | |
| 43 | |
| 44 | |
| 45 | |
| 46 | |
| 47 | |
| 48 | 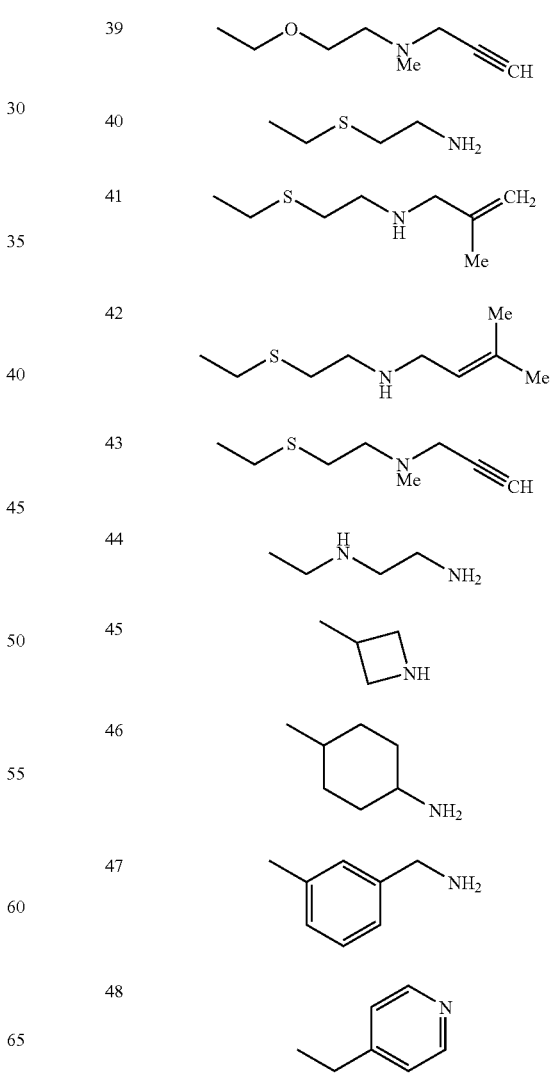 |

TABLE 47-continued (I-A-2-7)

| No | —D²—D³ |
|---|---|
| 49 | 3-aminophenyl-ethyl |
| 50 | 3-pyridyl-propyl |
| 51 | pyrrolidin-1-yl-butyl |
| 52 | pyrrolidin-1-yl-pentyl |
| 53 | 3-methoxypyrrolidin-1-yl-butyl |
| 54 | 3-methoxypyrrolidin-1-yl-pentyl |
| 55 | 3-methoxypyrrolidin-1-yl-(3,3-dimethyl)propyl |
| 56 | 3-methoxypyrrolidin-1-yl-(4,4-dimethyl)butyl |
| 57 | piperidin-1-yl-butyl |
| 58 | piperidin-1-yl-pentyl |
| 59 | 3-methoxypiperidin-1-yl-butyl |

TABLE 47-continued (I-A-2-7)

| No | —D²—D³ |
|---|---|
| 60 | 3-methoxypiperidin-1-yl-pentyl |

TABLE 48

(I-A-2-7)

| No | —D²—D³ |
|---|---|
| 61 | 4-methoxypiperidin-1-yl-butyl |
| 62 | 4-methoxypiperidin-1-yl-pentyl |
| 63 | 3-methoxypiperidin-1-yl-(3,3-dimethyl)propyl |
| 64 | 3-methoxypiperidin-1-yl-(4,4-dimethyl)butyl |
| 65 | 4-methoxypiperidin-1-yl-(3,3-dimethyl)propyl |

TABLE 48-continued (I-A-2-7)

| No | —D²—D³ |
|---|---|
| 66 | (CH₂)₃C(Me)₂CH₂-piperidine-4-OMe |
| 67 | butyl-tetrahydropyridine |
| 68 | pentyl-tetrahydropyridine |
| 69 | CH₂CH₂C(Me)₂CH₂-tetrahydropyridine |
| 70 | (CH₂)₃C(Me)₂CH₂-tetrahydropyridine |
| 71 | propyl-morpholine |
| 72 | butyl-morpholine |
| 73 | pentyl-morpholine |
| 74 | CH₂CH₂C(Me)₂CH₂-morpholine |
| 75 | (CH₂)₃C(Me)₂CH₂-morpholine |
| 76 | CH₂CH₂-O-CH₂CH₂-azetidine |
| 77 | CH₂CH₂-O-CH₂CH₂-pyrrolidine |
| 78 | CH₂CH₂-O-CH₂CH₂-piperidine |
| 79 | CH₂CH₂-O-CH₂CH₂-pyrrolidine-3-OMe |
| 80 | CH₂CH₂-O-CH₂CH₂-piperidine-3-OMe |
| 81 | CH₂CH₂-O-CH₂CH₂-piperidine-4-OMe |
| 82 | CH₂CH₂-O-CH₂CH₂-tetrahydropyridine |
| 83 | CH₂CH₂-O-CH₂CH₂-morpholine |
| 84 | CH₂CH₂-S-CH₂CH₂-pyrrolidine-3-OMe |
| 85 | CH₂CH₂-S-CH₂CH₂-piperidine-3-OMe |
| 86 | CH₂CH₂-S-CH₂CH₂-piperidine-4-OMe |

TABLE 48-continued (I-A-2-7)

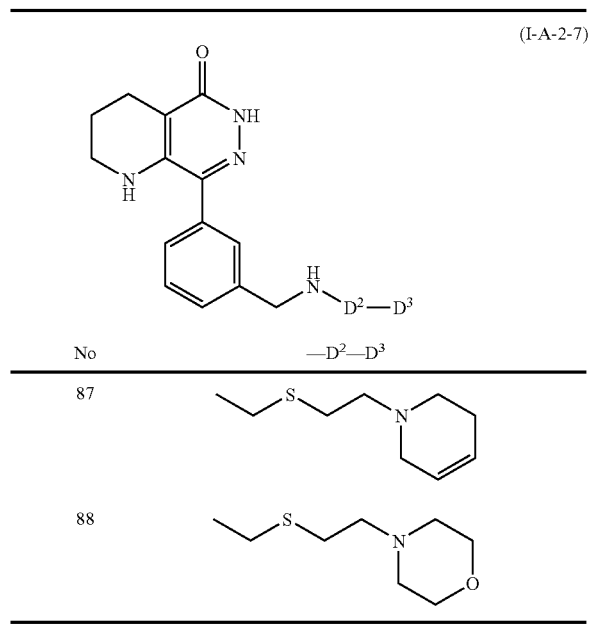

| No | —D²—D³ |
|----|--------|
| 87 | (ethylthio-ethyl-tetrahydropyridine) |
| 88 | (ethylthio-ethyl-morpholine) |

TABLE 49

(I-A-2-8)

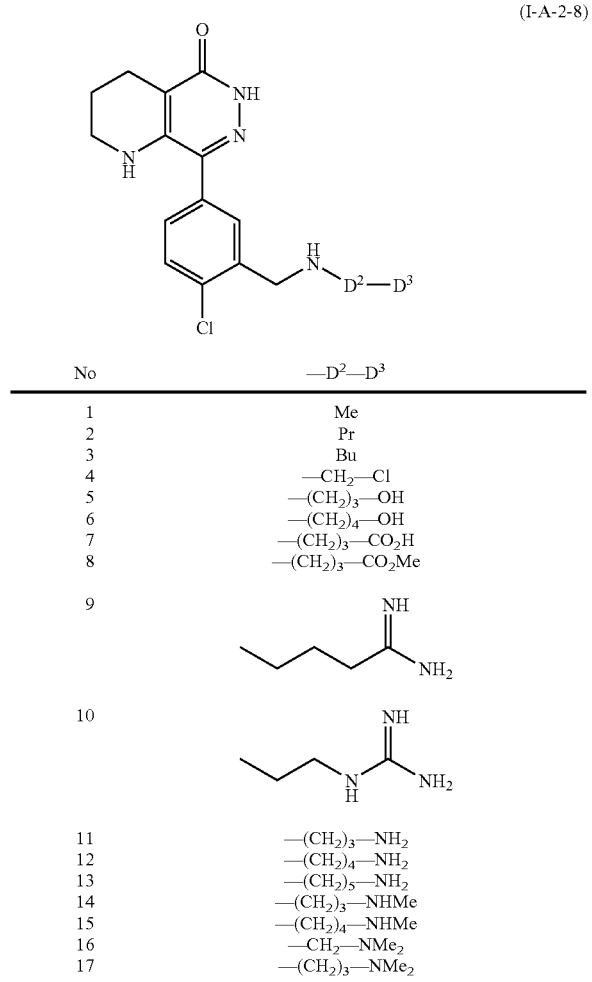

| No | —D²—D³ |
|----|--------|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | (butyl amidine) |
| 10 | (propyl guanidine) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |

TABLE 49-continued (I-A-2-8)

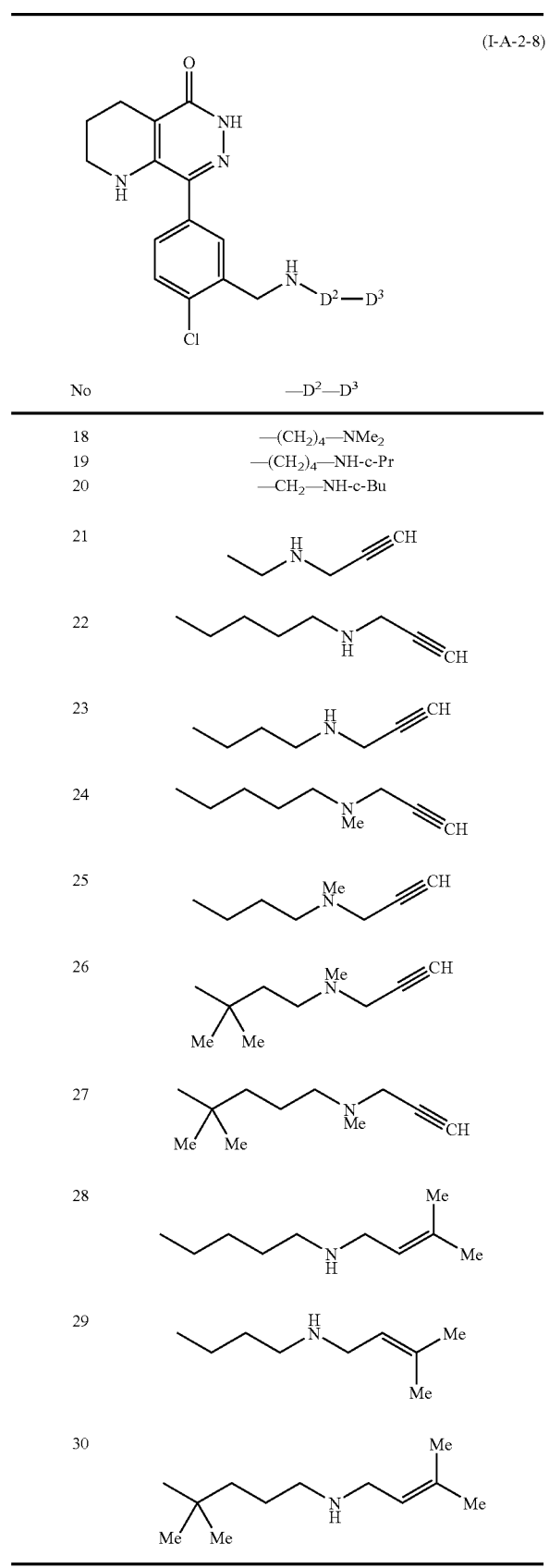

| No | —D²—D³ |
|----|--------|
| 18 | —(CH₂)₄—NMe₂ |
| 19 | —(CH₂)₄—NH-c-Pr |
| 20 | —CH₂—NH-c-Bu |
| 21 | (ethyl-NH-propargyl) |
| 22 | (pentyl-NH-propargyl) |
| 23 | (butyl-NH-propargyl) |
| 24 | (pentyl-NMe-propargyl) |
| 25 | (butyl-NMe-propargyl) |
| 26 | (neohexyl-NMe-propargyl) |
| 27 | (dimethylpentyl-NMe-propargyl) |
| 28 | (pentyl-NH-prenyl) |
| 29 | (butyl-NH-prenyl) |
| 30 | (dimethylpentyl-NH-prenyl) |

TABLE 50
(I-A-2-8)
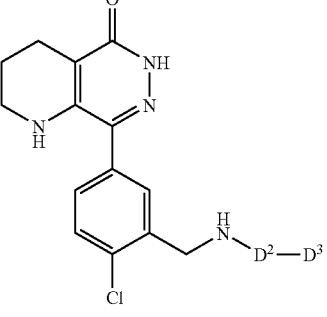
| No | —D²—D³ |
|---|---|
| 31 | 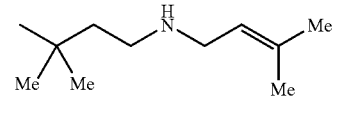 |
| 32 | 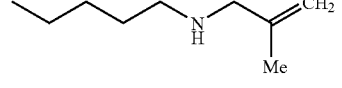 |
| 33 | 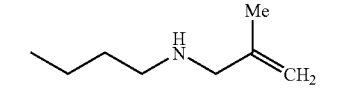 |
| 34 | 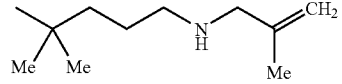 |
| 35 | 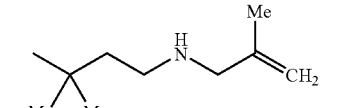 |
| 36 | 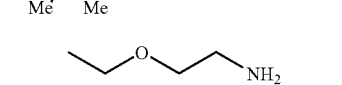 |
| 37 | 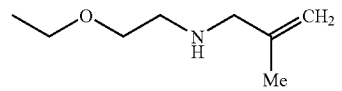 |
| 38 | 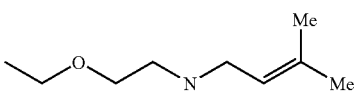 |
| 39 | 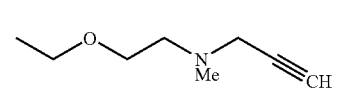 |
| 40 | 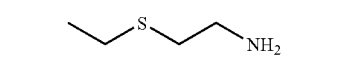 |
| 41 | 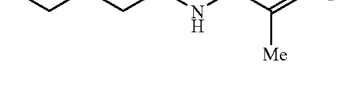 |
| 42 | 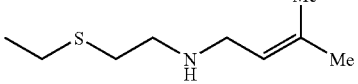 |
TABLE 50-continued
(I-A-2-8)
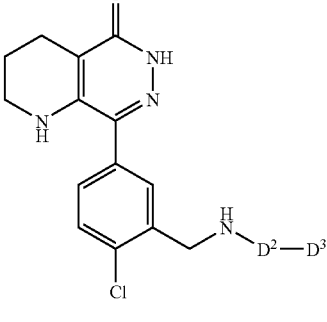
| No | —D²—D³ |
|---|---|
| 43 | 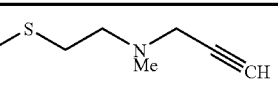 |
| 44 | 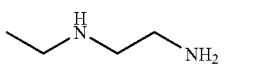 |
| 45 |  |
| 46 | 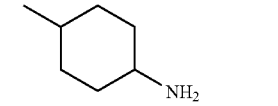 |
| 47 | 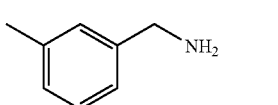 |
| 48 | 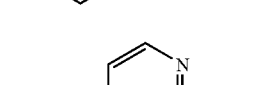 |
| 49 | 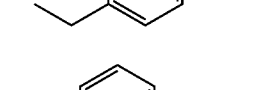 |
| 50 | 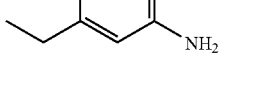 |
| 51 | 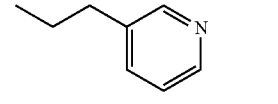 |
| 52 | 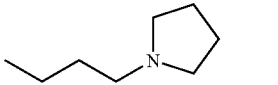 |
| 53 | 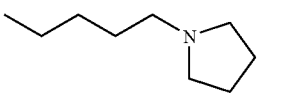 |

TABLE 50-continued and TABLE 51 (chemical structure tables, not transcribed).

TABLE 51-continued
(I-A-2-8)
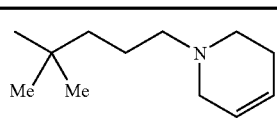
| No | —D²—D³ |
|---|---|
| 70 | 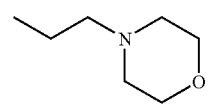 |
| 71 | 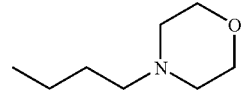 |
| 72 | 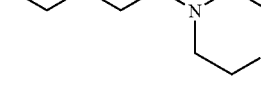 |
| 73 | 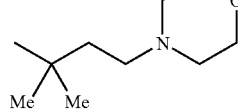 |
| 74 | 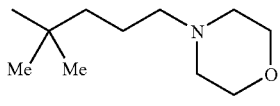 |
| 75 | 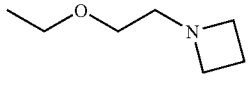 |
| 76 |  |
| 77 |  |
| 78 | 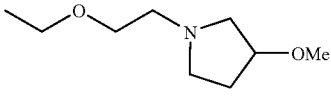 |
TABLE 51-continued
(I-A-2-8)
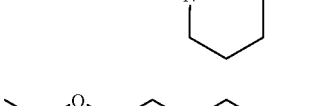
| No | —D²—D³ |
|---|---|
| 79 | 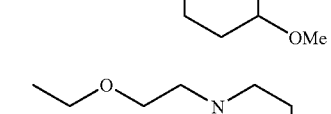 |
| 80 | 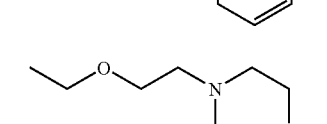 |
| 81 | 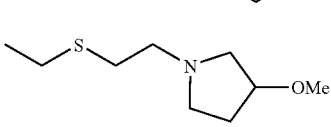 |
| 82 | 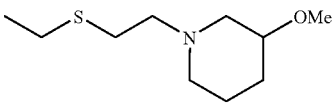 |
| 83 | 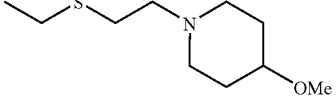 |
| 84 | 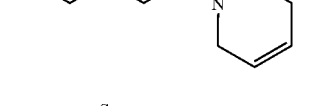 |
| 85 | 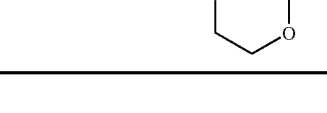 |
| 86 |  |
| 87 | |
| 88 | |

TABLE 52

(I-A-2-9)

Structure: 5,6,7,8-tetrahydropyrido[2,3-d]pyridazin-4(3H)-one with phenyl substituent bearing CF₃ and CH₂-NH-D²-D³ groups.

| No | —D²—D³ |
|---|---|
| 1 | Me |
| 2 | Pr |
| 3 | Bu |
| 4 | —CH₂—Cl |
| 5 | —(CH₂)₃—OH |
| 6 | —(CH₂)₄—OH |
| 7 | —(CH₂)₃—CO₂H |
| 8 | —(CH₂)₃—CO₂Me |
| 9 | butyl-C(=NH)NH₂ (amidine) |
| 10 | propyl-NH-C(=NH)NH₂ (guanidine) |
| 11 | —(CH₂)₃—NH₂ |
| 12 | —(CH₂)₄—NH₂ |
| 13 | —(CH₂)₅—NH₂ |
| 14 | —(CH₂)₃—NHMe |
| 15 | —(CH₂)₄—NHMe |
| 16 | —CH₂—NMe₂ |
| 17 | —(CH₂)₃—NMe₂ |
| 18 | —(CH₂)₄—NMe₂ |
| 19 | —(CH₂)₄—NH-c-Pr |
| 20 | —CH₂—NH-c-Bu |
| 21 | Et-NH-CH₂-C≡CH |
| 22 | pentyl-NH-CH₂-C≡CH |
| 23 | butyl-NH-CH₂-C≡CH |
| 24 | pentyl-N(Me)-CH₂-C≡CH |
| 25 | butyl-N(Me)-CH₂-C≡CH |
| 26 | Me₂C(Me)CH₂CH₂-N(Me)-CH₂-C≡CH |
| 27 | Me₂C(Me)CH₂CH₂CH₂-N(Me)-CH₂-C≡CH |

TABLE 52-continued (I-A-2-9)

| No | —D²—D³ |
|---|---|
| 28 | pentyl-NH-CH₂-CH=C(Me)₂ |
| 29 | butyl-NH-CH₂-CH=C(Me)₂ |
| 30 | Me₃C-CH₂CH₂-NH-CH₂-CH=C(Me)₂ |

TABLE 53

(I-A-2-9)

| No | —D²—D³ |
|---|---|
| 31 | Me₃C-CH₂CH₂CH₂-NH-CH₂-CH=C(Me)₂ |
| 32 | pentyl-NH-CH₂-C(Me)=CH₂ |
| 33 | butyl-NH-CH₂-C(Me)=CH₂ |

TABLE 53-continued (I-A-2-9)

| No | —D²—D³ |
|---|---|
| 34 | (CH₂)₃C(Me)₂-CH₂CH₂CH₂-NH-CH₂-C(=CH₂)Me |
| 35 | Me₂C(Me)-CH₂CH₂-NH-CH₂-C(=CH₂)Me |
| 36 | EtO-CH₂CH₂-NH₂ |
| 37 | EtO-CH₂CH₂-NH-CH₂-C(=CH₂)Me |
| 38 | EtO-CH₂CH₂-NH-CH₂-CH=C(Me)₂ |
| 39 | EtO-CH₂CH₂-N(Me)-CH₂-C≡CH |
| 40 | EtS-CH₂CH₂-NH₂ |
| 41 | EtS-CH₂CH₂-NH-CH₂-C(=CH₂)Me |
| 42 | EtS-CH₂CH₂-NH-CH₂-CH=C(Me)₂ |
| 43 | EtS-CH₂CH₂-N(Me)-CH₂-C≡CH |
| 44 | Et-NH-CH₂CH₂-NH₂ |
| 45 | 2-methylazetidine |

TABLE 53-continued (I-A-2-9)

| No | —D²—D³ |
|---|---|
| 46 | 4-methylcyclohexylamine |
| 47 | 3-methylbenzylamine |
| 48 | 4-ethylpyridine |
| 49 | 3-ethylaniline |
| 50 | 3-propylpyridine |
| 51 | 1-butylpyrrolidine |
| 52 | 1-pentylpyrrolidine |
| 53 | 1-butyl-3-methoxypyrrolidine |
| 54 | 1-pentyl-3-methoxypyrrolidine |
| 55 | 1-(3,3-dimethylbutyl)-3-methoxypyrrolidine |
| 56 | 1-(4,4-dimethylpentyl)-3-methoxypyrrolidine |

TABLE 53-continued
(I-A-2-9)
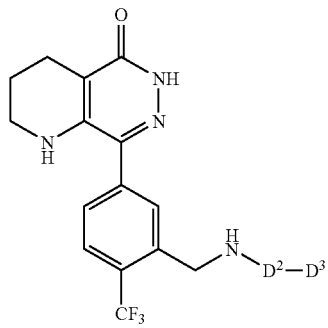
| No | —D²—D³ |
|---|---|
| 57 | |
| 58 | |
| 59 | |
| 60 | |
TABLE 54
(I-A-2-9)
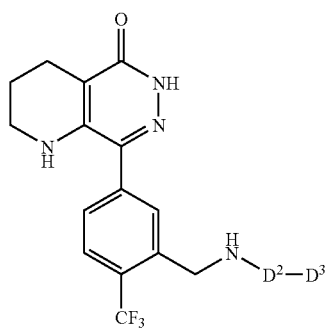
| No | —D²—D³ |
|---|---|
| 61 | |
| 62 | |
TABLE 54-continued
(I-A-2-9)
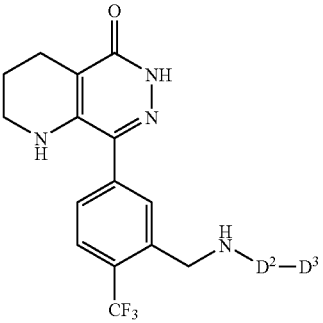
| No | —D²—D³ |
|---|---|
| 63 | |
| 64 | |
| 65 | |
| 66 | |
| 67 | |
| 68 | |
| 69 | |
| 70 | |
| 71 | |
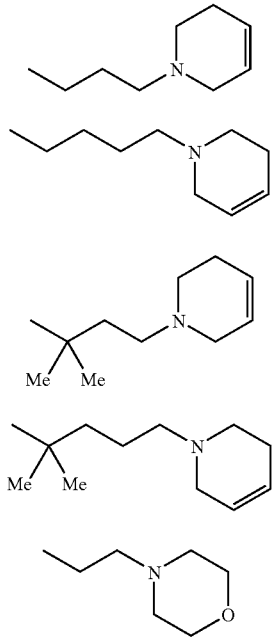

TABLE 54-continued (I-A-2-9)

| No | —D²—D³ |
|---|---|
| 72 | (butyl-morpholine) |
| 73 | (pentyl-morpholine) |
| 74 | (3,3-dimethylbutyl-morpholine) |
| 75 | (4,4-dimethylpentyl-morpholine) |
| 76 | (ethoxyethyl-azetidine) |
| 77 | (ethoxyethyl-pyrrolidine) |
| 78 | (ethoxyethyl-piperidine) |
| 79 | (ethoxyethyl-3-methoxypyrrolidine) |
| 80 | (ethoxyethyl-3-methoxypiperidine) |
| 81 | (ethoxyethyl-4-methoxypiperidine) |
| 82 | (ethoxyethyl-tetrahydropyridine) |
| 83 | (ethoxyethyl-morpholine) |
| 84 | (ethylthioethyl-3-methoxypyrrolidine) |
| 85 | (ethylthioethyl-3-methoxypiperidine) |
| 86 | (ethylthioethyl-4-methoxypiperidine) |
| 87 | (ethylthioethyl-tetrahydropyridine) |

TABLE 54-continued (I-A-2-9)

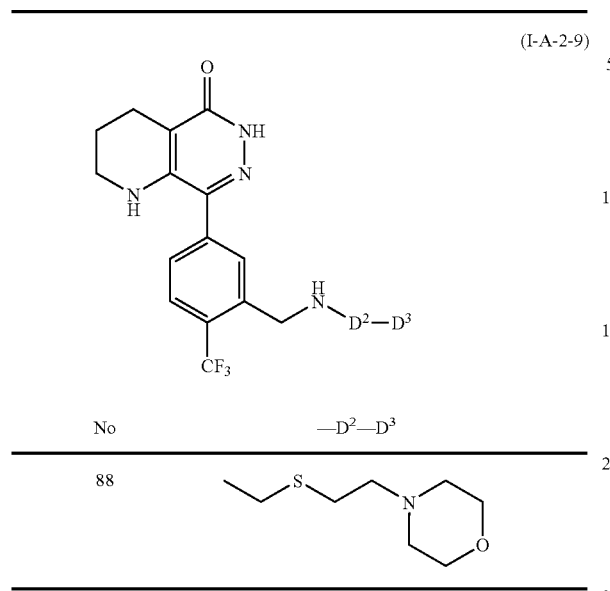

| No | —D²—D³ |
|---|---|
| 88 | 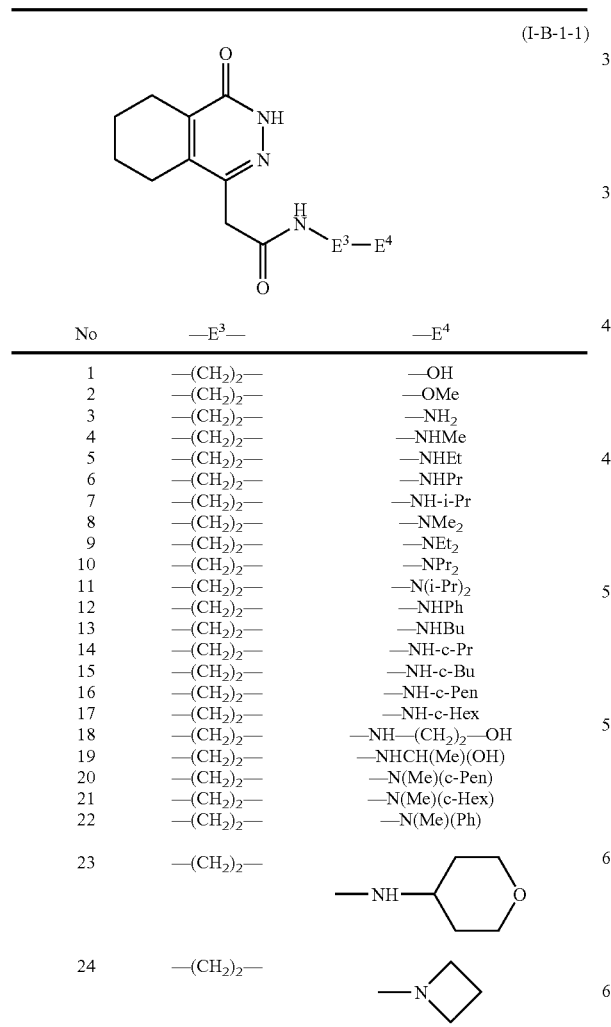 |

TABLE 55

(I-B-1-1)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | |
| 24 | —(CH₂)₂— | |

TABLE 55-continued (I-B-1-1)

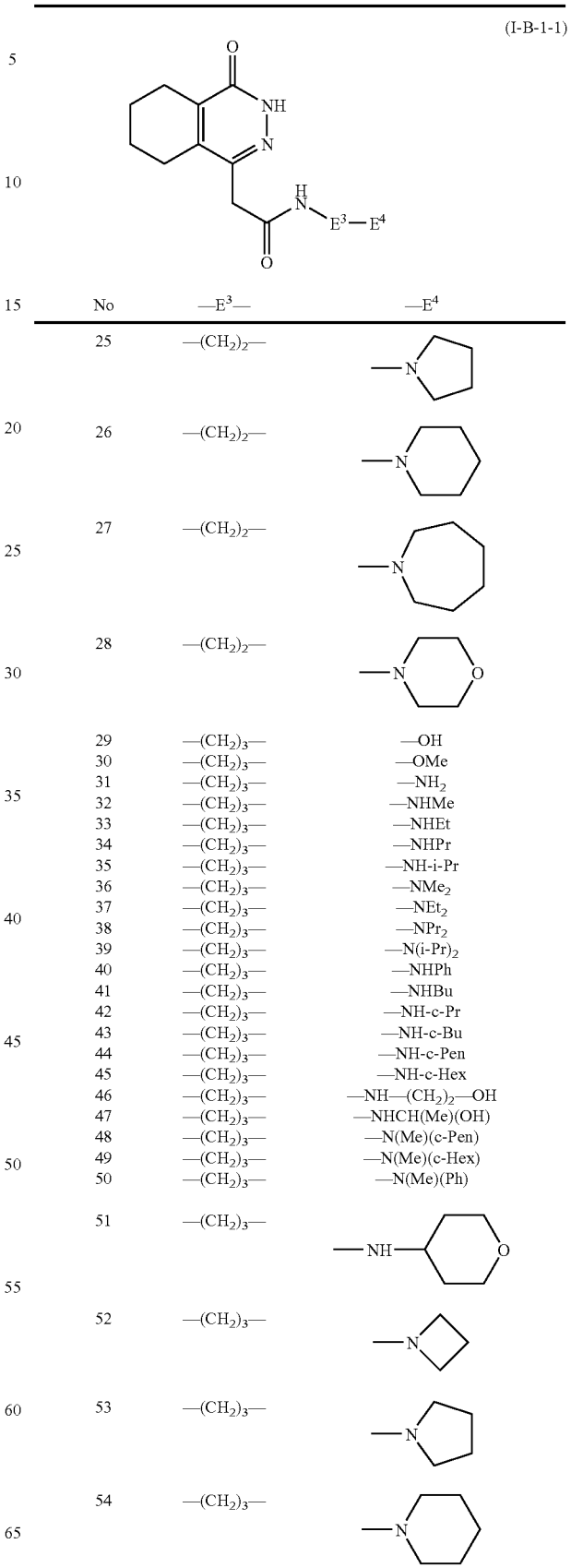

| No | —E³— | —E⁴ |
|---|---|---|
| 25 | —(CH₂)₂— | |
| 26 | —(CH₂)₂— | |
| 27 | —(CH₂)₂— | |
| 28 | —(CH₂)₂— | |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | |
| 52 | —(CH₂)₃— | |
| 53 | —(CH₂)₃— | |
| 54 | —(CH₂)₃— | |

TABLE 55-continued (I-B-1-1)

Structure: 5,6,7,8-tetrahydrophthalazin-1(2H)-one with −CH₂−C(=O)−NH−E³−E⁴ substituent

| No | —E³— | —E⁴ |
|---|---|---|
| 55 | —(CH₂)₃— | N-azepanyl (1-azepanyl ring) |
| 56 | —(CH₂)₃— | 4-morpholinyl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | 1-azetidinyl |
| 81 | —(CH₂)₄— | 1-pyrrolidinyl |
| 82 | —(CH₂)₄— | 1-piperidinyl |
| 83 | —(CH₂)₄— | 1-azepanyl |
| 84 | —(CH₂)₄— | 4-morpholinyl |

TABLE 56

(I-B-1-2)

Structure: 5,6,7,8-tetrahydrophthalazin-1(2H)-one with −CH₂−C(=O)−N(Me)−E³−E⁴ substituent

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | 1-azetidinyl |
| 25 | —(CH₂)₂— | 1-pyrrolidinyl |
| 26 | —(CH₂)₂— | 1-piperidinyl |
| 27 | —(CH₂)₂— | 1-azepanyl |
| 28 | —(CH₂)₂— | 4-morpholinyl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |

TABLE 56-continued (I-B-1-2)

[Structure: 4-oxo-3,4,5,6,7,8-hexahydrophthalazine with -CH2-C(=O)-N(Me)-E3-E4 substituent]

| No | —E³— | —E⁴ |
|---|---|---|
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N-azetidinyl |
| 53 | —(CH₂)₃— | —N-pyrrolidinyl |
| 54 | —(CH₂)₃— | —N-piperidinyl |
| 55 | —(CH₂)₃— | —N-azepanyl |
| 56 | —(CH₂)₃— | —N-morpholinyl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |

TABLE 56-continued (I-B-1-2)

[Structure: 4-oxo-3,4,5,6,7,8-hexahydrophthalazine with -CH2-C(=O)-N(Me)-E3-E4 substituent]

| No | —E³— | —E⁴ |
|---|---|---|
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | —N-azetidinyl |
| 81 | —(CH₂)₄— | —N-pyrrolidinyl |
| 82 | —(CH₂)₄— | —N-piperidinyl |
| 83 | —(CH₂)₄— | —N-azepanyl |
| 84 | —(CH₂)₄— | —N-morpholinyl |

TABLE 57

(I-B-1-3)

[Structure: 4-oxo-3,4,5,6,7,8-hexahydrophthalazine with -CH2-C(=O)-N(Et)-E3-E4 substituent]

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |

TABLE 57-continued (I-B-1-3)

[Structure: 4-oxo-3,4,5,6,7,8-hexahydrophthalazine with -CH2-C(=O)-N(Et)-E3-E4 substituent]

| No | —E³— | —E⁴ |
|---|---|---|
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | —N-azetidinyl |
| 25 | —(CH₂)₂— | —N-pyrrolidinyl |
| 26 | —(CH₂)₂— | —N-piperidinyl |
| 27 | —(CH₂)₂— | —N-azepanyl |
| 28 | —(CH₂)₂— | —N-morpholinyl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N-azetidinyl |
| 53 | —(CH₂)₃— | —N-pyrrolidinyl |
| 54 | —(CH₂)₃— | —N-piperidinyl |
| 55 | —(CH₂)₃— | —N-azepanyl |
| 56 | —(CH₂)₃— | —N-morpholinyl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |

TABLE 57-continued (I-B-1-3)

| No | —E³— | —E⁴ |
|---|---|---|
| 80 | —(CH₂)₄— | azetidinyl (N-azetidine) |
| 81 | —(CH₂)₄— | pyrrolidinyl |
| 82 | —(CH₂)₄— | piperidinyl |
| 83 | —(CH₂)₄— | azepanyl |
| 84 | —(CH₂)₄— | morpholinyl |

TABLE 58

(I-B-1-4)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |

TABLE 58-continued (I-B-1-4)

| No | —E³— | —E⁴ |
|---|---|---|
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | azetidinyl |
| 25 | —(CH₂)₂— | pyrrolidinyl |
| 26 | —(CH₂)₂— | piperidinyl |
| 27 | —(CH₂)₂— | azepanyl |
| 28 | —(CH₂)₂— | morpholinyl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |

TABLE 58-continued (I-B-1-4)

| No | —E³— | —E⁴ |
|---|---|---|
| 52 | —(CH₂)₃— | azetidinyl (N-linked 4-membered ring) |
| 53 | —(CH₂)₃— | pyrrolidinyl |
| 54 | —(CH₂)₃— | piperidinyl |
| 55 | —(CH₂)₃— | azepanyl |
| 56 | —(CH₂)₃— | morpholinyl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-tetrahydropyran-4-yl |
| 80 | —(CH₂)₄— | azetidinyl |
| 81 | —(CH₂)₄— | pyrrolidinyl |
| 82 | —(CH₂)₄— | piperidinyl |
| 83 | —(CH₂)₄— | azepanyl |
| 84 | —(CH₂)₄— | morpholinyl |

TABLE 59

(I-B-1-5)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-tetrahydropyran-4-yl |

TABLE 59-continued (I-B-1-5)

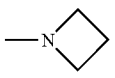

| No | —E³— | —E⁴ |
|---|---|---|
| 24 | —(CH₂)₂— | 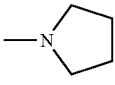 azetidine |
| 25 | —(CH₂)₂— | pyrrolidine |
| 26 | —(CH₂)₂— | piperidine |
| 27 | —(CH₂)₂— | azepane |
| 28 | —(CH₂)₂— | morpholine |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-tetrahydropyran |
| 52 | —(CH₂)₃— | azetidine |
| 53 | —(CH₂)₃— | pyrrolidine |

TABLE 59-continued (I-B-1-5)

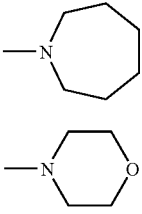

| No | —E³— | —E⁴ |
|---|---|---|
| 54 | —(CH₂)₃— | piperidine |
| 55 | —(CH₂)₃— | azepane |
| 56 | —(CH₂)₃— | morpholine |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-tetrahydropyran |
| 80 | —(CH₂)₄— | azetidine |
| 81 | —(CH₂)₄— | pyrrolidine |
| 82 | —(CH₂)₄— | piperidine |
| 83 | —(CH₂)₄— | azepane |

TABLE 59-continued (I-B-1-5)

| No | —E³— | —E⁴ |
|---|---|---|
| 84 | —(CH₂)₄— | -N-morpholine |

TABLE 60

(I-B-1-6)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | tetrahydropyran-4-yl |
| 12 | —CH₂— | 1-Bn-piperidin-4-yl |
| 13 | —CH₂— | —(CH₂)₂-(1-Bn-piperidin-4-yl) |
| 14 | —CH₂— | —(CH₂)₂-(4-OH-C₆H₄) |
| 15 | —CH₂— | —(CH₂)₂-(4-OMe-C₆H₄) |

TABLE 60-continued (I-B-1-6)

| No | —E¹— | —E³—E⁴ |
|---|---|---|
| 16 | —CH₂— | —(CH₂)₂-(4-NH₂-C₆H₄) |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | tetrahydropyran-4-yl |
| 28 | —(CH₂)₂— | 1-Bn-piperidin-4-yl |
| 29 | —(CH₂)₂— | —(CH₂)₂-(1-Bn-piperidin-4-yl) |
| 30 | —(CH₂)₂— | —(CH₂)₂-(4-OH-C₆H₄) |
| 31 | —(CH₂)₂— | —(CH₂)₂-(4-OMe-C₆H₄) |
| 32 | —(CH₂)₂— | —(CH₂)₂-(4-NH₂-C₆H₄) |

TABLE 61

(I-B-1-7)

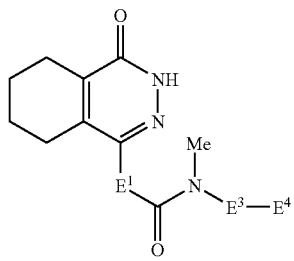

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | (tetrahydropyran-4-yl) |
| 12 | —CH₂— | (1-Bn-piperidin-4-yl) |
| 13 | —CH₂— | —(CH₂)₂-(1-Bn-piperidin-4-yl) |
| 14 | —CH₂— | —(CH₂)₂-(4-OH-phenyl) |
| 15 | —CH₂— | —(CH₂)₂-(4-OMe-phenyl) |
| 16 | —CH₂— | —(CH₂)₂-(4-NH₂-phenyl) |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | (tetrahydropyran-4-yl) |
| 28 | —(CH₂)₂— | (1-Bn-piperidin-4-yl) |

TABLE 61-continued (I-B-1-7)

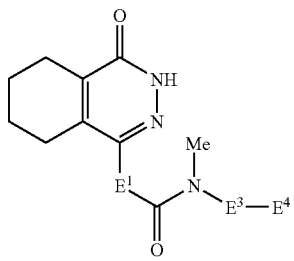

| No | —E¹— | —E³—E⁴ |
|---|---|---|
| 29 | —(CH₂)₂— | —(CH₂)₂-(1-Bn-piperidin-4-yl) |
| 30 | —(CH₂)₂— | —(CH₂)₂-(4-OH-phenyl) |
| 31 | —(CH₂)₂— | —(CH₂)₂-(4-OMe-phenyl) |
| 32 | —(CH₂)₂— | —(CH₂)₂-(4-NH₂-phenyl) |

TABLE 62

(I-B-1-8)

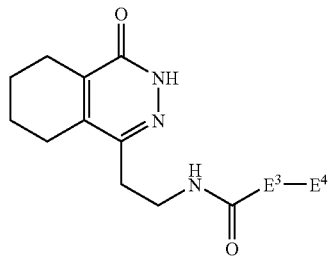

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |

TABLE 62-continued (I-B-1-8)

| No | —E³— | —E⁴ |
|---|---|---|
| 23 | —(CH₂)₂— | —NH-(tetrahydropyran-4-yl) |
| 24 | —(CH₂)₂— | —N(azetidinyl) |
| 25 | —(CH₂)₂— | —N(pyrrolidinyl) |
| 26 | —(CH₂)₂— | —N(piperidinyl) |
| 27 | —(CH₂)₂— | —N(azepanyl) |
| 28 | —(CH₂)₂— | —N(morpholinyl) |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N(azetidinyl) |
| 53 | —(CH₂)₃— | —N(pyrrolidinyl) |
| 54 | —(CH₂)₃— | —N(piperidinyl) |
| 55 | —(CH₂)₃— | —N(azepanyl) |
| 56 | —(CH₂)₃— | —N(morpholinyl) |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | —N(azetidinyl) |
| 81 | —(CH₂)₄— | —N(pyrrolidinyl) |
| 82 | —(CH₂)₄— | —N(piperidinyl) |

TABLE 62-continued (I-B-1-8)

| No | —E³— | —E⁴ |
|---|---|---|
| 83 | —(CH₂)₄— | N-methylazepane |
| 84 | —(CH₂)₄— | N-methylmorpholine |

TABLE 63

(I-B-1-9)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | tetrahydropyran-4-yl |
| 12 | —CH₂— | 1-Bn-piperidin-4-yl |
| 13 | —CH₂— | —(CH₂)₂-(1-Bn-piperidin-4-yl) |
| 14 | —CH₂— | —(CH₂)₂-C₆H₄-OH |

TABLE 63-continued (I-B-1-9)

| No | —E¹— | —E³—E⁴ |
|---|---|---|
| 15 | —CH₂— | —(CH₂)₂-C₆H₄-OMe |
| 16 | —CH₂— | —(CH₂)₂-C₆H₄-NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | tetrahydropyran-4-yl |
| 28 | —(CH₂)₂— | 1-Bn-piperidin-4-yl |
| 29 | —(CH₂)₂— | —(CH₂)₂-(1-Bn-piperidin-4-yl) |
| 30 | —(CH₂)₂— | —(CH₂)₂-C₆H₄-OH |
| 31 | —(CH₂)₂— | —(CH₂)₂-C₆H₄-OMe |
| 32 | —(CH₂)₂— | —(CH₂)₂-C₆H₄-NH₂ |

TABLE 64

(I-B-1-10)

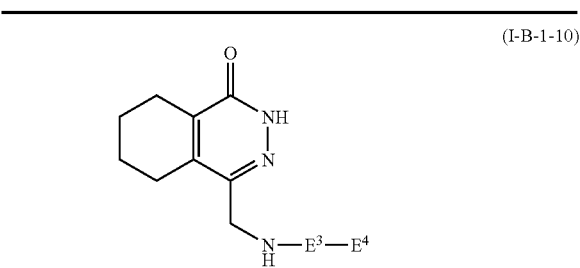

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | 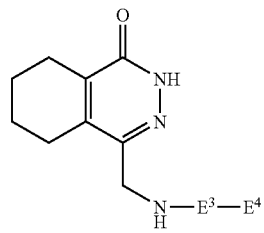 |
| 24 | —(CH₂)₂— | (azetidine) |
| 25 | —(CH₂)₂— | (pyrrolidine) |
| 26 | —(CH₂)₂— | (piperidine) |
| 27 | —(CH₂)₂— | (azepane) |
| 28 | —(CH₂)₂— | (morpholine) |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | (tetrahydropyran-NH) |
| 52 | —(CH₂)₃— | (azetidine) |
| 53 | —(CH₂)₃— | (pyrrolidine) |
| 54 | —(CH₂)₃— | (piperidine) |
| 55 | —(CH₂)₃— | (azepane) |
| 56 | —(CH₂)₃— | (morpholine) |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |

TABLE 64-continued (I-B-1-10)

| No | —E³— | —E⁴ |
|---|---|---|
| 79 | —(CH₂)₄— | —NH-(tetrahydropyran-4-yl) |
| 80 | —(CH₂)₄— | azetidin-1-yl |
| 81 | —(CH₂)₄— | pyrrolidin-1-yl |
| 82 | —(CH₂)₄— | piperidin-1-yl |
| 83 | —(CH₂)₄— | azepan-1-yl |
| 84 | —(CH₂)₄— | morpholin-4-yl |

TABLE 65

(I-B-1-11)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |

TABLE 65-continued (I-B-1-11)

| No | —E³— | —E⁴ |
|---|---|---|
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |

TABLE 65-continued (I-B-1-11)

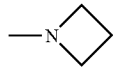

| No | —E³— | —E⁴ |
|---|---|---|
| 52 | —(CH₂)₃— | 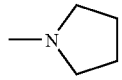 |
| 53 | —(CH₂)₃— | 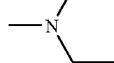 |
| 54 | —(CH₂)₃— | 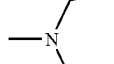 |
| 55 | —(CH₂)₃— | 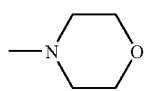 |
| 56 | —(CH₂)₃— | 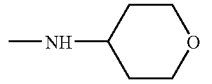 |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | 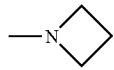 |
| 80 | —(CH₂)₄— | 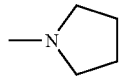 |
| 81 | —(CH₂)₄— | 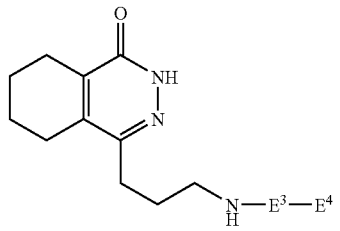 |

TABLE 65-continued (I-B-1-11)

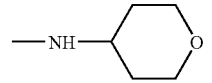

| No | —E³— | —E⁴ |
|---|---|---|
| 82 | —(CH₂)₄— | (piperidine) |
| 83 | —(CH₂)₄— | (azepane) |
| 84 | —(CH₂)₄— | (morpholine) |

TABLE 66

(I-B-1-12)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | (tetrahydropyranyl-NH) |

TABLE 66-continued (I-B-1-12)

[Structure: 5,6,7,8-tetrahydrophthalazin-1(2H)-one with 4-(3-(NH-E³-E⁴)propyl) substituent]

| No | —E³— | —E⁴ |
|---|---|---|
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl (hexamethyleneimino) |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | azetidin-1-yl |
| 53 | —(CH₂)₃— | pyrrolidin-1-yl |
| 54 | —(CH₂)₃— | piperidin-1-yl |
| 55 | —(CH₂)₃— | azepan-1-yl |
| 56 | —(CH₂)₃— | morpholin-4-yl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | azetidin-1-yl |
| 81 | —(CH₂)₄— | pyrrolidin-1-yl |
| 82 | —(CH₂)₄— | piperidin-1-yl |
| 83 | —(CH₂)₄— | azepan-1-yl |

TABLE 66-continued (I-B-1-12)

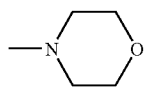

| No | —E³— | —E⁴ |
|---|---|---|
| 84 | —(CH₂)₄— | (N-morpholinyl) |

TABLE 67

(I-B-1-13)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | (tetrahydropyran-4-yl) |
| 12 | —CH₂— | (1-Bn-piperidin-4-yl) |
| 13 | —CH₂— | —(CH₂)₂—(1-Bn-piperidin-4-yl) |
| 14 | —CH₂— | —(CH₂)₂—C₆H₄—OH |
| 15 | —CH₂— | —(CH₂)₂—C₆H₄—OMe |
| 16 | —CH₂— | —(CH₂)₂—C₆H₄—NH₂ |
| 17 | —(CH₂)₂— | Me |

TABLE 67-continued (I-B-1-13)

| No | —E¹— | —E³—E⁴ |
|---|---|---|
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | (tetrahydropyran-4-yl) |
| 28 | —(CH₂)₂— | (1-Bn-piperidin-4-yl) |
| 29 | —(CH₂)₂— | —(CH₂)₂—(1-Bn-piperidin-4-yl) |
| 30 | —(CH₂)₂— | —(CH₂)₂—C₆H₄—OH |
| 31 | —(CH₂)₂— | —(CH₂)₂—C₆H₄—OMe |
| 32 | —(CH₂)₂— | —(CH₂)₂—C₆H₄—NH₂ |
| 33 | —(CH₂)₃— | Me |
| 34 | —(CH₂)₃— | Et |
| 35 | —(CH₂)₃— | Pr |
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |
| 42 | —(CH₂)₃— | c-Hex |
| 43 | —(CH₂)₃— | (tetrahydropyran-4-yl) |
| 44 | —(CH₂)₃— | (1-Bn-piperidin-4-yl) |

TABLE 67-continued (I-B-1-13)

| No | —E¹— | —E³—E⁴ |
|---|---|---|
| 45 | —(CH₂)₃— | —(CH₂)₂—(piperidine-N-Bn) |
| 46 | —(CH₂)₃— | —(CH₂)₂—(C₆H₄)—OH |
| 47 | —(CH₂)₃— | —(CH₂)₂—(C₆H₄)—OMe |
| 48 | —(CH₂)₃— | —(CH₂)₂—(C₆H₄)—NH₂ |

TABLE 68

(I-B-1-14)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | —(tetrahydropyran-4-yl) |
| 12 | —CH₂— | —(piperidine-N-Bn) |

TABLE 68-continued (I-B-1-14)

| No | —E¹— | —E³—E⁴ |
|---|---|---|
| 13 | —CH₂— | —(CH₂)₂—(piperidine-N-Bn) |
| 14 | —CH₂— | —(CH₂)₂—(C₆H₄)—OH |
| 15 | —CH₂— | —(CH₂)₂—(C₆H₄)—OMe |
| 16 | —CH₂— | —(CH₂)₂—(C₆H₄)—NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | —(tetrahydropyran-4-yl) |
| 28 | —(CH₂)₂— | —(piperidine-N-Bn) |
| 29 | —(CH₂)₂— | —(CH₂)₂—(piperidine-N-Bn) |
| 30 | —(CH₂)₂— | —(CH₂)₂—(C₆H₄)—OH |
| 31 | —(CH₂)₂— | —(CH₂)₂—(C₆H₄)—OMe |
| 32 | —(CH₂)₂— | —(CH₂)₂—(C₆H₄)—NH₂ |
| 33 | —(CH₂)₃— | Me |
| 34 | —(CH₂)₃— | Et |
| 35 | —(CH₂)₃— | Pr |

TABLE 68-continued (I-B-1-14)

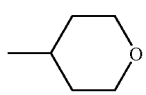

| No | —E¹— | —E³—E⁴ |
|---|---|---|
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |
| 42 | —(CH₂)₃— | c-Hex |
| 43 | —(CH₂)₃— | 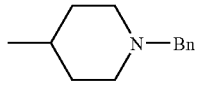 |
| 44 | —(CH₂)₃— | 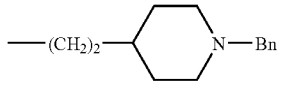 |
| 45 | —(CH₂)₃— | —(CH₂)₂— 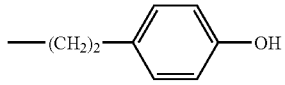—Bn |
| 46 | —(CH₂)₃— | —(CH₂)₂—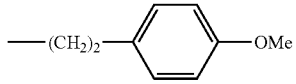—OH |
| 47 | —(CH₂)₃— | —(CH₂)₂—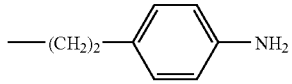—OMe |
| 48 | —(CH₂)₃— | —(CH₂)₂—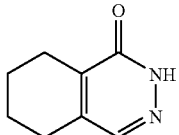—NH₂ |

TABLE 69

(I-B-1-15)

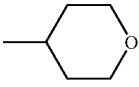

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |

TABLE 69-continued (I-B-1-15)

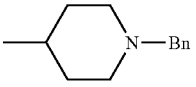

| No | —E¹— | —E³—E⁴ |
|---|---|---|
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | 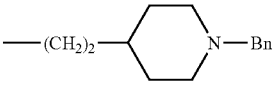 |
| 12 | —CH₂— | 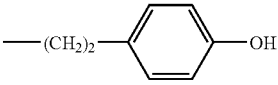 |
| 13 | —CH₂— | —(CH₂)₂—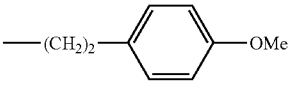—Bn |
| 14 | —CH₂— | —(CH₂)₂—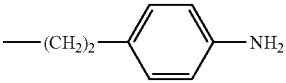—OH |
| 15 | —CH₂— | —(CH₂)₂—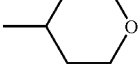—OMe |
| 16 | —CH₂— | —(CH₂)₂—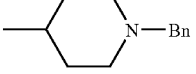—NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | 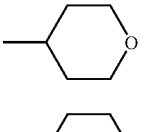 |
| 28 | —(CH₂)₂— | 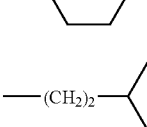 |
| 29 | —(CH₂)₂— | —(CH₂)₂——Bn |

TABLE 69-continued (I-B-1-15)

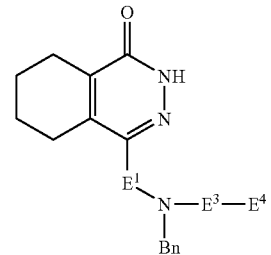

| No | —E¹— | —E³—E⁴ |
|---|---|---|
| 30 | —(CH₂)₂— | —(CH₂)₂—C₆H₄—OH (4-) |
| 31 | —(CH₂)₂— | —(CH₂)₂—C₆H₄—OMe (4-) |
| 32 | —(CH₂)₂— | —(CH₂)₂—C₆H₄—NH₂ (4-) |
| 33 | —(CH₂)₃— | Me |
| 34 | —(CH₂)₃— | Et |
| 35 | —(CH₂)₃— | Pr |
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |
| 42 | —(CH₂)₃— | c-Hex |
| 43 | —(CH₂)₃— | tetrahydropyran-4-yl |
| 44 | —(CH₂)₃— | 1-benzylpiperidin-4-yl |
| 45 | —(CH₂)₃— | —(CH₂)₂-(1-benzylpiperidin-4-yl) |
| 46 | —(CH₂)₃— | —(CH₂)₂—C₆H₄—OH (4-) |
| 47 | —(CH₂)₃— | —(CH₂)₂—C₆H₄—OMe (4-) |
| 48 | —(CH₂)₃— | —(CH₂)₂—C₆H₄—NH₂ (4-) |

TABLE 70

(I-B-2-1)

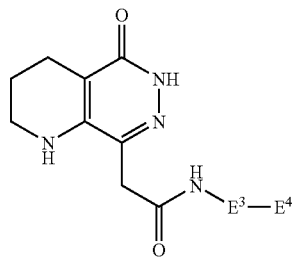

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |

TABLE 70-continued (I-B-2-1)

| No | —E³— | —E⁴ |
|---|---|---|
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N(azetidinyl) |
| 53 | —(CH₂)₃— | —N(pyrrolidinyl) |
| 54 | —(CH₂)₃— | —N(piperidinyl) |
| 55 | —(CH₂)₃— | —N(azepanyl) |
| 56 | —(CH₂)₃— | —N(morpholinyl) |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | —N(azetidinyl) |
| 81 | —(CH₂)₄— | —N(pyrrolidinyl) |
| 82 | —(CH₂)₄— | —N(piperidinyl) |
| 83 | —(CH₂)₄— | —N(azepanyl) |
| 84 | —(CH₂)₄— | —N(morpholinyl) |

TABLE 71

(I-B-2-2)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |

TABLE 71-continued (I-B-2-2)

| No | —E³— | —E⁴ |
|---|---|---|
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | azetidin-1-yl |
| 53 | —(CH₂)₃— | pyrrolidin-1-yl |
| 54 | —(CH₂)₃— | piperidin-1-yl |
| 55 | —(CH₂)₃— | azepan-1-yl |
| 56 | —(CH₂)₃— | morpholin-4-yl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |

TABLE 71-continued (I-B-2-2)

| No | —E³— | —E⁴ |
|---|---|---|
| 80 | —(CH₂)₄— | azetidin-1-yl |
| 81 | —(CH₂)₄— | pyrrolidin-1-yl |
| 82 | —(CH₂)₄— | piperidin-1-yl |
| 83 | —(CH₂)₄— | azepan-1-yl |
| 84 | —(CH₂)₄— | morpholin-4-yl |

TABLE 72

(I-B-2-3)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |

TABLE 72-continued (I-B-2-3)

| No | —E³— | —E⁴ |
|---|---|---|
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |

TABLE 72-continued (I-B-2-3)

[Structure: tetrahydropyrido-pyridazinone with -CH₂-C(O)-N(Et)-E³-E⁴ substituent]

| No | —E³— | —E⁴ |
|---|---|---|
| 52 | —(CH₂)₃— | azetidin-1-yl |
| 53 | —(CH₂)₃— | pyrrolidin-1-yl |
| 54 | —(CH₂)₃— | piperidin-1-yl |
| 55 | —(CH₂)₃— | azepan-1-yl |
| 56 | —(CH₂)₃— | morpholin-4-yl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | azetidin-1-yl |
| 81 | —(CH₂)₄— | pyrrolidin-1-yl |

TABLE 72-continued (I-B-2-3)

[Structure: same as above]

| No | —E³— | —E⁴ |
|---|---|---|
| 82 | —(CH₂)₄— | piperidin-1-yl |
| 83 | —(CH₂)₄— | azepan-1-yl |
| 84 | —(CH₂)₄— | morpholin-4-yl |

TABLE 73

(I-B-2-4)

[Structure: tetrahydropyrido-pyridazinone with -CH₂-C(O)-N(i-Pr)-E³-E⁴ substituent]

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |

TABLE 73-continued (I-B-2-4)

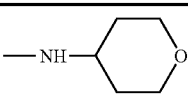

| No | —E³— | —E⁴ |
|---|---|---|
| 23 | —(CH₂)₂— | —NH-(tetrahydropyran-4-yl) |
| 24 | —(CH₂)₂— | azetidin-1-yl |
| 25 | —(CH₂)₂— | pyrrolidin-1-yl |
| 26 | —(CH₂)₂— | piperidin-1-yl |
| 27 | —(CH₂)₂— | azepan-1-yl |
| 28 | —(CH₂)₂— | morpholin-4-yl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | azetidin-1-yl |
| 53 | —(CH₂)₃— | pyrrolidin-1-yl |
| 54 | —(CH₂)₃— | piperidin-1-yl |
| 55 | —(CH₂)₃— | azepan-1-yl |
| 56 | —(CH₂)₃— | morpholin-4-yl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | azetidin-1-yl |
| 81 | —(CH₂)₄— | pyrrolidin-1-yl |
| 82 | —(CH₂)₄— | piperidin-1-yl |

TABLE 73-continued (I-B-2-4)

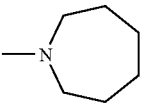

| No | —E³— | —E⁴ |
|---|---|---|
| 83 | —(CH₂)₄— | 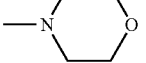 |
| 84 | —(CH₂)₄— | 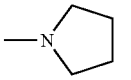 |

TABLE 74

(I-B-2-5)

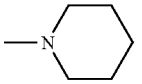

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— |  |
| 24 | —(CH₂)₂— | 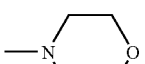 |

TABLE 74-continued (I-B-2-5)

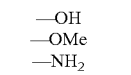

| No | —E³— | —E⁴ |
|---|---|---|
| 25 | —(CH₂)₂— | 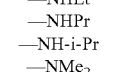 |
| 26 | —(CH₂)₂— | 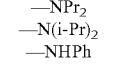 |
| 27 | —(CH₂)₂— | 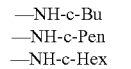 |
| 28 | —(CH₂)₂— | 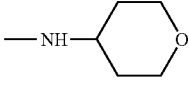 |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | 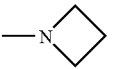 |
| 52 | —(CH₂)₃— | 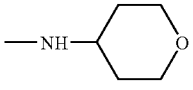 |
| 53 | —(CH₂)₃— | 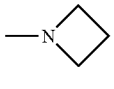 |
| 54 | —(CH₂)₃— | 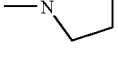 |

TABLE 74-continued (I-B-2-5)

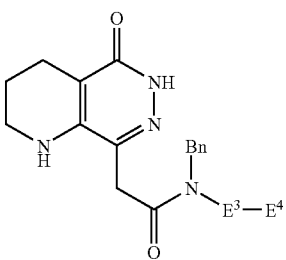

| No | —E³— | —E⁴ |
|---|---|---|
| 55 | —(CH₂)₃— | N-methylazepane |
| 56 | —(CH₂)₃— | N-methylmorpholine |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | N-methylazetidine |
| 81 | —(CH₂)₄— | N-methylpyrrolidine |
| 82 | —(CH₂)₄— | N-methylpiperidine |
| 83 | —(CH₂)₄— | N-methylazepane |
| 84 | —(CH₂)₄— | N-methylmorpholine |

TABLE 75

(I-B-2-6)

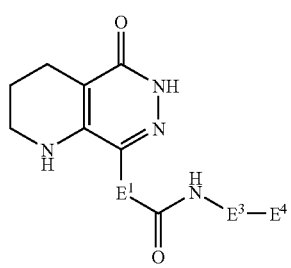

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | tetrahydropyran-4-yl |
| 12 | —CH₂— | 1-Bn-piperidin-4-yl |
| 13 | —(CH₂)₂— | 1-Bn-piperidin-4-yl |
| 14 | —CH₂— | —(CH₂)₂—C₆H₄—OH |
| 15 | —CH₂— | —(CH₂)₂—C₆H₄—OMe |
| 16 | —CH₂— | —(CH₂)₂—C₆H₄—NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | tetrahydropyran-4-yl |
| 28 | —(CH₂)₂— | 1-Bn-piperidin-4-yl |

TABLE 75-continued (I-B-2-6)

| No | —E¹— | —E³—E⁴ |
|----|------|--------|
| 29 | —(CH₂)₂— | —(CH₂)₂-(4-piperidinyl)-N-Bn |
| 30 | —(CH₂)₂— | —(CH₂)₂-C₆H₄-OH |
| 31 | —(CH₂)₂— | —(CH₂)₂-C₆H₄-OMe |
| 32 | —(CH₂)₂— | —(CH₂)₂-C₆H₄-NH₂ |

TABLE 76

(I-B-2-7)

| No | —E¹— | —E³—E⁴ |
|----|------|--------|
| 1  | —CH₂— | Me |
| 2  | —CH₂— | Et |
| 3  | —CH₂— | Pr |
| 4  | —CH₂— | i-Pr |
| 5  | —CH₂— | Ph |
| 6  | —CH₂— | Bn |
| 7  | —CH₂— | c-Pr |
| 8  | —CH₂— | c-Bu |
| 9  | —CH₂— | c-Pen |
| 10 | —CH₂— | c-Hex |
| 11 | —CH₂— | 4-tetrahydropyranyl |
| 12 | —CH₂— | 1-Bn-4-piperidinyl |

TABLE 76-continued (I-B-2-7)

| No | —E¹— | —E³—E⁴ |
|----|------|--------|
| 13 | —CH₂— | —(CH₂)₂-(1-Bn-4-piperidinyl) |
| 14 | —CH₂— | —(CH₂)₂-C₆H₄-OH |
| 15 | —CH₂— | —(CH₂)₂-C₆H₄-OMe |
| 16 | —CH₂— | —(CH₂)₂-C₆H₄-NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | 4-tetrahydropyranyl |
| 28 | —(CH₂)₂— | 1-Bn-4-piperidinyl |
| 29 | —(CH₂)₂— | —(CH₂)₂-(1-Bn-4-piperidinyl) |
| 30 | —(CH₂)₂— | —(CH₂)₂-C₆H₄-OH |
| 31 | —(CH₂)₂— | —(CH₂)₂-C₆H₄-OMe |
| 32 | —(CH₂)₂— | —(CH₂)₂-C₆H₄-NH₂ |

TABLE 77

(I-B-2-8)

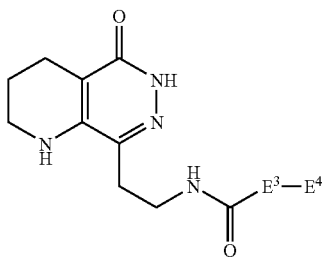

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | —N-(azetidin-1-yl) |
| 25 | —(CH₂)₂— | —N-(pyrrolidin-1-yl) |
| 26 | —(CH₂)₂— | —N-(piperidin-1-yl) |
| 27 | —(CH₂)₂— | —N-(azepan-1-yl) |
| 28 | —(CH₂)₂— | —N-(morpholin-4-yl) |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |

TABLE 77-continued (I-B-2-8)

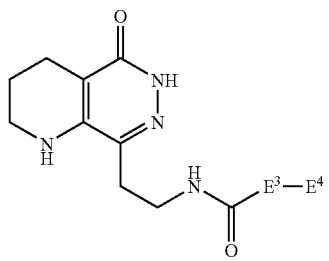

| No | —E³— | —E⁴ |
|---|---|---|
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N-(azetidin-1-yl) |
| 53 | —(CH₂)₃— | —N-(pyrrolidin-1-yl) |
| 54 | —(CH₂)₃— | —N-(piperidin-1-yl) |
| 55 | —(CH₂)₃— | —N-(azepan-1-yl) |
| 56 | —(CH₂)₃— | —N-(morpholin-4-yl) |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |

TABLE 77-continued (I-B-2-8)

| No | —E³— | —E⁴ |
|---|---|---|
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | N-azetidinyl |
| 81 | —(CH₂)₄— | N-pyrrolidinyl |
| 82 | —(CH₂)₄— | N-piperidinyl |
| 83 | —(CH₂)₄— | N-azepanyl |
| 84 | —(CH₂)₄— | N-morpholinyl |

TABLE 78

(I-B-2-9)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | tetrahydropyran-4-yl |
| 12 | —CH₂— | 1-Bn-piperidin-4-yl |
| 13 | —CH₂— | —(CH₂)₂-(1-Bn-piperidin-4-yl) |
| 14 | —CH₂— | —(CH₂)₂—C₆H₄—OH |
| 15 | —CH₂— | —(CH₂)₂—C₆H₄—OMe |
| 16 | —CH₂— | —(CH₂)₂—C₆H₄—NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | tetrahydropyran-4-yl |
| 28 | —(CH₂)₂— | 1-Bn-piperidin-4-yl |
| 29 | —(CH₂)₂— | —(CH₂)₂-(1-Bn-piperidin-4-yl) |
| 30 | —(CH₂)₂— | —(CH₂)₂—C₆H₄—OH |
| 31 | —(CH₂)₂— | —(CH₂)₂—C₆H₄—OMe |

TABLE 78-continued (I-B-2-9)

| No | —E¹— | —E³—E⁴ |
|---|---|---|
| 32 | —(CH₂)₂— | —(CH₂)₂—C₆H₄—NH₂ |

TABLE 79

(I-B-2-10)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBu |
| 14 | —(CH₂)₂— | —NH-c-Pr |
| 15 | —(CH₂)₂— | —NH-c-Bu |
| 16 | —(CH₂)₂— | —NH-c-Pen |
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | —N(azetidinyl) |
| 25 | —(CH₂)₂— | —N(pyrrolidinyl) |
| 26 | —(CH₂)₂— | —N(piperidinyl) |
| 27 | —(CH₂)₂— | —N(azepanyl) |
| 28 | —(CH₂)₂— | —N(morpholinyl) |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N(azetidinyl) |
| 53 | —(CH₂)₃— | —N(pyrrolidinyl) |
| 54 | —(CH₂)₃— | —N(piperidinyl) |
| 55 | —(CH₂)₃— | —N(azepanyl) |

TABLE 79-continued (I-B-2-10)

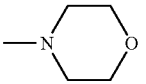

| No | —E³— | —E⁴ |
|---|---|---|
| 56 | —(CH$_2$)$_3$— | 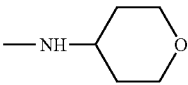 (morpholine) |
| 57 | —(CH$_2$)$_4$— | —OH |
| 58 | —(CH$_2$)$_4$— | —OMe |
| 59 | —(CH$_2$)$_4$— | —NH$_2$ |
| 60 | —(CH$_2$)$_4$— | —NHMe |
| 61 | —(CH$_2$)$_4$— | —NHEt |
| 62 | —(CH$_2$)$_4$— | —NHPr |
| 63 | —(CH$_2$)$_4$— | —NH-i-Pr |
| 64 | —(CH$_2$)$_4$— | —NMe$_2$ |
| 65 | —(CH$_2$)$_4$— | —NEt$_2$ |
| 66 | —(CH$_2$)$_4$— | —NPr$_2$ |
| 67 | —(CH$_2$)$_4$— | —N(i-Pr)$_2$ |
| 68 | —(CH$_2$)$_4$— | —NHPh |
| 69 | —(CH$_2$)$_4$— | —NHBu |
| 70 | —(CH$_2$)$_4$— | —NH-c-Pr |
| 71 | —(CH$_2$)$_4$— | —NH-c-Bu |
| 72 | —(CH$_2$)$_4$— | —NH-c-Pen |
| 73 | —(CH$_2$)$_4$— | —NH-c-Hex |
| 74 | —(CH$_2$)$_4$— | —NH—(CH$_2$)$_2$—OH |
| 75 | —(CH$_2$)$_4$— | —NHCH(Me)(OH) |
| 76 | —(CH$_2$)$_4$— | —N(Me)(c-Pen) |
| 77 | —(CH$_2$)$_4$— | —N(Me)(c-Hex) |
| 78 | —(CH$_2$)$_4$— | —N(Me)(Ph) |
| 79 | —(CH$_2$)$_4$— | 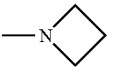 (—NH-tetrahydropyranyl) |
| 80 | —(CH$_2$)$_4$— | 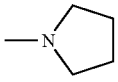 (azetidinyl) |
| 81 | —(CH$_2$)$_4$— | 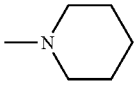 (pyrrolidinyl) |
| 82 | —(CH$_2$)$_4$— | 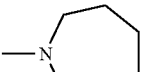 (piperidinyl) |
| 83 | —(CH$_2$)$_4$— | 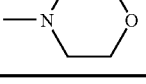 (azepanyl) |
| 84 | —(CH$_2$)$_4$— | 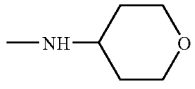 (morpholinyl) |

TABLE 80

(I-B-2-11)

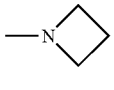

| No | —E³— | —E⁴ |
|---|---|---|
| 1 | —(CH$_2$)$_2$— | —OH |
| 2 | —(CH$_2$)$_2$— | —OMe |
| 3 | —(CH$_2$)$_2$— | —NH$_2$ |
| 4 | —(CH$_2$)$_2$— | —NHMe |
| 5 | —(CH$_2$)$_2$— | —NHEt |
| 6 | —(CH$_2$)$_2$— | —NHPr |
| 7 | —(CH$_2$)$_2$— | —NH-i-Pr |
| 8 | —(CH$_2$)$_2$— | —NMe$_2$ |
| 9 | —(CH$_2$)$_2$— | —NEt$_2$ |
| 10 | —(CH$_2$)$_2$— | —NPr$_2$ |
| 11 | —(CH$_2$)$_2$— | —N(i-Pr)$_2$ |
| 12 | —(CH$_2$)$_2$— | —NHPh |
| 13 | —(CH$_2$)$_2$— | —NHBu |
| 14 | —(CH$_2$)$_2$— | —NH-c-Pr |
| 15 | —(CH$_2$)$_2$— | —NH-c-Bu |
| 16 | —(CH$_2$)$_2$— | —NH-c-Pen |
| 17 | —(CH$_2$)$_2$— | —NH-c-Hex |
| 18 | —(CH$_2$)$_2$— | —NH—(CH$_2$)$_2$—OH |
| 19 | —(CH$_2$)$_2$— | —NHCH(Me)(OH) |
| 20 | —(CH$_2$)$_2$— | —N(Me)(c-Pen) |
| 21 | —(CH$_2$)$_2$— | —N(Me)(c-Hex) |
| 22 | —(CH$_2$)$_2$— | —N(Me)(Ph) |
| 23 | —(CH$_2$)$_2$— | 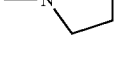 (—NH-tetrahydropyranyl) |
| 24 | —(CH$_2$)$_2$— | 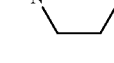 (azetidinyl) |
| 25 | —(CH$_2$)$_2$— | (pyrrolidinyl) |
| 26 | —(CH$_2$)$_2$— | 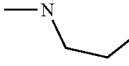 (piperidinyl) |
| 27 | —(CH$_2$)$_2$— | (azepanyl) |
| 28 | —(CH$_2$)$_2$— | 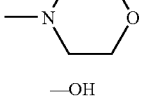 (morpholinyl) |
| 29 | —(CH$_2$)$_3$— | —OH |
| 30 | —(CH$_2$)$_3$— | —OMe |
| 31 | —(CH$_2$)$_3$— | —NH$_2$ |
| 32 | —(CH$_2$)$_3$— | —NHMe |
| 33 | —(CH$_2$)$_3$— | —NHEt |
| 34 | —(CH$_2$)$_3$— | —NHPr |
| 35 | —(CH$_2$)$_3$— | —NH-i-Pr |
| 36 | —(CH$_2$)$_3$— | —NMe$_2$ |
| 37 | —(CH$_2$)$_3$— | —NEt$_2$ |
| 38 | —(CH$_2$)$_3$— | —NPr$_2$ |
| 39 | —(CH$_2$)$_3$— | —N(i-Pr)$_2$ |
| 40 | —(CH$_2$)$_3$— | —NHPh |

TABLE 80-continued (I-B-2-11)

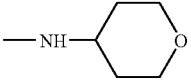

| No | —E³— | —E⁴ |
|---|---|---|
| 41 | —(CH₂)₃— | —NHBu |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— |  |
| 52 | —(CH₂)₃— |  |
| 53 | —(CH₂)₃— | 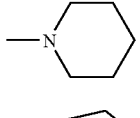 |
| 54 | —(CH₂)₃— | 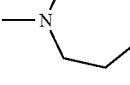 |
| 55 | —(CH₂)₃— | 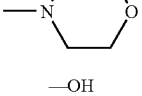 |
| 56 | —(CH₂)₃— | 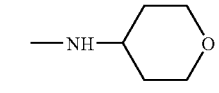 |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBu |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |

TABLE 80-continued (I-B-2-11)

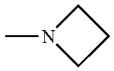

| No | —E³— | —E⁴ |
|---|---|---|
| 79 | —(CH₂)₄— | 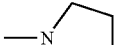 |
| 80 | —(CH₂)₄— | 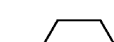 |
| 81 | —(CH₂)₄— | 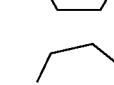 |
| 82 | —(CH₂)₄— | 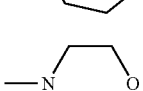 |
| 83 | —(CH₂)₄— |  |
| 84 | —(CH₂)₄— |  |

TABLE 81

(I-B-2-12)

| No | —E³— | —E⁴ |
|---|---|---|
| 1 | —(CH₂)₂— | —OH |
| 2 | —(CH₂)₂— | —OMe |
| 3 | —(CH₂)₂— | —NH₂ |
| 4 | —(CH₂)₂— | —NHMe |
| 5 | —(CH₂)₂— | —NHEt |
| 6 | —(CH₂)₂— | —NHPr |
| 7 | —(CH₂)₂— | —NH-i-Pr |
| 8 | —(CH₂)₂— | —NMe₂ |
| 9 | —(CH₂)₂— | —NEt₂ |
| 10 | —(CH₂)₂— | —NPr₂ |
| 11 | —(CH₂)₂— | —N(i-Pr)₂ |
| 12 | —(CH₂)₂— | —NHPh |
| 13 | —(CH₂)₂— | —NHBn |
| 14 | —(CH₂)₂— | —NH-c-Pr |
| 15 | —(CH₂)₂— | —NH-c-Bu |
| 16 | —(CH₂)₂— | —NH-c-Pen |

TABLE 81-continued (I-B-2-12)

| No | —E³— | —E⁴ |
|---|---|---|
| 17 | —(CH₂)₂— | —NH-c-Hex |
| 18 | —(CH₂)₂— | —NH—(CH₂)₂—OH |
| 19 | —(CH₂)₂— | —NHCH(Me)(OH) |
| 20 | —(CH₂)₂— | —N(Me)(c-Pen) |
| 21 | —(CH₂)₂— | —N(Me)(c-Hex) |
| 22 | —(CH₂)₂— | —N(Me)(Ph) |
| 23 | —(CH₂)₂— | —NH-(tetrahydropyran-4-yl) |
| 24 | —(CH₂)₂— | —N-azetidinyl |
| 25 | —(CH₂)₂— | —N-pyrrolidinyl |
| 26 | —(CH₂)₂— | —N-piperidinyl |
| 27 | —(CH₂)₂— | —N-azepanyl |
| 28 | —(CH₂)₂— | —N-morpholinyl |
| 29 | —(CH₂)₃— | —OH |
| 30 | —(CH₂)₃— | —OMe |
| 31 | —(CH₂)₃— | —NH₂ |
| 32 | —(CH₂)₃— | —NHMe |
| 33 | —(CH₂)₃— | —NHEt |
| 34 | —(CH₂)₃— | —NHPr |
| 35 | —(CH₂)₃— | —NH-i-Pr |
| 36 | —(CH₂)₃— | —NMe₂ |
| 37 | —(CH₂)₃— | —NEt₂ |
| 38 | —(CH₂)₃— | —NPr₂ |
| 39 | —(CH₂)₃— | —N(i-Pr)₂ |
| 40 | —(CH₂)₃— | —NHPh |
| 41 | —(CH₂)₃— | —NHBn |
| 42 | —(CH₂)₃— | —NH-c-Pr |
| 43 | —(CH₂)₃— | —NH-c-Bu |
| 44 | —(CH₂)₃— | —NH-c-Pen |
| 45 | —(CH₂)₃— | —NH-c-Hex |
| 46 | —(CH₂)₃— | —NH—(CH₂)₂—OH |
| 47 | —(CH₂)₃— | —NHCH(Me)(OH) |
| 48 | —(CH₂)₃— | —N(Me)(c-Pen) |
| 49 | —(CH₂)₃— | —N(Me)(c-Hex) |
| 50 | —(CH₂)₃— | —N(Me)(Ph) |
| 51 | —(CH₂)₃— | —NH-(tetrahydropyran-4-yl) |
| 52 | —(CH₂)₃— | —N-azetidinyl |
| 53 | —(CH₂)₃— | —N-pyrrolidinyl |
| 54 | —(CH₂)₃— | —N-piperidinyl |
| 55 | —(CH₂)₃— | —N-azepanyl |
| 56 | —(CH₂)₃— | —N-morpholinyl |
| 57 | —(CH₂)₄— | —OH |
| 58 | —(CH₂)₄— | —OMe |
| 59 | —(CH₂)₄— | —NH₂ |
| 60 | —(CH₂)₄— | —NHMe |
| 61 | —(CH₂)₄— | —NHEt |
| 62 | —(CH₂)₄— | —NHPr |
| 63 | —(CH₂)₄— | —NH-i-Pr |
| 64 | —(CH₂)₄— | —NMe₂ |
| 65 | —(CH₂)₄— | —NEt₂ |
| 66 | —(CH₂)₄— | —NPr₂ |
| 67 | —(CH₂)₄— | —N(i-Pr)₂ |
| 68 | —(CH₂)₄— | —NHPh |
| 69 | —(CH₂)₄— | —NHBn |
| 70 | —(CH₂)₄— | —NH-c-Pr |
| 71 | —(CH₂)₄— | —NH-c-Bu |
| 72 | —(CH₂)₄— | —NH-c-Pen |
| 73 | —(CH₂)₄— | —NH-c-Hex |
| 74 | —(CH₂)₄— | —NH—(CH₂)₂—OH |
| 75 | —(CH₂)₄— | —NHCH(Me)(OH) |
| 76 | —(CH₂)₄— | —N(Me)(c-Pen) |
| 77 | —(CH₂)₄— | —N(Me)(c-Hex) |
| 78 | —(CH₂)₄— | —N(Me)(Ph) |
| 79 | —(CH₂)₄— | —NH-(tetrahydropyran-4-yl) |
| 80 | —(CH₂)₄— | —N-azetidinyl |
| 81 | —(CH₂)₄— | —N-pyrrolidinyl |

TABLE 81-continued
(I-B-2-12)
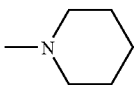
| No | —E³— | —E⁴ |
|---|---|---|
| 82 | —(CH₂)₄— | 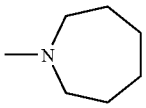 |
| 83 | —(CH₂)₄— | 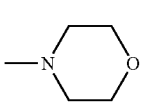 |
| 84 | —(CH₂)₄— | 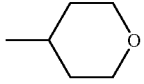 |
TABLE 82
(I-B-2-13)
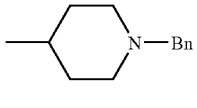
| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | 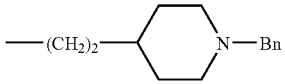 |
| 12 | —CH₂— | 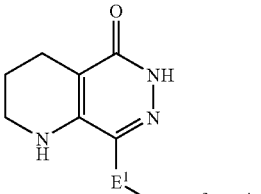 |
| 13 | —CH₂— | 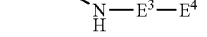 |
TABLE 82-continued
(I-B-2-13)
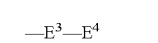
| No | —E¹— | —E³—E⁴ |
|---|---|---|
| 14 | —CH₂— |  |
| 15 | —CH₂— |  |
| 16 | —CH₂— |  |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— |  |
| 28 | —(CH₂)₂— | 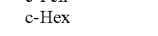 |
| 29 | —(CH₂)₂— | 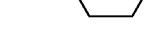 |
| 30 | —(CH₂)₂— | 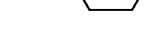 |
| 31 | —(CH₂)₂— |  |
| 32 | —(CH₂)₂— |  |
| 33 | —(CH₂)₃— | Me |
| 34 | —(CH₂)₃— | Et |
| 35 | —(CH₂)₃— | Pr |
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |

TABLE 82-continued (I-B-2-13)

| No | —E¹— | —E³—E⁴ |
|---|---|---|
| 42 | —(CH₂)₃— | c-Hex |
| 43 | —(CH₂)₃— | (4-tetrahydropyranyl) |
| 44 | —(CH₂)₃— | (4-(N-Bn)piperidinyl) |
| 45 | —(CH₂)₃— | —(CH₂)₂-(4-(N-Bn)piperidinyl) |
| 46 | —(CH₂)₃— | —(CH₂)₂-(4-OH-phenyl) |
| 47 | —(CH₂)₃— | —(CH₂)₂-(4-OMe-phenyl) |
| 48 | —(CH₂)₃— | —(CH₂)₂-(4-NH₂-phenyl) |

TABLE 83

(I-B-2-14)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |

TABLE 83-continued (I-B-2-14)

| No | —E¹— | —E³—E⁴ |
|---|---|---|
| 11 | —CH₂— | (4-tetrahydropyranyl) |
| 12 | —CH₂— | (4-(N-Bn)piperidinyl) |
| 13 | —CH₂— | —(CH₂)₂-(4-(N-Bn)piperidinyl) |
| 14 | —CH₂— | —(CH₂)₂-(4-OH-phenyl) |
| 15 | —CH₂— | —(CH₂)₂-(4-OMe-phenyl) |
| 16 | —CH₂— | —(CH₂)₂-(4-NH₂-phenyl) |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | (4-tetrahydropyranyl) |
| 28 | —(CH₂)₂— | (4-(N-Bn)piperidinyl) |
| 29 | —(CH₂)₂— | —(CH₂)₂-(4-(N-Bn)piperidinyl) |
| 30 | —(CH₂)₂— | —(CH₂)₂-(4-OH-phenyl) |

TABLE 83-continued (I-B-2-14)

| No | —E¹— | —E³—E⁴ |
|---|---|---|
| 31 | —(CH₂)₂— | —(CH₂)₂—C₆H₄—OMe |
| 32 | —(CH₂)₂— | —(CH₂)₂—C₆H₄—NH₂ |
| 33 | —(CH₂)₃— | Me |
| 34 | —(CH₂)₃— | Et |
| 35 | —(CH₂)₃— | Pr |
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |
| 42 | —(CH₂)₃— | c-Hex |
| 43 | —(CH₂)₃— | tetrahydropyran-4-ylmethyl |
| 44 | —(CH₂)₃— | (1-benzylpiperidin-4-yl)methyl |
| 45 | —(CH₂)₃— | —(CH₂)₂—(1-benzylpiperidin-4-yl) |
| 46 | —(CH₂)₃— | —(CH₂)₂—C₆H₄—OH |
| 47 | —(CH₂)₃— | —(CH₂)₂—C₆H₄—OMe |
| 48 | —(CH₂)₃— | —(CH₂)₂—C₆H₄—NH₂ |

TABLE 84

(I-B-2-15)

| No | —E¹— | —E³—E⁴ |
|---|---|---|
| 1 | —CH₂— | Me |
| 2 | —CH₂— | Et |
| 3 | —CH₂— | Pr |
| 4 | —CH₂— | i-Pr |
| 5 | —CH₂— | Ph |
| 6 | —CH₂— | Bn |
| 7 | —CH₂— | c-Pr |
| 8 | —CH₂— | c-Bu |
| 9 | —CH₂— | c-Pen |
| 10 | —CH₂— | c-Hex |
| 11 | —CH₂— | tetrahydropyran-4-ylmethyl |
| 12 | —CH₂— | (1-benzylpiperidin-4-yl)methyl |
| 13 | —CH₂— | —(CH₂)₂—(1-benzylpiperidin-4-yl) |
| 14 | —CH₂— | —(CH₂)₂—C₆H₄—OH |
| 15 | —CH₂— | —(CH₂)₂—C₆H₄—OMe |
| 16 | —CH₂— | —(CH₂)₂—C₆H₄—NH₂ |
| 17 | —(CH₂)₂— | Me |
| 18 | —(CH₂)₂— | Et |
| 19 | —(CH₂)₂— | Pr |
| 20 | —(CH₂)₂— | i-Pr |
| 21 | —(CH₂)₂— | Ph |
| 22 | —(CH₂)₂— | Bn |
| 23 | —(CH₂)₂— | c-Pr |
| 24 | —(CH₂)₂— | c-Bu |
| 25 | —(CH₂)₂— | c-Pen |
| 26 | —(CH₂)₂— | c-Hex |
| 27 | —(CH₂)₂— | tetrahydropyran-4-ylmethyl |
| 28 | —(CH₂)₂— | (1-benzylpiperidin-4-yl)methyl |

TABLE 84-continued (I-B-2-15)

[Structure: tetrahydropyrido-pyridazinone with E¹–N(Bn)–E³–E⁴ substituent]

| No | —E¹— | —E³—E⁴ |
|---|---|---|
| 29 | —(CH₂)₂— | —(CH₂)₂—(piperidine-N-Bn) |
| 30 | —(CH₂)₂— | —(CH₂)₂—C₆H₄—OH |
| 31 | —(CH₂)₂— | —(CH₂)₂—C₆H₄—OMe |
| 32 | —(CH₂)₂— | —(CH₂)₂—C₆H₄—NH₂ |
| 33 | —(CH₂)₃— | Me |
| 34 | —(CH₂)₃— | Et |
| 35 | —(CH₂)₃— | Pr |
| 36 | —(CH₂)₃— | i-Pr |
| 37 | —(CH₂)₃— | Ph |
| 38 | —(CH₂)₃— | Bn |
| 39 | —(CH₂)₃— | c-Pr |
| 40 | —(CH₂)₃— | c-Bu |
| 41 | —(CH₂)₃— | c-Pen |
| 42 | —(CH₂)₃— | c-Hex |
| 43 | —(CH₂)₃— | tetrahydropyran-4-yl |
| 44 | —(CH₂)₃— | 4-(N-Bn)piperidinyl |
| 45 | —(CH₂)₃— | —(CH₂)₂—(piperidine-N-Bn) |
| 46 | —(CH₂)₃— | —(CH₂)₂—C₆H₄—OH |
| 47 | —(CH₂)₃— | —(CH₂)₂—C₆H₄—OMe |
| 48 | —(CH₂)₃— | —(CH₂)₂—C₆H₄—NH₂ |

TABLE 85

(I-C-1-1)

[Structure: hexahydrophthalazinone with —CH₂—Cyc1—G² substituent]

| No | -Cyc1-G² |
|---|---|
| 1 | azetidin-1-yl |
| 2 | pyrrolidin-1-yl |
| 3 | piperidin-1-yl |
| 4 | azepan-1-yl |
| 5 | morpholin-4-yl |
| 6 | piperazin-1-yl (NH) |
| 7 | 4-Me-piperazin-1-yl |
| 8 | 4-Et-piperazin-1-yl |
| 9 | 4-Pr-piperazin-1-yl |
| 10 | 4-i-Pr-piperazin-1-yl |
| 11 | 4-Ph-piperazin-1-yl |
| 12 | 4-Bn-piperazin-1-yl |
| 13 | 4-(CH₂)₂—OH-piperazin-1-yl |

TABLE 85-continued
(I-C-1-1)
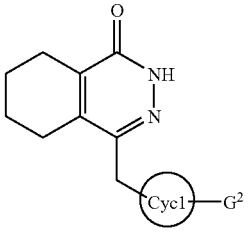
| No | -Cyc1-G² |
|----|----------|
| 14 | 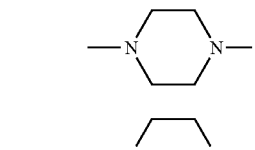 |
| 15 | 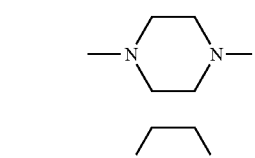 |
| 16 | 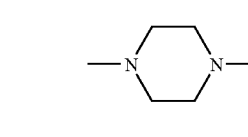 |
| 17 | 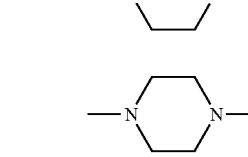 |
| 18 | 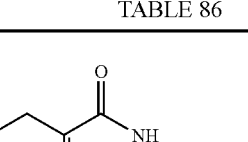 |
| 19 | 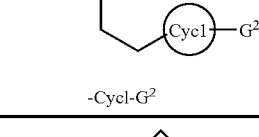 |
| 20 | 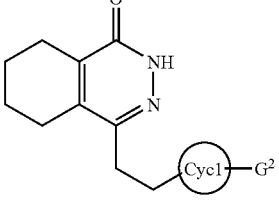 |
TABLE 86
(I-C-1-2)
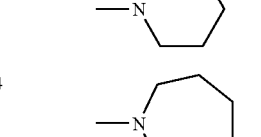
| No | -Cyc1-G² |
|----|----------|
| 1 | 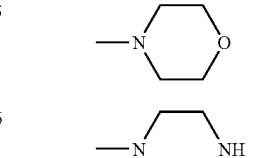 |
| 2 | 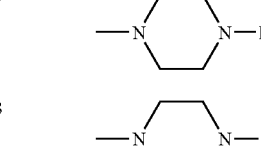 |
| 3 | 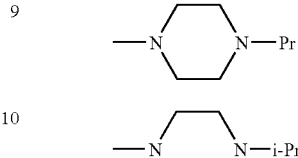 |
| 4 | 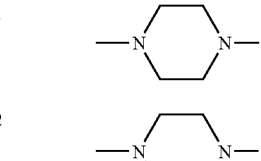 |
| 5 | 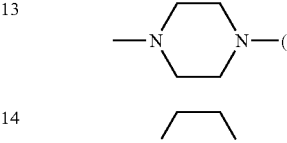 |
| 6 | 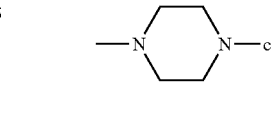 |
| 7 | 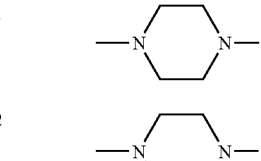 |
| 8 | 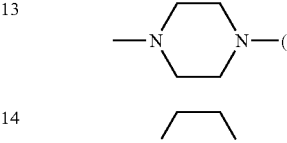 |
| 9 | 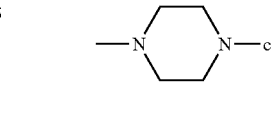 |
| 10 | 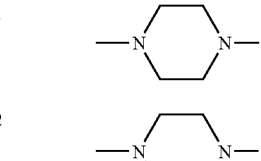 |
| 11 | 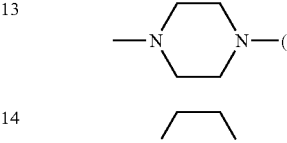 |
| 12 | 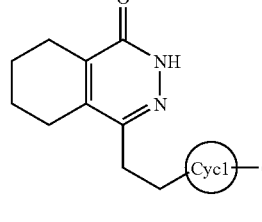 |
| 13 | —N◯N—(CH₂)₂—OH |
| 14 | —N◯N—c-Pr |
| 15 | —N◯N—c-Bu |

TABLE 86-continued (I-C-1-2)

| No | -Cyc1-G² |
|----|----------|
| 16 | –N(piperazine)N–c-Pen |
| 17 | –N(piperazine)N–c-Hex |
| 18 | –N(piperazine)N–(tetrahydropyran-4-yl) |
| 19 | –N(piperazine)N–cycloheptyl |
| 20 | –N(piperazine)N–(pyridin-4-yl) |

TABLE 87

(I-C-1-3)

| No | -Cyc1-G² |
|----|----------|
| 1 | –N(azetidine) |
| 2 | –N(pyrrolidine) |
| 3 | –N(piperidine) |
| 4 | –N(azepane) |

TABLE 87-continued (I-C-1-3)

| No | -Cyc1-G² |
|----|----------|
| 5 | –N(morpholine) |
| 6 | –N(piperazine)NH |
| 7 | –N(piperazine)N–Me |
| 8 | –N(piperazine)N–Et |
| 9 | –N(piperazine)N–Pr |
| 10 | –N(piperazine)N–i-Pr |
| 11 | –N(piperazine)N–Ph |
| 12 | –N(piperazine)N–Bn |
| 13 | –N(piperazine)N–(CH₂)₂–OH |
| 14 | –N(piperazine)N–c-Pr |
| 15 | –N(piperazine)N–c-Bu |
| 16 | –N(piperazine)N–c-Pen |
| 17 | –N(piperazine)N–c-Hex |

TABLE 87-continued
(I-C-1-3)
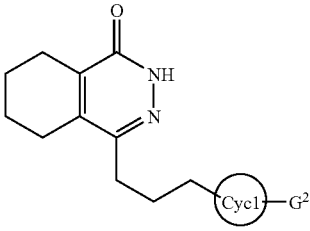
| No | -Cyc1-G² |
|----|----------|
| 18 | 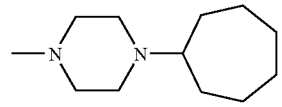 |
| 19 | 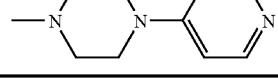 |
| 20 | 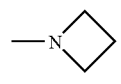 |
TABLE 88
(I-C-2-1)
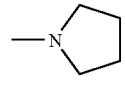
| No | -Cyc1-G² |
|----|----------|
| 1 | 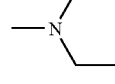 |
| 2 | 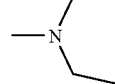 |
| 3 | 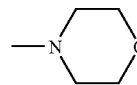 |
| 4 | 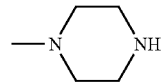 |
| 5 | 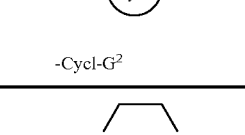 |
| 6 | 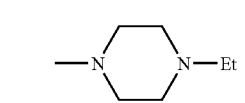 |
TABLE 88-continued
(I-C-2-1)
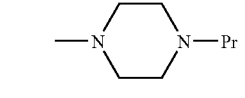
| No | -Cyc1-G² |
|----|----------|
| 7 | —N⟨⟩N—Me |
| 8 | —N⟨⟩N—Et |
| 9 | —N⟨⟩N—Pr |
| 10 | —N⟨⟩N—i-Pr |
| 11 | —N⟨⟩N—Ph |
| 12 | —N⟨⟩N—Bn |
| 13 | —N⟨⟩N—(CH₂)₂—OH |
| 14 | —N⟨⟩N—c-Pr |
| 15 | —N⟨⟩N—c-Bu |
| 16 | —N⟨⟩N—c-Pen |
| 17 | —N⟨⟩N—c-Hex |
| 18 | 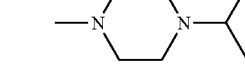 |

TABLE 88-continued (I-C-2-1)

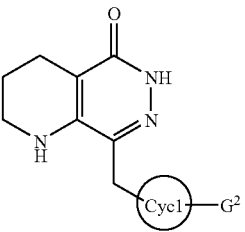

| No | -Cyc1-G² |
|---|---|
| 19 | —N⟨piperazine⟩N—cycloheptyl |
| 20 | —N⟨piperazine⟩N—(4-pyridyl) |

TABLE 89

(I-C-2-2)

| No | -Cyc1-G² |
|---|---|
| 1 | —N⟨azetidine⟩ |
| 2 | —N⟨pyrrolidine⟩ |
| 3 | —N⟨piperidine⟩ |
| 4 | —N⟨azepane⟩ |
| 5 | —N⟨morpholine⟩O |
| 6 | —N⟨piperazine⟩NH |
| 7 | —N⟨piperazine⟩N—Me |

TABLE 89-continued (I-C-2-2)

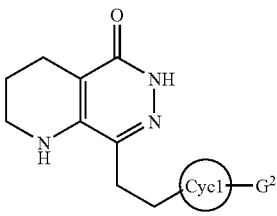

| No | -Cyc1-G² |
|---|---|
| 8 | —N⟨piperazine⟩N—Et |
| 9 | —N⟨piperazine⟩N—Pr |
| 10 | —N⟨piperazine⟩N—i-Pr |
| 11 | —N⟨piperazine⟩N—Ph |
| 12 | —N⟨piperazine⟩N—Bn |
| 13 | —N⟨piperazine⟩N—(CH₂)₂—OH |
| 14 | —N⟨piperazine⟩N—c-Pr |
| 15 | —N⟨piperazine⟩N—c-Bu |
| 16 | —N⟨piperazine⟩N—c-Pen |
| 17 | —N⟨piperazine⟩N—c-Hex |
| 18 | —N⟨piperazine⟩N—(tetrahydropyranyl) |
| 19 | —N⟨piperazine⟩N—cycloheptyl |
| 20 | —N⟨piperazine⟩N—(4-pyridyl) |

TABLE 90

(I-C-2-3)

| No | -Cyc1-G² |
|---|---|
| 1 | azetidinyl |
| 2 | pyrrolidinyl |
| 3 | piperidinyl |
| 4 | azepanyl |
| 5 | morpholinyl |
| 6 | piperazinyl-NH |
| 7 | piperazinyl-Me |
| 8 | piperazinyl-Et |
| 9 | piperazinyl-Pr |
| 10 | piperazinyl-i-Pr |
| 11 | piperazinyl-Ph |
| 12 | piperazinyl-Bn |
| 13 | piperazinyl-(CH₂)₂-OH |

TABLE 90-continued (I-C-2-3)

| No | -Cyc1-G² |
|---|---|
| 14 | piperazinyl-c-Pr |
| 15 | piperazinyl-c-Bu |
| 16 | piperazinyl-c-Pen |
| 17 | piperazinyl-c-Hex |
| 18 | piperazinyl-tetrahydropyranyl |
| 19 | piperazinyl-cycloheptyl |
| 20 | piperazinyl-pyridyl |

Processes for the Preparation of the Compound of the Present Invention:

The compound represented by formula (I) can be prepared by the following method described in Example.

(1) The compounds of the present invention represented by formula (I), a compound in which A represents $A^1$, and $D^1$ represents —$NR^6C(O)$— or —$CH_2$—$NR^6C(O)$—, i.e., a compound represented by formula (IA-1)

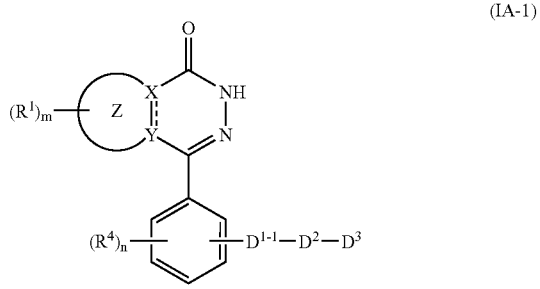

(IA-1)

(wherein $D^{1-1}$ is —$NR^6C(O)$— or —$CH_2$—$NR^6C(O)$—, and other symbols have the same meanings as described above.) can be prepared by the following method.

The compound represented by formula (IA-1) can be prepared by the amidation of the compounds of formula (II)

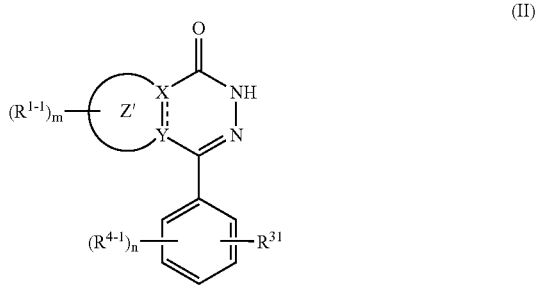

(wherein $R^{31}$ is $NHR^6$ or —$CH_2$—$NHR^6$, and $R^{1-1}$, $R^{4-1}$ and

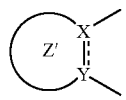

are $R^1$, $R^4$ and

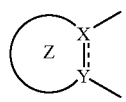

respectively. With proviso that, hydroxyl or amino in the group represented by $R^{1-1}$, hydroxyl or amino represented by $R^{4-1}$, and amino in the group represented by

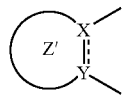

may be protected, if necessary. Other symbols have the same meanings as defined above.) and a compound represented by formula (III)

$$HOOC\text{-}D^{2-1}\text{-}D^{3-1} \qquad (III)$$

(wherein $D^{2-1}$ and $D^{3-1}$ are $D^2$ and $D^3$ respectively. With proviso that, amino in the group represented by $D^{2-1}$, and carboxy, hydroxy, amino, amidino or guanidino in $D^{3-1}$ may be protected, if necessary.), if necessary, followed by removal of the protective group from the resulting product.

The method of amidation is known. For example, it includes the method (1) an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g., oxalyl chloride or thionyl chloride etc.) in an organic solvent (e.g., chloroform, methylene chloride, diethyl ether or tetrahydrofuran) or without a solvent at −20° C. to reflux temperature. And then the obtained acyl halide derivative may be reacted with amine in an inert organic solvent (e.g., chloroform, methylene chloride, diethyl ether or tetrahydrofuran) in the presence of tertiary amine (e.g., pyridine, triethylamine, dimethylaniline or dimethylaminopyridine etc.) at 0 to 40° C. As an alternative, the obtained acyl halide derivative may be reacted in an organic solvent (dioxane, tetrahydrofuran) using an alkaline aqueous solution (e.g., sodium bicarbonate, sodium hydroxide) at 0 to 40° C.

(2) The method via a mixed acid anhydride may be carried out, for example, by reacting carboxylic acid with an acyl halide (e.g., pivaloyl chloride, tosyl chloride or mesyl chloride) or an acid derivative (ethyl chloroformate or isobutyl chloroformate) in an organic solvent (e.g., chloroform, methylene chloride, diethyl ether, tetrahydrofuran) or without a solvent, in the presence of tertiary amine (e.g., pyridine, triethylamine, dimethylaniline or dimethylaminopyridine) at 0 to 40° C. And then the obtained mixed acid anhydride derivative may be reacted with amine in an organic solvent (e.g., chloroform, methylene chloride, diethyl ether or tetrahydrofuran), at 0 to 40° C.

(3) The method using a condensing agent may be carried out, for example, by reacting carboxylic acid with amine in an organic solvent (e.g., chloroform, methylene chloride, dimethylformamide, diethyl ether or tetrahydrofuran) or without a solvent, in the presence or absence of tertiary amine (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzotiazole (HOBt), at 0 to 40° C.

The reaction described in (1), (2) and (3) may be carried out under an inert gas (e.g., argon, nitrogen) to avoid water in order to obtain a preferable result.

The removal of the protective group may be carried out by following method.

The reaction for removing the protective group for carboxyl, hydroxyl, amino, amidino or guanidino is well known, including, for example, the following:

(1) alkali hydrolysis,
(2) deprotection under acidic condition,
(3) deprotection through hydrogenolysis,
(4) silyl deprotection.

These methods are explained as follows.

(1) The deprotection through alkali hydrolysis may be effected, for example, in an organic solvent (e.g., methanol, tetrahydrofuran, dioxane) by the use of an alkali metal hydroxide (e.g., sodium hydroxide, potassium hydroxide, lithium hydroxide), an alkaline earth metal hydroxide (e.g., barium hydroxide, calcium hydroxide) or a carbonate (e.g., sodium carbonate, potassium carbonate), or an aqueous solution thereof or their mixture, at 0 to 40° C.

(2) The deprotection under acidic condition may be effected, for example, in an organic solvent (e.g., dichloromethane, chloroform, dioxane, ethyl acetate, anisole) with an organic solvent (e.g., acetic acid, trifluoroacetic acid, methanesulfonic acid, p-toluenesulfonic acid) or an inorganic acid (e.g., hydrochloric acid, sulfuric acid) or their mixture (hydrogen bromide/acetic acid), at 0 to 100° C.

(3) The deprotection through hydrogenolysis may be effected, for example, in a solvent (e.g., ether-type (e.g., tetrahydrofuran, dioxane, dimethoxyethane, diethyl ether), alcohol-type (e.g., methanol, ethanol), benzene-type (e.g., benzene, toluene), ketone-type (e.g., acetone, methyl ethyl ketone), nitrile-type (e.g., acetonitrile), amide-type (e.g., dimethylformamide), water, ethyl acetate, acetic acid, or mixed solvent of two or more of these), in the presence of a catalyst (e.g., palladium-carbon, palladium-black, palladium hydroxide, platinum oxide, Raney nickel), in a normal-pressure or increased-pressure hydrogen atmosphere or in the presence of ammonium formate, at 0 to 200° C.

(4) The silyl deprotection may be effected, for example, in a water-miscible organic solvent (e.g., tetrahydrofuran, acetonitrile) by the use of tetrabutylammonium fluoride, at 0 to 40° C.

The carboxyl-protective group includes, for example, methyl, ethyl, t-butyl and benzyl.

The hydroxyl-protective group includes, for example, methoxymethyl, 2-tetrahydropyranyl, t-butyldimethylsilyl, t-butyldiphenylsilyl, acetyl and benzyl.

The amino, amidino and guanidino-protective group includes, for example, benzyloxycarbonyl, t-butoxycarbonyl, trifluoroacetyl, 9-fluorenylmethoxycarbonyl and trimethylsilyl.

The carboxyl, hydroxyl, amino, amidino or guanidino-protective group may be any others than those mentioned above, capable of being readily and selectively removed, and are not specifically defined. For example, those described in T. W Greene, *Protective Groups in Organic Synthesis*, 3rd edition, Wiley, New York, 1999 may be used.

The intended compounds of the invention may be readily produced through selective use of the deprotecting reaction, which could be readily understood by anyone skilled in the art.

(2) Among the compounds of the present invention represented by formula (I), a compound in which A represents $A^1$, and $D^1$ represents —$NR^6SO_2$—, i.e., a compound represented by formula (IA-2)

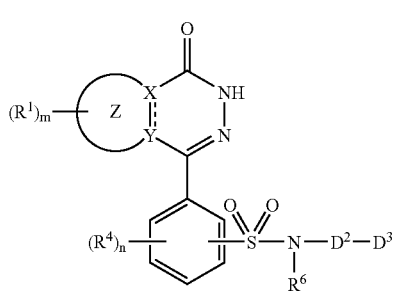

(wherein all symbols have the same meanings as described above.) can be prepared by the following method.

The compound represented by formula (IA-2) can be prepared by the sulfonamidation of the compounds of formula (II-1)

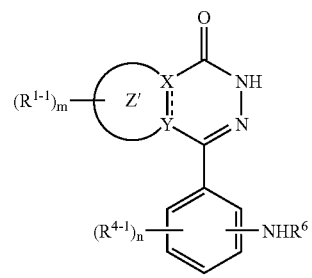

(wherein all symbols have the same meanings as defined above.) and a compound represented by formula (IV)

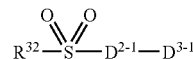

(wherein $R^{32}$ is halogen atom and other symbols have the same meanings as defined above.), if necessary, followed by removal of the protective group from the resulting product.

This sulfonamidation is known. For example, it is carried out at 0 to 40° C. in an inert organic solvent (e.g., chloroform, methylene chloride, diethyl ether or tetrahydrofuran) in the presence of tertiary amine (e.g., pyridine, triethylamine, dimethylaniline or dimethylaminopyridine).

The removal of the protective group may be carried out by the above method.

(3) Among the compounds of the present invention represented by formula (I), a compound in which A represents $A^1$, and $D^1$ represents —OC(O)—, i.e., a compound represented by formula (IA-3)

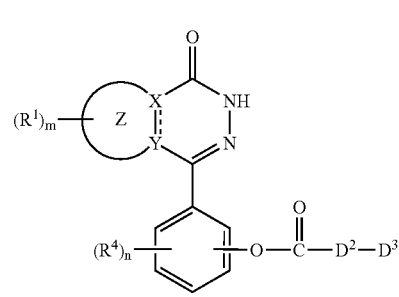

(wherein all symbols have the same meanings as described above.) can be prepared by the following method.

The compound represented by formula (IA-3) can be prepared by esterifying the compounds of formula (V)

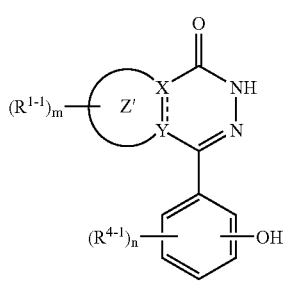

(wherein all symbols have the same meanings as defined above.) with the above compound represented by formula (III)

(wherein all symbols have the same meanings as defined above.), if necessary, followed by removal of the protective group from the resulting product.

The method of esterification is known. For example, it includes the method
(1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g., oxalyl chloride or thionyl chloride etc.) in an inert organic solvent (e.g., chloroform, methylene chloride, diethyl ether or tetrahydrofuran) or without a solvent at −20° C. to reflux temperature. And then the obtained acyl halide derivative may be reacted with alcohol in an inert organic solvent (e.g., chloroform, methylene chloride, diethyl ether or tetrahydrofuran) in the presence of tertiary amine (e.g., pyridine, triethylamine, dimethylaniline or dimethylaminopyridine etc.) at 0 to 40° C.

(2) The method via a mixed acid anhydride may be carried out, for example, by reacting carboxylic acid with an acyl halide (e.g., pivaloyl chloride, tosyl chloride or mesyl chloride) or an acid derivative (ethyl chloroformate or isobutyl chloroformate) in an inert organic solvent (e.g., chloroform, methylene chloride, diethyl ether, tetrahydrofuran) or without a solvent, in the presence of tertiary amine (e.g., pyridine, triethylamine, dimethylaniline or dimethylaminopyridine) at 0 to 40° C. And then the obtained mixed acid anhydride derivative may be reacted with alcohol in an inert organic solvent (e.g., chloroform, methylene chloride, diethyl ether or tetrahydrofuran), at 0 to 40° C.

(3) The method using a condensing agent may be carried out, for example, by reacting carboxylic acid with alcohol in an organic solvent (e.g., chloroform, methylene chloride, dimethylformamide, diethyl ether or tetrahydrofuran) or without a solvent, in the presence or absence of tertiary amine (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1′-carbodiimidazole (CDI) or 2-chloro-1-methylpyridinium iodide), in the presence or absence of 1-hydroxybenzotiazole (HOBt), at 0 to 40° C.

The reaction described in (1), (2) and (3) may be carried out under an inert gas (e.g., argon, nitrogen) to avoid water in order to obtain a preferable result.

The removal of the protective group may be carried out by the above method.

(4) Among the compounds of the present invention represented by formula (I), a compound in which A represents $A^1$, and $D^1$ represents —$CH_2$—O—, i.e., a compound represented by formula (IA-4)

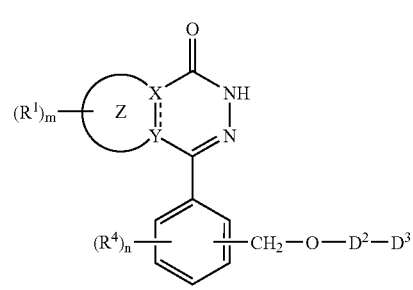

(wherein all symbols have the same meanings as described above.) can be prepared by the following method.

The compound represented by formula (IA-4) can be prepared by the etherification of the compounds of formula (VI-1)

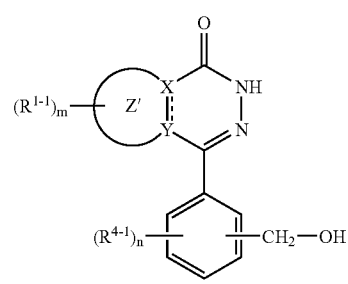

(wherein all symbols have the same meanings as described above.) and the compound of formula (VII-1)

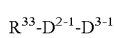

(wherein $R^{33}$ is a leaving group (halogen atom, mesyloxy or tosyloxy, etc.) and other symbols have the same meanings as described above.), if necessary, followed by removal of the protective group, by the etherification of the compounds of formula (VI-2)

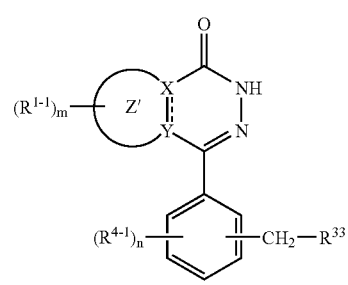

(wherein all symbols have the same meanings as described above.) and the compound of formula (VII-2)

$$HO\text{-}D^{2\text{-}1}\text{-}D^{3\text{-}1} \qquad (VII\text{-}2)$$

(wherein all symbols have the same meanings as described above.), if necessary, followed by removal of the protective group, or by the etherification of the above compounds of formula (VI-1)

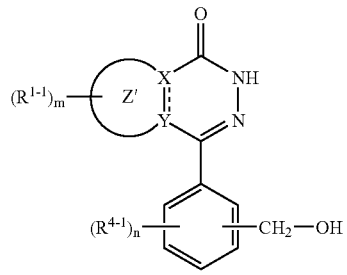

(VI-1)

(wherein all symbols have the same meanings as described above.) and the compound of formula (VII-2)

$$HO\text{-}D^{2\text{-}1}\text{-}D^{3\text{-}1} \qquad (VII\text{-}2)$$

(wherein all symbols have the same meanings as described above.), if necessary, followed by removal of the protective group.

This etherification of the compound of formula (VI-1) and the compound of formula (VII-1), and the compound of formula (VI-2) and the compound of formula (VII-2) is known. For example, it is carried out at 0 to 100° C. in an inert organic solvent (e.g., dimethylformamide, dimethylsulfoxide, chloroform, methylene chloride, diethyl ether or tetrahydrofuran) in the presence of an alkali metal hydroxide (e.g., sodium hydroxide, potassium hydroxide, lithium hydroxide), an alkaline earth metal hydroxide (e.g., barium hydroxide, calcium hydroxide) or a carbonate (e.g., sodium carbonate, potassium carbonate), or an aqueous solution thereof or their mixture.

This etherification of the compound of formula (VI-1) and the compound of formula (VII-2) is known. For example, it is carried out at 0 to 60° C. by reacting with a corresponding alcohol compound in an organic solvent (dichloromethane, diethyl ether, tetrahydrofuran, acetonitrile, benzene, toluene, etc.) in the presence of an azo compound (diethyl azodicarboxylate, diisopropyl azodicarboxylate, 1,1'-(azodicarbonyl)dipiperidine, 1,1'-azobis(N,N-dimethylformamide), etc.) and a phosphine compound (triphenylphosphine, tributylphosphine, trimethylphosphine, etc.).

The deprotection reaction of the protective group may be carried out by the methods described above.

(5) Among the compounds of the present invention represented by formula (I), a compound in which A represents $A^1$, and $D^1$ represents —$NR^6$—, i.e., a compound represented by formula (IA-5)

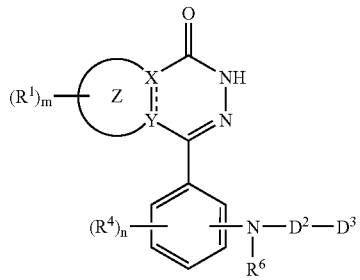

(IA-5)

(wherein all symbols have the same meanings as described above.) can be prepared by the following method.

The compound represented by formula (IA-5) can be prepared by reacting the above compound of formula (II-1)

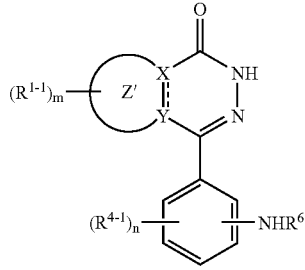

(II-1)

(wherein all symbols have the same meanings as described above.) with the compound of formula (VIII-1)

$$R^{32}\text{-}D^{2\text{-}1}\text{-}D^{3\text{-}1} \qquad (VIII\text{-}1)$$

(wherein all symbols have the same meanings as described above.), if necessary, followed by removal of the protecting group, or by reacting the compound of formula (IX)

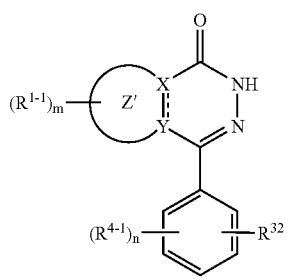

(IX)

(wherein all symbols have the same meanings as described above.) with the compound of formula (VIII-2)

$$R^6HN\text{-}D^{2\text{-}1}\text{-}D^{3\text{-}1} \qquad (VIII\text{-}2)$$

(wherein all symbols have the same meanings as described above.), if necessary, followed by removal of the protecting group.

This reaction of the compound of formula (II) and the compound of formula (VIII-1), and the compound of formula (IX) and the compound of formula (VIII-2) is known. For example, it is carried out at 0 to 100° C. in an inert organic solvent (e.g., dimethylformamide, dimethylsulfoxide, chloroform, methylene chloride, diethyl ether, tetrahydrofuran or acetonitrile) in the presence or absence of a base (e.g., triethylamine, pyridine).

The deprotection reaction of the protective group may be carried out by the methods described above.

Among the compounds of the present invention represented by formula (IA-5), a compound in which $D^2$ is C1-8 alkylene, C2-8 alkenylene, —(C1-4 alkylene)-O—(C1-4 alkylene)-, —(C1-4 alkylene)-S—(C1-4 alkylene)-, —(C1-4 alkylene)-$NR^8$—(C1-4 alkylene)-, —(C1-8 alkylene)-(Cyc2)- or —(C1-4 alkylene)-(Cyc2)—(C1-4 alkylene)-, i.e., a compound represented by formula (IA-5-1)

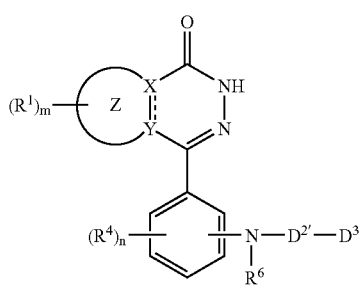

(IA-5-1)

(wherein $D^{2'}$ is C1-8 alkylene, C2-8 alkenylene, —(C1-4 alkylene)-O—(C1-4 alkylene)-, —(C1-4 alkylene)-S—(C1-4 alkylene)-, —(C1-4 alkylene)-$NR^8$—(C1-4 alkylene)-, —(C1-8 alkylene)-(Cyc2)- or —(C1-4 alkylene)-(Cyc2)-(C1-4 alkylene)- and other symbols have the same meanings as described above.) can be prepared by reductive amination of the above compound of formula (II-1)

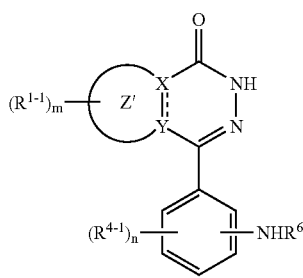

(II-1)

(wherein all symbols have the same meanings as described above.) and the compound of formula (VIII-3)

OHC-$D^{2''}$-$D^{3-1}$     (VIII-3)

(wherein $D^{2''}$ is C1-7 alkylene, C2-7 alkenylene, —(C1-3 alkylene)-O—(C1-4 alkylene)-, —(C1-3 alkylene)-S—(C1-4 alkylene)-, —(C1-3 alkylene)-$NR^8$—(C1-4 alkylene)-, —(C1-7 alkylene)-(Cyc2)- or —(C1-3 alkylene)-(Cyc2)—(C1-4 alkylene)- and other symbols have the same meanings as described above.), if necessary, followed by removal of the protecting group.

The reductive amination is well known. For example, it may be carried out in an organic solvent (e.g., methanol, ethanol) in the presence of reducing agent (e.g., sodium cyanoborohydride, sodium borohydride, sodium triacetoxyborohydride) and, if necessary, in the presence of an acid (e.g., acetic acid, hydrogen chloride) at −20 to 60° C.

The removal of the protective group may be carried out by the methods described above.

(6) Among the compounds of the present invention represent by formula (I), a compound in which A is $A^1$ and $D^1$ is —$CH_2$—$NR^6$—, i.e., a compound of formula (IA-6)

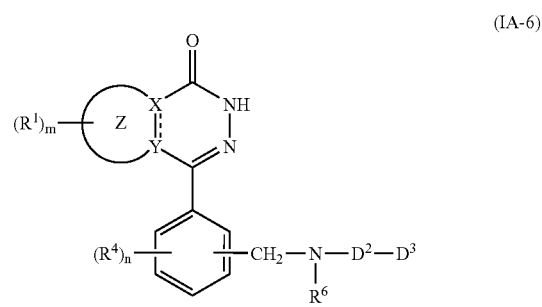

(IA-6)

(wherein all symbols have the same meanings as described above.) can be prepared by the following method.

The compound represented by formula (IA-6) can be prepared by reacting the compound of formula (X)

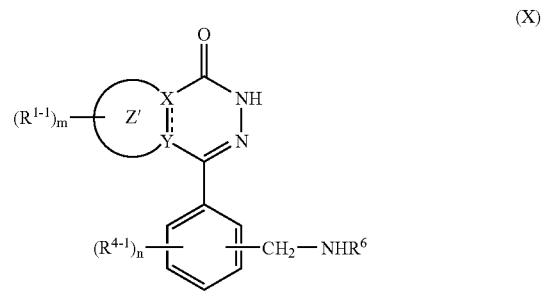

(X)

(wherein all symbols have the same meanings as described above.) with the above compound of formula (VIII-1)

$R^{32}$-$D^{2-1}$-$D^{3-1}$     (VIII-1)

(wherein all symbols have the same meanings as described above.), if necessary, followed by removal of the protecting group, or by reductive amination of the compound of formula (XI)

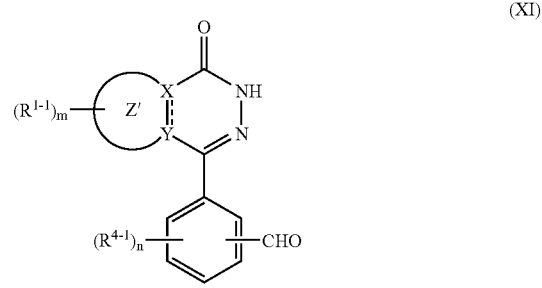

(XI)

(wherein all symbols have the same meanings as described above.) with the above compound of formula (VIII-2)

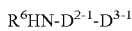  (VIII-2)

(wherein all symbols have the same meanings as described above.), if necessary, followed by removal of the protecting group.

The reaction of the compound of formula (X) and the compound of formula (VIII-1) may be carried out by the same method as the above reaction of the compound of formula (IX) and the compound of formula (VIII-2).

The reaction of the compound of formula (XI) and the compound of formula (VIII-2) may be carried out by the same method as the above reaction of the compound of formula (II-1) and the compound of formula (VIII-3).

The removal of the protective group may be carried out by the methods described above.

(7) Among the compounds represented by formula (I), a compound in which A is $A^1$ and $D^1$ is —$NR^6C(O)NR^7$—, i.e., a compound (IA-7)

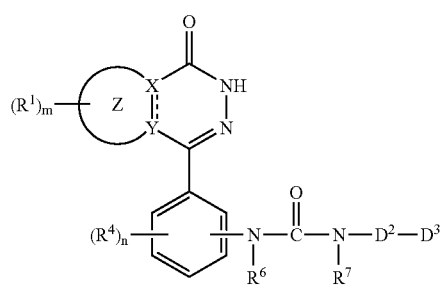

(wherein all symbols have the same meanings as described above.) can be prepared by the following method.

The compound represented by formula (IA-7) can be prepared by reacting the above compound of formula (II-1)

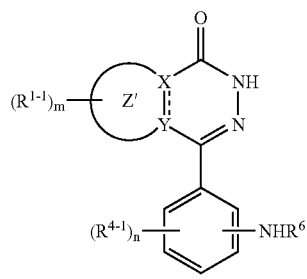

(wherein all symbols have the same meanings as described above.) with the compound of formula (XII)

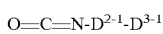  (XII)

(wherein all symbols have the same meanings as described above.), if necessary, followed by removal of the protecting group.

The reaction is known. It may be carried out in organic solvent (e.g., tetrahydrofuran, methylene chloride, diethyl ether) at 0 to 100° C.

The removal of the protective group may be carried out by the methods described above.

(8) Among the compounds represented by formula (I), a compound in which A is $A^1$ and $D^1$ is —$NR^6C(S)NR^7$—, i.e., a compound of formula (IA-8)

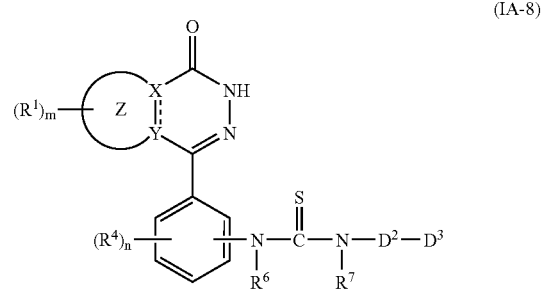

(wherein all symbols have the same meanings as described above.) can be prepared by the following method.

The compound represented by formula (IA-8) can be prepared by reacting the above compound of formula (II-1)

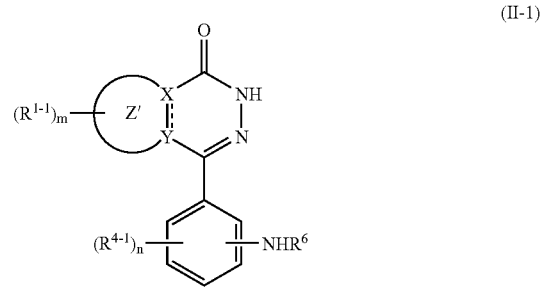

(wherein all symbols have the same meanings as described above.) with the compound of formula (XIII)

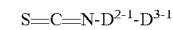  (XIII)

(wherein all symbols have the same meanings as described above.), if necessary, followed by removal of the protecting group.

The reaction is known. It may be carried out in an organic solvent (tetrahydrofuran, methylene chloride, diethyl ether) at 0 to 100° C.

The removal of the protective group may be carried out by the methods described above.

(9) Among the compound of the present invention represented by formula (I), a compound in which A is $A^1$ and $D^1$ is —$NR^6C(O)O$—, i.e., a compound of formula (IA-9)

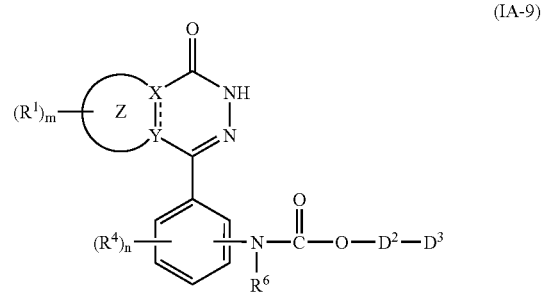

(wherein all symbols have the same meanings as described above.) can be prepared by the following method.

The compound represented by formula (IA-9) can be prepared by reacting the above compound of formula (II-1)

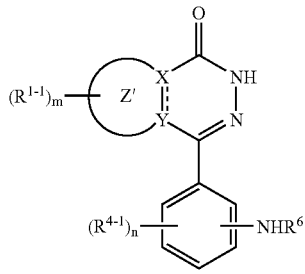

(wherein all symbols have the same meanings as described above.) with the compound of formula (XIV)

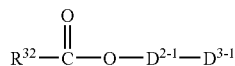

(wherein all symbols have the same meanings as described above.), if necessary, followed by removal of the protecting group.

The reaction is known. It may be carried out in an organic solvent (e.g., tetrahydrofuran, methylene chloride, diethyl ether) at −78 to 40° C.

The removal of the protective group may be carried out by the methods described above.

(10) Among the compounds of the present invention represented by formula (I), a compound in which A is $A^1$ and $D^1$ is —$NR^6C(S)$—, i.e., a compound of formula (IA-10)

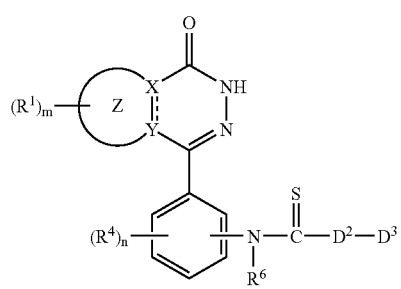

(wherein all symbols have the same meanings as described above.) can be prepared by the following method.

The compound represented by formula (IA-10) can be prepared by thiocarbonylation of the compound of formula (XV)

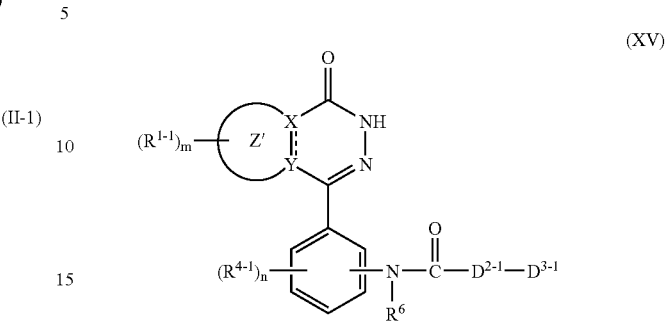

(wherein all symbols have the same meanings as described above.), if necessary, followed by removal of the protecting group.

The reaction is known. It may be carried out in an organic solvent (e.g., dioxane, benzene, toluene, xylene, tetrahydrofuran), using Lawesson reagent (2,4-bis(4-methoxyphenyl)-1,3-dithia-2,4-diphosphetane-2,4-disulfide) at 20 to 150° C.

The removal of the protective group may be carried out by the methods described above.

(11) Among the compound of the present invention represented by formula (I), a compound in which A is $A^1$ and $D^1$ is —$NR^6C(=NR^7)$—, i.e., a compound of formula (IA-11)

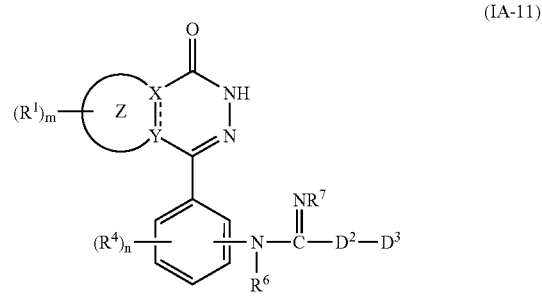

(wherein all symbols have the same meanings as described above.) can be prepared by the following method.

The compound of formula (IA-11) can be prepared by reacting the above compound of formula (II-1)

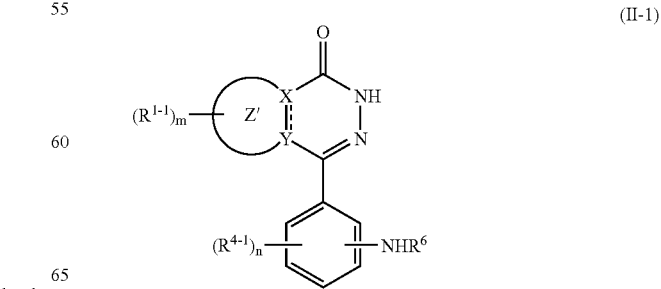

(wherein all symbols have the same meanings as described above.) with the compound of formula (XVI)

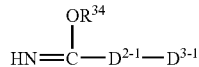
(XVI)

(wherein $R^{34}$ is C1-4 alkyl and other symbols have the same meanings as described above.), if necessary, followed by removal of the protecting group.

The reaction is known. For example, it may be carried out in an organic solvent (e.g., methanol, ethanol) at 0 to 50° C.

The removal of the protective group may be carried out by the methods described above.

(12) Among the compound of the present invention represented by formula (I), a compound in which A is $A^1$ and $D^3$ is —$NR^9R^{10}$ or hetero ring represented by

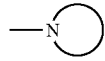

(among Cyc2, the hetero ring is a hetero ring having at least one nitrogen atom which binds to $D^2$), i.e., a compound of formula (IA-12)

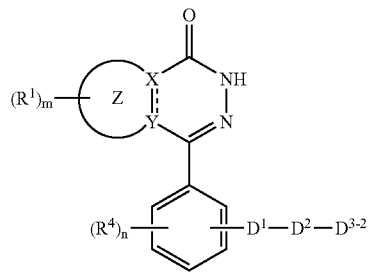
(IA-12)

(wherein $D^{3-2}$ is —$NR^9R^{10}$ or hetero ring represented by

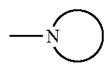

(among Cyc2, the hetero ring is a hetero ring having at least one nitrogen atom which binds to $D^2$ and other symbols have the same meanings as described above.) can be prepared by the following method.

The compound represented by formula (IA-12) cam be prepared by reacting a compound of formula (XVII)

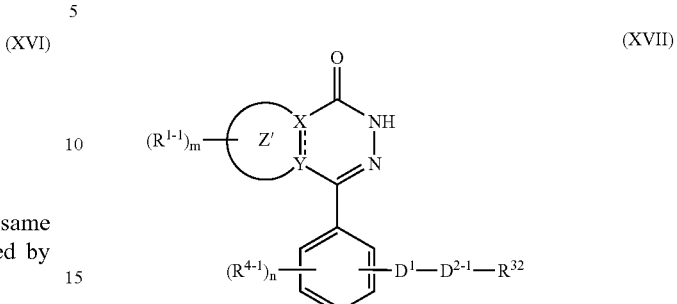
(XVII)

(wherein all symbols have the same meanings as described above.) with a compound of formula (XVIII)

$$H—NR^9R^{10} \quad (XVIII)$$

(wherein all symbols have the same meanings as described above.) or a compound of formula (XIX)

(XIX)

(wherein all symbols have the same meanings as described above.), if necessary, followed by removal of the protecting group.

The reaction of the compound of formula (XVII) and the compound of formula (XVIII) or (XIX) may be carried out by the same method as the above reaction of the compound of formula (IX) and the compound of formula (VIII-2).

The removal of the protective group may be carried out by the methods described above.

(13) Among the compounds of the present invention represented formula (I), a compound in which A is $A^2$, and $E^2$ is —$C(O)NR^{24}$—, i.e., a compound of formula (IB-1)

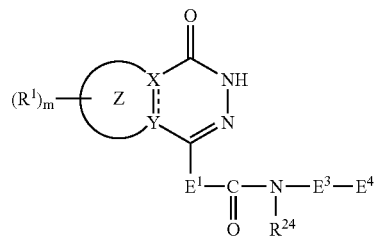
(IB-1)

(wherein all symbols have the same meanings as described above.) can be prepared by the following method.

The compound of formula (IB-1) can be prepared by amidation of a compound of formula (XX)

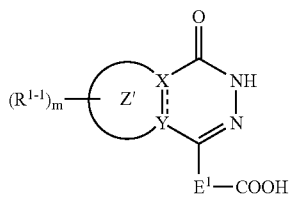
(XX)

(wherein all symbols have the same meanings as described above.) and the compound of formula (XXI)

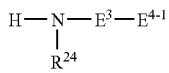
(XXI)

(wherein $E^{4-1}$ is $E^4$. With proviso that, hydroxyl, amino or carboxyl in the group represented by $E^{4-1}$ may be protected, if necessary. Other symbols have the same meanings as defined above.), if necessary, followed by removal of the protecting group.

The amidation and the removal of the protective group may be carried out by the methods described above.

(14) Among the compounds of the present invention represented by formula (I), a compound in which A is $A^2$ and $E^2$ is $—NR^{24}C(O)—$, i.e., a compound of formula (IB-2)

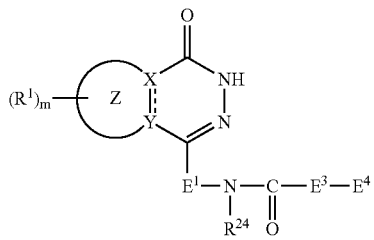
(IB-2)

(wherein all symbols have the same meanings as described above.) can be prepared by the following method.

The compound of formula (IB-2) can be prepared by amidation of a compound of formula (XXII)

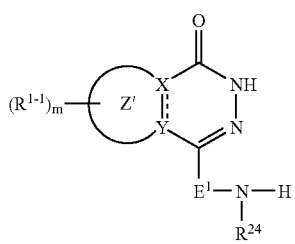
(XXII)

(wherein all symbols have the same meanings as described above.) and a compound of formula (XXIII)

(XXIII)

(wherein all symbols have the same meanings as described above.), if necessary, followed by removal of the protecting group.

The amidation and the removal of the protective group may be carried out by the methods described above.

(15) Among the compounds of the present invention represented by formula (I), a compound in which A is $A^2$ and $E^2$ is $—NR^{24}—$, i.e., a compound of formula (IB-3)

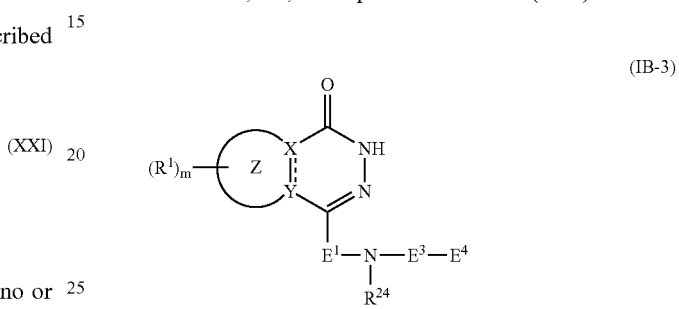
(IB-3)

(wherein all symbols have the same meanings as described above.) can be prepared by the following method.

The compound of formula (IB-3) can be prepared by reacting a compound of formula (XXIV)

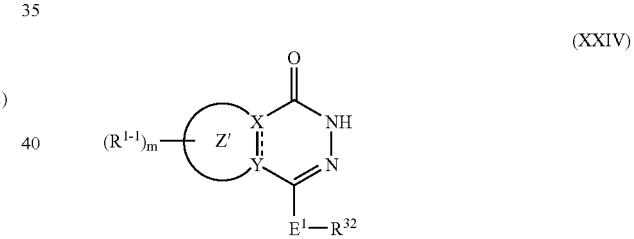
(XXIV)

(wherein all symbols have the same meanings as described above.) with the above compound of formula (XXI)

(XXI)

(wherein all symbols have the same meanings as described above.), if necessary, followed by removal of the protecting group.

The reaction of the compound of formula (XXIV) and the compound of formula (XXI) may be carried out by the same method as the above reaction of the compound of formula (IX) and the compound formula (VIII-2).

The removal of the protective group may be carried out by the methods described above.

(16) Among the compound of the present invention represented by formula (I), a compound in which A is $A^2$, and $E^2$ is —C(O)O—, i.e., a compound of formula (IB-4)

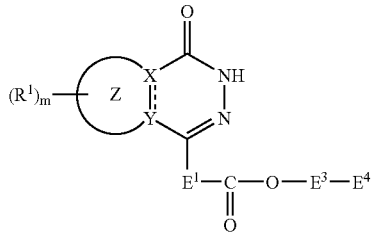
(IB-4)

(wherein all symbols have the same meanings as described above.) can be prepared by the following method.

The compound of formula (IB-4) can be prepared by esterifying the compound of formula (XX)

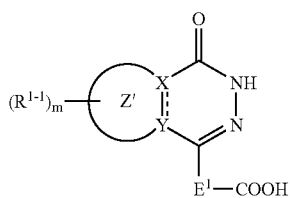
(XX)

(wherein all symbols have the same meanings as described above.) with a compound of formula (XXV)

 (XXV)

(wherein all symbols have the same meanings as described above.), if necessary, followed by removal of the protecting group.

The esterifying and the removal of the protective group may be carried out by the methods described above.

(17) Among the compounds of the present invention represented by formula (I), a compound in which A is $A^2$, and $E^2$ is —S—, i.e., a compound of formula (IB-5)

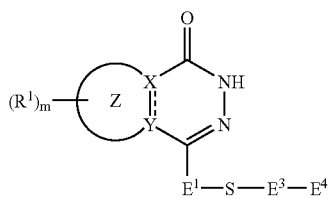
(IB-5)

(wherein all symbols have the same meanings as described above.) can be prepared by the following method.

The compound of formula (IB-5) can be prepared by reacting a compound of formula (XXVI)

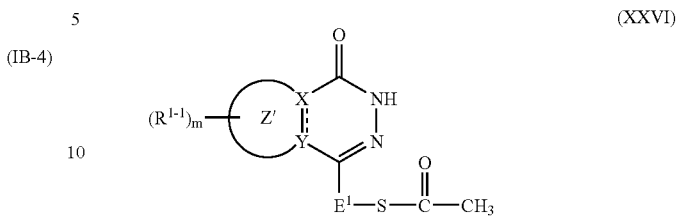
(XXVI)

(wherein all symbols have the same meanings as described above.) with a compound of formula (XXVII)

 (XXVII)

(wherein all symbols have the same meanings as described above.), if necessary, followed by removal of the protecting group.

The reaction is known. For example, it may be carried out in an inert organic solvent (e.g., dimethylformamide, dimethylsulfoxide, chloroform, methylene chloride, diethyl ether, tetrahydrofuran, acetonitrile) in the presence or absence of a base (e.g., triethylamine, pyridine) at 0 to 100° C.

The removal of the protective group may be carried out by the methods described above.

(18) Among the compounds of the present invention represented by formula (I), a compound in which A is $A^2$, and $E^4$ is —$NR^{25}R^{26}$ or hetero ring represented by

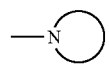

(The hetero ring is a hetero ring having at least one nitrogen atom (The nitrogen atom binds to $E^3$.) in Cyc5.), i.e., a compound of formula (IB-6)

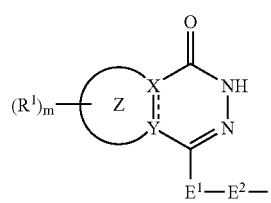
(IB-6)

(wherein $E^{4-2}$ is —$NR^{25}R^{26}$ or hetero ring represented by

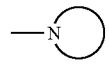

(The hetero ring is a hetero ring having at least one nitrogen atom (The nitrogen atom binds to $E^3$.) in Cyc5.) and other symbols have the same meanings as described above.) can be prepared by the following method.

The compound of formula (IB-6) can be prepared by reacting a compound of formula (XXVIII)

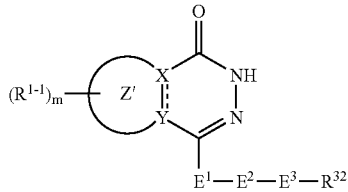
(XXVIII)

(wherein all symbols have the same meanings as described above.) with a compound of formula (XXIX)

H—NR$^{25}$R$^{26}$ (XXIX)

(wherein all symbols have the same meanings as described above.) or a compound of formula (XXX)

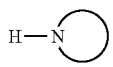
(XXX)

(wherein all symbols have the same meanings as described above.), if necessary, followed by removal of the protecting group.

The reaction of the compound of formula (XXVIII) and the compound of formula (XXIX) or (XXX) may be carried out by the same method as the above reaction of the compound of formula (IX) and the compound of formula (VIII-2).

The removal of the protective group may be carried out by the methods described above.

(19) Among the compounds of the present invention represented by formula (I), a compound in which A is A$^3$, i.e., a compound of formula (IC-1)

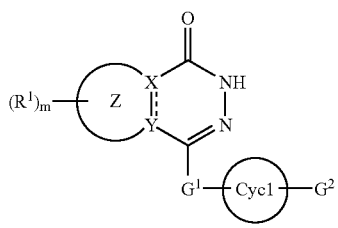
(IC-1)

(wherein all symbols have the same meanings as described above.) can be prepared by the following method.

The compound of formula (IC-1) can be prepared by reacting a compound of formula (XXXI)

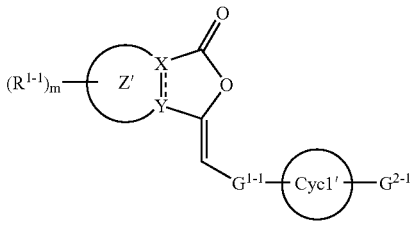
(XXXI)

(wherein G$^{1-1}$ is bond or C1-7 alkylene, Cyc1' and G$^{2-1}$ are Cyc1 and G$^2$ respectively. With proviso that amino in the group represented by Cyc1, and hydroxy and amino in the group represented by G$^{2-1}$ may be protected, if necessary. Other symbols have the same meanings as described above.) with hydrazine or a salt thereof (e.g., hydride, chloride), if necessary, followed by removal the protecting group.

The reaction is known. For example, it may be carried out in an organic solvent (e.g., methanol, ethanol, propanol, isopropanol, butanol, acetic acid, tetrahydrofuran) at 50° C. to reflux temperature.

The removal of the protective group may be carried out by the methods described above.

Moreover, among the compounds of the present invention represented by formula (IC-1), a compound in which Cyc1 is hetero ring represented by

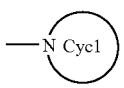

(The hetero ring is a hetero ring having at least one nitrogen atom (The nitrogen atom binds to G$^1$.) in Cyc1.), i.e., a compound of formula (IC-1-1)

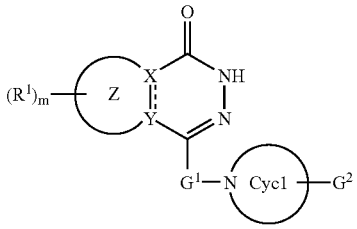
(IC-1-1)

(wherein

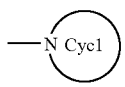

is a hetero ring having at least one nitrogen atom (The nitrogen atom binds to $G^1$.) in Cyc1 and other symbols have the same meanings as described above.) can be prepared by following method.

The compound of formula (IC-1-1) can be prepared by reacting a compound of formula (XXXII)

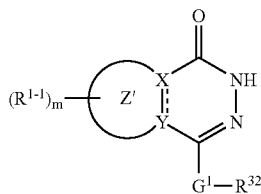
(XXXII)

(wherein all symbols have the same meanings as described above.) with a compound of formula (XXXIII)

(XXXIII)

(wherein all symbols have the same meanings as described above.), if necessary, followed by removal the protecting group.

The reaction of the compound of formula (XXXII) and the compound of formula (XXXII) may be carried out by the same method as the above reaction of the compound of formula (IX) and the compound of formula (VIII-2).

The removal of the protective group may be carried out by the methods described above.

(20) Among the compounds of the present invention represented by formula (I), a compound in which A is $A^4$ or $A^5$, i.e., a compound of (ID-1)

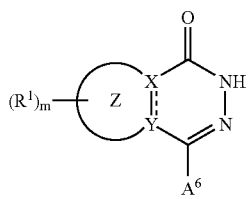
(ID-1)

(wherein $A^6$ is $A^4$ or $A^5$ and other symbols have the same meanings as described above.) can be prepared by the following a) to b).

a) The compound of formula (ID-1) can be prepared by reacting a compound of formula (XXXIV-1)

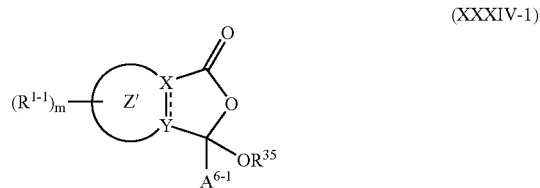
(XXXIV-1)

(wherein $R^{35}$ is C1-8 alkyl, and $A^{6-1}$ is $A^6$. With proviso that hydroxy or amino in the group represented by $A^{6-1}$ may be protected, if necessary. Other symbols have the same meanings as described above.) or a compound of formula (XXXIV-2)

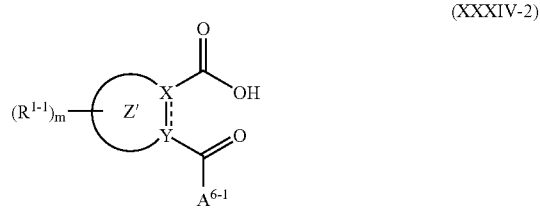
(XXXIV-2)

(wherein all symbols have the same meanings as described above.) with hydrazine or a salt thereof (e.g., hydride, chloride), if necessary, followed by removal the protecting group.

The reaction is known. For example, it may be carried out in an organic solvent (e.g., methanol, ethanol, propanol, isopropanol, butanol, acetic acid, tetrahydrofuran) at 50° C. to reflux temperature.

The removal of the protective group may be carried out by the methods described above.

b) The compound of formula (ID-1) can be prepared by reacting a compound of formula (XXXV)

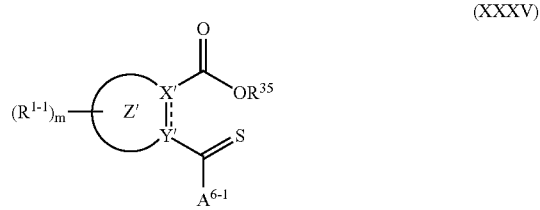
(XXXV)

(wherein all symbols have the same meanings as described above.) with hydrazine and a salt thereof (e.g., hydride, chloride), if necessary, followed by removal the protecting group.

The reaction is known. For example, it may be carried out in an organic solvent (e.g., methanol, ethanol, propanol, isopropanol, butanol, acetic acid, tetrahydrofuran) at 50° C. to reflux temperature.

The removal of the protective group may be carried out by the methods described above.

Moreover, among the compound of formula (ID-1), a compound in which X is N, is single bond, i.e., a compound of formula (ID-1-1)

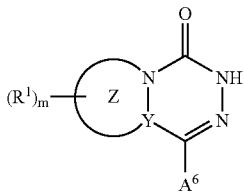

(ID-1-1)

(wherein all symbols have the same meanings as described above.) can be prepared by the following method.

The compound of formula (ID-1-1) can be prepared by reacting a compound of formula (XXXVI)

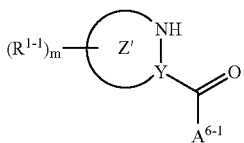

(XXXVI)

(wherein all symbols have the same meanings as described above.) with a compound of formula (XXXVII)

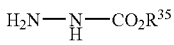

(XXXVII)

(wherein $R^{35}$ has the same meaning as described above.), if necessary, followed by removal of the protecting group.

The reaction may be carried out, for example, in an organic solvent (e.g., toluene, tetrahydrofuran, chloroform, methylene chloride) in the presence or absence of catalyst (e.g., p-toluenesulfonic acid, pyridine) at 50° C. to reflux temperature.

The removal of the protective group may be carried out by the methods described above.

The compounds represented by formulae (II), (II-1), (III), (IV), (V), (VI-1), (VI-2), (VII-1), (VII-2), (VIII-1), (VIII-2), (VIII-3), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX), (XXX), (XXXI), (XXXII), (XXXIII), (XXXIV-1), (XXXIV-2), (XXXV), (XXXVI) and (XXXVII) are known compounds or can be prepared by known methods or methods as described in Examples.

For example the compounds of formulae (II), (II-1), (V), (VI-1), (VI-2), (IX), (X), (XI), (XX), (XXII), (XXIV), (XXVI), (XXXI), (XXXIV-1), (XXXIV-2), (XXXV) and (XXXVI) can be prepared by the method described in reaction scheme 1, 2, 3 and 4.

In each reaction scheme, $R^{36}$ is $-NHR^6$, $-CH_2-NHR^6$, $-OH$, $-CH_2-OH$, $-CH_2-R^{33}$ or halogen atom. With proviso that hydroxy and amino in the group represented by $R^{36}$ may be protected, if necessary. $R^{37}$ is the protecting group of amino, $R^{38}$ is $-NHR^6$, $-CH_2-NHR^6$, $-OH$, $-CH_2-OH$, $-CH_2-R^{33}$ or halogen atom, BOP is benzotriazol-1-yloxy-tris(dimethylamino)phosphonium hexafluorophosphate, Me is methyl, Et is ethyl, $E^{1-1}$ is bond or C1-3 alkylene, Ph is phenyl, TBAF is tetrabutylammonium fluoride, $TMSN_3$ is trimethylsilylazide, and $R^{39}$ is COOH, $-NHR^{24}$, halogen atom or $-SCOCH_3$. With proviso that amino or carboxy in the group represented by $R^{39}$ may be protected, if necessary. $R^{40}$ is COOH, $-NHR^{24}$, halogen atom or $-SCOCH_3$, and other symbols have the same meanings as described above. The compound represented by formulae (XXXIX) and (XXXXXV) with bromo instead of chloro may be used, which could be readily understood by anyone skilled in the art.

Reaction Scheme 1

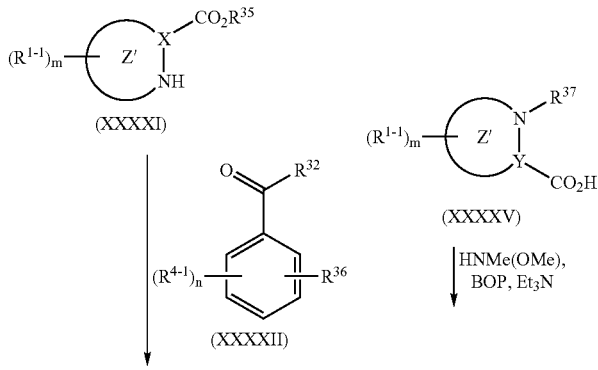

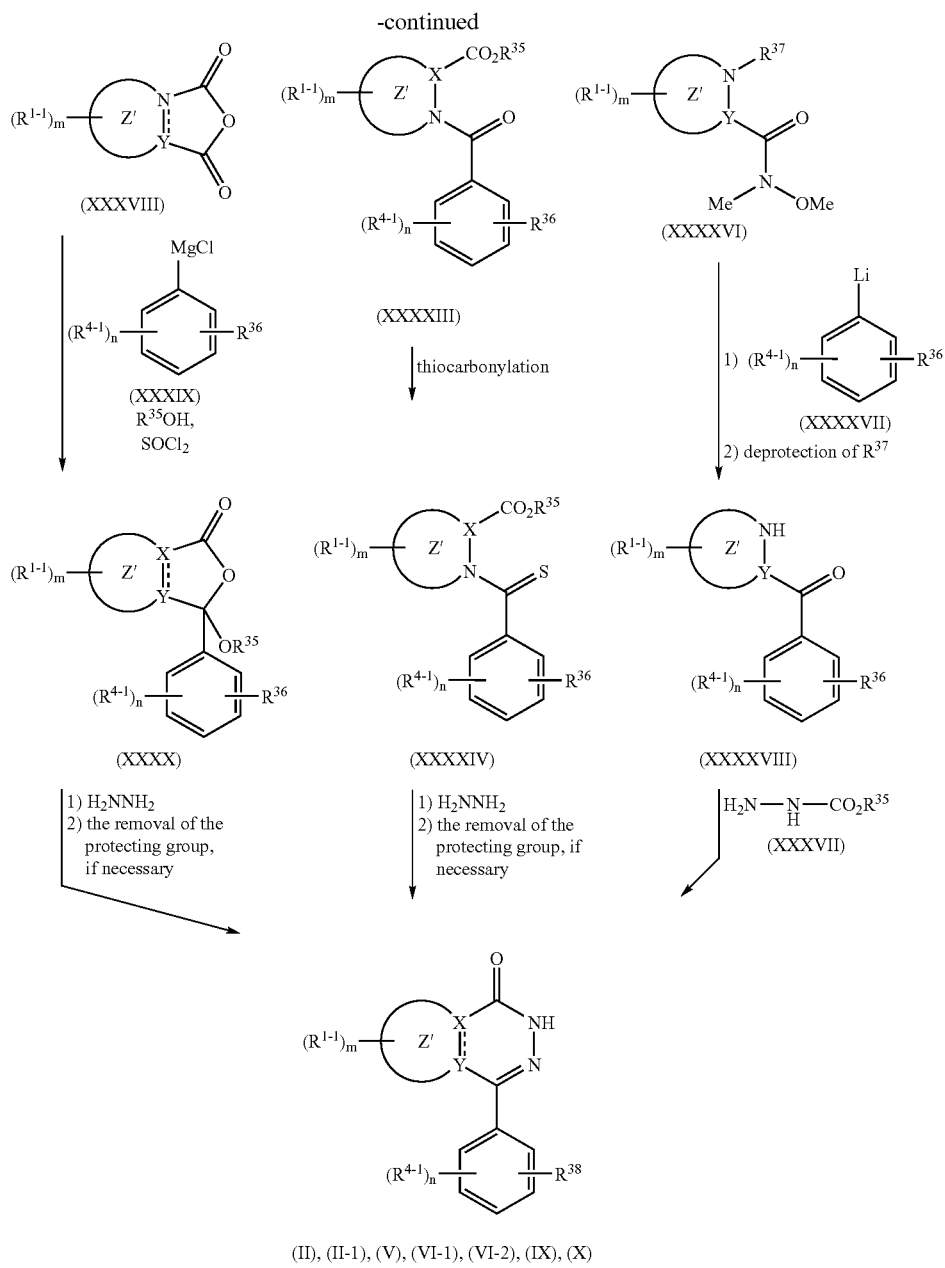
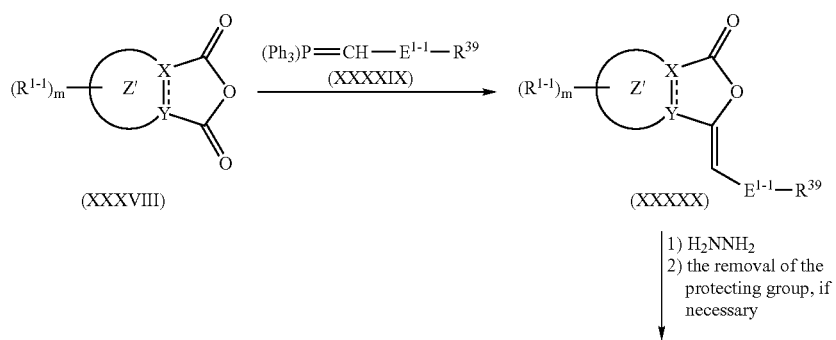
Reaction Scheme 2

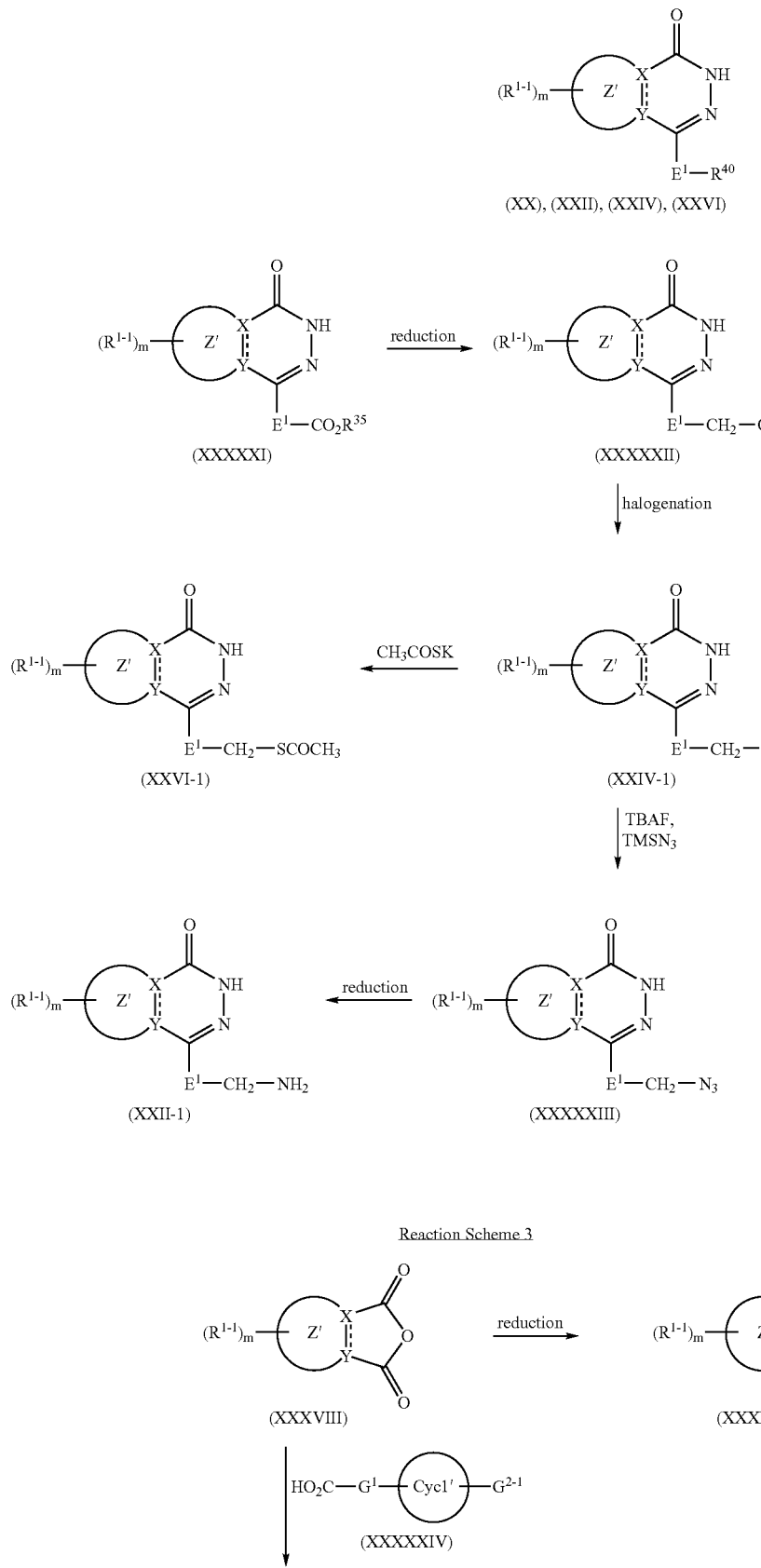

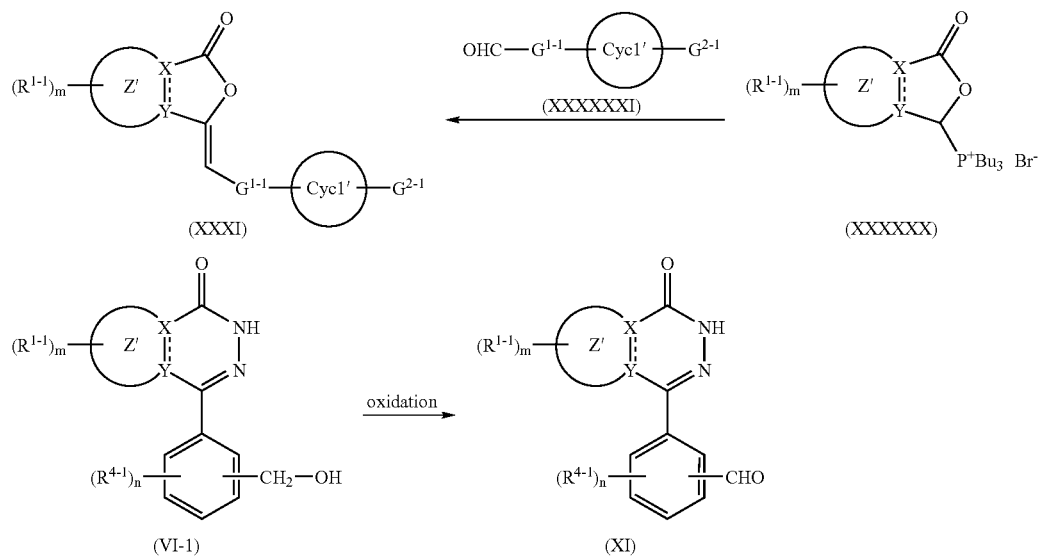
Reaction Scheme 4
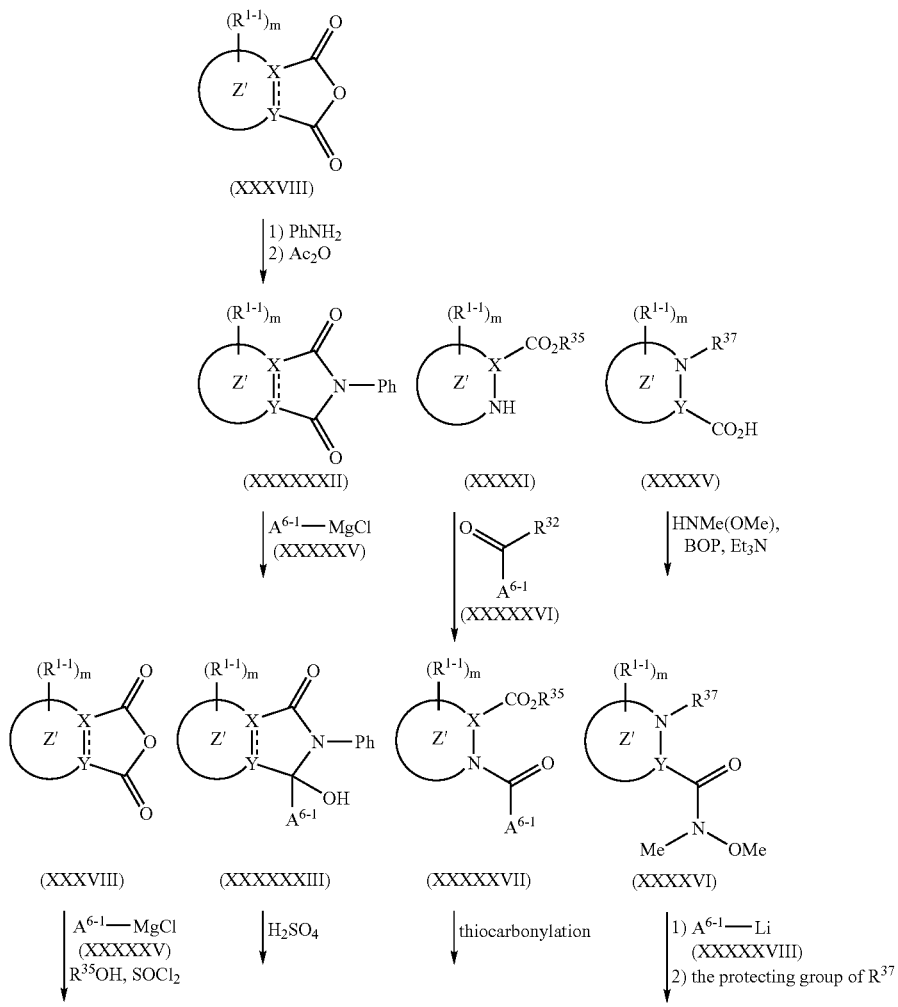

-continued

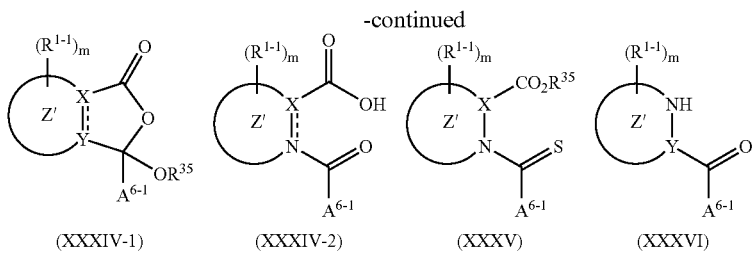

(XXXIV-1) (XXXIV-2) (XXXV) (XXXVI)

In Reaction Schemes 1, 2, 3 and 4, the compounds used as the starting materials are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

Pharmacological Activities:

It has been confirmed that the compounds of the present invention of formula (I) have PARP inhibitory activity by the following experimental results.

1) Enzyme Assay in Vitro

Methods

The below procedure was carried out with 96 well plate at room temperature. In a final volume of 80 µL, the reaction mixture contained each 10 µL of 500 mM Tris/HCl (pH 8.0, WAKO), 100 mM $MgCl_2$, 50 mM dithiothreitol (sigma), 1 mg/mL activated DNA and 1 mM NAD (containing $^3$H-NAD). The 10 µL of test compound was added to the reaction mixture and the reaction was started by addition of 10 µL of 0.1 U/µL PARP (TREVIGEN). The reaction was terminated at 10 minutes by addition of 100 µL of 20% trichloroacetic acid. Poly(ADP-ribose), which is the reaction product, was collected on a glass fiber filter (GF/C, PACKARD). The radioactivity was measured by topcount (PACKARD). Inhibitory activity of the compound was represented by 50% inhibitory concentration calculated as 100% of control (distilled water). The results were shown in Table 91.

TABLE 1

| Example No. | $IC_{50}(\mu M)$ |
|---|---|
| 6(9) | 0.61 |
| 11(4) | 0.10 |
| 30(4) | 0.29 |

2) Ischemia-reperfusion Injury Model (Brain and Heart)

Model of cerebral or coronary ischemia-reperfusion was prepared according to procedures described previously (*Jpn. J. Stroke*, 8, 1 (1986), Stroke, 27, 1624-1628 (1996) and *Eur. J. Pharmacol.*, 270, 45 (1994)). The compounds of the present invention were improvement effective of these diseases.

Toxicity:

The toxicity of the compounds of the present invention represented by formula (I) is very low (For example, as a result of administering the compounds of the present invention to rats, they did not affect circulatory parameters, such as blood pressure, an electrocardiogram, and heart rate.) and therefore the compounds may be considered safe for pharmaceutical use.

INDUSTRIAL APPLICABILITY

Application to Pharmaceutical:

Since the compound of the present invention represented by formula (I) has PARP inhibitory activity, it is useful for prevention and/or treatment of various diseases, for example, ischemic diseases (cerebral infarction, myocardial infarction, reperfusion injury or postoperative injury etc.), inflammatory diseases (inflammatory bowel disease, multiple sclerosis, arthritis or lung injury etc.), neurodegenerative disorders (extrapyramidal disease, Parkinson's disease, Alzheimer's disease, muscular dystrophy or lumbar spinal canal stenosis etc.), glaucoma, diabetes, diabetic complication, shock, head trauma, spinal cord injury, renal failure or hyperalgesia etc. Moreover, it is useful as an antiretroviral drug such as an anti HIV drug, a sensitizer of anticancer therapy or an immunosuppressant.

The compound represented by formula (I) or pharmaceutically acceptable salt thereof may be administered in combination with other pharmaceutical preparations to accomplish the following purposes:

1) To complement for and/or enhance the preventive and/or treatment effect of the compound to be combined;
2) To improve the kinetics/absorption of the compound to be combined and reduce the dose of the compound; and/or
3) To eliminate the side effect of the compound to be combined.

The compound represented by formula (I) and other pharmaceutical preparations may be administered in the form of formulation having these components incorporated in one preparation or may be administered in separate preparations. In the case where these pharmaceutical preparations are administered in separate preparations, they may be administered simultaneously or at different times. In the latter case, the compound represented by formula (I) may be administered before the other pharmaceutical preparations. Alternatively, the other pharmaceutical preparations may be administered before the compound represented by formula (I). The method for the administration of these pharmaceutical preparations may be the same or different.

The diseases on which the preventive and/or treatment effect of the aforementioned combined preparations works are not specifically limited but may be those for which the preventive and/or treatment effect of the compound represented by formula (I) is complemented and/or enhanced.

Examples of the other pharmaceutical preparations for complementing and/or enhancing the preventive and/or treatment effect of the compound represented by formula (I) on ischemic diseases include radical scavenger, astrocyto modulator, N-methyl-D-aspartate (NMDA) antagonist, alpha-amino-3-hydroxy-5-methylisoxazole-4-propionate (AMPA) antagonist, antithrombotic agent, thrombolytic agent, immunosuppressive agent, cell adhesion molecules inhibitor, nitrogen oxide synthase (NOS) inhibitor, neurotrophic factor and interleukin-8 inhibitor etc.

Examples of the other pharmaceutical preparations for complementing and/or enhancing the preventive and/or treatment effect of the compound represented by formula (I) on lumbar spinal canal stenosis include nitrogen oxide synthase (NOS) inhibitor, aldose reductase (AR) inhibitor, radical scavenger, N-methyl-D-aspartate (NMDA) antagonist, alpha-amino-3-hydroxy-5-methylisoxazole-4-propionate (AMPA) antagonist, neurotrophic factor and interleukin-8 inhibitor etc.

Examples of the radical scavenger include, for example, edaravone and ebselen (DR-3305) etc.

Examples of the astrocyto modulator include, for example, ONO-2506 etc.

Examples of the antithrombotic agent include, for example, sodium ozagrel, argatroban and aspirin etc.

Examples of the thrombolytic agent include, for example, tissue plasminogen activator (t-PA), urokinase and heparin etc.

Examples of the immunosuppressive agent include, for example, cyclosporin A, cyclophosphamide and tacrolimus etc.

Examples of the NOS inhibitor include, for example, L-NMMA and ONO-1714 etc.

Examples of the AR inhibitor include, for example, epalrestat, zenarestat, fidarestat, zopolrestat and AS-3201 etc.

The weight proportion of the compound represented by formula (I) and the other pharmaceutical preparations is not specifically limited.

Arbitrary two or more of the other pharmaceutical preparations may be administered in combination.

Examples of the other pharmaceutical preparations for complementing and/or enhancing the preventive and/or treatment effect of the compound represented by formula (I) include not only those which have so far been found but also those which will be found on the basis of the aforementioned mechanism.

In order to use the compound of the present invention represented by formula (I) or the pharmaceutically acceptable salt thereof, or the compound represented by formula (I) in combination with the other pharmaceutical preparations, these compounds are normally administered to the entire or local part of human body orally or parenterally.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compound represented by formula (I) or the pharmaceutically acceptable salt thereof, or the concomitant drug combined the compound represented by formula (I) with pharmaceutical preparations may be administered in the form of, for example, solid compositions, liquid compositions or other compositions each for oral administration, or injections, preparations for external use or suppositories, each for parenteral administration.

Solid compositions for oral administration include compressed tablets, pills, capsules, powders, and granules.

Capsules include hard capsules and soft capsules.

In such solid compositions, one or more of the active substance(s) may be admixed with at least one inert diluent such as lactose, mannitol, glucose, hydroxypropyl cellulose, microcrystalline cellulose, starch, polyvinylpyrrolidone or magnesium aluminometasilicate. The compositions may comprise, in accordance with the conventional process, additives other than the inert diluent, for example, lubricants such as magnesium stearate, disintegrants such as cellulose calcium glycolate, stabilizer such as lactose, and solubilizing agent such as glutamic acid or aspartic acid. Tablets or pills may be coated with a film of a gastric soluble or enteric substance such as sucrose, gelatin, hydroxypropyl cellulose or hydroxypropyl methylcellulose phthalate, or with two or more layers, if necessary. Furthermore, capsules made of a substance which can be absorbed in the body, for example, gelatin, are included.

Liquid compositions for oral administration include pharmaceutically acceptable emulsions, solutions, syrups and elixirs etc. Such liquid compositions comprise one or more of the active substance(s) and an ordinarily employed inert diluent(s) (for example, purified water or ethanol) dissolving the substance(s) therein. The compositions may comprise, in addition to the inert diluent, an adjuvant such as humectants or suspending agents, sweetening agents, flavoring agents, aromatic agents and antiseptics.

The other compositions for oral administration include sprays which comprise one or more active substance(s) and are formulated in a manner known per se in the art. The compositions may comprise, in addition to an inert diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

In the present invention, injections for parenteral administration include sterile aqueous and/or non-aqueous solutions, suspensions and emulsions. The aqueous solutions or suspensions include, for example, distilled water for injection and saline. The non-aqueous solutions or suspensions include propylene glycol, polyethylene glycol, vegetable oils such as olive oil, alcohol such as ethanol and Polysorbate 80 (trade mark). Furthermore, sterile aqueous and non-aqueous solutions, suspensions, and emulsions may be used in combination. Such compositions may additionally comprise adjuvants such as antisaptic, humectant, emulsfier, dispersant, stabilizer (such as lactose) and solubilizing agent (such as glutamic acid and aspartic acid). They are sterilized by filtration through a bacteria retaining filter, the addition of a sterilizer, or irradiation. Also, a sterile solid composition is prepared and then, for example, a freeze-dried product may be dissolved in sterilized or sterile distilled water for injection or another sterile solvent before use.

The other compositions for parenteral administration include liquids for external use, ointments, endermic liniments, suppositories for intrarectal administration and pessaries for vaginal administration which comprise one or more of the active substance(s) and may be prepared by methods known per se.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

3-(3-aminophenyl)-3-methoxy-4,5,6,7-tetrahydro-2-benzofuran-1(3H)-one

To a solution of 3,4,5,6-tetrahydrophthalic acid anhydride (3.04 g) in tetrahydrofuran (40.0 mL) was added a solution of 3-(bis(trimethylsilyl)amino)phenylmagnesium chloride in tetrahydrofuran (1M, 20.0 mL) at −78° C. The mixture was stirred for 1.5 hours. A saturated aqueous ammonium chloride solution was added to the reaction mixture, which was stirred at room temperature for 30 minutes. Anhydrous magnesium sulfate was added to the reaction mixture, which was filtrated. The filtrate was concentrated to give an oily product. Thionyl chloride (5.20 mL) was added dropwise to methanol (20.0 mL) at −10° C. and then the solution was stirred at 0° C. for 15 minutes. To the solution was added the oily product obtained previously and the solution was stirred at room temperature for 18 hours. The reaction mixture was concentrated. The obtained residue was dissolved in methylene chloride (20 mL) and thereto was added triethylamine (2.79 mL) at 0° C. Water was added to the reaction solution, which was extracted with methylene chloride. The extract was washed with water, a saturated aqueous sodium hydrogen carbonate solution and brine sequentially, dried over anhydrous magnesium sulfate and concentrated. The residue was purified by column chromatography on silica gel (ethyl acetate:hexane=3:7) to give the title compound (2.56 g) having the following physical data.

NMR (DMSO-$d_6$): δ 7.03 (t, J=7.8 Hz, 1H), 6.60-6.47 (m, 3H), 5.21 (brs, 2H), 3.20 (s, 3H), 2.17-1.60 (m, 8H).

EXAMPLE 1

4-(3-aminophenyl)-5,6,7,8-tetrahydrophthalazin-1 (2H)-one

A solution of the compound prepared in Reference example 1 (2.56 g) and hydrazine monohydrate (503 mg) in ethanol (30.0 mL) was refluxed for 18 hours. After cooling the reaction mixture to room temperature, the deposited crystal was collected by filtration. It was washed with hexane and dried under reduced pressure. 4N hydrogen chloride in dioxane (0.10 mL) was added dropwise to a suspension of the obtained solid (32.0 mg) in methanol (1.00 mL) and the mixture was stirred at room temperature for 30 minutes. The reaction mixture was concentrated. The obtained crystal was dried under reduced pressure to give the compound of the present invention (36.2 mg) having the following physical data. Moreover, the compound was converted to methanesulfonate thereof by conventional method.

Hydrochloride:
TLC: Rf 0.27 (ethyl acetate:hexane=2:1);
NMR (DMSO-$d_6$): δ 12.95 (s, 1H), 9.40 (brs, 3H), 7.47 (t, J=8.1 Hz, 1H), 7.32-7.26 (m, 3H), 2.43-1.59 (m, 8H).

Methanesulfonate:
TLC: Rf 0.55 (methanol:methylene chloride=1:9);
NMR (DMSO-$d_6$): δ 12.94 (s, 1H), 8.31 (s, 1H), 7.44 (t, J=7.8 Hz, 1H), 7.26-7.21 (m, 2H), 7.18 (s, 1H), 2.48-2.34 (m, 4H), 2.31 (s, 3H), 1.71-1.60 (m, 4H).

EXAMPLE 2 TO EXAMPLE 2(2)

By the same procedure as described in Reference Example 1→Example 1, if necessary, by converting to corresponding salts by conventional method, using 3,4,5,6-tetrahydrophthalic acid anhydride in tetrahydrofuran or a corresponding derivative, and 3-(bis(trimethylsilyl)amino)phenylmagnesium chloride or a corresponding derivative, the following compounds of the present invention were obtained.

EXAMPLE 2

4-(3-aminophenyl)-4a,5,8,8a-tetrahydrophthalazin-1 (2H)-one methanesulfonate

TLC: Rf 0.50 (methanol:methylene chloride=1:9);
NMR (CD$_3$OD): δ 7.66-7.58 (m, 2H), 7.51-7.44 (m, 2H), 5.82 (m, 1H), 5.73 (m, 1H), 3.21 (m, 1H), 2.74 (s, 3H), 2.72-2.47 (m, 3H), 2.27 (m, 1H), 1.92 (m, 1H).

EXAMPLE 2(1)

4-(3-aminophenyl)-2,5,6,7,8,9-hexahydro-1H-cyclohepta[d]pyridazin-1-one

Methanesulfonate
TLC: Rf 0.47 (chloroform:methanol=9:1);
NMR (DMSO-$d_6$): δ 13.01 (br-s, 1H), 7.45 (m, 1H), 7.20-7.09 (m, 3H), 2.86-2.80 (m, 2H), 2.58-2.52 (m, 2H), 2.31 (s, 3H), 1.86-1.76 (m, 2H), 1.58-1.46 (m, 4H).

EXAMPLE 2(2)

4-(3-nitro-4-chlorophenyl)-5,6,7,8-tetrahydrophthalazin-1(2H)-one

TLC: Rf 0.24 (ethyl acetate:hexane=1:1);
NMR (DMSO-$d_6$): δ 13.07 (s, 1H), 8.17 (d, J=1.5 Hz, 1H), 7.86 (d, J=8.4 Hz, 1H), 7.80 (dd, J=8.4, 1.5 Hz, 1H), 2.48-2.38 (m, 4H), 1.71-1.58 (m, 4H).

REFERENCE EXAMPLE 2

4-(3-nitrobenzoyl)thiomorpholine-3-carboxylic acid ethyl ester

To a solution of thiomorpholin-3-ylcarboxylic acid ethyl ester (5.05 g) in methylene chloride (120 mL) were added dimethylaminopyridine (352 mg), triethylamine (4.9 mL) and 3-nitrobenzoyl chloride (5.62 g) in ice bath and then the mixture was stirred at room temperature overnight. 2N hydrochloric acid was added to the reaction mixture, which was extracted with methylene chloride. The extract was wash with a saturated aqueous sodium hydrogen carbonate solution and brine sequentially, dried over anhydrous magnesium sulfate and concentrated. The residue was purified by column chromatography on silica gel (hexane:ethyl acetate=2:1) to give the title compound (5.91 g) having the following physical data.

TLC: Rf 0.23 (hexane:ethyl acetate=2:1);

NMR (CDCl$_3$): δ 8.32-8.30 (m, 2H), 7.79-7.62 (m, 2H), 5.78 and 4.57 (m, 1H), 4.98-4.93 and 3.84-3.79 (m, 1H), 4.23 (q, J=7.2 Hz, 2H), 3.71-3.63 and 3.28-3.02 and 2.91-2.70 (m, 4H), 2.61-2.57 and 2.43-2.39 (m, 1H), 1.36 (t, J=7.2 Hz, 3H).

REFERENCE EXAMPLE 3

4-((3-nitrophenyl)carbonothioyl)thiomorpholine-3-carboxylic acid ethyl ester To a solution of the compound prepared in Reference example 2 (5.88 g) in toluene (90 mL) was added Lawesson's reagent (2,4-bis(4-methoxyphenyl)-1,3-dithia-2,4-diphosphetane-2,4-disulfide) (8.62 g) and the mixture was refluxed for 2 hours. After cooling to room temperature, the raction mixture was filtrated and concentrated. The residue was purified by column chromatography on silica gel (hexane:ethyl acetate=4:1) to give the title compound (6.16 g) having the following physical data.

TLC: Rf 0.27 (hexane:ethyl acetate=4:1);

NMR (CDCl$_3$): δ 8.24-8.17 (m, 2H), 7.66-7.55 (m, 2H), 6.96-6.93 and 4.88-4.86 (m, 1H), 5.96-5.90 and 4.13-4.06 (m, 1H), 4.39-4.32 (m, 2H), 3.83-3.73 and 3.59-3.50 (m, 1H), 3.37-3.30 and 3.12-3.07 (m, 1H), 3.20-3.14 and 3.02-2.94 (m, 1H), 2.94-2.88 and 2.80-2.71 (m, 1H), 2.72-2.64 and 2.49-2.41 (m, 1H), 1.40-1.28 (m, 3H).

EXAMPLE 3

4-(3-nitrophenyl)-6,7,9,9a-tetrahydro[1,4]thiazino[4,3-d][1,2,4]triazin-1(2H)-one To a solution of the compound prepared in Reference example 3 (4.78 g) in ethanol (50 mL) was added hydrazine monohydrate (2.0 mL) and the mixture was refluxed overnight. The reaction mixture was cooled to room temperature and the precipitate was collected by filtration to give the compound of the present invention (2.30 g) having the following physical data.

TLC: Rf 0.45 (chloroform:methanol=19:1);

NMR (DMSO-d$_6$): δ 10.65 (s, 1H), 8.30-8.27 (m, 2H), 7.89-7.86 (m, 1H), 7.76-7.70 (m, 1H), 4.24 (dd, J=10.8, 2.7 Hz, 1H), 3.49 (dt, J=13.8, 2.7 Hz, 1H), 3.17-3.08 (m, 1H), 2.97 (dd, J=13.2, 10.8 Hz, 1H), 2.88-2.82 (m, 1H), 2.71 (dt, J=12.6, 2.7 Hz, 1H), 2.32-2.27 (m, 1H).

EXAMPLE 4 TO EXAMPLE 4(32)

By the same procedure as described in Reference example 2→Reference example 3→Example 3, using thiomorpholin-3-ylcarboxylic acid ethyl ester or a corresponding derivative, and 3-nitrobenzoyl chloride or a corresponding derivative, the following compounds of the present invention were obtained.

EXAMPLE 4

4-(3-nitrophenyl)-7,8,9,9a-tetrahydro-2H-pyrido[1,2-d][1,2,4]triazin-1(6H)-one TLC: Rf 0.50 (chloroform:methanol=9:1);

NMR (DMSO-d$_6$): δ 10.48 (s, 1H), 8.28 (d, J=8.1 Hz, 1H), 8.22 (s, 1H), 7.86 (d, J=8.1 Hz, 1H), 7.73 (t, J=8.1 Hz, 1H), 3.91 (m, 1H), 3.17 (m, 1H), 2.87 (m, 1H), 2.10 (m, 1H), 1.86 (m, 1H), 1.43 (m, 4H).

EXAMPLE 4(1)

4-phenyl-6,7,9,9a-tetrahydro[1,4]thiazino[4,3-d][1,2,4]triazin-1(2H)-one

TLC: Rf 0.18 (hexane:ethyl acetate=2:1);

NMR (DMSO-d$_6$): δ 10.53 (s, 1H), 7.50-7.38 (m, 5H), 4.23 (dd, J=9.6, 3.6 Hz, 1H), 3.52 (m, 1H), 3.08 (m, 1H), 2.94-2.80 (m, 2H), 2.68 (m, 1H), 2.30 (d, J=10.5 Hz, 1H).

EXAMPLE 4(2)

(9aR)-4-(3-nitrophenyl)-6,7,9,9a-tetrahydro[1,4]thiazino[4,3-d][1,2,4]triazin-1(2H)-one TLC: Rf 0.18 (hexane:ethyl acetate=1:1);

NMR (CDCl$_3$): δ8.32 (dd, J=8.1, 1.5 Hz, 1H), 8.27 (s, 1H), 8.14 (br, H), 7.72 (d, J=8.1 Hz, 1H), 7.66 (t, J=8.1 Hz, 1H), 4.39 (dd, J=10.8, 2.7 Hz, 1H), 3.72 (dt, J=14.1, 2.7 Hz, 1H), 3.24 (m, 1H), 3.13 (m, 1H), 2.99 (dd, J=14.1, 10.8 Hz, 1H), 2.77 (m, 1H), 2.32 (m, 1H);

[α]$_D$=−71.9 (c, 0.16, MeOH).

EXAMPLE 4(3)

4-(4-nitrophenyl)-6,7,9,9a-tetrahydro[1,4]thiazino[4,3-d][1,2,4]triazin-1(2H)-one TLC: Rf 0.28 (ethyl acetate:hexane=1:1);

NMR (DMSO-d$_6$): δ 10.69 (s, 1H), 8.28 (d, J=8.4 Hz, 2H), 7;73 (d, J=8.4 Hz, 2H), 4.26 (dd, J=10.2, 3.0 Hz, 1H), 3.48 (d, J=14.4 Hz, 1H), 3.17-2.29 (m, 5H).

EXAMPLE 4(4)

4-(3-methoxyphenyl)-6,7,9,9a-tetrahydro[1,4]thiazino[4,3-d][1,2,4]triazin-1(2H)-one TLC: Rf 0.17 (hexane:ethyl acetate=1:1);

NMR (DMSO-d$_6$): δ 10.50 (s, 1H), 7.33 (t, J=8.1 Hz, 1H), 7.00-6.93 (m, 3H), 4.20 (dd, J=10.5, 3.0 Hz, 1H), 3.76 (s, 3H), 3.53 (dt, J=13.8, 3.0 Hz, 1H), 3.10-3.01 (m, 1H), 2.93-2.78 (m, 2H) 2.73-2.63 (m, 1H), 2.32-2.27 (m, 1H).

EXAMPLE 4(5)

4-(4-methoxyphenyl)-6,7,9,9a-tetrahydro[1,4]thiazino[4,3-d][1,2,4]triazin-1(2H)-one TLC: Rf 0.50 (chloroform:methanol=8:1);

NMR (DMSO-d$_6$): δ 7.40-7.26 (m, 2H), 7.04-6.92 (m, 2H), 4.20 (dd, J=9.3, 4.2 Hz, 1H), 3.77 (s, 3H), 3.57 (dt, J=14.1, 2.7 Hz, 1H), 3.06 (m, 1H), 2.94-2.78 (m, 2H), 2.68 (m, 1H), 2.30 (m, 1H).

EXAMPLE 4(6)

4-(2-nitrophenyl)-6,7,9,9a-tetrahydro[1,4]thiazino[4,3-d][1,2,4]triazin-1(2H)-one TLC: Rf 0.50 (methylene chloride:methanol=10:1);
NMR (CDCl$_3$): δ 8.14 (br, 1H), 7.21 (ddd, J=8.4, 7.5, 2.1 Hz, 1H), 7.09 (t, J=7.5 Hz, 1H), 6.80 (td, J=7.5, 1.2 Hz, 1H), 6.74 (dd, J=8.4, 1.2 Hz, 1H), 4.35 (dd, J=10.5, 3.0 Hz, 1H), 3.72 (dt, J=13.8, 3.0 Hz, 1H), 3.14 (m, 1H), 3.08-2.90 (m, 2H), 2.79 (m, 1H), 2.21 (dd, J=13.8, 1.2 Hz, 1H).

EXAMPLE 4(7)

4-(3-nitrophenyl)-6,7-dihydro[1,4]thiazino[4,3-d][1,2,4]triazin-1(2H)-one

TLC: Rf 0.27 (methylene chloride:methanol=20:1);
NMR (DMSO-d$_6$): δ 11.02 (brs, 1H), 8.32 (d, J=8.1 Hz, 1H), 8.28 (s, 1H), 7.92 (d, J=8.1 Hz, 1H), 7.76 (t, J=8.1 Hz, 1H), 6.28 (s, 1H), 3.61 (m, 2H), 3.16 (m, 2H).

EXAMPLE 4(8)

4-phenyl-6,7-dihydro[1,4]thiazino[4,3-d][1,2,4]triazin-1(2H)-one

TLC: Rf 0.51 (methanol:methylene chloride=1:10);
NMR (DMSO-d$_6$): δ 10.89 (s, 1H), 7.45 (m, 5H), 6.24 (s, 1H), 3.60 (m, 2H), 3.14 (m, 2H).

EXAMPLE 4(9)

4-phenyl-7,8,10,10a-tetrahydro-6H-[1,2,4]triazino[5,4-c][1,4]thiazepin-1(2H)-one TLC: Rf 0.53 (chloroform:methanol=9:1);
NMR (DMSO-d$_6$): δ 10.57 (br-s, 1H), 7.50-7.40 (m, 5H), 4.29 (dd, J=6.9, 4.5 Hz, 1H), 3.44-3.36 (m, 1H), 3.16-3.00 (m, 3H), 2.78-2.70 (m, 2H), 1.80-1.64 (m, 1H), 1.55-1.40 (m, 1H).

EXAMPLE 4(10)

4-(3-nitrophenyl)-7,8,10,10a-tetrahydro-6H-[1,2,4]triazino[5,4-c][1,4]thiazepin-1(2H)-one TLC: Rf 0.60 (chloroform:methanol=9:1).

EXAMPLE 4(11)

4-(3-dimethylaminophenyl)-6,7,9,9a-tetrahydro[1,4]thiazino[4,3-d][1,2,4]triazin-1(2H)-one TLC: Rf 0.50 (chloroform:methanol=8:1);
NMR (DMSO-d$_6$): δ 7.21 (dd, J=8.1, 7.2 Hz, 1H), 6.75 (m, 1H), 6.72-6.58 (m, 2H), 4.20 (dd, J=10.5, 3.0 Hz, 1H), 3.58 (dt, J=13.8, 2.7 Hz, 1H), 3.04 (m, 1H), 2.98-2.76 (m, 2H), 2.90 (s, 6H), 2.68 (m, 1H), 2.30 (m, 1H).

EXAMPLE 4(12)

(8aR)-4-(3-nitrophenyl)-8,8a-dihydro[1,3]thiazolo[3,4-d][1,2,4]triazin-1(2H)-one TLC: Rf 0.39 (methylene chloride:methanol=10:1);
NMR (DMSO-d$_6$): δ 11.07 (s, 1H), 8.33 (m, 2H), 8.02 (d, J=7.8 Hz, 1H), 7.76 (t, J=7.8 Hz, 1H), 4.53 (m, 2H), 4.28 (m, 1H), 3.46 (m, 2H).

EXAMPLE 4(13)

4-(3-amino-5-nitrophenyl)-6,7,9,9a-tetrahydro[1,4]thiazino[4,3-d][1,2,4]triazin-1(2H)-one TLC: Rf 0.44 (chloroform:methanol=8:1);
NMR (DMSO-d$_6$): δ 7.41 (dd, J=2.1, 2.1 Hz, 1H), 7.32 (dd, J=2.1, 1.2 Hz, 1H), 6.94 (dd, J=2.1, 1.2 Hz, 1H), 6.52 (brs, 1H), 6.01 (brs, 2H), 4.23 (dd, J=7.5, 3.0 Hz, 1H), 3.57 (m, 1H), 3.10 (m, 1H), 3.00-2.76 (m, 2H), 2.68 (m, 1H), 2.33 (m, 1H).

EXAMPLE 4(14)

(9aS)-4-(3-nitrophenyl)-6,7,9,9a-tetrahydro[1,4]thiazino[4,3-d][1,2,4]triazin-1(2H)-one TLC: Rf 0.51 (methylene chloride:methanol=10:1).

EXAMPLE 4(15)

(7R,8aS)-7-benzyloxy-4-phenyl-6,7,8,8a-tetrahydropyrrolo[1,2-d][1,2,4]triazin-1(2H)-one TLC: Rf 0.26 (hexane:ethyl acetate 1:1);
NMR (DMSO-d$_6$): δ 10.55 (s, 1H), 7.50-7.24 (m, 10H), 4.53 (d, J=12.3 Hz, 1H), 4.48 (d, J=12.3 Hz, 1H), 4.16 (dd, J=8.7, 7.2 Hz, 1H), 4.09-4.03 (m, 1H), 3.54 (dd, J=10.8, 3.0 Hz, 1H), 3.44 (dd, J=10.8, 4.8 Hz, 1H), 2.39-2.31 (m, 1H), 2.24-2.15 (m, 1H).

EXAMPLE 4(16a)

(7R,8aS)-7-benzyloxy-4-(3-nitrophenyl)-6,7,8,8a-tetrahydropyrrolo[1,2-d][1,2,4]triazin-1(2H)-one TLC: Rf 0.10 (hexane:ethyl acetate=1:1);
NMR (DMSO-d$_6$): δ 10.73 (s, 1H), 8.31-8.27 (m, 2H), 7.95 (dt, J=7.5, 1.5 Hz, 1H), 7.75-7.69 (m, 1H), 7.34-7.24 (m, 5H), 4.53 (d, J=12.0 Hz, 1H), 4.50 (d, J=12.0 Hz, 1H), 4.24-4.19 (m, 1H), 4.11-4.04 (m, 1H), 3.57 (dd, J=10.5, 3.0 Hz, 1H), 3.50 (dd, J=10.5, 5.1 Hz, 1H), 2.41-2.33 (m, 1H), 2.28-2.19 (m, 1H).

EXAMPLE 4(16b)

(7R,8aS)-7-benzyloxy-4-(3-aminophenyl)-6,7,8,8a-tetrahydropyrrolo[1,2-d][1,2,4]triazin-1(2H)-one TLC: Rf 0.51 (chloroform:methanol=9:1);
NMR (DMSO-d$_6$): δ 10.45 (s, 1H), 7.34-7.24 (m, 5H), 7.03 (t, J=7.8 Hz, 1H), 6.72 (t, J=1.8 Hz, 1H), 6.60 (dd, J=7.8, 1.8 Hz, 1H), 5.19 (s, 2H), 4.53 (d, J=12.0 Hz, 1H), 4.48 (d, J=12.0 Hz, 1H), 4.14-4.01 (m, 2H), 3.54 (dd, J=10.8, 2.4 Hz, 1H), 3.46 (dd, J=10.8, 4.8 Hz, 1H), 2.38-2.30 (m, 1H), 2.22-2.13 (m, 1H).

EXAMPLE 4(17)

4-phenyl-9,9a-dihydro-2H-[1,3]thiazino[3,4-d][1,2,4]triazin-1(8H)-one

TLC: Rf 0.55 (chloroform:methanol=9:1);
NMR (DMSO-$d_6$): δ 10.55 (br-s, 1H), 7.53-7.43 (m, 5H), 4.43 (d, J=13.8 Hz, 1H), 4.20 (dd, J=12.0, 2.4 Hz, 1H), 4.06 (dd, J=13.8, 2.4 Hz, 1H), 3.21 (m, 1H), 2.88 (m, 1H), 2.07 (m, 1H), 1.80 (m, 1H).

EXAMPLE 4(18)

4-(3-nitrophenyl)-9,9a-dihydro-2H-[1,3]thiazino[3,4-d][1,2,4]triazin-1(8H)-one

TLC: Rf 0.55 (chloroform:methanol=9:1);
NMR (DMSO-$d_6$): δ 10.70 (br-s, 1H), 8.40 (m, 1H), 8.33 (m, 1H), 7.96 (m, 1H), 7.75 (m, 1H), 4.48 (d, J=14.1 Hz, 1H), 4.24 (dd, J=12.0, 2.1 Hz, 1H), 4.14 (dd, J=14.1, 2.1 Hz, 1H), 3.23 (m, 1H), 2.91 (m, 1H), 2.08 (m, 1H), 1.86 (m, 1H).

EXAMPLE 4(19)

4-(3-nitro-4-methylphenyl)-6,7-dihydro[1,4]thiazino[4,3-d][1,2,4]triazin-1(2H)-one TLC: Rf 0.33 (methylene chloride:methanol=20:1);
NMR (DMSO-$d_6$): δ 10.97 (brs, 1H), 8.04 (d, J=1.8 Hz, 1H), 7.70 (dd, J=7.8, 1.8 Hz, 1H), 7.59 (d, J=7.8 Hz, 1H), 6.27 (s, 1H), 3.61 (m, 2H), 3.14 (m, 2H), 2.55 (s, 3H).

EXAMPLE 4(20)

4-(3-cyanophenyl)-6,7,9,9a-tetrahydro[1,4]thiazino[4,3-d][1,2,4]triazin-1(2H)-one TLC: Rf 0.20 (hexane:ethyl acetate=1:1);
NMR (CDCl$_3$): δ 8.10 (br, 1H), 7.75 (dt, J=6.9, 1.8 Hz, 1H), 7.68 (m, 1H), 7.62-7.55 (m, 2H), 4.36 (dd, J=11.1, 2.7 Hz, 1H), 3.69 (dt, J=11.1, 2.7 Hz, 1H), 3.21 (ddd, J=14.1, 12.0, 2.7 Hz, 1H), 3.12 (dt, J=10.8, 2.4 Hz, 1H), 2.96 (dd, J=14.1, 11.1 Hz, 1H), 2.74 (m, 1H), 2.32 (ddd, J=11.1, 4.5, 2.4 Hz, 1H).

EXAMPLE 4(21)

4-(3-nitro-4-methylphenyl)-6,7,9,9a-tetrahydro[1,4]thiazino[4,3-d][1,2,4]triazin-1(2H)-one TLC: Rf 0.59 (chloroform:methanol=9:1).

EXAMPLE 4(22)

4-(3-fluorophenyl)-6,7,9,9a-tetrahydro[1,4]thiazino[4,3-d][1,2,4]triazin-1(2H)-one TLC: Rf 0.63 (chloroform:methanol=9:1);
NMR (DMSO-$d_6$): δ 7.56-7.46 (m, 1H), 7.36-7.24 (m, 3H), 4.20 (dd, J=10.2, 3.6 Hz, 1H), 3.54-3.44 (m, 1H), 3.16-3.02 (m, 1H), 2.96-2.78 (m, 2H), 2.76-2.64 (m, 1H), 2.36-2.24 (m, 1H).

EXAMPLE 4(23)

4-(3-nitro-5-fluorophenyl)-6,7,9,9a-tetrahydro[1,4]thiazino[4,3-d][1,2,4]triazin-1(2H)-one TLC: Rf 0.66 (chloroform:methanol=9:1).

EXAMPLE 4(24)

4-(2-methyl-5-nitrophenyl)-6,7,9,9a-tetrahydro[1,4]thiazino[4,3-d][1,2,4]triazin-1(2H)-one TLC: Rf 0.59 (chloroform:methanol=9:1).

EXAMPLE 4(25)

4-(4-nitrophenyl)-6,7-dihydro[1,4]thiazino[4,3-d][1,2,4]triazin-1(2H)-one

TLC: Rf 0.54 (chloroform:methanol=9:1);
NMR (DMSO-$d_6$): δ 11.03 (brs, 1H), 8.32-8.25 (m, 2H), 7.77-7.70 (m, 2H), 6.29 (s, 1H), 3.64-3.54 (m, 2H), 3.20-3.12 (m, 2H).

EXAMPLE 4(26)

4-(2-methyl-3-nitrophenyl)-6,7,9,9a-tetrahydro[1,4]thiazino[4,3-d][1,2,4]triazin-1(2H)-one TLC: Rf 0.49 (chloroform:methanol=9:1);
NMR (CDCl$_3$): δ 8.64 (s, 1H), 7.93 (dd, J=7.8, 1.5 Hz, 1H), 7.50-7.40 (m, 2H), 4.34 (dd, J=11.1, 2.4 Hz, 1H), 3.41 (dt, J=11.1, 2.7 Hz, 1H), 3.24-3.00 (m, 2H), 2.91 (dd, J=13.5, 11.1 Hz, 1H), 2.70-2.40 (m, 4H), 2.30-2.26 (m, 1H).

EXAMPLE 4(27)

4-(3-methoxyphenyl)-6,7-dihydro[1,4]thiazino[4,3-d][1,2,4]triazin-1(2H)-one

TLC: Rf 0.46 (hexane:ethyl acetate=1:1);
NMR (DMSO-$d_6$): δ 10.85 (s, 1H), 7.37 (t, J=7.6 Hz, 1H), 7.08-6.96 (m, 3H), 6.23 (s, 1H), 3.77 (s, 3H), 3.64-3.56 (m, 2H), 3.16-3.08 (m, 2H).

EXAMPLE 4(28)

4-(3-nitro-4-methoxyphenyl)-6,7-dihydro[1,4]thiazino[4,3-d][1,2,4]triazin-1(2H)-one TLC: Rf 0.30 (chloroform:methanol=9:1);
NMR (DMSO-$d_6$): δ 10.92 (s, 1H), 7.95 (d, J=2.1 Hz, 1H), 7.73 (dd, J=8.7, 2.1 Hz, 1H), 7.42 (d, J=8.7 Hz, 1H), 6.25 (s, 1H), 3.96 (s, 3H), 3.65-3.60 (m, 2H), 3.20-3.15 (m, 2H).

EXAMPLE 4(29)

4-benzyl-6,7,9,9a-tetrahydro[1,4]thiazino[4,3-d][1,2,4]triazin-1(2H)-one

TLC: Rf 0.37 (methylene chloride:methanol=10:1);
NMR (CDCl$_3$): δ 8.03 (br, 1H), 7.39-7.24 (m, 5H), 4.17 (dd, J=10.8, 2.7 Hz, 1H), 3.93 (dt, J=14.4, 2.7 Hz, M1), 3.06 (ddd, J=14.4, 12.0, 2.7 Hz, 1H), 2.89 (dt, J=13.5, 2.7 Hz, 1H), 2.78 (dd, J=13.5, 10.8 Hz, 1H), 2.21 (ddd, J=14.4, 12.0, 2.7 Hz, 1H), 2.06 (dq, J=14.4, 2.7 Hz, 1H).

EXAMPLE 4(30)

4-3-nitrobenzyl-6,7-dihydro[1,4]thiazino[4,3-d][1,2,4]triazin-1(2H)-one

TLC: Rf 0.60 (chloroform:methanol=9:1);
NMR (CDCl$_3$): δ 8.61 (s, 1H), 8.20-8.10 (m, 2H), 7.64-7.54 (m, 2H), 6.39 (s, 1H), 3.82 (s, 2H), 3.80-3.74 (m, 2H), 2.76-2.72 (m, 2H).

EXAMPLE 4(31)

4-phenyl-7,8,9,9a-tetrahydro-2H-pyrido[1,2-d][1,2,4]triazin-1(6H)-one

TLC: Rf 0.67 (methanol:methylene chloride=1:10);
NMR (DMSO-d$_6$): δ 10.34 (s, 1H), 7.44-7.34 (m, 5H), 3.86 (dd, J=11.1, 3.0 Hz, 1H), 3.20 (dt, J=13.2, 2.1 Hz, 1H), 2.77 (td, J=13.2, 2.1 Hz, 1H), 2.06 (m, 1H), 1.85 (m, 1H), 1.49-1.26 (m, 4H).

EXAMPLE 4(32)

5-phenyl-2,3-dihydro-7H-[1,3]thiazolo[3,2-d][1,2,4]triazin-8(8aH)-one

TLC: Rf 0.30 (ethyl acetate:hexane=1:1);
NMR (DMSO-d$_6$): δ 10.99 (s, 1H), 7.48 (m, 5H), 5.39 (s, 1H), 3.97 (ddd, J=12.0, 6.3, 1.2 Hz, 1H), 3.35-3.25 (m, 1H), 2.92 (ddd, J=10.0, 6.3, 1.2 Hz, 1H), 2.59-2.48 (m, 1H).

EXAMPLE 5

4-(3-nitro-4-hydroxyphenyl)-6,7-dihydro[1,4]thiazino[4,3-d][1,2,4]triazin-1(2H)-one The compound prepared in Example 4(28) (150 mg) and lithium chloride (59 mg) were dissolved in dimethylformamide (2.0 mL) and the mixture was refluxed for 16 hours. After cooling to room temperature, to the reaction mixture was added 1N hydrochloric acid. The precipitate was collected by filtration. It was dried to give the compound of the present invention (126 mg) having the following physical data.

TLC: Rf 0.19 (hexane:ethyl acetate=1:1);
NMR (DMSO-d$_6$): δ 11.45 (brs, 1H), 10.89 (s, 1H), 7.92 (d, J=2.4 Hz, 1H), 7.58 (dd, J=9.0, 2.4 Hz, 1H), 7.16 (d, J=9.0 Hz, 1H), 6.24 (s, 1H), 3.65-3.60 (m, 2H), 3.20-3.15 (m, 2H).

EXAMPLE 6

4-(3-aminophenyl)-6,7,9,9a-tetrahydro[1,4]thiazino[4,3-d][1,2,4]triazin-1(2H)-one To a solution of the compound prepared in Example 3 (537 mg) in ethanol (4 mL) was added tin chloride dihydrate (2.07 g) and the mixture was refluxed for 30 minutes. After cooling to room temperature, a saturated aqueous sodium hydrogen carbonate solution was added to the reaction mixture, which was extracted with ethyl acetate. The extract was washed with brine, dried over anhydrous magnesium sulfate and concentrated. To methanol (2 mL) was added the obtained solid (137 mg) and then 4N hydrogen chloride in dioxane (0.26 mL) was added to the mixture, which was stirred at room temperature for 3 hours. The reaction mixture was concentrated. The residue was recrystallized from a mixture solvent (isopropanol:ethanol=4:1) to give the compound of the present invention (144 mg) having the following physical data. Moreover, the compound was converted to methanesulfonate thereof by conventional method.

Hydrochloride:
TLC: Rf 0.42 (chloroform:methanol=9:1);
NMR (DMSO-d$_6$): δ 10.90-10.70 (br, 1H), 7.51 (t, J=7.8 Hz, 1H), 7.40-7.36 (m, 3H), 4.25 (dd, J=10.2, 3.0 Hz, 1H), 3.58-3.49 (m, 1H), 3.14-3.06 (m, 1H), 2.96-2.82 (m, 2H), 2.77-2.67 (m, 1H), 2.34-2.30 (m, 1H).

Methanesulfonate:
TLC: Rf 0.36 (chloroform:methanol=9:1);
NMR (DMSO-d$_6$): δ 10.84-10.48 (br, 1H), 7.44 (t, J=7.8 Hz, 1H), 7.25-7.18 (m, 3H), 4.24 (dd, J=9.9, 3.3 Hz, 1H), 3.56-3.49 (m, 1H), 3.15-3.05 (m, 1H), 2.95-2.81 (m, 2H), 2.75-2.65 (m, 1H), 2.33-2.30 (m, 4H).

EXAMPLE 6(1) TO EXAMPLE 6(19)

By the same procedure as described in Example 6, if necessary, by converting to corresponding salts by conventional method, using the compounds prepared in Example 4, 4(2), 4(3), 4(6), 4(7), 4(10), 4(12), 4(14), 4(13), 4(18), 4(19), 4(21), 4(23)-4(26), 4(28), 4(30) or 5 instead of the compound prepared in Example 3, the following compounds of the present invention were obtained.

EXAMPLE 6(1)

4-(3-aminophenyl)-7,8,9,9a-tetrahydro-2H-pyrido[1,2-d][1,2,4]triazin-1(6H)-one methanesulfonate TLC: Rf 0.44 (methanol:methylene chloride=1:9);
NMR (DMSO-d$_6$): δ 10.65 (brs, 1H), 7.38 (t, J=7.8 Hz, 1H), 7.13-7.04 (m, 3H), 3.93 (m, 1H), 3.26 (d, J=13.2 Hz, 1H), 2.82 (m, 1H), 2.31 (s, 3H), 2.07 (m, 1H), 1.86 (m, 1H), 1.46 (m, 4H).

EXAMPLE 6(2)

(9aR)-4-(3-aminophenyl)-6,7,9,9a-tetrahydro[1,4]thiazino[4,3-d][1,2,4]triazin-1(2H)-one TLC: Rf 0.27 (methylene chloride:methanol=10:1);
NMR (DMSO-d$_6$): δ 10.44 (s, 1H), 7.04 (t, J=7.5 Hz, 1H), 6.57 (d, J=7.5 Hz, 1H), 6.53 (s, 1H), 6.47 (d, J=7.5 Hz, 1H), 5.23 (s, 2H), 4.19 (t, J=6.6 Hz, 1H), 3.62 (m, 1H), 3.03 (m, 1H), 2.84-2.80 (m, 2H), 2.66 (m, 1H), 2.31 (d, J=13.2 Hz, 1H).

EXAMPLE 6(3)

4-(4-aminophenyl)-6,7,9,9a-tetrahydro[1,4]thiazino[4,3-d][1,2,4]triazin-1(2H)-one Methanesulfonate TLC: Rf 0.39 (methanol:methylene chloride=1:10);
NMR (DMSO-d$_6$): δ 10.87 (brs, 1H), 7.24 (d, J=8.4 Hz, 2H), 6.86 (d, J=8.4 Hz, 2H), 4.26 (dd, J=10.6, 3.0 Hz, 1H), 3.66 (brd, J=14.1 Hz, 1H), 3.16-2.35 (m, 5H), 2.30 (s, 3H).

EXAMPLE 6(4)

4-(2-aminophenyl)-6,7,9,9a-tetrahydro[1,4]thiazino[4,3-d][1,2,4]triazin-1(2H)-one TLC: Rf 0.22 (methylene chloride:methanol=10:1);
NMR (CDCl$_3$): δ 8.24 (brs, 1H), 7.21 (t, J=7.5 Hz, 1H), 7.09 (d, J=7.5 Hz, 1H), 6.80 (t, J=7.5 Hz, 1H), 6.74 (d, J=7.5 Hz, 1H), 4.34 (dd, J=11.7, 2.7 Hz, 1H), 3.95 (brs, 2H), 3.72 (m, 1H), 3.13 (m, 1H), 3.08-2.92 (m, 2H), 2.80 (m, 1H), 2.21 (m, 1H).

EXAMPLE 6(5)

4-(3-aminophenyl)-6,7-dihydro[1,4]thiazino[4,3-d][1,2,4]triazin-1(2H)-one

Free Form:
TLC: Rf 0.31 (methanol:methylene chloride=1:10);
NMR (DMSO-d$_6$): δ 10.81 (s, 1H), 7.07 (t, J=7.8 Hz, 1H), 6.63 (d, J=7.8 Hz, 1H), 6.56 (s, 1H), 6.50 (d, J=7.8 Hz, 1H), 6.21 (s, 1H), 5.28 (s, 2H), 3.62 (m, 2H), 3.14 (m, 2H).

Methanesulfonate:
TLC: Rf 0.48 (methanol:methylene chloride=1:9);
NMR (DMSO-d$_6$): δ 10.93 (s, 1H), 7.44 (t, J=7.8 Hz, 1H), 7.19 (m, 3H), 6.26 (s, 1H), 3.60 (m, 2H), 3.15 (m, 2H), 2.33 (s, 3H).

EXAMPLE 6(6)

4-(3-aminophenyl)-7,8,10,10a-tetrahydro-6H-[1,2,4]triazino[5,4-c][1,4]thiazepin-1(2H)-one TLC: Rf 0.44 (chloroform:methanol=9:1);
NMR (DMSO-d$_6$): δ 10.47 (br-s, 1H), 7.04 (m, 1H), 6.62-6.52 (m, 3H), 5.21 (br-s, 2H), 4.25 (dd, J=6.9, 4.5 Hz, 1H), 3.52-3.42 (m, 1H), 3.14-2.96 (m, 3H), 2.76-2.60 (m, 2H), 1.82-1.56 (m, 2H).

EXAMPLE 6(7)

(8aR)-4-(3-aminophenyl)-8,8a-dihydro[1,3]thiazolo[3,4-d][1,2,4]triazin-1(2H)-one TLC: Rf 0.56 (methanol:methylene chloride=1:9);
NMR (DMSO-d$_6$): δ 10.81 (s, 1H), 7.07 (t, J=7.8 Hz, 1H), 6.72 (s, 1H), 6.63 (m, 2H), 5.25 (s, 2H), 4.50 (d, J=9.3 Hz, 1H), 4.41 (d, J=9.3 Hz, H), 4.16 (t, J=7.2 Hz, 1H), 3.36 (m, 2H).

EXAMPLE 6(8)

(9aS)-4-(3-aminophenyl)-6,7,9,9a-tetrahydro[1,4]thiazino[4,3-d][1,2,4]triazin-1(2H)-one TLC: Rf 0.44 (methylene chloride:methanol=10:1);
NMR (CDCl$_3$): δ 8.01 (br, 1H), 7.20 (t, J=8.1 Hz, 1H), 6.76-6.69 (m, 2H), 6.64 (t, J=1.8 Hz, 1H), 4.33 (dd, J=10.8, 3.0 Hz, 1H), 3.85 (dt, J=10.8, 3.0 Hz, 1H), 3.78 (br, 2H), 3.11 (m, 1H), 3.05 (m, 1H), 2.94 (dd, J=13.5, 10.8 Hz, 1H), 2.74 (m, 1H), 2.25 (m, 1H).

EXAMPLE 6(9)

4-(3,5-diaminophenyl)-6,7,9,9a-tetrahydro[1,4]thiazino[4,3-d][1,2,4]triazin-1(2H)-one TLC: Rf 0.25 (chloroform:methanol=8:1);
NMR (DMSO-d$_6$): δ 5.82 (t, J=1.8 Hz, 1H), 5.75 (d, J=1.8 Hz, 2H), 4.86 (brs, 4H), 4.15 (dd, J=9.3, 4.2 Hz, 1H), 3.72 (m, 1H), 3.00 (m, 1H), 2.84-2.50 (m, 3H), 2.32 (m, 1H).

EXAMPLE 6(10)

4-(3-aminophenyl)-9,9a-dihydro-2H-[1,3]thiazino[3,4-d][1,2,4]triazin-1(8H)-one methanesulfonate TLC: Rf 0.40 (chloroform:methanol=9:1);
NMR (DMSO-d$_6$): δ 10.61 (br-s, 1H), 7.42 (m, 1H), 7.29-7.16 (m, 3H), 4.45 (d, J=13.8 Hz, 1H), 4.21 (dd, J=12.0, 2.4 Hz, 1H), 4.11 (dd, J=13.8, 2.4 Hz, 1H), 3.21 (m, 1H), 2.88 (m, 1H), 2.32 (s, 3H), 2.08 (m, 1H), 1.78 (m, 1H).

EXAMPLE 6(11)

4-(3-amino-4-methylphenyl)-6,7-dihydro[1,4]thiazino[4,3-d][1,2,4]triazin-1(2H)-one methanesulfonate TLC: Rf 0.38 (methanol:methylene chloride=1:10);
NMR (DMSO-d$_6$): δ 10.88 (s, 1H), 8.30 (s, 1H), 7.26 (d, J=7.8 Hz, 1H), 7.09 (s, 1H), 7.04 (d, J=7.8 Hz, 1H), 6.25 (s, 1H), 3.61 (m, 2H), 3.16 (m, 2H), 2.32 (s, 3H), 2.24 (s, 3H).

EXAMPLE 6(12)

4-(3-amino-4-methylphenyl)-6,7,9,9a-tetrahydro[1,4]thiazino[4,3-d][1,2,4]triazin-1(2H)-one Methanesulfonate TLC: Rf 0.42 (chloroform:methanol=9:1);
NMR (DMSO-d$_6$): δ 7.40-7.35 (m, 1H), 7.30-7.25 (m, 2H), 4.25 (dd, J=10.2, 3.6 Hz, 1H), 3.60-3.50 (m, 1H), 3.20-3.05 (m, 1H), 2.95-2.80 (m, 2H), 2.80-2.65 (m, 1H), 2.40-2.25 (m, 7H).

EXAMPLE 6(13)

4-(3-amino-5-fluorophenyl)-6,7,9,9a-tetrahydro[1,4]thiazino[4,3-d][1,2,4]triazin-1(2H)-one methanesulfonate TLC: Rf 0.37 (chloroform:methanol=9:1);
NMR (DMSO-d$_6$): δ 10.65 (brs, 1H), 6.55-6.40 (m, 3H), 4.21 (dd, J=10.2, 3.3 Hz, 1H), 3.64-3.54 (m, 1H), 3.14-3.02 (m, 1H), 2.94-2.78 (m, 2H), 2.76-2.64 (m, 1H), 2.40-2.30 (m, 4H).

EXAMPLE 6(14)

4-(2-methyl-5-aminophenyl)-6,7,9,9a-tetrahydro[1,4]thiazino[4,3-d][1,2,4]triazin-1(2H)-one TLC: Rf 0.40 (chloroform:methanol=9:1);
NMR (DMSO-d$_6$): δ 10.43 (s, 1H), 6.88 (d, J=8.1 Hz, 1H), 6.51 (dd, J=8.1, 2.4 Hz, 1H), 6.45 (brs, 1H), 4.20-4.12 (m, 1H), 3.40-3.26 (m, 1H), 3.06-2.94 (m, 1H), 2.90-2.70 (m, 2H), 2.58-2.46 (m, 1H), 2.34-2.22 (m, 1H), 2.02 (s, 3H).

EXAMPLE 6(15)

4-(4-aminophenyl)-6,7-dihydro[1,4]thiazino[4,3-d][1,2,4]triazin-1(2H)-one methanesulfonate TLC: Rf 0.39 (chloroform:methanol=9:1);
NMR (DMSO-$d_6$): δ 10.85 (brs, 1H), 7.40-7.32 (d, J=8.4 Hz, 2H), 7.12-7.05 (d, J=8.4 Hz, 2H), 6.24 (s, 1H), 3.64-3.58 (m, 2H), 3.20-3.12 (m, 2H), 2.34 (s, 3H).

EXAMPLE 6(16)

4-(2-methyl-3-aminophenyl)-6,7,9,9a-tetrahydro[1,4]thiazino[4,3-d][1,2,4]triazin-1(2H)-one methanesulfonate TLC: Rf 0.41 (chloroform:methanol=9:1);
NMR (DMSO-$d_6$): δ 7.35-7.27 (m, 2H), 7.20 (brs, 1H), 4.34-4.21 (m, 1H), 3.26-3.16 (m, 1H), 3.10-2.98 (m, 1H), 2.96-2.78 (m, 2H), 2.58-2.48 (m, 1H), 2.34 (s, 3H), 2.32-2.22 (m, 1H), 2.17 (s, 3H).

EXAMPLE 6(17)

4-(3-amino-4-methoxyphenyl)-6,7-dihydro[1,4]thiazino[4,3-d][1,2,4]triazin-1(2H)-one methanesulfonate TLC: Rf 0.53 (chloroform:methanol=9:1);
NMR (DMSO-$d_6$): δ 10.86 (s, 1H), 7.24-7.10 (m, 3H), 6.25 (s, 1H), 3.90 (s, 3H), 3.65-3.58 (m, 2H), 3.20-3.13 (m, 2H), 2.32 (s, 3H).

EXAMPLE 6(18)

4-(3-amino-4-hydroxyphenyl)-6,7-dihydro[1,4]thiazino[4,3-d][1,2,4]triazin-1(2H)-one TLC: Rf 0.14 (chloroform:methanol=9:1);
NMR (DMSO-$d_6$): δ 10.72 (s, 1H), 9.45 (brs, 1H), 6.66 (d, J=7.5 Hz, 1H), 6.60 (d, J=2.1 Hz, 1H), 6.42 (dd, J=7.5, 2.1 Hz, 1H), 6.19 (s, 1H), 4.70 (brs, 2H), 3.70-3.60 (m, 2H), 3.20-3.10 (m, 2H).

EXAMPLE 6(19)

4-3-aminobenzyl-6,7-dihydro[1,4]thiazino[4,3-d][1,2,4]triazin-1(2H)-one

TLC: Rf 0.29 (chloroform:methanol=9:1);
NMR (DMSO-$d_6$): δ 10.69 (s, 1H), 6.95 (dt, J=1.2, 7.2 Hz, 1H), 6.44-6.32 (m, 3H), 6.06 (s, 1H), 5.08 (s, 2H), 3.72-3.64 (m, 2H), 3.58 (s, 2H), 2.76-2.66 (m, 2H).

EXAMPLE 7

(7R,8aS)-7-hydroxy-4-(3-nitrophenyl)-6,7,8,8a-tetrahydropyrrolo[1,2-d][1,2,4]triazin-1(2H)-one To a solution of the compound prepared in Example 4(16a) (76 mg) in methylene chloride (0.5 mL) was added boron tribromide (2 mL; 1.0 M in methylene chloride) at −40° C. and the mixture was stirred for 1.5 hours. To the reaction mixture was added sodium hydrogen carbonate (ca 1 g). The reaction mixture was allowed to return to room temperature slowly and then brine was added to the reaction mixture, which was extracted with methylene chloride. The extract was dried over anhydrous magnesium sulfate and concentrated. The residue was purified by column chromatography on silica gel (chloroform:methanol=19:1→9:1) to give the compound of the present invention (57 mg) having the following physical data.

TLC: Rf 0.37 (chloroform:methanol=9:1);
NMR (DMSO-$d_6$): δ 10.69 (s, 1H), 8.30-8.27 (m, 2H), 7.99-7.96 (m, 1H), 7.76-7.71 (m, 1H), 5.21 (d, J=3.6 Hz, 1H), 4.22-4.13 (m, 2H), 3.40 (d, J=3.6 Hz, 2H), 2.17-2.12 (m, 2H).

EXAMPLE 8

(7R,8aS)-7-hydroxy-4-(3-aminophenyl)-6,7,8,8a-tetrahydropyrrolo[1,2-d][1,2,4]triazin-1(2H)-one methanesulfonate To a solution of the compound prepared in Example 4(16b) (188 mg) in methylene chloride (2 mL) was added aluminum trichloride (153 mg) and the mixture was stirred at room temperature overnight. Moreover, aluminum trichloride (151 mg) was added to the reaction mixture, which was stirred at room temperature for 7 hours. Sodium hydrogen carbonate (ca 1 g), small amount of water and methanol were added, sequentially, to the reaction mixture, which was stirred for 30 minutes. The reaction mixture was filtrated through Celite. The filtrate was concentrated. The residue was purified by column chromatography on silica gel (chloroform:methanol=19:1→9:1→4:1). To methanol (1 mL) was added the obtained solid and thereto was added a solution of methanesulfonic acid (42 mg) in methanol (1 mL). The mixture was stirred at room temperature for 10 minutes. The reaction mixture was concentrated to give the compound of the present invention (147 mg) having the following physical data.

TLC: Rf 0.17 (chloroform:methanol=9:1);
NMR (DMSO-$d_6$): δ 10.90-10.62 (br, 1H), 7.44 (t, J=7.8 Hz, 1H), 7.34-7.21 (m, 3H), 4.24-4.16 (m, 2H), 3.44 (dd, J=10.5, 2.4 Hz, 1H), 3.39 (dd, J=10.5, 4.8 Hz, 1H), 2.32 (s, 3H), 2.16-2.12 (m, 2H).

EXAMPLE 9

4-(3-aminomethylphenyl)-6,7,9,9a-tetrahydro[1,4]thiazino[4,3-d][1,2,4]triazin-1(2H)-one methanesulfonate To a solution of 4-((3-chloromethylphenyl)carbonothioyl)thiomorpholine-3-carboxylic acid ethyl ester (131 mg, It was prepared by the same procedure as described in Reference example 2→Reference example 3, using 3-chloromethylbenzoyl chloride instead of 3-nitrobenzoyl chloride) in dimethylformamide (1.5 mL) was added phthalimide potassium salt (70 mg) and the mixture was stirred at room temperature overnight. Water was added to the reaction mixture, which was extracted with a mixed solvent (hexane:ethyl acetate=1:1). The extract was washed with water and brine sequentially, dried over anhydrous sodium sulfate and concentrated. To a solution of the obtained solid in ethanol (2 mL) was added hydrazine monohydrate (92 μL) and the mixture was refluxed for 1 hour. After cooling the reaction mixture to room temperature, the precipitate was separated by filtration and the filtrate was concentrated. The precipitate and the residue were purified by column chromatography on silica gel (chloroform:methanol:water=8:2:0.2), respectively. To the obtained solid was added a solution of methanesulfonic acid in methanol (1M, 0.11 mL) and the mixture was concentrated. To the obtained residue was added ethyl acetate and the precipitate was separated by filtration. The precipitate was dried under reduced pressure to give the compound of the present invention (40 mg) having the following physical data.

TLC: Rf 0.11 (methylene chloride:methanol=10:1);

NMR (DMSO-$d_6$): δ 10.59 (s, 1H), 8.14 (br, 3H), 7.60-7.40 (m, 41), 4.25 (t, J=6.6 Hz, 1H), 4.12-4.02 (m, 2H), 3.52 (m, 1H), 3.12 (m, 1H), 2.88-2.83 (m, 2H), 2.72 (m, 1H), 2.30 (m, 1H), 2.28 (s, 3H).

EXAMPLE 10

4-(3-amino-4-fluorophenyl)-6,7-dihydro[1,4]thiazino[4,3-d][1,2,4]triazin-1(2H)-one By the same procedure as described in Reference example 2→Example 6→Reference example 3→Example 3 using 3,4-dihydro-2H-1,4-thiazine-5-carboxylic acid ethyl ester instead of thiomorpholin-3-ylcarboxylic acid ethyl ester, and 3-nitro-4-fluorobenzoyl chloride instead of 3-nitrobenzoyl chloride, the compound of the present invention having the following physical data.

TLC: Rf 0.41 (methanol:methylene chloride=1:10);

NMR (DMSO-$d_6$): δ 10.81 (s, 1H), 7.04 (dd, J=11.4, 7.8 Hz, 1H), 6.79 (d, J=7.8 Hz, 1H), 6.55 (m, 1H), 6.22 (s, 1H), 5.34 (s, 2H), 3.61 (m, 2H), 3.12 (m, 2H).

EXAMPLE 11

8-phenyl-2,3,4,6-tetrahydropyrido[2,3-d]pyridazin-5(1H)-one

Under an atmosphere of hydrogen, a mixture of 8-phenylpyrido[2,3-d]pyridazin-5(6H)-one (100 mg; It was prepared by the same procedure as described in Reference example 1→Example 1 using furo[3,4-b]pyridine-5,7-dione instead of 4,5,6,7-tetrahydro-2-benzofuran-1,3-dione, and phenylmagnesium chloride instead of 3-(bis(trimethylsilyl)amino)phenylmagnesium chloride), platinum(IV)oxide (10 mg), 1N hydrochloric acid (0.5 mL) and dimethylformamide (5 mL) was stirred at room temperature for 6 hours. The reaction mixture was filtrated through Celite. The filtrate was concentrated. The residue was diluted with ethyl acetate. The diluted solution was washed with a saturated aqueous sodium hydrogen carbonate solution and brine sequentially, dried over anhydrous sodium sulfate and concentrated. The residue was recrystallized from ethanol to give the compound of the present invention (42 mg) having the following physical data. Moreover, the compound was converted to a corresponding salt thereof by conventional method.

Free Form:

TLC: Rf 0.43 (chloroform:methanol=9:1);

NMR (DMSO-$d_6$): δ 12.11 (br-s, 1H), 7.52-7.40 (m, 5H), 5.72 (br-s, 1H), 3.13 (m, 2H), 2.39 (t, J=6.6 Hz, 2H), 1.72 (m, 2H).

Hydrochloride:

TLC: Rf 0.40 (chloroform:methanol=8:1);

NMR (DMSO-$d_6$): δ 12.41 (brs, 1H), 7.52-7.40 (m, 5H), 5.88 (brs, 2H), 3.16 (t, J=5.4 Hz, 2H), 2.43 (t, J=6.3 Hz, 2H), 1.73 (tt, J=6.3, 5.4 Hz, 2H).

Methanesulfonate:

TLC: Rf 0.39 (chloroform:methanol=8:1);

NMR (DMSO-$d_6$): δ 12.37 (s, 1H), 7.54-7.40 (m, 5H), 4.53 (brs, 2H), 3.22-3.08 (m, 2H), 2.42 (t, J=6.0 Hz, 2H), 2.35 (s, 3H), 1.82-1.64 (m, 2H).

EXAMPLE 11(1) TO EXAMPLE 11(4)

By the same procedure as described in Example 11, if necessary, by converting to corresponding salts by conventional method, using a corresponding derivative instead of 8-phenylpyrido[2,3-d]pyridazin-5(6H)-one, the following compounds of the present invention were obtained.

EXAMPLE 11(1)

4-phenyl-5,6,7,8-tetrahydropyrido[3,4-d]pyridazin-1(2H)-one methanesulfonate

TLC: Rf 0.30 (chloroform:methanol=9:1);

NMR (DMSO-$d_6$): δ 13.30 (s, 1H), 8.94 (br-s, 2H), 7.55-7.43 (m, 5H), 4.00 (s, 2H), 3.37 (t, J=6.0 Hz, 2H), 2.74 (t, J=6.0 Hz, 2H), 2.30 (s, 3H).

EXAMPLE 11(2)

1-phenyl-5,6,7,8-tetrahydropyrido[3,4-d]pyridazin-4(3H)-one

TLC: Rf 0.29 (chloroform:methanol=9:1);

NMR (DMSO-$d_6$): δ 12.93 (br-s, 1H), 7.52-7.40 (m, 5H), 3.61 (br-s, 2H), 2.79 (t, J=5.7 Hz, 2H), 2.32 (m, 2H).

EXAMPLE 11(3)

5-phenyl-1,3,4,7-tetrahydropyrido[2,3-d]pyridazin-8(2H)-one

TLC: Rf 0.49 (chloroform:methanol=9:1);

NMR (DMSO-$d_6$): δ 12.51 (br-s, 1H), 7.50-7.36 (m, 5H), 6.69 (br-s, 1H), 3.27 (m, 2H), 2.39 (t, J=5.7 Hz, 2H), 1.67 (m, 2H).

EXAMPLE 11(4)

8-(3-aminophenyl)-2,3,4,6-tetrahydropyrido[2,3-d]pyridazin-5(1H)-one

Hydrochloride:

TLC: Rf 0.40 (methylene chloride:methanol=9:1);

NMR (DMSO-$d_6$): δ 1.73 (m, 2 H) 2.41 (t, J=6.04 Hz, 2 H) 3.14 (m, 2 H) 5.92 (br. s., 1 H) 7.37 (m, 3 H) 7.52 (m, 1 H) 12.23 (br. s., 1 H).

Dihydrochloride:

TLC: Rf 0.33 (chloroform:methanol=8:1);

NMR (DMSO-$d_6$): δ 12.60 (brs, 1H), 7.64-7.42 (m, 4H), 6.07 (br, 4H), 3.24-3.08 (m, 2H), 2.44 (t, J=6.0 Hz, 2H), 1.84-1.64 (m, 2H).

REFERENCE EXAMPLE 4

6-methoxymethyl-8-phenylpyrido[2,3-d]pyridazin-5(6H)-one

After washing sodium hydride (103 mg; 62.6% in oil) with hexane, the mixture was suspended in dimethylformamide (1.5 mL). A solution of 8-phenylpyrido[2,3-d]pyridazin-5(6H)-one (200 mg; It was prepared by the same procedure as described in Reference example 1→Example 1 using furo[3,4-b]pyridine-5,7-dione instead of 4,5,6,7-tetrahydro-2-benzofuran-1,3-dione, and phenylmagnesium chloride instead of 3-(bis(trimethylsilyl)amino)phenylmagnesium chloride) in dimethylformamide (5.7 mL) was added dropwise to the suspension at 0° C. The mixture was stirred at room temperature for 40 minutes. Methoxymethyl chloride (0.27 mL) was added dropwise to the reaction mixture, which was stirred at room temperature overnight. The reaction mixture was concentrated. The obtained residue was diluted in a mixed solvent of water and ethyl acetate. The mixture was poured in a saturated aqueous sodium hydrogen carbonate solution and extracted with ethyl acetate. The extract was washed with brine, dried over anhydrous magnesium sulfate and concentrated to give the title compound (269 mg) having the following physical data. The obtained compound was used in next reaction without purification.

TLC: Rf 0.78 (chloroform:methanol=8:1).

REFERENCE EXAMPLE 5

6-methoxymethyl-8-phenyl-2,3,4,6-tetrahydropyrido[2,3-d]pyridazin-5(1H)-one

Under an atmosphere of argon, to platinum oxide (70 mg) was added dimethylformamide (1.0 mL). A solution of the compound prepared in Reference example 4 (269 mg) in dimethylformamide (8.0 mL) was added dropwise to the reaction mixture and 1N hydrochloric acid (0.9 mL) was added thereto. Under an atmosphere of hydrogen, the mixture was stirred at room temperature for 4 hours. Under an atmosphere of argon, the reaction mixture was filtrated through Celite. The filtrate was concentrated. The residue was purified by column chromatography on silica gel (methylene chloride:methanol=40:1→30:1) to give the title compound (224 mg) having the following physical data.

TLC: Rf 0.16 (hexane:ethyl acetate=1:1);
NMR (DMSO-$d_6$): δ 7.56-7.40 (m, 5H), 5.92 (brs, 1H), 5.23 (s, 2H), 3.29 (s, 3H), 3.20-3.06 (m, 2H), 2.43 (t, J=6.0 Hz, 2H), 1.84-1.64 (m, 2H).

REFERENCE EXAMPLE 6

6-methoxymethyl-1-methyl-8-phenyl-2,3,4,6-tetrahydropyrido[2,3-d]pyridazin-5(1H)-one After washing sodium hydride (141 mg; 62.6% in oil) with hexane, the mixture was suspended in dimethylformamide (1.0 mL). A solution of the compound prepared in Reference example 5 (200 mg) in dimethylformamide (6.4 mL) was added dropwise thereto at 0° C. and the mixture was stirred at room temperature for 1 hour. Methyl iodide (0.37 mL) was added dropwise to the reaction mixture, which was stirred at room temperature overnight. After adding water to the reaction mixture, it was poured in ice water and extracted with ethyl acetate. The extract was washed with brine, dried over anhydrous magnesium sulfate and concentrated. The residue was purified by column chromatography on silica gel (methylene chloride:methanol=100:1→50:1) to give the title compound (116 mg) having the following physical data.

TLC: Rf 0.23 (hexane:ethyl acetate=1:1).

EXAMPLE 12

1-methyl-8-phenyl-2,3,4,6-tetrahydropyrido[2,3-d]pyridazin-5(1H)-one 6N hydrochloric acid (2.4 mL) was added dropwise to a solution of the compound prepared in Reference example 6 (110 mg) in methanol (1.2 mL), which was stirred at room temperature overnight. 6N hydrochloric acid (2.4 mL) was added dropwise to the reaction mixture, which was stirred at 110° C. overnight. After cooling the reaction mixture to room temperature, it was poured in cold water. After neutralizing with 5N sodium hydroxide solution, the solution was extracted with ethyl acetate. The extract was washed with brine, dried over anhydrous magnesium sulfate and concentrated. The residue was washed with ethyl acetate to give the compound of the present invention (39 mg) having the following physical data.

TLC: Rf 0.44 (chloroform:methanol=4:1);
NMR (DMSO-$d_6$): δ 12.50 (s, 1H), 7.58-7.34 (m, 5H), 3.12-3.00 (m, 2H), 2.41 (t, J=6.0 Hz, 2H), 2.27 (s, 3H), 1.84-1.66 (m, 2H).

REFERENCE EXAMPLE 7

N-methyl-N-methoxy-1-t-butoxycarbonylpiperidine-2-carboxamide

To a solution of 1-t-butoxycarbonylpiperidine-2-carboxylic acid (2.29 g) in methylene chloride (30 mL) were added N,O-dimethylhydroxyamine hydrochloride (1.17 g), benzotriazol-1-yloxy-tris(dimethylamino)phosphoniumhexafluorophosphate (4.87 g, BOP reagent) and triethylamine (4.88 mL) and the mixture was stirred at room temperature overnight. The reaction mixture was concentrated. The residue was diluted with ethyl acetate. The diluted solution was washed water, 1N hydrochloric acid, water, a saturated aqueous sodium hydrogen carbonate solution and brine sequentially, dried over anhydrous sodium sulfate and concentrated to give the title compound (2.59 g) having the following physical data.

TLC: Rf 0.54 (hexane:ethyl acetate=3:1);
NMR (CDCl$_3$): δ 5.30-4.86 (m, 1H), 4.06-3.84 (m, 1H), 3.77 (br-s, 3H), 3.56-3.36 (m, 1H), 3.19 (s, 3H), 2.04-1.96 (m, 1H), 1.76-1.32 (m, 14H).

REFERENCE EXAMPLE 8

2-benzoylpiperidine-1-carboxylic acid t-butyl ester

A solution of phenyllithium in cyclohexane-ether (1.06 M, 6.23 mL) was added dropwise to a solution of the compound prepared in Reference example 7 (1.63 g) in tetrahydrofuran (30 mL) at −25° C. and the mixture was stirred at −25° C. for 3 hours. The reaction mixture was poured in 1M sodium dihydrogen phosphate solution and extracted with ethyl acetate. The extract was washed with water and brine sequentially, dried over anhydrous sodium sulfate and concentrated. The residue was purified by column chromatography on silica gel (hexane:ethyl acetate=9:1) to give the title compound (850 mg) having the following physical data.

TLC: Rf 0.56 (hexane:ethyl acetate=4:1);
NMR (CDCl$_3$): δ 7.96-7.84 (m, 2H), 7.66-7.40 (m, 3H), 5.70-5.44 (m, 1H), 4.04-3.86 (m, 1H), 3.30-3.08 (m, 1H), 2.20-1.98 (m, 1H), 1.92-1.76 (m, 1H), 1.74-1.20 (m, 13H).

REFERENCE EXAMPLE 9

2-benzoylpiperidine hydrochloride

To the compound prepared in Reference example 8 (270 mg) was added 4N hydrogen chloride-ethyl acetate solution (4 mL) and the mixture was stirred at room temperature for 15 minutes. The reaction mixture was concentrated to give the title compound (211 mg) having the following physical data.

TLC: Rf 0.48 (chloroform:methanol:acetic acid=40:10:1);

NMR (DMSO-d$_6$): δ 9.02 (br-s, 2H), 8.05 (m, 2H), 7.75 (m, 1H), 7.61 (m, 2H), 5.09 (dd, J=12.0, 3.0 Hz, 1H), 2.97 (m, 1H), 2.09 (m, 1H), 1.82-1.58 (m, 4H), 1.44 (m, 1H).

EXAMPLE 13

1-phenyl-3,6,7,8,9,9a-hexahydro-4H-pyrido[1,2-d][1,2,4]triazin-4-one (compound a) and 1-phenyl-3,6,7,8-tetrahydro-4H-pyrido[1,2-d][1,2,4]triazin-4-one (compound b)

The compound prepared in Reference example (199 mg) was separated with ethyl acetate and a saturated aqueous sodium hydrogen carbonate solution and the water layer was extracted with ethyl acetate. The combined organic layer was washed with brine, dried over anhydrous sodium sulfate and concentrated. The obtained powder was dissolved in toluene (10 mL). Thereto were added hydrazine carboxylic acid ethyl ester (184 mg) and p-toluenesulfonic acid monohydrate (8.4 mg) and the mixture was refluxed overnight. After cooling the reaction mixture to room temperature, it was diluted in ethyl acetate. The diluted solution was washed with 1N hydrochloric acid, water and brine sequentially, dried over anhydrous sodium sulfate and concentrated. The residue was purified by column chromatography on silica gel (hexane:ethyl acetate=2:1→1:1). The more polar fraction was recrystallized from ethyl acetate to give the compound a (16.3 mg) having the following physical data. The less polar fraction was recrystallized from a mixed solution of ethyl acetate and hexane (1:1) to give the compound b (13.6 mg) having the following physical data.

Compound a:
TLC: Rf 0.30 (hexane:ethyl acetate=1:1);
NMR (DMSO-d$_6$): δ 10.14 (s, 1H), 7.76-7.66 (m, 2H), 7.46-7.34 (m, 3H), 4.77 (dd, J=11.7, 2.7 Hz, 1H), 4.18 (m, 1H), 2.72 (m, 1H), 1.88-1.34 (m, 6H).

Compound b:
TLC: Rf 0.46 (hexane:ethyl acetate=1:1);
NMR (DMSO-d$_6$): δ 10.74 (s, 1H), 7.56-7.34 (m, 5H), 4.82 (t, J=4.5 Hz, 1H), 3.64 (m, 2H), 2.10 (m, 2H), 1.71 (m, 2H).

EXAMPLE 14

1-phenyl-3,8,9,9a-tetrahydro-4H-[1,3]thiazino[3,4-d][1,2,4]triazin-4-one

By the same procedure as described in Reference example 7→Reference example 8→Reference example 9→Example 13 using 3-t-butoxycarbonyl-1,3-thiazinane-4-carboxylic acid instead of 1-t-butoxycarbonylpiperidine-2-carboxylic acid, the compound of the present invention having the following physical data was obtained.
TLC: Rf 0.48 (hexane:ethyl acetate=1:1);
NMR (DMSO-d$_6$): δ 10.42 (s, 1H), 7.75-7.70 (m, 2H), 7.46-7.38 (m, 3H), 5.10 (dd, J=11.4, 2.7 Hz, 1H), 4.90 (dd, J=13.2, 2.7 Hz, 1H), 4.34 (d, J=13.2 Hz, 1H), 3.36 (m, 1H), 2.75 (m, 1H), 1.88-1.62 (m, 2H).

REFERENCE EXAMPLE 10

((E)-3-oxo-4,5,6,7-tetrahydro-2-benzofuran-1(3H)-ylidene)acetic acid methyl ester A solution of 3,4,5,6-tetrahydrophthalic acid anhydride (3.04 g) and (triphenylphosphoranylidene)acetic acid methyl ester (6.69 g) in chloroform (50.0 mL) was refluxed for 3 hours. After cooling the reaction mixture to room temperature, it was concentrated. The residue was purified by column chromatography on silica gel (ethyl acetate:hexane=1:9→3:7) to give the title compound (1.93 g) having the following physical data.
TLC: Rf 0.71 (ethyl acetate:hexane=1:1);
NMR (CDCl$_3$): δ 5.92 (s, 1H), 3.76 (s, 3H), 2.81 (m, 2H), 2.38 (m, 2H), 1.76 (m, 4H).

EXAMPLE 15

4-methoxycarbonylmethyl-5,6,7,8-tetrahydro-phthalazin-1(2H)-one

A solution of the compound prepared in Reference example 10 (1.04 g) and hydrazine monohydrate (250 mg) in ethanol (10.0 mL) was refluxed for 18 hours. After cooling the reaction mixture to room temperature, it was concentrated. The obtained crystal was washed with ethanol and ethyl acetate, and dried under reduced pressure to give the compound of the present invention (672 mg) having the following physical data.
TLC: Rf 0.45 (methanol:methylene chloride=1:9);
NMR (DMSO-d$_6$): δ 12.66 (brs, 1H), 3.65 (s, 2H), 3.63 (s, 3H), 2.38 (m, 4H), 1.64 (m, 4H).

EXAMPLE 16

4-(1-ethoxycarbonylethyl)-5,6,7,8-tetrahydro-phthalazin-1(2H)-one

By the same procedure as described in Reference example 10→Example 15 using 2-(triphenylphosphoranylidene)propanoic acid ethyl ester instead of (triphenylphosphoranylidene)acetic acid methyl ester, the compound of the present invention having the following physical data was obtained.
TLC: Rf 0.56 (methanol:methylene chloride=1:10);
NMR (DMSO-d$_6$): δ 12.67 (brs, 1H), 4.07 (q, J=6.9 Hz, 2H), 3.91 (q, J=6.9 Hz, 1H), 2.48-2:33 (m, 4H), 1.65 (m, 4H), 1.33 (d, J=6.9 Hz, 3H), 1.13 (t, J=6.9 Hz, 3H).

REFERENCE EXAMPLE 11

4-carboxymethyl-5,6,7,8-tetrahydrophthalazin-1(2H)-one 5N sodium hydroxide solution (1.72 mL) was added dropwise to a suspension of the compound prepared in Example 15 (635 mg) in methanol (10.0 mL) in ice bath and the mixture was stirred at room temperature for 3 hours. The reaction mixture was concentrate. 2N hydrochloric acid was added to the residue, which was adjusted to pH 2. The deposited crystal was collected by filtration. It was washed with hexane and dried under reduced pressure to give the title compound (478 mg) having the following physical data.
TLC: Rf 0.62 (methanol:methylene chloride:acetic acid=2:8:0.1);
NMR (DMSO-d$_6$): δ 12.62 (brs, 2H), 3.54 (s, 2H), 2.39 (m, 4H), 1.64 (m, 4H).

REFERENCE EXAMPLE 11(1)

4-(1-carboxyethyl)-5,6,7,8-tetrahydrophthalazin-1(2H)-one

By the same procedure as described in Reference example 11 using the compound prepared in Example 16 instead of the compound prepared in Example 15, the title compound having the following physical data was obtained.
TLC: Rf 0.28 (methanol:methylene chloride=1:4);
NMR (DMSO-$d_6$): δ 12.64 (s, 1H), 12.48 (brs, 1H), 3.81 (q, J=7.5 Hz, 1H), 2.48-2.37 (m, 4H), 1.65 (brs, 4H), 1.32 (d, J=7.5 Hz, 3H).

EXAMPLE 17 TO EXAMPLE 17(1)

By the same procedure as described in Reference example 10→Example 15→Example 11, if necessary, by converting to corresponding salts by conventional method, using a corresponding derivative instead of 4,5,6,7-tetrahydro-2-benzofuran-1,3-dione, and (triphenylphosphoranylidene)acetic acid ethyl ester instead of (triphenylphosphoranylidene)acetic acid methyl ester, the following compounds of the present invention were obtained.

EXAMPLE 17

8-ethoxycarbonylmethyl-2,3,4,6-tetrahydropyrido[2,3-d]pyridazin-5(1H)-one

TLC: Rf 0.46 (chloroform:methanol=9:1);
NMR (DMSO-$d_6$): δ 11.88 (br-s, 1H), 6.32 (br-s, 1H), 4.07 (q, J=7.2 Hz, 2H), 3.54 (s, 2H), 3.15 (m, 2H), 2.33 (t, J=6.3 Hz, 2H), 1.69 (m, 2H), 1.18 (t, J=7.2 Hz, 3H).

EXAMPLE 17(1)

5-ethoxycarbonylmethyl-1,3,4,7-tetrahydropyrido[2,3-d]pyridazin-8(2H)-one hydrochloride TLC: Rf 0.48 (chloroform:methanol=9:1);
NMR (DMSO-$d_6$): δ 12.60 (br-s, 1H), 4.10 (q, J=7.2 Hz, 2H), 3.75 (br-s, 2H), 3.28 (m, 2H), 2.45 (m, 2H), 1.77 (m, 2H), 1.18 (t, J=7.2 Hz, 3H).

REFERENCE EXAMPLE 12

4-(2-hydroxyethyl)-5,6,7,8-tetrahydrophthalazin-1(2H)-one

The compound prepared in Example 15 (350 mg) was dissolved in tetrahydrofuran (8.0 mL). Under an atmosphere of argon, sodium borohydride (239 mg) was added thereto at 0° C. and the mixture was refluxed for 13 hours. After cooling to 0° C., 1N hydrochloric acid was added to the reaction mixture, which was adjusted to pH 5. The deposited solid was collected by filtration. The filtrate was concentrated and extracted with chloroform. The extract was dried over anhydrous magnesium sulfate and concentrated to give the title compound having the following physical data.
TLC: Rf 0.32 (chloroform:methanol=9:1);
NMR (CD$_3$OD): δ 3.87 (t, J=6.6 Hz, 2H), 2.80 (t, J=6.6 Hz, 2H), 2.64-2.58 (m, 2H), 2.54-2.48 (m, 2H), 1.88-1.70 (m, 4H).

REFERENCE EXAMPLE 13

4-(2-chloroethyl)-5,6,7,8-tetrahydrophthalazin-1(2H)-one

To a solution of the compound prepared in Reference example 12 g (2.47 g) and pyridine (201 mg) in methylene chloride (60 mL) was added thionyl chloride (2.25 g) and the mixture was stirred at room temperature for 20 hours. Chloroform and a saturated aqueous sodium hydrogen carbonate solution were added to the reaction mixture, which was separated. The organic layer was washed with a saturated aqueous sodium hydrogen carbonate solution, water and brine sequentially, dried over anhydrous magnesium sulfate and concentrated to give the title compound (2.58 g) having the following physical data.
TLC: Rf 0.52 (chloroform:methanol=9:1);
NMR (CD$_3$OD): δ 3.88 (t, J=7.2 Hz, 2H), 3.05 (t, J=7.2 Hz, 2H), 2.60-2.50 (m, 4H), 1.85-1.70 (m, 4H).

REFERENCE EXAMPLE 14

4-(2-azidoethyl)-5,6,7,8-tetrahydrophthalazin-1(2H)-one

A solution of the compound prepared in Reference example 13 (106 mg), trimethylsilylazide (86.4 mg) and tetrabutylammonium fluoride (237 mg) in tetrahydrofuran (2.00 mL) was refluxed for 24 hours. The reaction mixture was concentrated. The residue was purified by column chromatography on silica gel (ethyl acetate:hexane=1:1) to give the title compound (85.0 mg) having the following physical data.
TLC: Rf 0.52 (ethyl acetate:hexane=4:1);
NMR (DMSO-$d_6$): δ 12.62 (brs, 1H), 3.63 (t, J=6.9 Hz, 2H), 2.79 (t, J=6.9 Hz, 2H), 2.48-2.37 (m, 4H), 1.67 (m, 4H).

REFERENCE EXAMPLE 15

4-(2-aminoethyl)-5,6,7,8-tetrahydrophthalazin-1(2H)-one hydrochloride

Under an atmosphere of hydrogen, a suspension of the compound prepared in Reference example 14 (50.0 mg) and 5% palladium on calcium carbonate (20.0 mg) in ethanol (3.0 mL) was stirred at room temperature for 6 hours. The reaction mixture was filtrated through Celite. The filtrate was concentrated. 4N hydrogen chloride-ethyl acetate solution (0.5 mL) was added dropwise to a solution of the obtained solid (44.0 mg) in methanol (3.0 mL) and the mixture was stirred at room temperature for 1 hour. The reaction mixture was concentrated. The residue was recrystallized from a mixed solvent of methanol and ethyl acetate to give the title compound (45.9 mg) having the following physical data.
TLC: Rf 0.39 (methanol:methylene chloride:saturated aqueous ammonia=1:4:0.1);
NMR (DMSO-$d_6$): δ 12.65 (s, 1H), 8.07 (brs, 3H), 3.07 (m, 2H), 2.83 (t, J=7.2 Hz, 2H), 2.44 (m, 2H), 2.38 (m, 2H), 1.66 (m, 4H).

REFERENCE EXAMPLE 16

4-(2-cyanoethyl)-5,6,7,8-tetrahydrophthalazin-1(2H)-one

To a suspension of the compound prepared in Reference example 13 (500 mg) in tetrahydrofuran (12 mL) were added trimethylsilyl cyanide (0.94 mL) and tetrabutylammonium fluoride (1.84 g) and the mixture was stirred at 80° C. overnight. After cooling to room temperature, the reaction mixture was poured in a cold saturated aqueous ammonium chloride solution and extracted with ethyl acetate. The extracted was washed with brine, dried over anhydrous magnesium sulfate and concentrated. The residue was purified by column chromatography on silica gel (methylene chloride:methanol=20:1). The obtained solid was washed with t-butyl methyl ether to give the title compound (249 mg) having the following physical data.

TLC: Rf 0.52 (chloroform:methanol=8:1);

NMR (DMSO-$d_6$): δ 12.66 (s, 1H), 2.94-2.72 (m, 4H), 2.60-2.26 (m, 4H), 1.78-1.54 (m, 4H).

REFERENCE EXAMPLE 17

4-(2-carboxyethyl)-5,6,7,8-tetrahydrophthalazin-1(2H)-one

To a suspension of the compound prepared in Reference example 16 (130 mg) in ethanol (3.2 mL) was added 5N sodium hydroxide solution (0.64 mL) and the mixture was stirred at 90° C. for 1 day. After cooling to 0° C., the reaction mixture was poured in cold water and washed with ethyl acetate. The water layer was neutralized with 2N hydrochloric acid and concentrated. The residue was washed with water. The solid was washed water and ether to give the title compound (131 mg) having the following physical data.

TLC: Rf 0.36 (chloroform:methanol=4:1);

NMR (DMSO-$d_6$): δ 12.51 (s, 1H), 12.08 (brs, 1H), 2.71 (t, J=6.9 Hz, 2H), 2.56 (t, J=6.9 Hz, 2H), 2.54-2.26 (m, 4H), 1.78-1.54 (m, 4H).

EXAMPLE 18

3-(4-oxo-3,4,5,6,7,8-hexahydrophthalazin-1-yl)phenylsulfamic acid pyridine salt

To a suspension of the compound prepared in Example 1 (100 mg) in methylene chloride (1.5 mL) and dimethylformamide (1.5 mL) was added sulfur trioxide pyridine complex (144 mg) and the mixture was stirred at room temperature for 4 hours. The reaction mixture was concentrated. The residue was washed with ethyl acetate to give the compound of the present invention (160 mg) having the following physical data.

TLC: Rf 0.17 (chloroform:methanol=4:1);

NMR (CD$_3$OD): δ 8.90-8.78 (m, 2H), 8.59 (dddd, J=7.8, 7.8, 1.5, 1.5 Hz, 1H), 8.12-7.98 (m, 2H), 7.48-7.14 (m, 3H), 6.89 (m, 1H), 2.66-2.52 (m, 2H), 2.52-2.38 (m, 2H), 1.90-1.60 (m, 4H).

EXAMPLE 19

4-(3-amidinophenyl)-6,7,9,9a-tetrahydro[1,4]thiazino[4,3-d][1,2,4]triazin-1(2H)-one methanesulfonate To a solution of the compound prepared in Example 4(20) (127 mg) in dimethylformamide (3 mL) were added sodium hydrosulfide (215 mg) and magnesium chloride hexahydrate (474 mg) and the mixture was stirred at room temperature for 3 hours under an atmosphere of argon. To the reaction mixture was added ethyl acetate and the precipitate was separated by filtration. The filtrate was wash with water and brine sequentially, dried over anhydrous sodium sulfate and concentrated. To a solution of the obtained solid (277 mg) in acetone (2 mL) was added methyl iodide (0.15 mL) and the mixture was stirred at room temperature for 3 hours. The reaction mixture was concentrated. To the residue were added methanol (2 mL) and ammonium acetate (43 mg) and the mixture was refluxed for 2 hours. The reaction mixture was concentrated. The residue was purified by column chromatography on silica gel (chloroform:methanol:water=9:1:0.1→8:2:0.2). The obtained solid was washed with a mixed solvent of methanol, ethyl acetate and hexane and converted to methanesulfonate thereof by conventional method to give the compound of the present invention (149 mg) having the following physical data.

TLC: Rf 0.22 (methylene chloride:methanol=10:1);

NMR (DMSO-$d_6$): δ 10.68 (s, 1H), 9.36 (s, 2H), 9.02 (s, 2H), 7.86 (d, J=7.8 Hz, 1H), 7.84-7.77 (m, 2H), 7.69 (t, J=7.8 Hz, 1H), 4.26 (dd, J=8.7, 4.8 Hz, 1H), 3.50 (m, 1H), 3.16 (m, 1H), 2.95-2.84 (m, 2H), 2.71 (m, 1H), 2.366 and 2.362 (s, 3H), 2.30 (d, J=13.8 Hz, 1H).

EXAMPLE 20

4-(3-hydroxyphenyl)-6,7,9,9a-tetrahydro[1,4]thiazino[4,3-d][1,2,4]triazin-1(2H)-one To a solution of the compound prepared in Example 4(4) (175 mg) in methylene chloride (1.3 mL) was added boron tribromide (1.3 mL; 1.0 M in methylene chloride) in ice bath and the mixture was stirred at room temperature for 5 hours. To the reaction mixture was added boron tribromide (1.3 mL; 1.0 M in methylene chloride) and the mixture was stirred at room temperature overnight. Methanol was added to the reaction mixture, which was concentrated. The residue was washed with methylene chloride. Water was added thereto and the mixture was extracted with ethyl acetate. The extract was washed with brine, dried over anhydrous magnesium sulfate and concentrated. The residue was recrystallized from acetonitrile to give the compound of the present invention (73 mg) having the following physical data.

TLC: Rf 0.43 (chloroform:methanol=9:1);

NMR (DMSO-$d_6$): δ 10.47 (s, 1H), 9.67 (bs, 1H), 7.20 (t, J=7.8 Hz, 1H), 6.81-6.73 (m, 3H), 4.19 (dd, J=9.3, 3.9 Hz, 1H), 3.56 (dt, J=14.1, 3.0 Hz, 1H), 3.09-2.99 (m, 1H), 2.90-2.79 (m, 2H) 2.69-2.60 (m, 1H), 2.33-2.28 (m, 1H).

EXAMPLE 20(1) TO EXAMPLE 20(2)

By the same procedure as described in Example 20 using the compound prepared in Example 4(5) or 4(27) instead of the compound prepared in Example 4(4), the following compounds of the present invention were obtained.

EXAMPLE 20(1)

4-(4-hydroxyphenyl)-6,7,9,9a-tetrahydro[1,4]thiazino[4,3-d][1,2,4]triazin-1(2H)-one TLC: Rf 0.32 (chloroform:methanol=8:1);

NMR (DMSO-$d_6$): δ 9.74 (brs, 1H), 7.24-7.14 (m, 2H), 6.84-6.74 (m, 2H), 4.18 (dd, J=8.1, 5.1 Hz, 1H), 3.60 (dt, J=14.1, 2.7 Hz, 1H), 3.05 (m, 1H), 2.92-2.78 (m, 2H), 2.68 (m, 1H), 2.31 (m, 1H).

EXAMPLE 20(2)

4-(3-hydroxyphenyl)-6,7-dihydro[1,4]thiazino[4,3-d][1,2,4]triazin-1(2H)-one

TLC: Rf 0.40 (chloroform:methanol=9:1);

NMR (DMSO-$d_6$): δ 10.83 (s, 1H), 9.70 (s, 1H), 7.24 (t, J=7.8 Hz, 1H), 6.88-6.75 (m, 3H), 6.22 (s, 1H), 3.66-3.56 (m, 2H), 3.16-3.06 (m, 2H).

EXAMPLE 21

N-(3-(4-oxo-3,4,5,6,7,8-hexahydrophthalazin-1-yl)phenyl)ethanimidamide hydrobromide To a suspension of the compound prepared in Example 1 (60 mg) in ethanol (2.5 mL) was added 2-naphthylmethylethanimidothioate (74 mg) and the mixture was stirred at room temperature for 4 hours. Methanol (1.5 mL) and 2-naphthylmethylethanimidothioate (222 mg) were added to the reaction mixture, which was stirred at 75° C. overnight. After cooling to room temperature, the reaction mixture was concentrated. The residue was purified by column chromatography on silica gel (methylene chloride:methanol=20:1→6:1) to give the compound of the present invention (84 mg) having the following physical data.

TLC: Rf 0.24 (chloroform:methanol=4:1);

NMR (DMSO-$d_6$): δ 12.97 (s, 1H), 7.59 (dd, J=8.1, 8.1 Hz, 1H), 7.50 (m, 1H), 7.44-7.34 (m, 2H), 2.54-2.32 (m, 4H), 2.34 (s, 3H), 1.80-1.50 (m, 4H).

EXAMPLE 21(1) TO EXAMPLE 21(3)

By the same procedure as described in Example 21 using the compound prepared in Example 6, 6(5) or 11(4) instead of the compound prepared in Example 1, the following compounds of the present invention were obtained.

EXAMPLE 21(1)

N-(3-(1-oxo-1,2,6,7,9,9a-hexahydro[1,4]thiazino[4,3-d][1,2,4]triazin-4-yl)phenyl)ethanimidamide hydrobromide TLC: Rf 0.25 (chloroform:methanol:water=8:2:0.2);

NMR (DMSO-$d_6$): δ 11.13 (br, 1H), 10.60 (s, 1H), 9.43 (br, 1H), 8.56 (br, 1H), 7.59 (t, J=7.8 Hz, 1H), 7.47 (d, J=7.8 Hz, if), 7.38 (d, J=7.8 Hz, 1H), 7.36 (s, 1H), 4.24 (dd, J=9.6, 3.9 Hz, 1H), 3.63 (d, J=13.8 Hz, 1H), 3.10 (d, J=12.0 Hz, 1H), 2.96-2.82 (m, 2H), 2.72 (m, 1H), 2.32 (s, 3H), 2.29 (m, 1H).

EXAMPLE 21(2)

N-(3-(1-oxo-1,2,6,7-tetrahydro[1,4]thiazino[4,3-d][1,2,4]triazin-4-yl)phenyl)ethanimidamide hydrobromide TLC: Rf 0.24 (chloroform:methanol:water=8:2:0.2);

NMR (DMSO-$d_6$): δ 10.95 (s, 1H), 9.30 (br, 1H), 8.87 (br, 1H), 8.35 (br, 1H), 7.60 (m, 1H), 7.48 (m, 1H), 7.42-7.36 (m, 2H), 6.28 (s, 1H), 3.72-3.64 (m, 2H), 3.20-3.12 (m, 2H), 2.30(brs, 3H).

EXAMPLE 21(3)

N-(3-(5-oxo-1,2,3,4,5,6-hexahydropyrido[2,3-d]pyridazin-8-yl)phenyl)ethanimidamide TLC: Rf 0.14 (chloroform:methanol=4:1).

EXAMPLE 22

4-(3-methylaminophenyl)-6,7-dihydro[1,4]thiazino[4,3-d][1,2,4]triazin-1(2H)-one

To a suspension of the compound prepared in Example 6(5) (100 mg) in methanol (1.1 mL) were added a solution of sodium methylate in methanol (0.5 mL; 28% solution) and paraformaldehyde (32 mg) and the mixture was stirred at room temperature for 3 hours. Methanol (1.1 mL) and sodium borohydride (22 mg) were added to the reaction mixture, which was stirred at 75° C. for 1 hour. After cooling to room temperature, water was added to the reaction mixture, which was poured in cold water. The solution was concentrated. The residue was washed with a mixed solvent of methanol and methylene chloride and filtrated through Celite. The filtrate was concentrated. The residue was purified by column chromatography on silica gel (methylene chloride:methanol=15:1) to give the compound of the present invention (15 mg) having the following physical data.

TLC: Rf 0.44 (chloroform:methanol=8:1);

NMR (DMSO-$d_6$): δ 10.80 (s, 1H), 7.15 (dd, J=7.5, 7.5 Hz, 1H), 6.66-6.46 (m, 3H), 6.21 (s, 1H), 5.86 (q, J=4.8 Hz, 1H), 3.68-3.56 (m, 2H), 3.20-3.06 (m, 2H), 2.67 (d, J=4.8 Hz, 3H).

EXAMPLE 23

4-(N-(2-(N'-t-butoxycarbonylamino)ethyl)carbamoylmethyl)-5,6,7,8-tetrahydrophthalazin-1(2H)-one The mixture of the compound prepared in Reference example 11 (183 mg), triethylamine (178 mg), N-(2-aminoethyl)carbamic acid t-butyl ester (160 mg), 1-ethyl-3-(3-dimethylaminopropyl)carbodiimide hydrochloride (338 mg), 1-hydroxybenzotriazol (238 mg) and dimethylformamide (3.00 mL) was stirred at room temperature for 16 hours. The reaction mixture was concentrated. To the residue was added water and the deposited crystal was collected by filtration. It was washed with ethyl acetate and dried under reduced pressure to give the compound of the present invention (189 mg) having the following physical data.

TLC: Rf 0.50 (methylene chloride:methanol=9:1);

NMR (DMSO-$d_6$): δ 12.56 (s, 1H), 8.01 (brs, 1H), 6.77 (brs, 1H), 3.39 (s, 2H), 3.08-2.95 (m, 4H), 2.38 (m, 4H), 2.25 (m, 4H), 1.37 (s, 9H).

EXAMPLE 23(1) TO EXAMPLE 23(37)

By the same procedure as described in Example 23, if necessary, by converting to corresponding salts by conventional method, using the compound prepared in Example 11 or a corresponding carboxylic acid derivative, and N-(2-aminoethyl)carbamic acid t-butyl ester or a corresponding derivative, the following compounds of the present invention were obtained.

EXAMPLE 23(1)

4-N-(2-(morpholin-4-yl)ethyl)carbamoylmethyl)-5,6,7,8-tetrahydrophthalazin-1(2H)-one TLC: Rf 0.37 (methanol:methylene chloride=1:9);

NMR (DMSO-$d_6$): δ 12.60 (brs, 1H), 11.06 (brs, 1H), 8.45 (t, J=5.7 Hz, 1H), 3.95-3.77 (m, 4H), 3.47 (s, 2H), 3.43 (m, 4H), 3.18-3.02 (m, 4H), 2.37 (m, 4H), 1.64 (brs, 4H).

EXAMPLE 23(2)

4-(N-(2-(N',N'-dimethylamino)ethyl)carbamoylmethyl)-5,6,7,8-tetrahydrophthalazin-1(2H)-one Free Form:

TLC: Rf 0.60 (methanol:methylene chloride:saturated aqueous ammonia=1:4:0.1);

NMR (DMSO-$d_6$): δ 12.56 (brs, 1H), 7.94 (brt, J=6.2 Hz, 1H), 3.40 (s, 2H), 3.13 (td, J=6.2, 6.2 Hz, 2H), 2.43 (brs, 2H), 2.36 (brs, 2H), 2.26 (t, J=6.2 Hz, 2H), 2.12 (s, 6H), 1.63 (brs, 4H).

Hydrochloride:

TLC: Rf 0.69 (methanol:methylene chloride:saturated aqueous ammonia=2:8:0.1);

NMR (DMSO-$d_6$): δ 12.60 (s, 1H), 10.22 (brs, 1H), 8.39 (t, J=5.7 Hz, 1H), 3.41-2.98 (m, 4H), 2.24 (m, 8H), 2.48-2.36 (m, 4H), 1.64 (brs, 4H).

EXAMPLE 23(3)

4-(N-(3-(N'-t-butoxycarbonylamino)propyl)carbamoylmethyl)-5,6,7,8-tetrahydrophthalazin-1(2H)-one NMR (DMSO-$d_6$): δ 12.56 (s, 1H), 7.97 (t, J=5.1 Hz, 1H), 6.75 (m, 1H), 3.39 (s, 2H), 3.02 (q, J=6, 6 Hz, 2H), 2.90 (q, J=6.6 Hz, 2H), 2.46-2.33 (m, 4H), 1.68-1.58 (m, 4H), 1.55-1.44 (m, 2H), 1.36 (s, 9H).

EXAMPLE 23(4)

4-(N-(2-(N'-t-butoxycarbonyl-N'-methylamino)ethyl)carbamoylmethyl)-5,6,7,8-tetrahydrophthalazin-1(2H)-one TLC: Rf 0.59 (chloroform:methanol:water=8:2:0.2);

NMR (CDCl$_3$): δ 10.69 (br, 1H), 6.88 (br, 1H), 3.49 (s, 2H), 3.45-3.32 (m, 4H), 2.86 (s, 3H), 2.60-2.48 (m, 4H), 1.90-1.80 (m, 4H), 1.45 (s, 9H).

EXAMPLE 23(5)

4-N-(2-(pyrrolidin-1-yl)ethyl)carbamoylmethyl)-5,6,7,8-tetrahydrophthalazin-1(2H)-one hydrochloride TLC: Rf 0.24 (ethyl acetate:acetic acid:water=3:3:1);

NMR (DMSO-$d_6$): δ 12.60 (s, 1H), 10.46 (br, 1H), 8.39 (m, 1H), 3.61-3.50 (m, 2H), 3.47 (s, 2H), 3.40 (q, J=6.0 Hz, 2H), 3.17 (q, J=6.0 Hz, 2H), 3.04-2.90 (m, 2H), 2.50-2.34 (m, 4H), 2.04-1.90 (m, 2H), 1.90-1.80 (m, 2H), 1.70-1.60 (m, 4H).

EXAMPLE 23(6)

4-(2-hydroxyethoxycarbonylmethyl)-5,6,7,8-tetrahydrophthalazin-1(2H)-one

TLC: Rf 0.60 (chloroform:methanol:water=8:2:0.2);

NMR (DMSO-$d_6$): δ 12.66 (s, 1H), 4.80 (t, J=5.1 Hz, 1H), 4.07 (t, J=5.1 Hz, 2H), 3.66 (s, 2H), 3.55 (q, J=5.1 Hz, 2H), 2.45-2.34 (m, 4H), 1.70-1.60 (m, 4H).

EXAMPLE 23(7)

4-(N-(3-(N',N'-dimethylamino)propyl)carbamoylmethyl)-5,6,7,8-tetrahydrophthalazin-1(2H)-one hydrochloride TLC: Rf 0.12 (chloroform:methanol:water=7:3:0.3);

NMR (DMSO-$d_6$): δ 12.60 (s, 1H), 10.43 (br, 1H), 8.28 (m, 1H), 3.42 (s, 2H), 3.11 (q, J=6.0 Hz, 2H), 3.04-2.96 (m, 2H), 2.71 (s, 3H), 2.69 (s, 3H), 2.46-2.34 (m, 4H), 1.84-1.74 (m, 2H), 1.68-1.48 (m, 4H).

EXAMPLE 23(8)

4-(N-(3-(imidazol-1-yl)propyl)carbamoylmethyl)-5,6,7,8-tetrahydrophthalazin-1(2H)-one hydrochloride TLC: Rf 0.82 (chloroform:methanol:water=7:3:0.3);

NMR (DMSO-$d_6$): δ 14.64 (br, 1H), 12.60 (s, 1H), 9.17 (m, 1H), 8.39 (m, 1H), 7.81 (d, J=1.5 Hz, 1H), 7.68 (d, J=1.5 Hz, 1H), 4.22 (t, J=6.6 Hz, 2H), 3.44 (s, 2H), 3.03 (q, J=6.6 Hz, 2H), 2.46-2.32 (m, 4H), 1.93(quin, J=6.6 Hz, 2H), 1.68-1.46 (m, 4H).

EXAMPLE 23(9)

4-(1-(N-(2-(N'-t-butoxycarbonylamino)ethyl)carbamoyl)ethyl)-5,6,7,8-tetrahydrophthalazin-1(2H)-one TLC: Rf 0.44 (methanol:methylene chloride=1:10);

NMR (DMSO-$d_6$): δ 12.60 (s, 1H), 7.93 (t, J=5.1 Hz, 1H), 6.74 (brs, 1H), 3.66 (q, J=7.2 Hz, 1H), 3.05 (m, 2H), 2.96 (m, 2H), 2.48-2.30 (m, 4H), 1.63 (m, 4H), 1.36 (s, 9H), 1.30 (d, J=7.2 Hz, 3H).

EXAMPLE 23(10)

4-(N-(1-ethylpyrrolidin-2-ylmethyl)carbamoylmethyl)-5,6,7,8-tetrahydrophthalazin-1(2H)-one Hydrochloride TLC: Rf 0.59 (methanol:methylene chloride:saturated aqueous ammonia=2:8:0.1);

NMR (DMSO-$d_6$): δ 12.61 (s, 1H), 10.42 (brs, 1H), 8.56 (m, 1H), 3.58-2.96 (m, 9H), 2.42-2.36 (m, 4H), 2.08-1.64 (m, 8H), 1.24 (t, J=6.9 Hz, 3H).

EXAMPLE 23(11)

4-(N-(3-(morpholin-4-yl)propyl)carbamoylmethyl)-5,6,7,8-tetrahydrophthalazin-1(2H)-one TLC: Rf 0.48 (chloroform:methanol=4:1);

NMR (DMSO-$d_6$): δ 12.57 (s, 1H), 8.00 (brt, 1H), 3.64-3.48 (m, 4H), 3.46-3.18 (m, 6H), 3.14-2.96 (m, 2H), 2.50-2.14 (m, 6H), 1.74-1.44 (m, 6H).

EXAMPLE 23(12)

4-(N-(3-(pyrrolidin-1-yl)propyl)carbamoylmethyl)-5,6,7,8-tetrahydrophthalazin-1(2H)-one hydrochloride TLC: Rf 0.25 (chloroform:methanol:water=7:3:0.3);

NMR (DMSO-$d_6$): δ 12.59 (s, 1H), 10.59 (br, 1H), 8.25 (br, 1H), 3.52-3.38 (m, 4H), 3.17-3.00 (m, 4H), 2.98-2.84 (m, 2H), 2.46-2.32 (m, 4H), 2.00-1.75 (m, 6H), 1.69-1.58 (m, 4H).

EXAMPLE 23(13)

4-(N-(pyridin-3-yl)carbamoylmethyl)-5,6,7,8-tetrahydrophthalazin-1(2H)-one hydrochloride TLC: Rf 0.47 (methanol:methylene chloride=1:9);
NMR (DMSO-$d_6$): δ 12.67 (s, 1H), 11.31 (s, 1H), 9.12 (d, J=2.1 Hz, 1H), 8.55 (d, J=4.8 Hz, 1H), 8.43 (d, J=8.7 Hz, 1H), 7.86 (dd, J=8.7, 4.8 Hz, 1H), 3.78 (s, 2H), 2.48-2.39 (m, 4H), 1.65 (brs, 4H).

EXAMPLE 23(14)

4-(N-(2-(piperidin-1-yl)ethyl)carbamoylmethyl)-5,6,7,8-tetrahydrophthalazin-1(2H)-one hydrochloride TLC: Rf 0.53 (chloroform:methanol:water=7:3:0.3);
NMR (DMSO-$d_6$): δ 12.60 (s, 1H), 10.30 (br, 1H), 8.44 (br, 1H), 3.50-3.34 (m, 2H), 3.31 (s, 2H), 3.10-2.96 (br, 2H), 2.90-2.72 (br, 2H), 2.48-2.32 (m, 4H), 1.80-1.68 (br, 4H), 1.68-1.56 (br, 6H), 1.50-1.40 (br, 2H).

EXAMPLE 23(15)

4-(N-(2-(N',N'-dimethylamino)propyl)carbamoylmethyl)-5,6,7,8-tetrahydrophthalazin-1(2H)-one hydrochloride TLC: Rf 0.26 (chloroform:methanol:water=7:3:0.3);
NMR (DMSO-$d_6$): δ 12.60 (s, 1H), 10.40 (br, 1H), 8.32 (br, 1H), 3.48 (s, 2H), 3.42-3.12 (m, 3H), 2.58 (s, 6H), 2.46-2.32 (m, 4H), 1.68-1.58 (m, 4H), 1.12 (d, J=6.0 Hz, 3H).

EXAMPLE 23(16)

4-(N-(4-(N'-t-butoxycarbonylamino)butyl)carbamoylmethyl)-5,6,7,8-tetrahydrophthalazin-1(2H)-one NMR (CD$_3$OD): δ 8.12 (br, 1H), 6.59 (br, 1H), 3.54 (s, 2H), 3.23-3.15 (m, 2H), 3.08-2.98 (m, 2H), 2.56-2.47 (m, 4H), 1.82-1.74 (m, 4H), 1.56-1.46 (m, 4H), 1.42 (s, 9H).

EXAMPLE 23(17)

4-(N-(pyridin-2-yl)carbamoylmethyl)-5,6,7,8-tetrahydrophthalazin-1(2H)-one hydrochloride TLC: Rf 0.51 (methanol:methylene chloride=1:10);
NMR (DMSO-$d_6$): δ 12.64 (s, 1H), 11.08 (s, 1H), 8.33 (m, 1H), 7.97 (d, J=8.4 Hz, 1H), 7.87 (m, 1H), 7.18 (m, 1H), 3.77 (s, 2H), 2.45-2.38 (m, 4H), 1.65 (brs, 4H).

EXAMPLE 23(18)

4-(2-(N',N'-dimethylamino)ethoxycarbonylmethyl)-5,6,7,8-tetrahydrophthalazin-1(2H)-one Free Form:
TLC: Rf 0.51 (methylene chloride:methanol:water=8:2:0.2);
NMR (DMSO-$d_6$): δ 12.66 (s, 1H), 4.13 (t, J=5.7 Hz, 2H), 3.64 (s, 2H), 2.44 (t, J=5.7 Hz, 2H), 2.44-2.35 (m, 4H), 2.12 (s, 6H), 1.72-1.58 (m, 4H).

Hydrochloride:
TLC: Rf 0.51 (chloroform:methanol:water=8:2:0.2);
NMR (DMSO-$d_6$): δ 12.70 (s, 1H), 10.72 (br, 1H), 4.44-4.36 (m, 2H), 3.74 (s, 2H), 3.40-3.32 (m, 2H), 2.75 (s, 6H), 2.46-2.32 (m, 4H), 1.72-1.60 (m, 4H).

EXAMPLE 23(19)

4-(N-(2-(pyrrol-1-yl)ethyl)carbamoylmethyl)-5,6,7,8-tetrahydrophthalazin-1(2H)-one TLC: Rf 0.60 (chloroform:methanol:water=8:2:0.2);
NMR (DMSO-$d_6$): δ 12.57 (s, 1H), 8.11 (m, 1H), 6.69 (d, J=1.2 Hz, 2H), 5.96 (d, J=1,2 Hz, 2H), 3.92 (t, J=6.0 Hz, 2H), 3.38 (s, 2H), 3.35 (t, J=6.0 Hz, 2H), 2.40-2.24 (m, 4H), 1.68-1.58 (m, 4H).

EXAMPLE 23(20)

4-(N-(2-(imidazol-4-yl)ethyl)carbamoylmethyl)-5,6,7,8-tetrahydrophthalazin-1(2H)-one hydrochloride TLC: Rf 0.56 (chloroform:methanol:water=7:3:0.3);
NMR (DMSO-$d_6$): δ 12.56 (s, 1H), 8.10 (m, 1H), 7.73 (br, 1H), 6.86 (s, 1H), 3.39 (s, 2H), 3.34-3.23 (m, 2H), 2.74-2.62 (m, 2H), 2.40-2.30 (m, 4H), 1.66-1.56 (m, 4H).

EXAMPLE 23(21)

4-(1-(N-(4-(N'-t-butoxycarbonylamino)butyl)carbamoyl)ethyl)-5,6,7,8-tetrahydrophthalazin-1(2H)-one TLC: Rf 0.38 (methanol:methylene chloride=1:10);
NMR (DMSO-$d_6$): δ 12.59 (s, 1H), 7.93 (t, J=5.7 Hz, 1H), 6.77 (m, 1H), 3.66 (q, J=7.0 Hz, 1H), 3.01 (m, 2H), 2.88 (m, 2H), 2.48-2.26 (m, 4H), 1.63 (brs, 4H), 1.42-1.28 (m, 16H).

EXAMPLE 23(22)

4-(N-(pyridin-2-ylmethyl)carbamoylmethyl)-5,6,7,8-tetrahydrophthalazin-1(2H)-one TLC: Rf 0.85 (chloroform:methanol:water=8:2:0.2);
NMR (DMSO-$d_6$): δ 12.60 (s, 1H), 8.62 (t, J=6.0 Hz, 1H), 8.49 (m, 1H), 7.75 (dt, J=7.5, 1.8 Hz, 1H), 7.29 (m, 1H), 7.25 (m, 1H), 4.35 (d, J=6.0 Hz, 2H), 3.51 (s, 2H), 2.48-2.34 (m, 4H), 1.70-1.58 (m, 4H).

EXAMPLE 23(23)

4-(N-(2-bromoethyl)carbamoylmethyl)-5,6,7,8-tetrahydrophthalazin-1(2H)-one

TLC: Rf 0.64 (methylene chloride:methanol=10:1);
NMR (DMSO-$d_6$): δ 12.59 (s, 1H), 8.32 (m, 1H) 3.52-3.44 (m, 2H), 3.43 (s, 2H), 3.42-3.33 (m, 2H), 2.48-2.33 (m, 4H), 2.70-1.60 (m, 4H).

EXAMPLE 23(24)

4-(N-(3-bromopropyl)carbamoylmethyl)-5,6,7,8-tetrahydrophthalazin-1(2H)-one

TLC: Rf 0.60 (methylene chloride:methanol=10:1);
NMR (DMSO-$d_6$): δ 12.58 (s, 1H), 8.10 (t, J=6.0 Hz, 1H), 3.51 (t, J=6.0 Hz, 2H), 3.40 (s, 2H), 3.15 (q, J=6.0 Hz, 2H), 2.45-2.33 (m, 4H), 1.93 (quin, J=6.0 Hz, 2H), 1.68-1.59 (m, 4H).

EXAMPLE 23(25)

4-(N-(5-(N'-t-butoxycarbonylamino)pentyl)carbamoylmethyl)-5,6,7,8-tetrahydrophthalazin-1(2H)-one NMR (DMSO-$d_6$): δ 12.56 (s, 1H), 7.99 (t, J=6.0 Hz, 1H), 6.75 (t, J=6.0 Hz, 1H), 3.38 (s, 2H), 3.10 (q, J=6.0 Hz, 2H), 2.86 (q, J=6.0 Hz, 2H), 2.45-2.33 (m, 4H), 1.69-1.62 (m, 4H), 1.44-1.29 (m, 4H), 1.36 (s, 9H), 1.28-1.18 (m, 2H).

EXAMPLE 23(26)

4-(N-(5-methylthiazol-2-yl)carbamoylmethyl)-5,6,7,8-tetrahydrophthalazin-1(2H)-one TLC: Rf 0.57 (methanol:methylene chloride=1:10);
NMR (DMSO-$d_6$): δ 12.65 (brs, 1H), 12.12 (brs, 1H), 7.12 (s, 1H), 3.73 (s, 2H), 2.39 (m, 4H), 2.32 (s, 3H), 1.65 (brs, 4H).

EXAMPLE 23(27)

4-(N-(3-(N',N'-dimethylamino)propyl)-N-methylcarbamoylmethyl)-5,6,7,8-tetrahydrophthalazin-1(2H)-one hydrochloride TLC: Rf 0.11 (methylene chloride:methanol:water=7:3:0.3);
NMR (DMSO-$d_6$): δ 12.59 (s, 1H), 10.92 and 10.51 (br, 1H), 3.68 and 3.66 (s, 2H), 3.43 and 3.36 (t, J=6.6 Hz, 2H), 3.80-2.90 (m, 2H), 3.01 and 2.82 (s, 3H), 2.73 and 2.71 and 2.69 (s, 6H), 2.42-2.32 (m, 4H), 2.02-1.82 (m, 2H), 1.67-1.58 (m, 4H).

EXAMPLE 23(28)

4-(N-(2-(N',N'-dimethylamino)ethyl)-N-methylcarbamoylmethyl)-5,6,7,8-tetrahydrophthalazin-1(2H)-one hydrochloride TLC: Rf 0.21 (methylene chloride:methanol:water=7:3:0.3);
NMR (DMSO-$d_6$): δ 12.59 (s, 1H), 10.69 and 9.93 (br, 1H), 3.75 and 3.68 (s, 2H), 3.64 (t, J=6.0 Hz, 2H), 3.20 (q, J=6.0 Hz, 2H), 3.04 and 2.84 (s, 3H), 2.79 and 2.77 and 2.76 (s, 6H), 2.42-2.33 (m, 4H), 1.68-1.60 (m, 4H).

EXAMPLE 23(29)

4-(N-(4-bromobutyl)carbamoylmethyl)-5,6,7,8-tetrahydrophthalazin-1(2H)-one

TLC: Rf 0.65 (methylene chloride:methanol=10:1);
NMR (DMSO-$d_6$): δ 12.56 (s, 1H), 8.02 (t, J=6.3 Hz, 1H), 3.52 (t, J=6.3 Hz, 2H), 3.39 (s, 2H), 3.06 (q, J=6.3 Hz, 2H), 2.45-2.33 (m, 4H), 1.82-1.73 (m, 2H), 1.67-1.58 (m, 4H), 1.58-1.48 (m, 2H).

EXAMPLE 23(30)

4-(2-(N-t-butoxycarbonylamino)ethoxycarbonylmethyl)-5,6,7,8-tetrahydrophthalazin-1(2H)-one NMR (CD$_3$OD): δ 4.15 (t, J=5.7 Hz, 1H), 3.71 (m, 2H), 3.54 (t, J=5.7 Hz, 2H), 3.29 (t, J=5.7 Hz, 1H), 3.14 (t, J=5.7 Hz, 1H), 2.56-2.47 (m, 4H), 1.91-1.84 (m, 4H), 1.43 (s, 9H).

EXAMPLE 23(31)

4-(N-(4-oxo-4,5-dihydro-1,3-thiazol-2-yl)carbamoylmethyl)-5,6,7,8-tetrahydrophthalazin-1(2H)-one NMR (DMSO-$d_6$): δ 12.73 (brs, 1H), 12.67 (s, 1H), 3.88 (s, 2H), 3.80 (s, 2H), 2.38 (brs, 4H), 1.65 (brs, 4H).

EXAMPLE 23(32)

4-(N-(1-methyl-4-oxo-1,5-dihydro-4H-imidazol-2-yl)carbamoylmethyl)-5,6,7,8-tetrahydrophthalazin-1(2H)-one TLC: Rf 0.49 (methanol:methylene chloride=1:10);
NMR (DMSO-$d_6$): δ 12.52 (brs, 1H), 11.03 (brs, 1H), 4.00 (s, 2H), 3.58 (s, 2H), 2.90 (s, 3H), 2.41 (m, 4H), 1.63 (brs, 4H).

EXAMPLE 23(33)

4-(2-(N-(2-(N'-t-butoxycarbonylamino)ethyl)carbamoyl)ethyl)-5,6,7,8-tetrahydrophthalazin-1(2H)-one TLC: Rf 0.66 (chloroform:methanol=4:1);
NMR (DMSO-$d_6$): δ 12.50 (s, 1H), 7.87 (brt, 1H), 6.78 (brt, 1H), 3.12-2.84 (m, 4H), 2.78-2.62 (m, 2H), 2.56-2.26 (m, 6H), 1.76-1.54 (m, 4H), 1.36 (s, 9H).

EXAMPLE 23(34)

4-(N-(2-cyanoethyl)carbamoylmethyl)-5,6,7,8-tetrahydrophthalazin-1(2H)-one

TLC: Rf 0.79 (methylene chloride:methanol:water=8:2:0.2);
NMR (DMSO-$d_6$): δ 12.59 (s, 1H), 8.39 (t, J=5.7 Hz, 1H), 3.43 (s, 2H), 3.32-3.23 (m, 2H), 2.64 (t, J=6.3 Hz, 2H), 2.45-2.33 (m, 4H), 1.68-1.60 (m, 4H).

EXAMPLE 23(35)

4-(N-(4-(imidazol-1-yl)butyl)carbamoylmethyl)-5,6,7,8-tetrahydrophthalazin-1(2H)-one TLC: Rf 0.75 (methylene chloride:methanol:saturated aqueous ammonia=8:2:0.2);
NMR (DMSO-$d_6$): δ 12.57(s 1H), 8.03 (m, 1H), 7.60 (s, 1H), 7.13 (s, 1H), 6.87 (s, 1H), 3.94 (t, J=6.6 Hz, 2H), 3.38 (s, 2H), 3.05 (q, J=6.6 Hz, 2H), 2.46-2.33 (m, 4H), 1.74-1.60 (m, 6H), 1.31(quin, J=6.6 Hz, 2H).

EXAMPLE 23(36)

4-(N-(2-methoxycarbonylethyl)carbamoylmethyl)-5,6,7,8-tetrahydrophthalazin-1(2H)-one TLC: Rf 0.83 (methylene chloride:methanol:water=8:2:0.2);
NMR (DMSO-$d_6$): δ 12.57(s 1H), 8.13 (m, 1H), 3.58 (s, 3H), 3.38 (s, 2H), 3.32-3.24 (m, 2H), 2.50-2.43 (m, 2H), 2.42-2.32 (m, 4H), 1.68-1.60 (m, 4H).

EXAMPLE 23(37)

4-(N-methyl-N-(3-chloropropyl)carbamoylmethyl)-5,6,7,8-tetrahydrophthalazin-1(2H)-one TLC: Rf 0.81 (methylene chloride:methanol:water=8:2:0.2);

NMR (DMSO-$d_6$): δ 12.56 (s, 1H), 3.68 and 3.60 (m, 2H), 3.63 and 3.31 (s, 2H), 3.45 and 3.41 (t, J=6.3 Hz, 2H), 3.02 and 2.81 (s, 3H), 2.41-2.33 (m, 4H), 2.01 and 1.90 (m, 2H), 1.70-1.60 (m, 4H).

EXAMPLE 24

4-(N-(2-hydroxyethyl)carbamoylmethyl)-5,6,7,8-tetrahydrophthalazin-1(2H)-one

A mixture of the compound prepared in Example 15 (222 mg) and 2-aminoethanol (305 mg) was stirred at 100° C. for 1 hour. After cooling the reaction mixture to room temperature, the deposited crystal was washed with ethyl acetate. The obtained crystal was recrystallized from a mixed solvent methanol and ethyl acetate to give the compound of the present invention (190 mg) having the following physical data.

TLC: Rf 0.23 (methanol:methylene chloride=1:10);

NMR (DMSO-$d_6$): δ 12.55 (brs, 1H), 8.03 (t, J=5.4 Hz, 1H), 4.66 (t, J=5.4 Hz, 1H), 3.41 (s, 2H), 3.38 (m, 2H), 3.11 (m, 2H), 2.42 (brs, 2H), 2.36 (brs, 2H), 1.63 (brs, 4H).

EXAMPLE 24(1) TO EXAMPLE 24(48)

By the same procedure as described in Example 24, if necessary, by converting to corresponding salts by conventional method, using the compound prepared in Example 15 or a corresponding ester derivative, and a corresponding derivative instead of 2-aminoethanol, the following compounds of the present invention were obtained.

EXAMPLE 24(1)

8-(N-(2-aminoethyl)carbamoylmethyl)-2,3,4,6-tetrahydropyrido[2,3-d]pyridazin-5(1H)-one dihydrochloride TLC: Rf 0.36 (chloroform:methanol:28% ammonia water=15:5:1);

NMR (DMSO-$d_6$): δ 12.32 (br-s, 1H), 8.41 (t, J=5.4 Hz, 1H), 8.06 (br-s, 3H), 3.49 (s, 2H), 3.30 (m, 2H), 3.20 (m, 2H), 2.86 (m, 2H), 2.38 (t, J=6.0 Hz, 2H), 1.70 (m, 2H).

EXAMPLE 24(2)

4-(N-(2-methoxyethyl)carbamoylmethyl)-5,6,7,8-tetrahydrophthalazin-1(2H)-one

TLC: Rf 0.53 (methanol:methylene chloride=1:10);

NMR (DMSO-$d_6$): δ 12.56 (brs, 1H), 8.11 (t, J=5.4 Hz, 1H), 3.41 (s, 2H), 3.32 (m, 2H), 3.23 (s, 3H), 3.19 (m, 2H), 2.41-2.36 (m, 4H), 1.63 (brs, 4H).

EXAMPLE 24(3)

4-(N-(2-(N',N'-diethylamino)ethyl)carbamoylmethyl)-5,6,7,8-tetrahydrophthalazin-1(2H)-one TLC: Rf 0.35 (chloroform:methanol:water=8:2:0.2);

NMR (DMSO-$d_6$): δ 12.57 (s, 1H), 7.85 (t, J=5.4 Hz, 1H), 3.39 (s, 2H), 3.09 (q, J=6.6 Hz, 2H), 2.48-2.32 (m, 10H), 1.67-1.58 (m, 4H), 0.91 (t, J=7.2 Hz, 6H).

EXAMPLE 24(4)

4-(N-propylcarbamoylmethyl)-5,6,7,8-tetrahydrophthalazin-1(2H)-one

TLC: Rf 0.60 (chloroform:methanol:water=8:2:0.2);

NMR (DMSO-$d_6$): δ 12.56 (s, 1H), 8.00 (t, J=6.9 Hz, 1H), 3.39 (s, 2H), 2.99 (q, J=6.9 Hz, 2H), 2.46-2.32 (m, 4H), 1.68-1.58 (m, 4H), 1.39(sextet, J=6.9 Hz, 2H), 0.83 (t, J=6.9 Hz, 3H).

EXAMPLE 24(5)

4-(N-(4-hydroxybutyl)carbamoylmethyl)-5,6,7,8-tetrahydrophthalazin-1(2H)-one

TLC: Rf 0.68 (methanol:methylene chloride=1:4);

NMR (DMSO-$d_6$): δ 12.54 (brs, 1H), 8.00 (t, J=5.6 Hz, 1H), 4.37 (t, J=5.1 Hz, 1H), 3.38 (s, 2H), 3.36 (m, 2H), 3.02 (m, 2H), 2.42-2.36 (m, 4H), 1.63 (brs, 4H), 1.38 (m, 4H).

EXAMPLE 24(6)

4-(N-(furan-2-ylmethyl)carbamoylmethyl)-5,6,7,8-tetrahydrophthalazin-1(2H)-one

TLC: Rf 0.37 (methanol:methylene chloride=1:10);

NMR (DMSO-$d_6$): δ 12.58 (brs, 1H), 8.51 (t, J=5.4 Hz, 1H), 7.56 (m, 1H), 6.38 (m, 1H), 6.22 (m, 1H), 4.25 (d, J=5.4 Hz, 2H), 3.44 (s, 2H), 2.37 (m, 4H), 1.62 (brs, 4H).

EXAMPLE 24(7)

4-(N-(piperidin-4-ylmethyl)carbamoylmethyl)-5,6,7,8-tetrahydrophthalazin-1(2H)-one hydrochloride TLC: Rf 0.21 (methanol:methylene chloride:saturated aqueous ammonia=1:4:0.2);

NMR (DMSO-$d_6$): δ 12.59 (s, 1H), 8.92 (m, 1H), 8.63 (m, 1H), 8.19 (t, J=5.4 Hz, 1H), 3.42 (s, 2H), 3.21 (m, 2H), 2.97-2.72 (m, 4H), 2.38 (m, 4H), 1.76-1.26 (m, 9H).

EXAMPLE 24(8)

4-(N-(2,3,4,5-tetrahydrofuran-2-ylmethyl)carbamoylmethyl)-5,6,7,8-tetrahydrophthalazin-1(2H)-one TLC: Rf 0.45 (methanol:methylene chloride=1:10);

NMR (DMSO-$d_6$): δ 12.56 (brs, 1H), 8.10 (t, J=5.7 Hz, 1H), 3.85-3.56 (m, 3H), 3.42 (s, 2H), 3.18-3.04 (m, 2H), 2.41-2.36 (m, 4H), 1.90-1.42 (m, 8H).

EXAMPLE 24(9)

4-(1-(N-(2-(piperidin-1-yl)ethyl)carbamoyl)ethyl)-5,6,7,8-tetrahydrophthalazin-1(2H)-one TLC: Rf 0.20 (methanol:methylene chloride=1:4);
NMR (DMSO-$d_6$): δ 12.60 (brs, 1H), 7.80 (t, J=5.7 Hz, 1H), 3.69 (q, J=6.9 Hz, 1H), 3.20-3.05 (m, 2H), 2.48-2.25 (m, 10H), 1.65-1.34 (m, 10H), 1.30 (d, J=6.9 Hz, 3H).

EXAMPLE 24(10)

4-(N-(2-(pyridin-4-yl)ethyl)carbamoylmethyl)-5,6,7,8-tetrahydrophthalazin-1(2H)-one TLC: Rf 0.37 (methanol:methylene chloride=1:10);
NMR (DMSO-$d_6$): δ 12.53 (brs, 1H), 8.44 (d, J=6.3 Hz, 2H), 8.10 (t, J=5.7 Hz, 1H), 7.22 (d, J=6.3 Hz, 2H), 3.35 (m, 4H), 2.84-2.63 (m, 2H), 2.34-2.27 (m, 4H), 1.59 (brs, 4H).

EXAMPLE 24(11)

4-(N-(2-(pyridin-2-yl)ethyl)carbamoylmethyl)-5,6,7,8-tetrahydrophthalazin-1(2H)-one TLC: Rf 0.36 (methanol:methylene chloride=1:10);
NMR (DMSO-$d_6$): δ 12.57 (s, 1H), 8.48 (d, J=3.9 Hz, 1H), 8.09 (t, J=5.4 Hz, 1H), 7.70 (m, 1H), 7.23 (m, 2H), 3.42 (td, J=6.9, 5.4 Hz, 2H), 3.36 (s, 2H), 2.87 (t, J=6.9 Hz, 2H), 2.33 (m, 4H), 1.60 (brs, 4H).

EXAMPLE 24(12)

4-(N-(2,2-dimethyl-3-(N',N'-dimethylamino)propyl)carbamoylmethyl)-5,6,7,8-tetrahydrophthalazin-1(2H)-one TLC: Rf 0.24 (methanol:methylene chloride=1:4);
NMR (DMSO-$d_6$): δ 12.61 (s, 1H), 7.89 (t, J=6.0 Hz, 1H), 3.44 (s, 2H), 2.95 (d, J=6.0 Hz, 2H), 2.43 (m, 2H), 2.36 (m, 2H), 2.15 (s, 6H), 2.05 (s, 2H), 1.63 (brs, 4H), 0.78 (s, 6H).

EXAMPLE 24(13)

4-(N-(2-(N'-isopropylamino)ethyl)carbamoylmethyl)-5,6,7,8-tetrahydrophthalazin-1(2H)-one TLC: Rf 0.27 (ethyl acetate:acetic acid:water=3:1:1);
NMR (DMSO-$d_6$): δ 12.57 (br, 1H), 7.96 (m, 1H), 3.40 (s, 2H), 3.09 (q, J=6.0 Hz, 2H), 2.66 (m, 1H), 2.58-2.48 (m, 2H), 2.45-2.32 (m, 4H), 1.68-1.59 (m, 4H), 0.93 (d, J=6.0 Hz, 6H).

EXAMPLE 24(14)

4-(N-(2-(N'-ethylamino)ethyl)carbamoylmethyl)-5,6,7,8-tetrahydrophthalazin-1(2H)-one TLC: Rf 0.22 (ethyl acetate:acetic acid:water=3:1:1);
NMR (DMSO-$d_6$): δ 12.53 (br, 1H), 7.96 (m, 1H), 3.40 (s, 2H), 3.10 (q, J=6.0 Hz, 2H), 2.57-2.45 (m, 4H), 2.45-2.34 (m, 4H), 1.68-1.58 (m, 4H), 0.97 (t, J=6.9 Hz, 3H).

EXAMPLE 24(15)

4-(N-(3-(N'-methylamino)propyl)carbamoylmethyl)-5,6,7,8-tetrahydrophthalazin-1(2H)-one TLC: Rf 0.20 (ethyl acetate:acetic acid:water=3:1:1);
NMR (DMSO-$d_6$): δ 8.01 (t, J=6.9 Hz, 1H), 3.38 (s, 2H), 3.07 (q, J=6.9 Hz, 2H), 2.41 (t, J=6.9 Hz, 2H), 2.45-2.33 (m, 4H), 2.21 (s, 3H), 1.70-1.60 (m, 4H), 1.52 (quin, J=6.9 Hz, 2H).

EXAMPLE 24(16)

4-(N-(2-(pyridin-3-yl)ethyl)carbamoylmethyl)-5,6,7,8-tetrahydrophthalazin-1(2H)-one TLC: Rf 0.47 (methanol:methylene chloride=1:10);
NMR (DMSO-$d_6$): δ 12.56 (brs, 1H), 8.40 (m, 2H), 8.10 (t, J=5.7 Hz, 1H), 7.61 (m, 1H), 7.30 (m, 1H), 3.36 (s, 2H), 3.31 (m, 2H), 2.73 (t, J=6.9 Hz, 2H), 2.31 (m, 4H), 1.60 (brs, 4H).

EXAMPLE 24(17)

4-(N-(1-benzylpiperidin-4-yl)carbamoylmethyl)-5,6,7,8-tetrahydrophthalazin-1(2H)-one Free Form:
TLC: Rf 0.38 (methanol:methylene chloride=1:10);
NMR (CD$_3$OD): δ 7.36 (m, 5H), 3.76 (m, 1H), 3.69 (s, 2H), 3.59 (s, 2H), 3.01 (m, 2H), 2.56 (brs, 4H), 2.33 (m, 2H), 1.97-1.61 (m, 8H).

Hydrochloride:
TLC: Rf 0.49 (methanol:methylene chloride:saturated aqueous ammonia=1:9:0.1);
NMR (DMSO-$d_6$): δ 12.58 (s, 1H), 10.63 (brs, 1H), 8.33 (d, J=7.2 Hz, 1H), 7.58 (m, 2H), 7.44 (m, 3H), 4.29-2.92 (m, 9H), 2.38 (m, 4H), 1.94-1.70 (m, 4H), 1.62 (brs, 4H).

EXAMPLE 24(18)

4-(N-(2-(N'-phenylamino)ethyl)carbamoylmethyl)-5,6,7,8-tetrahydrophthalazin-1(2H)-one Free Form:
TLC: Rf 0.47 (methanol:methylene chloride=1:10);
NMR (DMSO-$d_6$): δ 12.58 (brs, 1H), 8.12 (t, J=5.7 Hz, 1H), 7.05 (dd, J=8.4, 7.2 Hz, 2H), 6.52 (m, 3H), 5.55 (t, J=5.7 Hz, 1H), 3.42 (s, 2H), 3.22 (m, 2H), 3.06 (m, 2H), 2.38 (m, 4H), 1.60 (brs, 4H).

Hydrochloride:
TLC: Rf 0.57 (methanol:methylene chloride=1:10);
NMR (DMSO-$d_6$): δ 12.60 (s, 1H), 8.31 (m, 1H), 7.35-7.04 (m, 5H), 3.44 (s, 2H), 3.33-3.23 (m, 4H), 2.38 (m, 4H), 1.62 (brs, 4H).

EXAMPLE 24(19)

4-(N-(2-(1-methylpyrrol-2-yl)ethyl)carbamoylmethyl)-5,6,7,8-tetrahydrophthalazin-1(2H)-one TLC: Rf 0.47 (methanol:methylene chloride=1:10);
NMR (DMSO-$d_6$): δ 12.57 (brs, 1H), 8.13 (t, J=5.7 Hz, 1H), 6.58 (t, J=2.4 Hz, 1H), 5.84 (t, J=2.4 Hz, 11), 5.76 (brs, 1H), 3.49 (s, 3H), 3.39 (s, 2H), 3.24 (m, 2H), 2.64 (t, J=7.2 Hz, 2H), 2.37 (m, 4H), 1.63 (brs, 4H).

EXAMPLE 24(20)

4-(N-(5-hydroxypentyl)carbamoylmethyl)-5,6,7,8-tetrahydrophthalazin-1(2H)-one

TLC: Rf 0.29 (methanol:methylene chloride=1:10);

NMR (DMSO-$d_6$): δ 12.56 (brs, 1H), 7.99 (t, J=5.4 Hz, 1H), 4.33 (t, J=5.4 Hz, 1H), 3.38 (s, 2H), 3.35 (m, 2H), 3.02 (td, J=6.3, 5.4 Hz, 2H), 2.39 (m, 4H), 1.63 (brs, 4H), 1.41-1.22 (m, 6H).

EXAMPLE 24(21)

4-(N-(2-(N'-benzylamino)ethyl)carbamoylmethyl)-5,6,7,8-tetrahydrophthalazin-1(2H)-one TLC: Rf 0.15 (methanol:methylene chloride=1:9);

NMR (DMSO-$d_6$): δ 12.55 (brs, 1H), 7.97 (t, J=6.0 Hz, 1H), 7.30-7.17 (m, 5H), 3.67 (s, 2H), 3.40 (s, 2H), 3.15 (q, J=6.0 Hz, 2H), 2.56-2.35 (m, 6H), 1.61 (brs, 4H).

EXAMPLE 24(22)

4-(N-(2-(furan-2-ylmethylthio)ethyl)carbamoylmethyl)-5,6,7,8-tetrahydrophthalazin-1(2H)-one TLC: Rf 0.38 (methanol:methylene chloride=1:10);

NMR (DMSO-$d_6$): δ 12.57 (brs, 1H), 8.16 (t, J=5.7 Hz, 1H), 7.56 (t, J=1.5 Hz, 1H), 6.37 (dd, J=3.0, 1.5 Hz, 1H), 6.26 (d, J=3.0 Hz, 1H), 3.77 (s, 2H), 3.40 (s, 2H), 3.22 (m, 2H), 2.53-2.36 (m, 6H), 1.63 (brs, 4H).

EXAMPLE 24(23)

4-(N-(3-(2-methylpiperidin-1-yl)propyl)carbamoylmethyl)-5,6,7,8-tetrahydrophthalazin-1(2H)-one TLC: Rf 0.43 (methanol:methylene chloride:saturated aqueous ammonia=2:8:0.1);

NMR (DMSO-$d_6$): δ 12.57 (brs, 1H), 8.00 (t, J=5.7 Hz, 1H), 3.38 (s, 2H), 3.03 (m, 2H), 2.73-1.96 (m, 11H), 1.63-1.13 (m, 10H), 0.94 (d, J=6.3 Hz, 3H).

EXAMPLE 24(24)

4-(N-(3-(N'-cyclohexylamino)propyl)carbamoylmethyl)-5,6,7,8-tetrahydrophthalazin-1(2H)-one TLC: Rf 0.41 (methanol:methylene chloride:saturated aqueous ammonia=2:8:0.1);

NMR (DMSO-$d_6$): δ 12.58 (brs, 1H), 8.01 (t, J=5.1 Hz, 11), 3.38 (s, 2H), 3.08 (m, 2H), 2.51-2.25 (m, 7H), 1.77-0.92 (m, 16H).

EXAMPLE 24(25)

4-(N-(2-(N'-butylamino)ethyl)carbamoylmethyl)-5,6,7,8-tetrahydrophthalazin-1(2H)-one TLC: Rf 0.66 (methanol:methylene chloride: saturated aqueous ammonia=2:8:0.1);

NMR (DMSO-$d_6$): δ 12.58 (brs, 1H), 7.95 (t, J=5.4 Hz, 1H), 3.40 (s, 2H), 3.11 (m, 2H), 2.55-2.36 (m, 8H), 1.63 (brs, 4H), 1.31 (m, 4H), 0.85 (t, J=6.9 Hz, 3H).

EXAMPLE 24(26)

4-(N-(2-(N'-(2-hydroxypropyl)amino)ethyl)carbamoylmethyl)-5,6,7,8-tetrahydrophthalazin-1(2H)-one TLC: Rf 0.51 (methanol:methylene chloride:saturated aqueous ammonia=1:10:0.1);

NMR (DMSO-$d_6$): δ 7.99 (t, J=5.1 Hz, 1H), 4.44 (brs, 1H), 3.62 (m, 1H), 3.40 (s, 2H), 3.11 (m, 2H), 2.57-2.37 (m, 8H), 1.63 (brs, 4H), 1.01 (d, J=6.3 Hz, 3H).

EXAMPLE 24(27)

4-(N-(3-(N'-methyl-N'-phenylamino)propyl)carbamoylmethyl)-5,6,7,8-tetrahydrophthalazin-1(2H)-one TLC: Rf 0.58 (methanol:methylene chloride=1:10);

NMR (DMSO-$d_6$): δ 12.58 (brs, 1H), 8.07 (t, J=5.4 Hz, 1H), 7.14 (t, J=7.5 Hz, 2H), 6.61 (m, 3H), 3.41 (s, 2H), 3.29 (m, 2H), 3.08 (m, 2H), 2.83 (s, 3H), 2.39 (m, 4H), 1.62 (m, 6H).

EXAMPLE 24(28)

4-(N-(3-hydroxypropyl)carbamoylmethyl)-5,6,7,8-tetrahydrophthalazin-1(2H)-one

TLC: Rf 0.26 (methanol:methylene chloride=1:10);

NMR (DMSO-$d_6$): δ 12.54 (brs, 1H), 7.99 (t, J=5.4 Hz, 1H), 4.41 (t, J=5.4 Hz, 1H), 3.40 (m, 2H), 3.39 (s, 2H), 3.09 (m, 2H), 2.39 (m, 4H), 1.63 (brs, 4H), 1.58-1.49 (m, 2H).

EXAMPLE 24(29)

4-(N-(2-(thiophen-2-yl)ethyl)carbamoylmethyl)-5,6,7,8-tetrahydrophthalazin-1(2H)-one TLC: Rf 0.48 (methanol:methylene chloride=1:10);

NMR (DMSO-$d_6$): δ 12.57 (brs, 1H), 8.16 (t, J=5.7 Hz, 1H), 7.32 (d, J=5.1 Hz, 1H), 6.94 (dd, J=5.1, 3.3 Hz, 1H), 6.67 (d, J=3.3 Hz, 1H), 3.39 (s, 2H), 3.30 (m, 2H), 2.92 (t, J=6.9 Hz, 2H), 2.35 (brs, 4H), 1.62 (brs, 4H).

EXAMPLE 24(30)

4-(N-(2-(1-methylpyrrolidin-2-yl)ethyl)carbamoylmethyl)-5,6,7,8-tetrahydrophthalazin-1(2H)-one TLC: Rf 0.30 (methanol:methylene chloride:saturated aqueous ammonia=2:8:0.1);

NMR (DMSO-$d_6$): δ 12.58 (brs, 1H), 8.01 (t, J=5.4 Hz, 1H), 3.38 (s, 2H), 3.07 (m, 2H), 2.88 (m, 1H), 2.38 (m, 4H), 2.15 (s, 3H), 2.03-1.24 (m, 12H).

EXAMPLE 24(31)

4-(N-(2-(1-benzylpiperidin-4-yl)ethyl)carbamoylmethyl)-5,6,7,8-tetrahydrophthalazin-1(2H)-one Free Form:

TLC: Rf 0.44 (methanol:methylene chloride:saturated aqueous ammonia=2:8:0.1);

NMR (DMSO-$d_6$): δ 12.56 (brs, 1H), 7.96 (t, J=5.4 Hz, 1H), 7.32-7.19 (m, 5H), 3.40 (s, 2H), 3.37 (s, 2H), 3.06 (m, 2H), 2.75 (m, 2H), 2.31 (m, 4H), 1.87-1.03 (m, 13H).

Hydrochloride:

TLC: Rf 0.48 (methanol:methylene chloride:saturated aqueous ammonia=1:9:0.1);

NMR (DMSO-$d_6$): δ 12.58 (s, 1H), 10.21 (brs, 1H), 8.05 (t, J=5.4 Hz, 1H), 7.56 (m, 2H), 7.45 (m, 3H), 4.24 (m, 2H), 3.38-2.78 (m, 8H), 2.37 (m, 4H), 1.83-1.31 (m, 11H).

EXAMPLE 24(32)

4-(N-(2-(N'-(2-hydroxyethyl)amino)ethyl)carbamoylmethyl)-5,6,7,8-tetrahydrophthalazin-1(2H)-one TLC: Rf 0.18 (ethyl acetate:acetic acid:water=3:1:1);

NMR (DMSO-$d_6$): δ 12.55 (br, 1H), 7.99 (t, J=6.0 Hz, 1H), 4.43 (m, 1H), 3.44-3.37 (m, 2H), 3.40 (s, 2H), 3.11 (q, J=6.0 Hz, 2H), 2.59-2.52 (m, 4H), 2.45-2.33 (m, 4H), 1.68-1.60 (m, 4H).

EXAMPLE 24(33)

4-(N-(3-methylthiopropyl)carbamoylmethyl)-5,6,7,8-tetrahydrophthalazin-1(2H)-one TLC: Rf 0.60 (methanol:methylene chloride=1:10);

NMR (DMSO-$d_6$): δ 12.57 (brs, 1H), 8.05 (t, J=5.4 Hz, 1H), 3.39 (s, 2H), 3.11 (m, 2H), 2.44-2.36 (m, 6H), 2.02 (s, 3H), 1.66 (m, 6H).

EXAMPLE 24(34)

4-(N-(2-(N'-ethyl-N'-(3-methylphenyl)amino)ethyl)carbamoylmethyl)-5,6,7,8-tetrahydrophthalazin-1(2H)-one TLC: Rf 0.63 (methanol:methylene chloride=1:10);

NMR (DMSO-$d_6$): δ 12.59 (brs, 1H), 8.12 (t, J=5.4 Hz, 1H), 7.00 (dd, J=7.2, 7.2 Hz, 1H), 6.50 (m, 2H), 6.37 (d, J=7.2 Hz, 1H), 3.40 (s, 2H), 3.33-3.18 (m, 6H), 2.38 (m, 4H), 2.20 (s, 3H), 1.62 (brs, 4H), 1.04 (t, J=6.9 Hz, 3H).

EXAMPLE 24(35)

4-(N-(4,4-dimethoxybutyl)carbamoylmethyl)-5,6,7,8-tetrahydrophthalazin-1(2H)-one TLC: Rf 0.34 (methanol:methylene chloride=1:10);

NMR (DMSO-$d_6$): δ 12.56 (brs, 1H), 8.01 (t, J=5.4 Hz, 1H), 4.31 (t, J=5.4 Hz, 1H), 3.39 (s, 2H), 3.19 (s, 6H), 3.01 (m, 2H), 2.39 (m, 4H), 1.63 (brs, 4H), 1.52-1.34 (m, 4H).

EXAMPLE 24(36)

4-(N-(3-(N',N'-diethylamino)propyl)carbamoylmethyl)-5,6,7,8-tetrahydrophthalazin-1(2H)-one TLC: Rf 0.34 (methylene chloride:methanol:saturated aqueous ammonia=8:2:0.2);

NMR (DMSO-$d_6$): δ 12.57 (s, 1H), 7.99 (t, J=5.7 Hz, 1H), 3.38 (s, 2H), 3.05 (q, J=5.7 Hz, 2H), 2.44-2.29 (m, 10H), 1.66-1.59 (m, 4H), 1.49(quin, J=5.7 Hz, 2H), 0.91 (t, J=6.9 Hz, 6H).

EXAMPLE 24(37)

4-(N-(3-(N'-isopropylamino)propyl)carbamoylmethyl)-5,6,7,8-tetrahydrophthalazin-1(2H)-one TLC: Rf 0.18 (methylene chloride:methanol:saturated aqueous ammonia=8:2:0.2);

NMR (DMSO-$d_6$): δ 12.52 (br, 1H), 8.00 (m, 1H), 3.38 (s, 2H), 3.08 (q, J=6.0 Hz, 2H), 2.62(sep, J=6.0 Hz, 1H), 2.48-2.32 (m, 6H), 1.68-1.60 (m, 4H), 1.49(quin, J=6.0 Hz, 2H), 0.92 (d, J=6.0 Hz, 6H).

EXAMPLE 24(38)

4-(N-(2-(1,3-dioxolan-2-yl)ethyl)carbamoylmethyl)-5,6,7,8-tetrahydrophthalazin-1(2H)-one TLC: Rf 0.41 (methanol:methylene chloride=1:10);

NMR (DMSO-$d_6$): δ 12.57 (brs, 1H), 8.01 (t, J=5.7 Hz, 1H), 4.79 (t, J=4.8 Hz, 1H), 3.89-3.71 (m, 4H), 3.38 (s, 2H), 3.13 (m, 2H), 2.38 (m, 4H), 1.70 (m, 2H), 1.63 (brs, 4H).

EXAMPLE 24(39)

4-(N-(3-(N'-propylamino)propyl)carbamoylmethyl)-5,6,7,8-tetrahydrophthalazin-1(2H)-one TLC: Rf 0.14 (methylene chloride:methanol:saturated aqueous ammonia=8:2:0.2);

NMR (DMSO-$d_6$): δ 12.60 (br, 1H), 8.00 (m, 1H), 3.38 (s, 2H), 3.08 (q, J=6.6 Hz, 2H), 2.47-2.34 (m, 8H), 1.70-1.60 (m, 4H), 1.50(quin, J=6.6 Hz, 2H), 1.38(sex, J=6.6 Hz, 2H), 0.83 (t, J=6.6 Hz, 3H).

EXAMPLE 24(40)

4-(N-(2-(N'-propylamino)ethyl)carbamoylmethyl)-5,6,7,8-tetrahydrophthalazin-1(2H)-one TLC: Rf 0.31 (methylene chloride:methanol:saturated aqueous ammonia=8:2:0.2);

NMR (DMSO-$d_6$): δ 12.59 (br, 1H), 7.96 (m, 1H), 3.40 (s, 2H), 3.11 (q, J=6.3 Hz, 2H), 2.57-2.47 (m, 2H), 2.45-2.33 (m, 6H), 1.70-1.60 (m, 4H), 1.37(sex, J=7.2 Hz, 2H), 0.84 (t, J=7.2 Hz, 3H).

EXAMPLE 24(41)

4-(N-(2-(4-methoxyphenyl)ethyl)carbamoylmethyl)-5,6,7,8-tetrahydrophthalazin-1(2H)-one TLC: Rf 0.47 (methanol:methylene chloride=1:10);

NMR (DMSO-$d_6$): δ 12.56 (brs, 1H), 8.04 (t, J=5.7 Hz, 1H), 7.10 (d, J=8.7 Hz, 2H), 6.83 (d, J=8.7 Hz, 2H), 3.70 (s, 3H), 3.36 (s, 2H), 3.24 (m, 2H), 2.63 (t, J=7.2 Hz, 2H), 2.33 (m, 4H), 1.60 (brs, 4H).

EXAMPLE 24(42)

4-(N-(2-(4-aminophenyl)ethyl)carbamoylmethyl)-5,6,7,8-tetrahydrophthalazin-1(2H)-one hydrochloride TLC: Rf 0.39 (methanol:methylene chloride=1:10);

NMR (DMSO-$d_6$): δ 12.58 (brs, 1H), 10.38 (brs, 3H), 8.19 (t, J=5.4 Hz, 1H), 7.31 (m, 4H), 3.37 (s, 2H), 3.29 (q, J=6.9 Hz, 2H), 2.73 (t, J=6.9 Hz, 2H), 2.35 (brs, 4H), 1.61 (brs, 4H).

EXAMPLE 24(43)

8-(N-(2-(N'-phenylamino)ethyl)carbamoylmethyl)-2,3,4,6-tetrahydropyrido[2,3-d]pyridazin-5(1H)-one dihydrochloride TLC: Rf 0.40 (methanol:methylene chloride=1:10);
NMR (DMSO-$d_6$): δ 12.27 (brs, 1H), 8.36 (m, 1H), 7.31 (t, J=7.8 Hz, 2H), 7.10-6.00 (m, 7H), 3.46 (s, 2H), 3.24 (m, 6H), 2.38 (t, J=6.3 Hz, 2H), 1.70 (m, 2H).

EXAMPLE 24(44)

8-(N-(2-(1-benzylpiperidin-4-yl)ethyl)carbamoylmethyl)-2,3,4,6-tetrahydropyrido[2,3-d]pyridazin-5(1H)-one methanesulfonate TLC: Rf 0.36 (methanol:methylene chloride:saturated aqueous ammonia=1:10:0.1);
NMR (DMSO-$d_6$): δ 11.87 (s, 1H), 9.20 (brs, 1H), 8.05 (t, J=5.1 Hz, 1H), 7.48 (m, 5H), 6.38 (brs, 1H), 4.27 (m, 2H), 3.33-3.06 (m, 8H), 2.83 (m, 2H), 2.33 (m, 2H), 2.30 (s, 3H), 1.87-1.22 (m, 9H).

EXAMPLE 24(45)

8-(N-(3-(morpholin-4-yl)propyl)carbamoylmethyl)-2,3,4,6-tetrahydropyrido[2,3-d]pyridazin-5(1H)-one TLC: Rf 0.31 (methanol:methylene chloride=1:4);
NMR (DMSO-$d_6$): δ 11.85 (s, 1H), 8.05 (t, J=5.4 Hz, 1H), 6.41 (s, 1H), 3.54 (m, 4H), 3.29 (m, 2H), 3.17 (brs, 2H), 3.06 (q, J=6.6 Hz, 2H), 2.28 (m, 8H), 1.69 (m, 2H), 1.53 (m, 2H).

EXAMPLE 24(46)

8-(N-(2-(piperidin-1-yl)ethyl)carbamoylmethyl)-2,3,4,6-tetrahydropyrido[2,3-d]pyridazin-5(1H)-one methanesulfonate TLC: Rf 0.14 (methanol:methylene chloride:acetic acid=1:4:0.2);
NMR (DMSO-$d_6$): δ 11.91 (s, 1H), 8.94 (brs, 1H), 8.29 (t, J=5.4 Hz, 1H), 6.30 (brs, 1H), 3.50-3.38 (m, 6H), 3.12 (m, 4H), 2.90 (m, 2H), 2.35 (m, 2H), 2.32 (s, 3H), 1.98-1.33 (m, 8H).

EXAMPLE 24(47)

8-(N-(2-(morpholin-4-yl)ethyl)carbamoylmethyl)-2,3,4,6-tetrahydropyrido[2,3-d]pyridazin-5(1H)-one TLC: Rf 0.29 (methanol:methylene chloride=1:4);
NMR (DMSO-$d_6$): δ 11.85 (s, 1H), 7.99 (t, J=5.4 Hz, 1H), 6.40 (s, 1H), 3.53 (m, 4H), 3.34 (s, 2H), 3.16 (m, 4H), 2.30 (m, 8H), 1.70 (m, 2H).

EXAMPLE 24(48)

8-(N-(3-(N'-t-butoxycarbonylamino)propyl)carbamoylmethyl)-2,3,4,6-tetrahydropyrido[2,3-d]pyridazin-5(1H)-one TLC: Rf 0.35 (methanol:methylene chloride=1:9);
NMR (DMSO-$d_6$): δ 11.84 (s, 1H), 8.02 (t, J=5.4 Hz, 1H), 6.76 (t, J=5.4 Hz, 1H), 6.38 (s, 1H), 3.31 (m, 2H), 3.18 (brs, 2H), 2.98 (td, J=6.6, 5.4 Hz, 2H), 2.90 (td, J=6.6, 5.4 Hz, 2H), 2.32 (t, J=6.3 Hz, 2H), 1.69 (m, 2H), 1.47 (m, 2H), 1.36 (s, 9H).

EXAMPLE 25

4-(3-(N-(5-chloropentanoyl)amino)phenyl)-5,6,7,8-tetrahydrophthalazin-1(2H)-one 5-chloropentanoyl chloride (171 mg) was added dropwise to a mixed solution of the compound prepared in Example 1 (241 mg) and potassium carbonate (89.8 mg) in tetrahydrofuran (3.00 mL) and water (1.00 mL) in ice bath and the mixture was stirred for 30 minutes. Moreover, potassium carbonate (45.0 mg) and 5-chloropentanoyl chloride (85.5 mg) was added the reaction mixture, which was stirred for 30 minutes. 1N hydrochloric acid was added to the reaction mixture, which was adjusted to pH 2. Water was added thereto and the deposited crystal was collected by filtration. It was washed with water and hexane sequentially and dried under reduced pressure to give the compound of the present invention (347 mg) having the following physical data.

NMR (DMSO-$d_6$): δ 12.88 (s, 1H), 10.00 (s, 1H), 7.69 (s, 1H), 7.59 (d, J=7.8 Hz, 1H), 7.35 (t, J=7.8 Hz, 1H), 7.08 (d, J=7.8 Hz, 1H), 3.65 (t, J=6.0 Hz, 2H), 2.56-2.32 (m, 6H), 1.75-1.59 (m, 8H).

EXAMPLE 25(1) TO EXAMPLE 25(13)

By the same procedure as described in Example 25 using a corresponding derivative instead of the compound prepared in Example 1, and a corresponding derivative instead of 5-chloropentanoyl chloride, the following compounds of the present invention were obtained.

EXAMPLE 25(1)

4-(3-(N-(5-bromopentanoyl)amino)phenyl)-5,6,7,8-tetrahydrophthalazin-1(2H)-one

TLC: Rf 0.28 (methanol:methylene chloride=1:20);
NMR (DMSO-$d_6$): δ 12.88 (s, 1H), 10.00 (s, 1H), 7.69 (t, J=1.2 Hz, 1H), 7.59 (dd, J=7.8, 1.2 Hz, 1H), 7.35 (t, J=7.8 Hz, 1H), 7.09 (dd, J=7.8, 1.2 Hz, 1H), 3.55 (t, J=6.6 Hz, 2H), 2.48-2.32 (m, 6H), 1.86-1.59 (m, 8H).

EXAMPLE 25(2)

4-(3-(N-(4-chlorobutanoyl)amino)phenyl)-6,7,9,9a-tetrahydro[1,4]thiazino[4,3-d][1,2,4]triazin-1(2H)-one TLC: Rf 0.50 (chloroform:methanol=9:1);
NMR (CDCl$_3$): δ 8.47-8.28 (br, 1H), 7.69 (bs, 1H), 7.62 (bs, 1H), 7.53 (d, J=7.8 Hz, 1H), 7.37 (t, J=7.8 Hz, 1H), 7.09 (d, J=7.8 Hz, 1H), 4.35 (dd, J=10.5, 2.7 Hz, 1H), 3.85 (dt, J=13.5, 2.7 Hz, 1H), 3.67 (t, J=6.3 Hz, 2H), 3.21-3.11 (m, 1H), 3.08-3.02 (m, 1H), 2.94 (dd, J=13.5, 10.5 Hz, 1H), 2.86-2.76 (m, 1H), 2.56 (t, J=7.2 Hz, 2H), 2.32-2.16 (m, 3H).

EXAMPLE 25(3)

4-(3-(N-acetylamino)phenyl)-6,7,9,9a-tetrahydro[1,4]thiazino[4,3-d][1,2,4]triazin-1(2H)-one TLC: Rf 0.40 (methylene chloride:methanol=10:1);
NMR (DMSO-$d_6$): δ 10.52 (s, 1H), 10.05 (s, 1H), 7.67 (s, 1H), 7.56 (d, J=8.1 Hz, 1H), 7.34 (t, J=8.1 Hz, 1H), 7.06 (d, J=8.1 Hz, 1H), 4.23 (dd, J=8.7, 4.8 Hz, 1H), 3.56 (m, 1H), 3.08 (m, 1H), 2.89-2.83 (m, 2H), 2.70 (m, 1H), 2.32 (m, 1H), 2.04 (s, 3H).

EXAMPLE 25(4)

4-(3-(N-acetylamino)phenyl)-6,7-dihydro[1,4]thiazino[4,3-d][1,2,4]triazin-1(2H)-one TLC: Rf 0.51 (methanol:methylene chloride=1:10);
NMR (DMSO-$d_6$): δ 10.88 (s, 1H), 10.08 (s, 1H), 7.70 (s, 1H), 7.61 (d, J=7.8 Hz, 1H), 7.38 (t, J=7.8 Hz, 1H), 7.09 (d, J=7.8 Hz, 1H), 6.26 (s, 1H), 3.61 (m, 2H), 3.15 (m, 2H), 2.05 (s, 3H).

EXAMPLE 25(5)

4-(3-(N-acetylamino)phenyl)-5,6,7,8-tetrahydrophthalazin-1(2H)-one

TLC: Rf 0.45 (methanol:methylene chloride=1:10);
NMR (DMSO-$d_6$): δ 12.87 (s, 1H), 10.02 (s, 1H), 7.67 (s, 1H), 7.58 (d, J=7.8 Hz, 1H), 7.35 (t, J=7.8 Hz, 1H), 7.08 (d, J=7.8 Hz, 1H), 2.39 (m, 4H), 2.04 (s, 3H), 1.64 (m, 4H).

EXAMPLE 25(6)

4-(3-(N-(4-chlorobutanoyl)amino)phenyl)-6,7-dihydro[1,4]thiazino[4,3-d][1,2,4]triazin-1(2H)-one NMR (DMSO-$d_6$): δ 10.89 (s, 1H), 10.12 (s, 1H), 7.71 (t, J=1.5 Hz, 1H), 7.62 (m, 1H), 7.38 (t, J=7.8 Hz, 1H), 7.10 (dt, J=7.8, 1.5 Hz, 1H), 6.26 (s, 1H), 3.70 (t, J=6.9 Hz, 2H), 3.64-3.58 (m, 2H), 3.18-3.13 (m, 2H), 2.35 (t, J=6.9 Hz, 2H), 2.03(quin, J=6.9 Hz, 2H).

EXAMPLE 25(7)

4-(3-(N-(2-chloroacetyl)amino)phenyl)-5,6,7,8-tetrahydrophthalazin-1(2H)-one

TLC: Rf 0.27 (methanol:methylene chloride=1:20);
NMR (DMSO-$d_6$): δ 12.90 (s, 1H), 10.40 (s, 1H), 7.68 (s, 1H), 7.60 (d, J=7.8 Hz, 1H), 7.40 (t, J=7.8 Hz, 1H), 7.15 (d, J=7.8 Hz, 1H), 4.25 (s, 2H), 2.39 (m, 4H), 1.68 (m, 2H), 1.59 (m, 2H).

EXAMPLE 25(8)

4-(3-(N-(3-bromopropanoyl)amino)phenyl)-5,6,7,8-tetrahydrophthalazin-1(2H)-one

TLC: Rf 0.20 (methanol:methylene chloride=1:20);
NMR (DMSO-$d_6$): δ 12.88 (s, 1H), 10.15 (s, 1H), 7.70 (s, 1H), 7.60 (d, J=7.8 Hz, 1H), 7.37 (t, J=7.8 Hz, 1H), 7.12 (d, J=7.8 Hz, 1H), 3.72 (t, J=6.3 Hz, 2H), 2.95 (t, J=6.3 Hz, 2H), 2.48-2.34 (m, 4H), 1.70 (m, 2H), 1.60 (m, 2H).

EXAMPLE 25(9)

8-(3-(N-acetylamino)phenyl)-2,3,4,6-tetrahydropyrido[2,3-d]pyridazin-5(1H)-one

Free Form:

TLC: Rf 0.31 (chloroform:methanol=8:1);
NMR (DMSO-$d_6$): δ 12.11 (s, 1H), 10.06 (s, 1H), 7.70 (m, 1H), 7.61 (m, 1H), 7.37 (dd, J=7.8, 7.8 Hz, 1H), 7.09 (m, 1H), 5.37 (s, 1H), 3.20-3.06 (m, 2H), 2.39 (t, J=6.3 Hz, 2H), 2.04 (s, 3H), 1.82-1.60 (m, 2H).

Methanesulfonate:

TLC: Rf 0.31 (methylene chloride:methanol=9:1);
NMR (DMSO-$d_6$): δ 12.31 (s, 1H), 10.06 (s, 1H), 7.70 (m, 1H), 7.62 (m, 1H), 7.38 (t, J=7.9 Hz, 1H), 7.09 (m, 1H), 3.14 (m, 2H), 2.41 (t, J=6.2 Hz, 2H), 2.33 (s, 3H), 2.04 (s, 3H), 1.73 (m, 2H).

EXAMPLE 25(10)

4-(3-(N-mesylamino)phenyl)-5,6,7,8-tetrahydrophthalazin-1(2H)-one

TLC: Rf 0.56 (methanol:methylene chloride=1:10);
NMR (DMSO-$d_6$): δ 12.89 (s, 1H), 9.86 (brs, 1H), 7.39 (t, J=7.8 Hz, 1H), 7.25 (d, J=7.8 Hz, 1H), 7.23 (s, 1H), 7.16 (d, J=7.8 Hz, 1H), 3.00 (s, 3H), 2.48-2.34 (m, 4H), 1.69 (m, 2H), 1.59 (m, 2H).

EXAMPLE 25(11)

8-(3-(N-(4-chlorobutanoyl)amino)phenyl)-2,3,4,6-tetrahydropyrido[2,3-d]pyridazin-5(1H)-one TLC: Rf 0.41 (chloroform:methanol=8:1);
NMR (DMSO-$d_6$): δ 12.11 (s, 1H), 10.09 (s, 1H), 7.72 (m, 1H), 7.63 (s, 1H), 7.38 (dd, J=7.8, 7.8 Hz, 1H), 7.09 (m, 1H), 5.74 (s, 1H), 3.69 (t, J=6.3 Hz, 2H), 3.22-3.04 (m, 2H), 2.60-2.32 (m, 4H), 2.12-1.94 (m, 2H), 1.82-1.64 (m, 2H).

EXAMPLE 25(12)

4-(2-(N-(2-bromoacetyl)amino)ethyl)-5,6,7,8-tetrahydrophthalazin-1(2H)-one

TLC: Rf 0.68 (chloroform:methanol=4:1);
NMR (DMSO-$d_6$): δ 12.56 (s, 1H), 8.33 (brt, J=5.1 Hz, 1H), 3.82 (s, 2H), 3.44-3.26 (m, 2H), 2.64 (t, J=6.9 Hz, 2H), 2.54-2.28 (m, 4H), 1.78-1.52 (m, 4H).

EXAMPLE 25(13)

4-(2-(N-(3-bromopropanoyl)amino)ethyl)-5,6,7,8-tetrahydrophthalazin-1(2H)-one

TLC: Rf 0.71 (chloroform:methanol=4:1);
NMR (DMSO-$d_6$): δ 12.55 (brs, 1H), 8.07 (brt, J=6.0 Hz, 1H), 3.61 (t, J=6.0 Hz, 2H), 3.44-3.24 (m, 2H), 2.72-2.28 (m, 8H), 1.78-1.54 (m, 4H).

EXAMPLE 26

4-(3-(N-(5-(N'-methyl-N'-t-butoxycarbonylamino)pentanoyl)amino)phenyl)-5,6,7,8-tetrahydrophthalazin-1(2H)-one A mixture of the compound prepared in Example 1 (277 mg), triethylamine (223 mg), 5-(N-methyl-N-t-butoxycarbonylamino)pentanoic acid (277 mg), 1-ethyl-3-(3-dimethylaminopropyl)carbodiimide hydrochloride (230 mg), 1-hydroxybenzotriazole (184 mg) and dimethylformamide (3.00 mL) was stirred at room temperature for 18 hours. The reaction mixture was concentrated. Water was added to the residue, which was extracted with ethyl acetate. The extract was washed with 1N hydrochloric acid, water, a saturated aqueous sodium hydrogen carbonate solution and brine sequentially, dried over anhydrous magnesium sulfate and concentrated. The residue was recrystallized from a mixed solvent of ethyl acetate and hexane to give the compound of the present invention (298 mg) having the following physical data.

TLC: Rf 0.49 (methylene chloride:methanol=9:1);
NMR (DMSO-$d_6$): δ 12.88 (s, 1H), 9.97 (s, 1H), 7.69 (s, 1H), 7.58 (d, J=8.1 Hz, 1H), 7.35 (t, J=8.1 Hz, 1H), 7.08 (d, J=8.1 Hz, 1H), 3.15 (t, J=6.8 Hz, 2H), 2.74 (s, 3H), 2.48-2.30 (m, 6H), 1.70-1.50 (m, 8H), 1.36 (s, 9H).

EXAMPLE 26(1) TO EXAMPLE 26(19)

By the same procedure as described in Example 26, if necessary, by converting to corresponding salts by conventional method, using the compound prepared in Example 1 or a corresponding derivative, and (N-methyl-N-t-butoxycarbonylamino)pentanoic acid or a corresponding derivative, the following compounds of the present invention were obtained.

EXAMPLE 26(1)

4-(3-(N-(5-(N'-methyl-N'-benzyloxycarbonylamino)pentanoyl)amino)phenyl)-5,6,7,8-tetrahydrophthalazin-1(2H)-one TLC: Rf 0.29 (methanol:methylene chloride=1:20);
NMR (DMSO-$d_6$): δ 12.88 (s, 1H), 9.98 (s, 1H), 7.70 (s, 1H), 7.58 (d, J=7.8 Hz, 1H), 7.32 (m, 6H), 7.08 (d, J=7.8 Hz, 1H), 5.04 (s, 2H), 3.28-2.33 (m, 11H), 1.69-1.51 (m, 8H).

EXAMPLE 26(2)

4-(3-(N-(4-chlorobutanoyl)amino)phenyl)-5,6,7,8-tetrahydrophthalazin-1(2H)-one

TLC: Rf 0.48 (methanol:methylene chloride=1:20);
NMR (DMSO-$d_6$): δ 12.88 (s, 1H), 10.07 (s, 1H), 7.69 (s, 1H), 7.59 (d, J=7.8 Hz, 1H), 7.35 (t, J=7.8 Hz, 1H), 7.09 (d, J=7.8 Hz, 1H), 3.69 (t, J=6.3 Hz, 2H), 2.46-1.59 (m, 12H).

EXAMPLE 26(3)

4-(3-(N-(5-(N',N'-dimethylamino)pentanoyl)amino)phenyl)-5,6,7,8-tetrahydrophthalazin-1(2H)-one methanesulfonate TLC: Rf 0.30 (methanol:methylene chloride:saturated aqueous ammonia=2:8:0.1);
NMR (CD$_3$OD): δ 7.75 (t, J=1.8 Hz, 1H), 7.63 (brd, J=8.1 Hz, 1H), 7.45 (t, J=8.1 Hz, 1H), 7.20 (brd, J=8.1 Hz, 1H), 3.16 (m, 2H), 2.89 (s, 6H), 2.74 (s, 3H), 2.66-2.50 (m, 6H), 1.81 (m, 8H).

EXAMPLE 26(4)

4-(3-(N-(5-(N'-benzyloxycarbonylamino)pentanoyl)amino)phenyl)-5,6,7,8-tetrahydrophthalazin-1(2H)-one TLC: Rf 0.79 (methanol:methylene chloride=1:4);
NMR (DMSO-$d_6$): δ 12.88 (s, 1H), 9.97 (s, 1H), 7.69 (s, 1H), 7.59 (d, J=7.8 Hz, 1H), 7.37-7.26 (m, 6H), 7.08 (d, J=7.8 Hz, 1H), 4.99 (s, 2H), 3.00 (m, 2H), 2.48-2.28 (m, 6H), 1.69-1.42 (m, 8H).

EXAMPLE 26(5)

4-(3-(N-(2-(2-chloroethoxy)acetyl)amino)phenyl)-5,6,7,8-tetrahydrophthalazin-1(2H)-one TLC: Rf 0.41 (methanol:methylene chloride=1:20);
NMR (DMSO-$d_6$): δ 12.89 (s, 1H), 9.81 (s, 1H), 7.73 (s, 1H), 7.67 (d, J=7.8 Hz, 1H), 7.38 (t, J=7.8 Hz, 1H), 7.13 (d, J=7.8 Hz, 1H), 4.14 (s, 2H), 3.81 (s, 4H), 2.48-2.34 (m, 4H), 1.70-1.59 (m, 4H).

EXAMPLE 26(6)

4-(3-(N-(5-(N'-methyl-N'-benzyloxycarbonylamino)pentanoyl)amino)phenyl)-7,8,9,9a-tetrahydro-2H-pyrido[1,2-d][1,2,4]triazin-1(6H)-one TLC: Rf 0.28 (methanol:methylene chloride=1:20);
NMR (DMSO-$d_6$): δ 10.34 (s, 1H), 9.98 (s, 1H), 7.68 (s, 1H), 7.56 (d, J=9.0 Hz, 1H), 7.33 (m, 6H), 7.01 (d, J=7.8 Hz, 1H), 5.04 (s, 2H), 3.86 (m, 1H), 3.25-1.42 (m, 19H).

EXAMPLE 26(7)

4-(3(5-(N'-methyl-N'-benzyloxycarbonylamino)pentanoyl)aminophenyl)-6,7,9,9a-tetrahydro[1,4]thiazino[4,3-d][1,2,4]triazin-1(2H)-one TLC: Rf 0.24 (methanol:chloroform=1:10);
NMR (DMSO-$d_6$): δ 10.53 (s, 1H), 10.01 (s, 1H), 7.67 (t, J=1.5 Hz, 1H), 7.58 (m, 1H), 7.34 (m, 6H), 7.06 (m, 1H), 5.04 (s, 2H), 4.23 (dd, J=8.6, 4.8 Hz, 1H), 3.57 (brd, J=13.8 Hz, 1H), 3.28 (m, 3H), 3.07 (t, J=12.0 Hz, 1H), 2.88-2.65 (m, 5H), 2.33 (m, 3H), 1.52 (m, 4H).

EXAMPLE 26(8)

4-(3-(N-(5-(N'-methyl-N'-benzyloxycarbonylamino)pentanoyl)amino)phenyl)-2,5,6,7,8,9-hexahydro-1H-cyclohepta[d]pyridazin-1-one TLC: Rf 0.54 (chloroform:methanol=9:1);
NMR (CDCl$_3$): δ 10.58 (br-s, 1H), 8.21 (br-s, 11), 7.69 (br-s, 1H), 7.60 (m, 1H), 7.40-7.28 (m, 6H), 7.04 (m, 1H), 5.13 (s, 2H), 3.42-3.28 (m, 2H), 3.00-2.86 (m, 5H), 2.70-2.64 (m, 2H), 2.46-2.30 (m, 2H), 1.94-1.84 (m, 2H), 1.80-1.60 (m, 8H).

EXAMPLE 26(9)

4-(3-(N-(4-(N'-methyl-N'-t-butoxycarbonylamino)butanoyl)amino)phenyl)-6,7,9,9a-tetrahydro[1,4]thiazino[4,3-d][1,2,4]triazin-1(2H)-one TLC: Rf 0.35 (methylene chloride:methanol=10:1).

EXAMPLE 26(10)

4-(3-(N-(6-(N'-methyl-N'-t-butoxycarbonylamino)hexanoyl)amino)phenyl)-6,7,9,9a-tetrahydro[1,4]thiazino[4,3-d][1,2,4]triazin-1(2H)-one TLC: Rf 0.35 (methylene chloride:methanol=10:1).

EXAMPLE 26(11)

4-(3-(N-(5-(N'-(3-methyl-2-butenyl)-N'-t-butoxycarbonylamino)pentanoyl)amino)phenyl)-5,6,7,8-tetrahydrophthalazin-1(2H)-one TLC: Rf 0.31 (hexane:ethyl acetate=1:3);
NMR (DMSO-$d_6$): δ 12.87 (s, 1H), 9.95 (s, 1H), 7.68 (m, 1H), 7.58 (m, 1H), 7.34 (dd, J=7.8, 7.8 Hz, 1H), 7.07 (m, 1H), 5.10 (m, 1H), 3.72 (d, J=6.6 Hz, 2H), 3.16-3.00 (m, 2H), 2.62-2.40 (m, 2H), 2.40-2.22 (m, 4H), 1.78-1.30 (m, 8H), 1.64 (s, 3H), 1.60 (s, 3H), 1.36 (s, 9H).

EXAMPLE 26(12)

4-(3-(N-(5-(N'-methyl-N'-benzyloxycarbonylamino)pentanoyl)amino)phenyl)-6,7-dihydro[1,4]thiazino[4,3-d][1,2,4]triazin-1(2H)-one TLC: Rf 0.63 (chloroform:methanol:water=8:2:0.2);
NMR (CD$_3$OD): δ 7.74 (s, 1H), 7.57 (d, J=7.8 Hz, 1H), 7.41 (t, J=7.8 Hz, 1H), 7.35-7.20 (m, 5H), 7.14 (d, J=7.8 Hz, 1H), 6.39 (s, 1H), 5.08 (s, 2H), 3.73-3.68 (m, 2H), 3.38-3.28 (m, 2H), 3.16-3.10 (m, 2H), 2.91(brs, 3H), 2.44-2.25 (m, 2H), 1.78-1.50 (m, 4H).

EXAMPLE 26(13)

4-(3-(N-(2-(N',N'-dimethylamino)acetyl)amino)phenyl)-5,6,7,8-tetrahydrophthalazin-1(2H)-one hydrochloride TLC: Rf 0.27 (chloroform:methanol=8:1);
NMR (DMSO-$d_6$): δ 12.92 (s, 1H), 10.97 (s, 1H), 9.96 (brs, 1H), 7.72 (m, 1H), 7.65 (m, 1H), 7.43 (dd, J=7.8, 7.8 Hz, 1l), 7.20 (m, 1H), 4.16 (s, 2H), 2.87 (s, 6H), 2.60-2.24 (m, 4l), 1.80-1.50 (m, 4H).

EXAMPLE 26(14)

4-(3-(N-(1-t-butoxycarbonylazetidin-3-ylcarbonyl)amino)phenyl)-5,6,7,8-tetrahydrophthalazin-1(2H)-one TLC: Rf 0.27 (chloroform:methanol=8:1);
NMR (DMSO-$d_6$): δ 12.88 (s, 1H), 10.13 (s, 1H), 7.71 (m, 1H), 7.60 (m, 1H), 7.37 (dd, J=7.5, 7.5 Hz, 1H), 7.12 (m, 1H), 4.08-3.84 (m, 4H), 3.46 (m, 1H), 2.54-2.28 (m, 4H), 1.78-1.52 (m, 4H), 1.38 (s, 9H).

EXAMPLE 26(15)

4-(3-(N-(1-t-butoxycarbonylpyrrolidin-2-ylcarbonyl)amino)phenyl)-5,6,7,8-tetrahydrophthalazin-1(2H)-one NMR (DMSO-$d_6$): δ 12.88 (s, 1H), 10.07 (s, 1H), 7.71 (s, 1H), 7.62 (d, J=7.8 Hz, 1H), 7.37 (t, J=7.8 Hz, 1H), 7.10 (d, J=7.8 Hz, 1H), 4.17 (m, 1H), 3.38-2.34 (m, 8H), 1.98-1.60 (m, 6H), 1.38 (s, 9H×⅓), 1.26 (s, 9H×⅔).

EXAMPLE 26(16)

4-(2-(N-(2-(N'-t-butoxycarbonylamino)acetyl)amino)ethyl)-5,6,7,8-tetrahydrophthalazin-1(2H)-one TLC: Rf 0.31 (chloroform:methanol=8:1);
NMR (DMSO-$d_6$): δ 12.54 (s, 1H), 7.82 (brt, 1H), 6.91 (brt, 1H), 3.47 (d, J=6.3 Hz, 2H), 3.40-3.26 (m, 2H), 2.61 (t, J=7.2 Hz, 2H), 2.56-2.30 (m, 4H), 1.76-1.54 (m, 4H), 1.36 (s, 9H).

EXAMPLE 26(17)

4-(2-(N-(3-(N'-t-butoxycarbonylamino)propanoyl)amino)ethyl)-5,6,7,8-tetrahydrophthalazin-1(2H)-one TLC: Rf 0.44 (chloroform:methanol=4:1);
NMR (DMSO-$d_6$): δ 12.54 (s, 1H), 7.92 (t, J=6.0 Hz, 1H), 6.72 (brt, 1H), 3.42-3.18 (m, 2H), 3.16-3.02 (m, 2H), 2.68-2.28 (m, 6H), 2.18 (t, J=7.2 Hz, 2H), 1.78-1.52 (m, 4H), 1.36 (s, 9H).

EXAMPLE 26(18)

4-(2-(N-(2-(N',N'-dimethylamino)acetyl)amino)ethyl)-5,6,7,8-tetrahydrophthalazin-1(2H)-one TLC: Rf 0.62 (chloroform:methanol=4:1);
NMR (DMSO-$d_6$): δ 12.54 (brs, 1H), 7.80 (t, J=5.7 Hz, 1H), 3.44-3.24 (m, 2H), 2.80 (s, 2H), 2.64 (t, J=7.2 Hz, 2H), 2.54-2.26 (m, 4H), 2.16 (s, 6H), 1.76-1.52 (m, 4H).

EXAMPLE 26(19)

4-(2-(N-(4-(N'-t-butoxycarbonylamino)butanoyl)amino)ethyl)-5,6,7,8-tetrahydrophthalazin-1(2H)-one TLC: Rf 0.67 (chloroform:methanol=4:1);
NMR (DMSO-$d_6$): δ 12.53 (s, 1H), 7.85 (t, J=5.4 Hz, 1H), 6.78 (t, J=5.7 Hz, 1H), 3.40-3.20 (m, 2H), 2.94-2.80 (m, 2H), 2.60 (t, J=7.2 Hz, 2H), 2.56-2.28 (m, 4H), 2.01 (t, J=7.2 Hz, 2H), 1.78-1.46 (m, 6H), 1.36 (s, 9H).

EXAMPLE 27

4-(2-(N-benzylamino)ethyl)-5,6,7,8-tetrahydrophthalazin-1(2H)-one

The compound prepared in Reference example 13 (40 mg), sodium iodide (8.4 mg) and benzylamine (0.21 mL) were stirred at room temperature for 10 hours. Methylene chloride and a saturated aqueous sodium hydrogen carbonate solution were added to the reaction mixture, which was separated. The organic layer was dried over anhydrous magnesium sulfate and concentrated. The residue was purified by column chromatography on silica gel (chloroform:methanol=50:1) to give the compound of the present invention (18 mg) having the following physical data.

TLC: Rf 0.29 (chloroform:methanol=9:1);

NMR (DMSO-$d_6$): δ 12.46 (s, 1H), 7.40-7.15 (m, 5H), 3.69 (s, 2H), 2.80-2.60 (m, 4H), 2.50-2.30 (m, 4H), 1.63 (brs, 4H).

EXAMPLE 27(1) TO EXAMPLE 27(80)

By the same procedure as described in Example 27, if necessary, by converting to corresponding salts by conventional method, using the compound prepared in Reference example 13 or a corresponding derivative, and a corresponding derivative instead of benzylamine, the following compounds of the present invention were obtained.

EXAMPLE 27(1)

4-(2-(morpholin-4-yl)ethyl)-5,6,7,8-tetrahydrophthalazin-1(2H)-one

Free Form:

TLC: Rf 0.38 (chloroform:methanol:acetic acid=90:10:1);

NMR (CD$_3$OD): δ 3.74-3.66 (m, 4H), 2.84-2.77 (m, 2H), 2.75-2.66 (m, 2H), 2.64-2.48 (m, 8H), 1.88-1.72 (m, 4H).

Hydrochloride:

TLC: Rf 0.24 (chloroform:methanol=9:1);

NMR (DMSO-$d_6$): δ 12.68 (s, 1H), 10.85 (brs, 1H), 4.02-3.92 (m, 2H), 3.82-3.70 (m, 2H), 3.54-3.44 (m, 2H), 3.44-3.32 (m, 2H), 3.15-3.05 (m, 2H), 3.05-2.96 (m, 2H), 2.53-2.33 (m, 4H), 1.76-1.58 (m, 4H).

EXAMPLE 27(2)

4-(2-(pyrrolidin-1-yl)ethyl)-5,6,7,8-tetrahydrophthalazin-1(2H)-one hydrochloride TLC: Rf 0.12 (chloroform:methanol=9:1);

NMR (CD$_3$OD): δ 3.78-3.66 (m, 2H), 3.63 (t, J=8.1 Hz, 2H), 3.26-3.10 (m, 2H), 3.06 (t, J=8.1 Hz, 2H), 2.62-2.48 (m, 4H), 2.26-1.96 (m, 4H), 1.90-1.72 (m, 4H).

EXAMPLE 27(3)

4-(2-(4-methylpiperazin-1-yl)ethyl)-5,6,7,8-tetrahydrophthalazin-1(2H)-one dihydrochloride TLC: Rf 0.32 (chloroform:methanol=9:1);

NMR (DMSO-$d_6$): δ 12.68 (s, 1H), 11.80 (brs, 2H), 4.00-3.20 (m, 10H), 3.10-2.95 (m, 2H), 2.80 (s, 3H), 2.50-2.30 (m, 4H), 1.75-1.55 (m, 4H).

EXAMPLE 27(4)

4-(2-(piperidin-1-yl)ethyl)-5,6,7,8-tetrahydrophthalazin-1(2H)-one hydrochloride TLC: Rf 0.34 (chloroform:methanol=9:1);

NMR (DMSO-$d_6$): δ 12.66 (s, 1H), 10.45 (brs, 1H), 3.52-3.42 (m, 2H), 3.34-3.22 (m, 2H), 3.06-2.96 (m, 2H), 2.96-2.80 (m, 2H), 2.54-2.32 (m, 4H), 1.84-1.56 (m, 9H), 1.46-1.26 (m, 1H).

EXAMPLE 27(5)

4-(2-(N-cyclohexylamino)ethyl)-5,6,7,8-tetrahydrophthalazin-1(2H)-one hydrochloride TLC: Rf 0.34 (chloroform:methanol=9:1);

NMR (DMSO-$d_6$): δ 12.65 (s, 1H), 8.85 (brs, 2H), 3.26-3.10 (m, 2H), 3.10-2.96 (m, 1H), 2.90 (t, J=7.2 Hz, 2H), 2.50-2.36 (m, 4H), 2.06-1.98 (m, 2H), 1.80-1.54 (m, 7H), 1.40-1.00 (m, 5H).

EXAMPLE 27(6)

4-(2-(azepan-1-yl)ethyl)-5,6,7,8-tetrahydrophthalazin-1(2H)-one hydrochloride

TLC: Rf 0.28 (chloroform:methanol=9:1);

NMR (DMSO-$d_6$): δ 12.66 (s, 1H), 10.55 (s, 1H), 3.46-3.28 (m, 4H), 3.20-3.06 (m, 2H), 3.06-2.98 (m, 2H), 2.56-2.46 (m, 2H), 2.44-2.34 (m, 2H), 1.90-1.50 (m, 12H).

EXAMPLE 27(7)

4-(2-(4-t-butoxycarbonylpiperazin-1-yl)ethyl)-5,6,7,8-tetrahydrophthalazin-1(2H)-one TLC: Rf 0.29 (chloroform:methanol=9:1);

NMR (DMSO-$d_6$): δ 12.51 (s, 1H), 3.32-3.24 (m, 6H), 2.70-2.60 (m, 2H), 2.60-2.50 (m, 2H), 2.40-2.30 (m, 6H), 1.72-1.56 (m, 4H), 1.37 (s, 9H).

EXAMPLE 27(8)

4-(2-(thiomorpholin-4-yl)ethyl)-5,6,7,8-tetrahydrophthalazin-1(2H)-one hydrochloride TLC: Rf 0.40 (chloroform:methanol=9:1);

NMR (DMSO-$d_6$): δ 12.67 (s, 1H), 10.90 (brs, 1H), 3.84-3.70 (m, 2H), 3.44-3.30 (m, 2H), 3.24-3.10 (m, 4H), 3.08-2.98 (m, 2H), 2.90-2.76 (m, 2H), 2.52-2.44 (m, 2H), 2.42-2.34 (m, 2H), 1.76-1.58 (m, 4H).

EXAMPLE 27(9)

4-(2-(N-(2-propynyl)amino)ethyl)-5,6,7,8-tetrahydrophthalazin-1(2H)-one hydrochloride TLC: Rf 0.28 (chloroform:methanol=9:1);

NMR (DMSO-$d_6$): δ 12.66 (s, 1H), 9.70-9.45 (m, 2H), 3.98-3.88 (m, 2H), 3.70 (t, J=2.4 Hz, 1H), 3.30-3.18 (m, 2H), 2.91 (t, J=7.8 Hz, 2H), 2.48-2.32 (m, 4H), 1.76-1.58 (m, 4H).

EXAMPLE 27(10)

4-(2-(4-ethylpiperazin-1-yl)ethyl)-5,6,7,8-tetrahydrophthalazin-1(2H)-one

TLC: Rf 0.19 (chloroform:methanol=5:1);

NMR (CD$_3$OD): δ 2.84-2.76 (m, 2H), 2.75-2.67 (m, 2H), 2.67-2.47 (m, 12H), 2.44 (q, J=7.5H, 2H), 1.79 (m, 4H), 1.10 (t, J=7.5 Hz, 3H).

EXAMPLE 27(11)

4-(2-(N-cyclohexylmethylamino)ethyl)-5,6,7,8-tetrahydrophthalazin-1(2H)-one hydrochloride TLC: Rf 0.49 (chloroform:methanol=4:1);

NMR (DMSO-$d_6$): δ 12.66 (s, 1H), 8.86 (brs, 2H), 3.26-3.08 (m, 2H), 3.02-2.88 (m, 2H), 2.86-2.70 (m, 2H), 2.58-2.30 (m, 4H), 1.88-1.50 (m, 10H), 1.32-0.82 (m, 5H).

EXAMPLE 27(12)

4-(2-(azocan-1-yl)ethyl)-5,6,7,8-tetrahydrophthalazin-1(2H)-one

TLC: Rf 0.41 (chloroform:methanol=5:1);

NMR (CD$_3$OD): δ 3.61 (t, J=6.6 Hz, 2H), 3.58-3.30 (m, 4H), 3.08 (t, J=6.6 Hz, 2H), 2.62-2.50 (m, 4H), 2.12-1.60 (m, 14H).

EXAMPLE 27(13)

4-(2-(4-methyl-1,4-diazepan-1-yl)ethyl)-5,6,7,8-tetrahydrophthalazin-1(2H)-one

TLC: Rf 0.29 (chloroform:methanol:saturated aqueous ammonia=5:1:0.1);

NMR (CD$_3$OD): δ 3.26 (m, 4H), 3.08-3.01 (m, 4H), 2.96 (t, J=6.0 Hz, 2H), 2.84 (m, 2H), 2.81 (s, 3H), 2.60 (m, 2H), 2.52 (m, 2H), 2.03 (m, 2H), 1.80 (m, 4H).

EXAMPLE 27(14)

4-(2-(N-(2-(N'-t-butoxycarbonylamino)ethyl)amino)ethyl)-5,6,7,8-tetrahydrophthalazin-1(2H)-one TLC: Rf 0.47 (chloroform:methanol=8:1);

NMR (DMSO-$d_6$): δ 12.52 (brs, 1H), 6.73 (brt, 1H), 3.34 (br, 1H), 3.06-2.94 (m, 2H), 2.80 (t, J=7.2 Hz, 2H), 2.70-2.54 (m, 4H), 2.54-2.28 (m, 4H), 1.76-1.54 (m, 4H), 1.36 (s, 9H).

EXAMPLE 27(15)

4-(2-(4-phenylpiperazin-1-yl)ethyl)-5,6,7,8-tetrahydrophthalazin-1(2H)-one

TLC: Rf 0.50 (chloroform:methanol=9:1);

NMR (CD$_3$OD): δ 7.23 (dd, J=7.5, 7.5 Hz, 2H), 6.97 (d, J=7.5 Hz, 2H), 6.83 (dd, J=7.5, 7.5 Hz, 1H), 3.20 (m, 4H), 2.90-2.70 (m, 8H), 2.62 (m, 2H), 2.52 (m, 2H), 1.80 (m, 4H).

EXAMPLE 27(16)

4-(2-(4-(2-chlorophenyl)piperazin-1-yl)ethyl)-5,6,7,8-tetrahydrophthalazin-1(2H)-one TLC: Rf 0.44 (chloroform:methanol=9:1);

NMR (CDCl$_3$): δ 10.61 (s, 1H), 7.36 (d, J=7.8 Hz, 1H), 7.22 (dd, J=7.8, 7.8 Hz, 1H), 7.05 (d, J=7.8 Hz, 1H), 6.98 (dd, J=7.8, 7.8 Hz, 1H), 3.11 (m, 4H), 2.78 (s, 4H), 2.74 (m, 4H), 2.59 (m, 2H), 2.53 (m, 2H), 1.78 (m, 4H).

EXAMPLE 27(17)

4-(2-(4-benzylpiperazin-1-yl)ethyl)-5,6,7,8-tetrahydrophthalazin-1(2H)-one

TLC: Rf 0.43 (chloroform:methanol=9:1);

NMR (CD$_3$OD): δ 7.36-7.22 (m, 5H), 3.54 (s, 2H), 2.84-2.64 (m, 4H), 2.64-2.45 (m, 12H), 1.86-1.72 (m, 4H).

EXAMPLE 27(18)

4-(2-(N-(4-trifluoromethylbenzyl)amino)ethyl)-5,6,7,8-tetrahydrophthalazin-1(2H)-one TLC: Rf 0.33 (chloroform:methanol=9:1);

NMR (CD$_3$OD): δ 7.63 (d, J=8.4 Hz, 2H), 7.54 (d, J=8.4 Hz, 2H), 3.90 (s, 2H), 2.96 (t, J=6.9 Hz, 2H), 2.80 (t, J=6.9 Hz, 2H), 2.52 (m, 4H), 1.77 (m, 4H).

EXAMPLE 27(19)

4-(2-(N-methyl-N-benzylamino)ethyl)-5,6,7,8-tetrahydrophthalazin-1(2H)-one

Free Form:

TLC: Rf 0.32 (chloroform:methanol=9:1);

NMR (CD$_3$OD): δ 7.28 (m, 5H), 3.56 (s, 2H), 2.83-2.65 (m, 4H), 2.49 (m, 4H), 2.31 (s, 3H), 1.73 (m, 4H).

Methanesulfonate:

TLC: Rf 0.44 (methylene chloride:methanol=9:1);

NMR (DMSO-$d_6$): δ 12.69 (s, 1H), 9.42 (m, 1H), 7.49 (m, 5H), 4.48 (m, 1H), 4.31 (m, 1H), 3.50-3.25 (m, 2H), 2.98 (m, 2H), 2.75 (m, 3H), 2.38 (m, 4H), 2.29 (s, 3H), 1.68 (m, 4H).

EXAMPLE 27(20)

4-(2-(N-(2-phenylethyl)amino)ethyl)-5,6,7,8-tetrahydrophthalazin-1(2H)-one

TLC: Rf 0.41 (methanol:methylene chloride=1:10);

NMR (CD$_3$OD): δ 7.37 (m, 5H), 3.52 (t, J=6.8 Hz, 2H), 3.38 (m, 2H), 3.07 (m, 4H), 2.60 (m, 4H), 1.85 (m, 4H).

EXAMPLE 27(21)

4-(2-(N-(4-trifluoromethoxybenzyl)amino)ethyl)-5,6,7,8-tetrahydrophthalazin-1(2H)-one TLC: Rf 0.37 (chloroform:methanol=0.9:1);

NMR (CD$_3$OD): δ 7.44 (d, J=7.5 Hz, 2H), 7.23 (d, J=7.5 Hz, 2H), 3.82 (s, 2H), 2.93 (t, J=6.9 Hz, 2H), 2.79 (t, J=6.9 Hz, 2H), 2.59-2.49 (m, 4H), 1.77 (m, 4H).

EXAMPLE 27(22)

4-(2-(4-(pyridin-2-yl)piperazin-1-yl)ethyl)-5,6,7,8-tetrahydrophthalazin-1(2H)-one TLC: Rf 0.55 (chloroform:methanol=9:1);

NMR (CD$_3$OD): δ 8.08 (m, 1H), 7.56 (m, 1H), 6.82 (d, J=8.4 Hz, 1H), 6.68 (dd, J=6.3, 4.8 Hz, 1H), 3.54 (t, J=5.1 Hz, 4H), 2.90-2.74 (m, 4H), 2.68 (t, J=5.1 Hz, 4H), 2.62 (m, 2H), 2.52 (m, 2H), 1.79 (m, 4H).

EXAMPLE 27(23)

4-(2-(N-(2-(N'-phenylamino)ethyl)amino)ethyl)-5,6,7,8-tetrahydrophthalazin-1(2H)-one TLC: Rf 0.26 (chloroform:methanol=9:1);
NMR (CD$_3$OD): δ 7.18-7.08 (m, 2H), 6.74-6.64 (m, 3H), 3.48-3.36 (m, 4H), 3.22 (t, J=6.0 Hz, 2H), 2.95 (t, J=6.6 Hz, 2H), 2.51 (m, 4H), 1.78 (m, 4H).

EXAMPLE 27(24)

4-(2-(4-acetylpiperazin-1-yl)ethyl)-5,6,7,8-tetrahydrophthalazin-1(2H)-one

TLC: Rf 0.21 (chloroform:methanol=9:1);
NMR (CD$_3$OD): δ 3.62-3.52 (m, 4H), 2.85-2.70 (m, 4H), 2.64-2.48 (m, 8H), 2.09 (s, 3H), 1.79 (m, 4H).

EXAMPLE 27(25)

4-(2-(N-(naphthalen-1-ylmethyl)amino)ethyl)-5,6,7,8-tetrahydrophthalazin-1(2H)-one TLC: Rf 0.45 (methanol:methylene chloride=1:9);
NMR (DMSO-d$_6$): δ 12.49 (brs, 1H), 8.15 (m, 1H), 7.89 (m, 1H), 7.79 (d, J=7.2 Hz, 1H), 7.53-7.40 (m, 4H), 4.15 (s, 2H), 2.87 (t, J=7.2 Hz, 2H), 2.69 (t, J=7.2 Hz, 2H), 2.35 (m, 4H), 1.62 (brs, 4H).

EXAMPLE 27(26)

4-(2-(N-ethyl-N-benzylamino)ethyl)-5,6,7,8-tetrahydrophthalazin-1(2H)-one

TLC: Rf 0.41 (chloroform:methanol=9:1);
NMR (CD$_3$OD): δ 7.30-7.20 (m, 5H), 3.60 (s, 2H), 2.72 (s, 4H), 2.62 (q, J=7.2 Hz, 2H), 2.48 (m, 2H), 2.40 (m, 2H), 1.70 (m, 4H), 1.10 (t, J=7.2 Hz, 3H).

EXAMPLE 27(27)

4-(2-(N-(1-benzylpiperidin-4-yl)amino)ethyl)-5,6,7,8-tetrahydrophthalazin-1(2H)-one TLC: Rf 0.17 (methylene chloride:methanol:water=9:1:0.1);
NMR (CD$_3$OD): δ 7.43-7.23 (m, 5H), 3.60 (s, 2H), 3.41 (t, J=6.6 Hz, 2H), 3.14 (m, 1H), 3.06-2.98 (m, 2H), 2.95 (t, J=6.6 Hz, 2H), 2.60-2.50 (m, 4H), 2.22-2.06 (m, 4H), 1.86-1.60 (m, 6H).

EXAMPLE 27(28)

4-(2-(N-(2-hydroxyethyl)-N-benzylamino)ethyl)-5,6,7,8-tetrahydrophthalazin-1(2H)-one TLC: Rf 0.44 (methylene chloride:methanol=9:1);
NMR (CD$_3$OD): δ 7.19 (m, 5H), 3.65 (t, J=8.7 Hz, 2H), 3.61 (s, 2H), 2.78-2.67 (m, 6H), 2.43 (m, 2H), 2.30 (m, 2H), 1.64 (m, 4H).

EXAMPLE 27(29)

4-(2-(4-cyclohexylpiperazin-1-yl)ethyl)-5,6,7,8-tetrahydrophthalazin-1(2H)-one

TLC: Rf 0.55 (methylene chloride:methanol=9:1);
NMR (CD$_3$OD): δ 3.30-2.70 (m, 13H), 2.59 (m, 2H), 2.51 (m, 2H), 2.05 (m, 2H), 1.91 (m, 2H), 1.86-1.65 (m, 6H), 1.44-1.20 (m, 4H).

EXAMPLE 27(30)

4-(2-(N-(4-fluorobenzyl)amino)ethyl)-5,6,7,8-tetrahydrophthalazin-1(2H)-one

Free Form:
TLC: Rf 0.50 (methylene chloride:methanol=4:1);
NMR (CD$_3$OD): δ 7.41 (m, 2H), 7.10 (dd, J=8.7, 8.7 Hz, 2H), 3.94 (s, 2H), 3.10 (t, J=6.9 Hz, 2H), 2.85 (t, J=6.9 Hz, 2H), 2.52 (m, 4H), 1.78 (m, 4H).

Hydrochloride:
TLC: Rf 0.43 (methylene chloride:methanol=4:1);
NMR (DMSO-d$_6$): δ 12.68 (s, 1H), 9.00 (s, 2H), 7.57 (m, 2H), 7.29 (m, 2H), 4.20 (m, 2H), 3.21 (m, 2H), 2.90 (m, 2H), 2.58-2.38 (m, 4H), 1.67 (m, 4H).

EXAMPLE 27(31)

4-(2-(N-(4-methoxybenzyl)amino)ethyl)-5,6,7,8-tetrahydrophthalazin-1(2H)-one

TLC: Rf 0.39 (methylene chloride:methanol:saturated aqueous ammonia=4:1:0.3);
NMR (CD$_3$OD): δ 7.40 (d, J=8.7 Hz, 2H), 6.99 (d, J=8.7 Hz, 2H), 4.15 (s, 2H), 3.81 (s, 3H), 3.37 (t, J=6.9 Hz, 2H), 2.95 (t, J=6.9 Hz, 2H), 2.53 (m, 4H), 1.78 (m, 4H).

EXAMPLE 27(32)

4-(2-(N-(1-phenylethyl)amino)ethyl)-5,6,7,8-tetrahydrophthalazin-1(2H)-one

TLC: Rf 0.38 (methylene chloride:methanol=9:1);
NMR (CD$_3$OD): δ 7.50 (m, 5H), 4.48 (q, J=6.9 Hz, 1H), 3.29 (m, 2H), 2.92 (t, J=6.6 Hz, 2H), 2.51 (m, 4H), 1.78 (m, 4H), 1.70 (d, J=6.9 Hz, 3H).

EXAMPLE 27(33)

4-(2-(N-(3-fluorobenzyl)amino)ethyl)-5,6,7,8-tetrahydrophthalazin-1(2H)-one

TLC: Rf 0.39 (methylene chloride:methanol=9:1);
NMR (CD$_3$OD): δ 7.48-7.06 (m, 4H), 4.06 (s, 2H), 3.20 (t, J=6.9 Hz, 2H), 2.90 (t, J=6.9 Hz, 2H), 2.53 (m, 4H), 1.77 (m, 4H).

EXAMPLE 27(34)

4-(2-(4-diphenylmethylpiperazin-1-yl)ethyl)-5,6,7,8-tetrahydrophthalazin-1(2H)-one TLC: Rf 0.48 (methylene chloride:methanol=9:1);
NMR (CD$_3$OD): δ 7.48-7.40 (m, 4H), 7.32-7.13 (m, 6H), 4.25 (s, 1H), 3.16 (t, J=5.1 Hz, 2H), 2.81-2.40 (m, 14H), 1.78 (m, 4H).

EXAMPLE 27(35)

4-(2-(N-(3-methoxybenzyl)amino)ethyl)-5,6,7,8-tetrahydrophthalazin-1(2H)-one

TLC: Rf 0.44 (methylene chloride:methanol=9:1);

NMR (CD$_3$OD): δ 7.32 (dd, J=8.1, 8.1 Hz, 1H), 7.02-6.90 (m, 3H), 4.05 (s, 2H), 3.81 (s, 3H), 3.24 (t, J=6.9 Hz, 2H), 2.90 (t, J=6.9 Hz, 2H), 2.51 (m, 4H), 1.77 (m, 4H).

EXAMPLE 27(36)

8-(2-(piperidin-1-yl)ethyl)-2,3,4,6-tetrahydropyrido[2,3-d]pyridazin-5(1H)-one hydrochloride TLC: Rf 0.26 (chloroform:methanol=4:1);

NMR (DMSO-d$_6$): δ 11.94 (s, 1H), 9.31 (brs, 1H), 6.39 (brs, 1H), 3.60-3.10 (m, 6H), 3.06-2.74 (m, 4H), 2.34 (t, J=6.6 Hz, 2H), 1.94-1.50 (m, 7H), 1.38 (m, 1H).

EXAMPLE 27(37)

4-(2-(N-(2-phenoxyethyl)amino)ethyl)-5,6,7,8-tetrahydrophthalazin-1(2H)-one

TLC: Rf 0.62 (methylene chloride:methanol:water=4:1:0.2);

NMR (CD$_3$OD): δ 7.26 (dd, J=8.1, 8.1 Hz, 2), 6.98-6.88 (m, 3H), 4.11 (t, J=5.1 Hz, 2H), 3.14-3.05 (m, 4H), 2.84 (t, J=6.6 Hz, 2H), 2.60-2.50 (m, 4H), 1.78 (m, 4H).

EXAMPLE 27(38)

4-(2-(4-benzyloxycarbonyl-1,4-diazepan-1-yl)ethyl)-5,6,7,8-tetrahydrophthalazin-1(2H)-one Free Form:

TLC: Rf 0.67 (methylene chloride:methanol:saturated aqueous ammonia=4:1:0.3);

NMR (CD$_3$OD): δ 7.34 (m, 5H), 5.11 (s, 2H), 3.54 (m, 4H), 2.82-2.70 (m, 8H), 2.60 (m, 2H), 2.52 (m, 2H), 1.90-1.72 (m, 6H).

Methanesulfonate:

TLC: Rf 0.64 (methylene chloride:methanol=9:1);

NMR (DMSO-d$_6$): δ 12.7 (s, M1), 9.35 (s, 1H), 7.40-7.30 (m, 5H), 5.11 (s, 2H), 3.89 (m, 1H), 3.72-3.40 (m, 7H), 3.35-3.16 (m, 2H), 2.95 (t, J=7.2 Hz, 2H), 2.65-2.50 (m, 4H), 2.30 (s, 3H), 1.85 (m, 2H), 1.67 (m, 4H).

EXAMPLE 27(39)

4-(2-(4-cyclopentylpiperazin-1-yl)ethyl)-5,6,7,8-tetrahydrophthalazin-1(2H)-one dihydrochloride TLC: Rf 0.14 (methylene chloride:methanol=9:1);

NMR (CD$_3$OD): δ 4.00-3.40 (m, 11H), 3.12 (t, J=7.5 Hz, 2H), 2.62-2.50 (m, 4H), 2.22-2.15 (m, 2H), 1.92-1.68 (m, 10H).

EXAMPLE 27(40)

4-(2-(4-butylpiperazin-1-yl)ethyl)-5,6,7,8-tetrahydrophthalazin-1(2H)-one dihydrochloride TLC: Rf 0.16 (methylene chloride:methanol=9:1);

NMR (CD$_3$OD): δ 4.10-3.45 (m, 8H), 3.74 (t, J=7.2 Hz, 2H), 3.30 (m, 2H), 3.16 (t, J=7.2 Hz, 2H), 2.60 (m, 2H), 2.53 (m, 2H), 1.90-1.75 (m, 6H), 1.45 (m, 2H), 1.01 (t, J=7.2 Hz, 3H).

EXAMPLE 27(41)

8-(2-(4-cyclohexylpiperazin-1-yl)ethyl)-2,3,4,6-tetrahydropyrido[2,3-d]pyridazin-5(1H)-one trihydrochloride TLC: Rf 0.36 (chloroform:methanol=4:1);

NMR (DMSO-d$_6$): δ 12.17 (s, 1H), 11.85 (brs, 1H), 5.09 (br, 3H), 3.98-3.08 (m, 11H), 2.96 (m, 2H), 2.36 (t, J=6.0 Hz, 2H), 2.10 (m, 2H), 1.94-0.98 (m, 12H).

EXAMPLE 27(42)

4-(2-(N-(4-chlorobenzyl)amino)ethyl)-5,6,7,8-tetrahydrophthalazin-1(2H)-one hydrochloride TLC: Rf 0.75 (methanol:methylene chloride=1:4);

NMR (DMSO-d$_6$): δ 12.66 (s, 1H), 9.39 (brs, 2H), 7.59 (d, J=8.4 Hz, 2H), 7.51 (d, J=8.4 Hz, 2H), 4.19 (m, 2H), 3.18 (m, 2H), 2.94 (t, J=7.5 Hz, 2H), 2.40 (m, 4H), 1.66 (m, 4H).

EXAMPLE 27(43)

4-(2-(4-hexylpiperazin-1-yl)ethyl)-5,6,7,8-tetrahydrophthalazin-1(2H)-one dihydrochloride TLC: Rf 0.68 (methylene chloride:methanol=4:1);

NMR (CD$_3$OD) δ 4.04-3.45 (m, 8H), 3.71 (t, J=7.2 Hz, 2H), 3.26 (m, 2H), 3.15 (t, J=7.2 Hz, 2H), 2.59 (m, 2H), 2.53 (m, 2H), 1.80 (m, 6H), 1.39 (m, 6H), 0.93 (t, J=6.9 Hz, 3H).

EXAMPLE 27(44)

4-(2-(4-isopropylpiperazin-1-yl)ethyl)-5,6,7,8-tetrahydrophthalazin-1(2H)-one dihydrochloride TLC: Rf 0.25 (methylene chloride:methanol=4:1);

NMR (CD$_3$OD): δ 4.12-3.58 (m, 11H), 3.18 (t, J=6.9 Hz, 2H), 2.60 (m, 2H), 2.53 (m, 2H), 1.80 (m, 4H), 1.44 (d, J=6.9 Hz, 6H).

EXAMPLE 27(45)

4-(2-(N-(2-fluorobenzyl)amino)ethyl)-5,6,7,8-tetrahydrophthalazin-1(2H)-one hydrochloride TLC: Rf 0.65 (methylene chloride:methanol=4:1);

NMR (CD$_3$OD): δ 7.61-7.50 (m, 2H), 7.32-7.20 (m, 2H), 4.39 (s, 2H), 3.51 (t, J=6.9 Hz, 2H), 3.02 (t, J=6.9 Hz, 2H), 2.52 (m, 4H), 1.79 (m, 4H).

EXAMPLE 27(46)

4-(2-(N-(3-methoxypropyl)amino)ethyl)-5,6,7,8-tetrahydrophthalazin-1(2H)-one hydrochloride TLC: Rf 0.42 (methylene chloride:methanol=4:1);
NMR (CD$_3$OD): δ 3.55 (t, J=6.6 Hz, 2H), 3.45 (t, J=6.9 Hz, 2H), 3.35 (s, 3H), 3.21 (t, J=6.9 Hz, 2H), 2.99 (t, J=6.6 Hz, 2H), 2.54 (m, 4H), 1.97 (m, 2H), 1.79 (m, 4H).

EXAMPLE 27(47)

8-(2-(N-(4-fluorobenzyl)amino)ethyl)-2,3,4,6-tetrahydropyrido[2,3-d]pyridazin-5(1H)-one dihydrochloride TLC: Rf 0.30 (chloroform:methanol=4:1);
NMR (DMSO-d$_6$): δ 12.41 (brs, 1H), 9.60 (brs, 2H), 7.65 (dd, J=8.4, 5.7 Hz, 2H), 7.27 (dd, J=8.4, 8.4 Hz, 2H), 6.00 (brs, 2H), 4.16 (m, 2H), 3.34-3.06 (m, 4H), 2.95 (t, J=7.2 Hz, 2H), 2.39 (t, J=6.0 Hz, 2H), 1.71 (m, 2H).

EXAMPLE 27(48)

4-(2-(N-(furan-2-ylmethyl)amino)ethyl)-5,6,7,8-tetrahydrophthalazin-1(2H)-one hydrochloride TLC: Rf 0.32 (methanol:methylene chloride=1:10);
NMR (DMSO-d$_6$): δ 12.66 (s, 1H), 9.33 (brs, 2H), 7.78 (d, J=1.5 Hz, 1H), 6.65 (d, J=3.3 Hz, 1H), 6.53 (dd, J=3.3, 1.5 Hz, 1H), 4.27 (m, 2H), 3.18 (m, 2H), 2.90 (t, J=7.6 Hz, 2H), 2.40 (m, 4H), 1.66 (m, 4H).

EXAMPLE 27(49)

4-(2-(N-(4-methylbenzyl)amino)ethyl)-5,6,7,8-tetrahydrophthalazin-1(2H)-one hydrochloride TLC: Rf 0.16 (methanol:methylene chloride=1:10);
NMR (DMSO-d$_6$): δ 12.66 (s, 1H), 9.23 (brs, 2H), 7.43 (d, J=7.8 Hz, 2H), 7.24 (d, J=7.8 Hz, 2H), 4.13 (m, 2H), 3.16 (m, 2H), 2.92 (t, J=7.2 Hz, 2H), 2.40 (m, 4H), 2.31 (s, 3H), 1.66 (m, 4H).

EXAMPLE 27(50)

4-(2-(N-(2-methoxybenzyl)amino)ethyl)-5,6,7,8-tetrahydrophthalazin-1(2H)-one hydrochloride TLC: Rf 0.34 (methylene chloride:methanol=4:1);
NMR (CD$_3$OD): δ 7.50-7.42 (m, 2H), 7.15-7.00 (m, 2H), 4.29 (s, 2H), 3.92 (s, 3H), 3.48 (t, J=6.6 Hz, 2H), 3.00 (t, J=6.6 Hz, 2H), 2.53 (m, 4H), 1.78 (m, 4H).

EXAMPLE 27(51)

4-(2-(N-(3-methylthiopropyl)amino)ethyl)-5,6,7,8-tetrahydrophthalazin-1(2H)-one hydrochloride TLC: Rf 0.069 (methylene chloride:methanol=4:1);
NMR (CD$_3$OD): δ 3.47 (t, J=6.6 Hz, 2H), 3.20 (t, J=7.2 Hz, 2H), 3.00 (t, J=6.6 Hz, 2H), 2.62 (t, J=7.2 Hz, 2H), 2.63-2.50 (m, 4H), 2.12 (s, 3H), 2.01 (m, 2H), 1.90-1.75 (m, 4H).

EXAMPLE 27(52)

4-(2-(N-(pyridin-4-ylmethyl)amino)ethyl)-5,6,7,8-tetrahydrophthalazin-1(2H)-one

TLC: Rf 0.39 (methylene chloride:methanol=4:1);
NMR (CD$_3$OD): δ 8.53 (d, J=6.0 Hz, 2H), 7.48 (d, J=6.0 Hz, 2H), 4.06 (s, 2H), 3.15 (t, J=6.9 Hz, 2H), 2.89 (t, J=6.9 Hz, 2H), 2.60-2.45 (m, 4H), 1.88-1.72 (m, 4H).

EXAMPLE 27(53)

8-(2-(4-ethylpiperazin-1-yl)ethyl)-2,3,4,6-tetrahydropyrido[2,3-d]pyridazin-5(1H)-one trihydrochloride TLC: Rf 0.26 (chloroform:methanol=4:1);
NMR (DMSO-d$_6$): δ 12.24 (s, 1H), 11.73 (brs, 1H), 5.59 (br, 3H), 4.00-3.06 (m, 14H), 2.97 (t, J=8.1 Hz, 2H), 2.37 (t, J=6.0 Hz, 2H, 1.73 (m, 2H), 1.26 (t, J=6.9 Hz, 3H).

EXAMPLE 27(54)

4-(2-(4-(4-fluorophenyl)piperazin-1-yl)ethyl)-5,6,7,8-tetrahydrophthalazin-1(2H)-one dihydrochloride TLC: Rf 0.60 (methylene chloride:methanol=9:1);
NMR (CD$_3$OD): δ 7.10-7.00 (m, 4H), 3.82-3.72 (m, 4H), 3.67 (t, J=7.2 Hz, 2H), 3.42-3.30 (m, 4H), 3.15 (t, J=7.2 Hz, 2H), 2.65-2.50 (m, 4H), 1.82 (m, 4H).

EXAMPLE 27(55)

4-(2-(4-(pyridin-4-yl)piperazin-1-yl)ethyl)-5,6,7,8-tetrahydrophthalazin-1(2H)-one trihydrochloride TLC: Rf 0.14 (methylene chloride:methanol=4:1);
NMR (CD$_3$OD): δ 8.28 (d, J=8.1 Hz, 2H), 7.33 (d, J=8.1 Hz, 2H), 4.50 (m, 2H), 3.95-3.30 (m, 6H), 3.71 (t, J=6.9 Hz, 2H), 3.18 (t, J=6.9 Hz, 2H), 2.62 (m, 2H), 2.53 (m, 2H), 1.81 (m, 4H).

EXAMPLE 27(56)

8-(2-(4-cyclopentylpiperazin-1-yl)ethyl)-2,3,4,6-tetrahydropyrido[2,3-d]pyridazin-5(1H)-one trihydrochloride TLC: Rf 0.45 (chloroform:methanol=4:1);
NMR (DMSO-d$_6$): δ 12.23 (s, 1H), 12.22 (brs, 1H), 4.66 (br, 3H), 4.00-3.30 (m, 11H), 3.23 (m, 2H), 2.98 (m, 2H), 2.37 (t, J=6.0 Hz, 2H), 2.00 (m, 2H), 1.92-1.40 (m, 8H).

EXAMPLE 27(57)

8-(2-(4-isopropylpiperazin-1-yl)ethyl)-2,3,4,6-tetrahydropyrido[2,3-d]pyridazin-5(1H)-one trihydrochloride TLC: Rf 0.26 (chloroform:methanol=4:1);
NMR (DMSO-d$_6$): δ 12.18 (s, 1H), 11.86 (brs, 1H), 4.55 (br, 3H), 3.98-3.30 (m, 11H), 3.22 (m, 2H), 2.97 (m, 2H), 2.37 (t, J=6.3 Hz, 2H), 1.72 (m, 2H), 1.30 (d, J=6.3 Hz, 6H).

EXAMPLE 27(58)

4-(2-(N-(thiophen-2-ylmethyl)amino)ethyl)-5,6,7,8-tetrahydrophthalazin-1(2H)-one hydrochloride TLC: Rf 0.32 (methanol:methylene chloride=1:10);
NMR (DMSO-$d_6$): δ 12.65 (s, 1H), 9.59 (brs, 2H), 7.62 (d, J=5.1 Hz, 1H), 7.37 (d, J=2.7 Hz, 1H), 7.09 (dd, J=5.1, 2.7 Hz, 1H), 4.41 (s, 2H), 3.18 (m, 2H), 2.96 (t, J=7.8 Hz, 2H), 2.40 (m, 4H), 1.66 (m, 4H).

EXAMPLE 27(59)

4-(2-(4-(2-methoxyphenyl)piperazin-1-yl)ethyl)-5,6,7,8-tetrahydrophthalazin-1(2H)-one dihydrochloride TLC: Rf 0.72 (methylene chloride:methanol=9:1);
NMR (CD$_3$OD): δ 7.15-6.90 (m, 4H), 3.87 (s, 3H), 3.82-3.05 (m, 8H), 3.67 (t, J=6.9 Hz, 2H), 3.13 (t, J=6.9 Hz, 2H), 2.62-2.50 (m, 4H), 1.80 (m, 4H).

EXAMPLE 27(60)

4-(2-(N-methyl-N-(2-(N',N'-dimethylamino)ethyl)amino)ethyl)-5,6,7,8-tetrahydrophthalazin-1(2H)-one TLC: Rf 0.13 (methylene chloride:methanol:saturated aqueous ammonia=4:1:0.5);
NMR (CD$_3$OD): δ 3.16 (t, J=6.3 Hz, 2H), 3.00 (t, J=6.9 Hz, 2H), 2.94-2.83 (m, 4H), 2.78 (s, 6H) 2.61 (m, 2H), 2.52 (m, 2H), 2.48 (s, 3H), 1.80 (m, 4H).

EXAMPLE 27(61)

4-(2-(4-(3-methoxyphenyl)piperazin-1-yl)ethyl)-5,6,7,8-tetrahydrophthalazin-1(2H)-one dihydrochloride TLC: Rf 0.54 (methylene chloride:methanol=9:1);
NMR (CD$_3$OD): δ 7.20 (dd, J=8.4, 8.4 Hz, 1H), 6.66-6.52 (m, 3H), 3.90-3.08 (m, 8H), 3.77 (s, 3H), 3.67 (t, J=7.2 Hz, 2H), 3.14 (t, J=7.2 Hz, 2H), 2.61 (m, 2H), 2.54 (m, 2H), 1.81 (m, 4H).

EXAMPLE 27(62)

4-(2-(4-((2E)-3-phenyl-2-propenyl)piperazin-1-yl)ethyl)-5,6,7,8-tetrahydrophthalazin-1(2H)-one dihydrochloride TLC: Rf 0.53 (methylene chloride:methanol=9:1);
NMR (CD$_3$OD): δ 7.52 (m, 2H), 7.42-7.32 (m, 3H), 6.96 (d, J=16.2 Hz, 1H), 6.36 (dt, J=16.2, 7.2 Hz, 1H), 4.04 (d, J=7.2 Hz, 2H), 3.90-3.45 (m, 10H), 3.13 (t, J=7.2 Hz, 2H), 2.59 (m, 2H), 2.53 (m, 2H), 1.79 (m, 4H).

EXAMPLE 27(63)

4-(2-(4-(1-methylpropyl)piperazin-1-yl)ethyl)-5,6,7,8-tetrahydrophthalazin-1(2H)-one dihydrochloride TLC: Rf 0.13 (methylene chloride:methanol=9:1);
NMR (CD$_3$OD): δ 4.15-3.40 (m, 11H), 3.15 (t, J=6.9 Hz, 2H), 2.60 (m, 2H), 2.53 (m, 2H), 2.02-1.58 (m, 6H), 1.41 (d, J=6.6 Hz, 3H), 1.06 (t, J=7.5 Hz, 3H).

EXAMPLE 27(64)

4-(2-(4-(furan-2-ylcarbonyl)piperazin-1-yl)ethyl)-5,6,7,8-tetrahydrophthalazin-1(2H)-one hydrochloride TLC: Rf 0.42 (methylene chloride:methanol=9:1);
NMR (CD$_3$OD): δ 7.73 (dd, J=1.8, 0.9 Hz, 1H), 7.17 (dd, J=2.4, 0.9 Hz, 1H), 6.63 (dd, J=2.4, 1.8 Hz, 1H), 4.80-4.65 (m, 2H), 3.90-3.25 (m, 6H), 3.66 (t, J=7.2 Hz, 2H), 3.13 (t, J=7.2 Hz, 2H), 2.60 (m, 2H), 2.53 (m, 2H), 1.80 (m, 4H).

EXAMPLE 27(65)

4-(2-(N-(3-chlorobenzyl)amino)ethyl)-5,6,7,8-tetrahydrophthalazin-1(2H)-one methanesulfonate TLC: Rf 0.38 (methylene chloride:methanol=9:1);
NMR (CD$_3$OD): δ 7.60 (s, 1H), 7.47 (s, 3H), 4.31 (s, 2H), 3.49 (t, J=6.9 Hz, 2H), 3.02 (t, J=6.9 Hz, 2H), 2.72 (s, 3H), 2.54 (m, 4H), 1.79 (m, 4H).

EXAMPLE 27(66)

8-(2-(N-benzylamino)ethyl)-2,3,4,6-tetrahydropyrido[2,3-d]pyridazin-5(1H)-one

TLC: Rf 0.42 (methylene chloride:methanol=4:1);
NMR (CD$_3$OD): δ 7.58-7.45 (m, 5H), 4.28 (s, 2H), 3.47 (t, J=6.6 Hz, 2H), 3.34 (m, 2H), 2.89 (t, J=6.6 Hz, 2H), 2.52 (t, J=6.6 Hz, 2H), 1.86 (m, 2H).

EXAMPLE 27(67)

8-(2-(N-(2-(N'-phenylamino)ethyl)amino)ethyl)-2,3,4,6-tetrahydropyrido[2,3-d]pyridazin-5(1H)-one TLC: Rf 0.23 (methylene chloride:methanol=4:1);
NMR (CD$_3$OD): δ 7.15 (m, 2H), 6.69 (m, 3H), 3.50 (m, 4H), 3.32 (m, 4H), 2.89 (t, J=6.6 Hz, 2H), 2.51 (t, J=6.6 Hz, 2H), 1.84 (m, 2H).

EXAMPLE 27(68)

8-(2-(4-hexylpiperazin-1-yl)ethyl)-2,3,4,6-tetrahydropyrido[2,3-d]pyridazin-5(1H)-one trihydrochloride TLC: Rf 0.51 (methylene chloride:methanol=4:1);
NMR (CD$_3$OD): δ 4.10-3.55 (m, 10H), 3.47 (t, J=5.7 Hz, 2H), 3.30 (m, 2H), 3.18 (t, J=7.2 Hz, 2H), 2.63 (t, J=6.3 Hz, 2H), 1.92 (m, 2H), 1.81 (m, 2H), 1.39 (m, 6H), 0.93 (m, 3H).

EXAMPLE 27(69)

4-(2-(N-(2,4-difluorobenzyl)amino)ethyl)-5,6,7,8-tetrahydrophthalazin-1(2H)-one

TLC: Rf 0.15 (methanol:methylene chloride=1:10).

EXAMPLE 27(70)

4-(2-(4-(2-methylpropyl)piperazin-1-yl)ethyl)-5,6,7,8-tetrahydrophthalazin-1(2H)-one dihydrochloride TLC: Rf 0.63 (methylene chloride:methanol=4:1);

NMR (CD$_3$OD): δ 4.05-3.50 (m, 8H), 3.78 (t, J=7.2 Hz, 2H), 3.24-3.15 (m, 4H), 2.60 (m, 2H), 2.53 (m, 2H), 2.20 (m, 1H), 1.80 (m, 4H), 1.10 (d, J=6.6 Hz, 6H).

EXAMPLE 27(71)

8-(2-(4-(4-fluorophenyl)piperazin-1-yl)ethyl)-2,3,4,6-tetrahydropyrido[2,3-d]pyridazin-5(1H)-one trihydrochloride TLC: Rf 0.69 (methylene chloride:methanol=9:1);

NMR (CD$_3$OD): δ 7.12-7.00 (m, 4H), 3.85-3.70 (m, 6H), 3.51 (t, J=5.7 Hz, 2H), 3.50-3.18 (m, 6H), 2.67 (t, J=6.3 Hz, 2H), 1.95 (m, 2H).

EXAMPLE 27(72)

8-(2-(4-(pyridin-4-yl)piperazin-1-yl)ethyl)-2,3,4,6-tetrahydropyrido[2,3-d]pyridazin-5(1H)-one methanesulfonate TLC: Rf 0.12 (methylene chloride:methanol=4:1);

NMR (CD$_3$OD): δ 8.15 (d, J=7.8 Hz, 2H), 7.20 (d, J=7.8 Hz, 2H), 3.90-3.75 (m, 4H), 3.35 (m, 2H), 3.05-2.78 (m, 8H), 2.69 (s, 3H), 2.52 (t, J=6.3 Hz, 2H), 1.86 (m, 2H).

EXAMPLE 27(73)

8-(2-(4-(4-methoxyphenyl)piperazin-1-yl)ethyl)-2,3,4,6-tetrahydropyrido[2,3-d]pyridazin-5(1H)-one methanesulfonate TLC: Rf 0.65 (methylene chloride:methanol=9:1);

NMR (DMSO-d$_6$): δ 12.0 (s, 1H), 9.53 (brs, 1H), 6.97 (d, J=9.0 Hz, 2H), 6.85 (d, J=9.0 Hz, 2H), 6.42 (s, 1H), 3.80-3.60 (m, 4H), 3.69 (s, 3H), 3.50 (m, 2H), 3.30-3.18 (m, 4H), 2.98-2.80 (m, 4H), 2.35 (m, 2H), 2.32 (s, 3H), 1.73 (m, 2H).

EXAMPLE 27(74)

4-(2-(N-methyl-N-(3-(N',N'-dimethylamino)propyl)amino)ethyl)-5,6,7,8-tetrahydrophthalazin-1(2H)-one TLC: Rf 0.10 (methylene chloride:methanol:saturated aqueous ammonia=4:1:0.5%);

NMR (CD$_3$OD): δ 2.77 (m, 4H), 2.64-2.45 (m, 6H), 2.36 (m, 2H), 2.33 (s, 3H), 2.26 (s, 6H), 1.85-1.65 (m, 6H).

EXAMPLE 27(75)

4-(2-(N-(2-(N',N'-diethylamino)ethyl)amino)ethyl)-5,6,7,8-tetrahydrophthalazin-1(2H)-one TLC: Rf 0.13 (methylene chloride:methanol:saturated aqueous ammonia=4:1:0.5%);

NMR (CD$_3$OD): δ 3.38 (t, J=6.6 Hz, 2H), 3.24 (m, 2H), 3.10 (m, 2H), 3.05-2.92 (m, 6H), 2.62-2.48 (m, 4H), 1.80 (m, 4H), 1.21 (t, J=7.2H, 6H).

EXAMPLE 27(76)

8-(2-(morpholin-4-yl)ethyl)-2,3,4,6-tetrahydropyrido[2,3-d]pyridazin-5(1H)-one

Free Form:

TLC: Rf 0.60 (methanol:methylene chloride=1:4);

NMR (DMSO-d$_6$): δ 11.73 (s, 1H), 6.58 (s, 1H), 3.58-3.55 (m, 4H), 3.17 (m, 2H), 2.58 (m, 4H), 2.41 (m, 4H), 2.32 (t, J=6.0 Hz, 2H), 1.71-1.67 (m, 2H).

Methanesulfonate:

TLC: Rf 0.52 (methanol:methylene chloride=1:4);

NMR (DMSO-d$_6$): δ 11.96 (s, 1H), 9.65 (brs, 1H), 6.36 (s, 1H), 4.01 (m, 2H), 3.65 (t, J=11.7 Hz, 2H), 3.45 (m, 4H), 3.16 (m, 4H), 2.83 (t, J=7.8 Hz, 2H), 2.35 (m, 2H), 2.31 (s, 3H), 1.72 (m, 2H).

EXAMPLE 27(77)

8-(2-(4-methyl-1,4-diazepan-1-yl)ethyl)-2,3,4,6-tetrahydropyrido[2,3-d]pyridazin-5(1H)-one methanesulfonate TLC: Rf 0.41 (methanol:methylene chloride:saturated aqueous ammonia=1:4:0.1);

NMR (DMSO-d$_6$): δ 11.85 (s, 1H), 10.28 (brs, 1H), 6.41 (s, 1H), 3.32-2.78 (m, 16H), 2.42-2.20 (m, 6H), 2.12 (m, 2H), 1.71 (m, 2H).

EXAMPLE 27(78)

4-(2-(4-cyclohexylmethylpiperazin-1-yl)ethyl)-5,6,7,8-tetrahydrophthalazin-1(2H)-one dihydrochloride TLC: Rf 0.52 (methylene chloride:methanol=4:1);

NMR (CD$_3$OD): δ 4.10-3.50 (m, 8H), 3.76 (t, J=6.9H, 2H), 3.20-3.12 (m, 4H), 2.65-2.48 (m, 4H), 1.98-1.65 (m, 12H), 1.48-1.00 (m, 3H).

EXAMPLE 27(79)

8-(2-(4-butylpiperazin-1-yl)ethyl)-2,3,4,6-tetrahydropyrido[2,3-d]pyridazin-5(1H)-one trihydrochloride TLC: Rf 0.28 (methylene chloride:methanol=4:1);

NMR (CD$_3$OD): δ 4.15-3.60 (m, 8H), 3.80 (t, J=7.2 Hz, 2H), 3.48 (t, J=5.7 Hz, 2H), 3.28 (m, 2H), 3.19 (t, J=7.2 Hz, 2H), 2.65 (t, J=6.6 Hz, 2H), 1.94 (m, 2H), 1.80 (m, 2H), 1.45 (m, 2H), 1.01 (t, J=7.2 Hz, 3H).

EXAMPLE 27(80)

4-(5-(morpholin-4-yl)pentyl)-5,6,7,8-tetrahydrophthalazin-1(2H)-one

TLC: Rf 0.43 (methylene chloride:methanol=10:1);

NMR (DMSO-d$_6$): δ 12.48 (s, 1H), 3.54 (t, J=7.5 Hz, 4H), 2.54-2.43 (m, 4H), 2.40-2.28 (m, 6H), 2.22 (t, J=7.5 Hz, 2H), 1.74-1.60 (m, 4H), 1.64-1.48 (m, 2H), 1.50-1.37 (m, 2H), 1.40-1.26 (m, 2H).

EXAMPLE 28

4-(3-(N-(5-(morpholin-4-yl)pentanoyl)amino)phenyl)-5,6,7,8-tetrahydrophthalazin-1(2H)-one methanesulfonate A mixture of the compound prepared in Example 25(1) (115 mg) and morpholine (0.5 mL) was refluxed for 3 hours. The reaction mixture was concentrated. Water was added to the residue, which was extracted with ethyl acetate. The extract was washed with a saturated aqueous sodium hydrogen carbonate solution and brine sequentially, dried over anhydrous magnesium sulfate and concentrated. The residue was recrystallized from a mixed solvent of isopropanol and hexane. A solution of the obtained solid (56.2 mg) and methanesulfonic acid (13.2 mg) in methanol (3.0 mL) was stirred at room temperature for 1 hour. The reaction mixture was concentrated to give the compound of the present invention (67.9 mg) having the following physical data.

TLC: Rf 0.41 (methanol:methylene chloride=1:4);
NMR (DMSO-$d_6$): δ 12.90 (s, 1H), 10.04 (s, 1H), 9.42 (brs, 1H), 7.70 (s, 1H), 7.60 (d, J=8.1 Hz, 1H), 7.36 (t, J=8.1 Hz, 1H), 7.10 (d, J=8.1 Hz, 1H), 3.96 (m, 2H), 3.61 (t, J=11.4 Hz, 2H), 3.43-2.30 (m, 12H), 2.29 (s, 3H), 1.63 (m, 8H).

EXAMPLE 28(1) TO EXAMPLE 28(42)

By the same procedure as described in Example 28, if necessary, by converting to corresponding salts by conventional method, using the compound prepared in Example 25(1) or the compound prepared in Example 23(23), 23(24), 23(29), 23(37), 25, 25(2), 25(6) to 25(8), 25(11) to 25(13), 26(2) or 26(5), and morpholine or a corresponding derivative, the following compounds of the present invention were obtained.

EXAMPLE 28(1)

4-(3-(N-(4-(morpholin-4-yl)butanoyl)amino)phenyl)-5,6,7,8-tetrahydrophthalazin-1(2H)-one methanesulfonate TLC: Rf 0.22 (methanol:methylene chloride=1:9);
NMR (DMSO-$d_6$): δ 12.90 (s, 1H), 10.12 (s, 1H), 9.54 (brs, 1H), 7.70 (s, 1H), 7.59 (d, J=7.8 Hz, 1H), 7.37 (t, J=7.8 Hz, 1H), 7.11 (d, J=7.8 Hz, 1H), 3.98 (m, 2H), 3.63 (t, J=11.6 Hz, 2H), 3.43-2.32 (m, 12H), 2.30 (s, 3H), 1.95 (m, 2H), 1.64 (m, 4H).

EXAMPLE 28(2)

4-(3-(N-(5-(4-methoxypiperidin-1-yl)pentanoyl)amino)phenyl)-5,6,7,8-tetrahydrophthalazin-1(2H)-one methanesulfonate TLC: Rf 0.29 (methanol:methylene chloride=2:3);
NMR (DMSO-$d_6$): δ 12.89 (s, 1H), 10.04 (s, 1H), 8.95 (brs, 1H), 7.70 (s, 1H), 7.59 (d, J=7.8 Hz, 1H), 7.36 (t, J=7.8 Hz, 1H), 7.10 (d, J=7.8 Hz, 1H), 3.52-2.33 (m, 13H), 3.24 (s, 3H), 2.29 (s, 3H), 2.15-1.46 (m, 12H).

EXAMPLE 28(3)

4-(3-(N-(2-(2-(morpholin-4-yl)ethoxy)acetyl)amino)phenyl)-5,6,7,8-tetrahydrophthalazin-1(2H)-one methanesulfonate TLC: Rf 0.50 (methanol:methylene chloride=1:9);
NMR (DMSO-$d_6$): δ 12.91 (s, 1H), 10.00 (s, 1H), 9.78 (brs, 1H), 7.70 (s, 1H), 7.64 (d, J=7.8 Hz, 1H), 7.40 (t, J=7.8 Hz, 1H), 7.15 (d, J=7.8 Hz, 1H), 4.20 (s, 2H), 4.05-3.40 (m, 10H), 3.16 (m, 2H), 2.56-2.33 (m, 4H), 2.31 (s, 3H), 1.70-1.59 (m, 4H).

EXAMPLE 28(4)

4-(3-(N-(4-(morpholin-4-yl)butanoyl)amino)phenyl)-6,7,9,9a-tetrahydro[1,4]thiazino[4,3-d][1,2,4]triazin-1(2H)-one methanesulfonate TLC: Rf 0.16 (chloroform:methanol=9:1);
NMR (DMSO-$d_6$): δ 10.53 (s, 1H), 10.15 (s, 1H), 9.59 (bs, 1H), 7.70 (s, 1H), 7.58-7.55 (m, 1H), 7.35 (t, J=7.8 Hz, 1H), 7.07 (d, J=7.8 Hz, 1H), 4.28-4.18 (m, 1H), 3.99-3.94 (m, 2H), 3.68-3.42 (m, 5H), 3.17-3.00 (m, 5H), 2.90-2.80 (m, 2H), 2.74-2.64 (m, 1H), 2.43 (t, J=6.9 Hz, 2H), 2.33-2.26 (m, 4H), 2.00-1.90 (m, 2H).

EXAMPLE 28(5)

4-(3-(N-(5-(N'-(2-propynyl)amino)pentanoyl)amino)phenyl)-5,6,7,8-tetrahydrophthalazin-1(2H)-one methanesulfonate TLC: Rf 0.30 (methanol:methylene chloride=1:9);
NMR (DMSO-$d_6$): δ 12.88 (s, 1H), 10.03 (s, 1H), 8.93 (brs, 2H), 7.70 (s, 1H), 7.60 (d, J=7.8 Hz, 1H), 7.36 (t, J=7.8 Hz, H), 7.09 (d, J=7.8 Hz, 1H), 3.92 (m, 2H), 3.72 (t, J=2.4 Hz, 1H), 2.96 (m, 2H), 2.48-2.32 (m, 6H), 2.31 (s, 3H), 1.65 (m, 8H).

EXAMPLE 28(6)

4-(3-(N-(5-(N'-(2-methyl-2-propenyl)amino)pentanoyl)amino)phenyl)-5,6,7,8-tetrahydrophthalazin-1(2H)-one methanesulfonate TLC: Rf 0.36 (methanol:methylene chloride:saturated aqueous ammonia=1:9:0.1);
NMR (DMSO-$d_6$): δ 12.88 (brs, 1H), 10.07 (s, 1H), 8.54 (brs, 2H), 7.71 (s, 1H), 7.61 (d, J=7.8 Hz, 1H), 7.35 (t, J=7.8 Hz, 1H), 7.09 (d, J=7.8 Hz, 1H), 5.08 (s, 1H), 5.07 (s, 1H), 3.51 (t, J=6.0 Hz, 2H), 2.89 (m, 2H), 2.48-2.34 (m, 9H), 1.77 (s, 3H), 1.69-1.59 (m, 8H).

EXAMPLE 28(7)

4-(3-(N-(5-(1,2,3,6-tetrahydropyridin-1-yl)pentanoyl)amino)phenyl)-5,6,7,8-tetrahydrophthalazin-1(2H)-one methanesulfonate TLC: Rf 0.48 (chloroform:methanol=4:1);
NMR (DMSO-$d_6$): δ 12.88 (s, 1H), 10.05 (s, 1H), 9.43 (brs, 1H), 7.70 (s, 1H), 7.60 (m, 1H), 7.36 (dd, J=7.8, 7.8 Hz, 1H), 7.09 (d, J=7.8 Hz, 1H), 5.90 (m, 1H), 5.70 (m, 1H), 3.80 (m, 1H), 3.54 (m, 1H), 3.22-2.98 (m, 4H), 2.60-2.18 (m, 8H), 2.50 (s, 3H), 1.82-1.50 (m, 8H).

EXAMPLE 28(8)

4-(3-(N-(5-(N'-cyclopropylamino)pentanoyl)amino)phenyl)-5,6,7,8-tetrahydrophthalazin-1(2H)-one methanesulfonate TLC: Rf 0.35 (chloroform:methanol=4:1);
NMR (DMSO-$d_6$): δ 12.88 (s, 1H), 10.06 (s, 1H), 8.56 (brs, 2H), 7.70 (s, 1H), 7.60 (m, 1H), 7.36 (dd, J=7.8, 7.8 Hz, 1H), 7.09 (m, 1H), 3.08-2.90 (m, 2H), 2.69 (m, 1H), 2.56-2.20 (m, 6H), 2.34 (s, 3H), 1.80-1.46 (m, 8H), 0.84-0.64 (m, 4H).

EXAMPLE 28(9)

4-(3-(N-(4-(morpholin-4-yl)butanoyl)amino)phenyl)-6,7-dihydro[1,4]thiazino[4,3-d][1,2,4]triazin-1(2H)-one methanesulfonate TLC: Rf 0.69 (chloroform:methanol:water=8:2:0.2);
NMR (DMSO-$d_6$): δ 10.89 (s, 1H), 10.16 (s, 1H), 9.52 (br, 1H), 7.74 (s, 1H), 7.61 (d, J=7.8 Hz, 1H), 7.40 (t, J=7.8 Hz, 1H), 7.12 (d, J=7.8 Hz, 1H), 6.27 (s, 1H), 4.02-3.94 (m, 2H), 3.69-3.58 (m, 4H), 3.50-3.42 (m, 2H), 3.20-3.01 (m, 6H), 2.48-2.42 (m, 2H), 2.02-1.92 (m, 2H).

EXAMPLE 28(10)

4-(3-(N-(2-(2-(piperidin-1-yl)ethoxy)acetyl)amino)phenyl)-5,6,7,8-tetrahydrophthalazin-1(2H)-one hydrochloride TLC: Rf 0.30 (methanol:methylene chloride=1:9);
NMR (DMSO-$d_6$): δ 12.89 (s, 1H), 10.19 (s, 2H), 7.83 (s, 1H), 7.79 (d, J=8.1 Hz, 1H), 7.38 (t, J=8.1 Hz, 1H), 7.13 (d, J=8.1 Hz, 1H), 4.16 (s, 2H), 3.85 (t, J=5.1 Hz, 2H), 3.28 (m, 2H), 2.58 (m, 2H), 2.48-2.35 (m, 6H), 1.82-1.59 (m, 10H).

EXAMPLE 28(11)

4-(3-(N-(2-(2-(pyrrolidin-1-yl)ethoxy)acetyl)amino)phenyl)-5,6,7,8-tetrahydrophthalazin-1(2H)-one hydrochloride TLC: Rf 0.55 (methanol:methylene chloride:saturated aqueous ammonia=1:9:0.1);
NMR (DMSO-$d_6$): δ 12.88 (s, 1H), 10.66 (brs, 1H), 10.17 (s, 1H), 7.86 (s, 1H), 7.83 (d, J=7.8 Hz, 1H), 7.37 (t, J=7.8 Hz, 1H), 7.12 (d, J=7.8 Hz, 1H), 4.16 (s, 2H), 3.82-3.55 (m, 4H), 3.38 (m, 2H), 3.03 (m, 2H), 2.48-2.36 (m, 4H), 1.99-1.59 (m, 8H).

EXAMPLE 28(12)

4-(3-(N-(5-(3-methoxypiperidin-1-yl)pentanoyl)amino)phenyl)-5,6,7,8-tetrahydrophthalazin-1(2H)-one hydrochloride TLC: Rf 0.45 (chloroform:methanol=4:1);
NMR (DMSO-$d_6$): δ 12.88 (s, 1H), 10.51 (brs, ½H), 10.24 (s, ½H), 10.20 (s, ½H), 9.11 (brs, ½H), 7.73 (s, 1H), 7.64 (m, 1H), 7.35 (dd, J=7.8, 7.8 Hz, 1H), 7.09 (m, 1H), 3.74-3.20 (m, 8H), 3.14-2.94 (m, 2H), 2.80-2.24 (m, 8H), 2.16-1.10 (m, 10H).

EXAMPLE 28(13)

4-(3-(N-(2-(morpholin-4-yl)acetyl)amino)phenyl)-5,6,7,8-tetrahydrophthalazin-1(2H)-one hydrochloride TLC: Rf 0.44 (methanol:methylene chloride=1:10);
NMR (DMSO-$d_6$): δ 12.92 (s, 1H), 10.92 (brs, 1H), 10.52 (brs, 1H), 7.71 (s, 1H), 7.64 (d, J=7.8 Hz, 1H), 7.43 (t, J=7.8 Hz, 1H), 7.20 (d, J=7.8 Hz, 1H), 4.20-2.27 (m, 14H), 1.69 (m, 2H), 1.60 (m, 2H).

EXAMPLE 28(14)

4-(3-(N-(2-(N'-(2-propynyl)amino)acetyl)amino)phenyl)-5,6,7,8-tetrahydrophthalazin-1(2H)-one hydrochloride TLC: Rf 0.43 (methanol:methylene chloride=1:10);
NMR (DMSO-$d_6$): δ 12.92 (s, 1H), 10.88 (s, 1H), 9.64 (brs, 2H), 7.69 (s, 1H), 7.62 (d, J=7.8 Hz, 1H), 7.43 (t, J=7.8 Hz, 1H), 7.18 (d, J=7.8 Hz, 1H), 4.02 (s, 2H), 3.97 (s, 2H), 3.76 (t, J=2.1 Hz, 1H), 2.48-2.35 (m, 4H), 1.69 (m, 2H), 1.60 (m, 2H).

EXAMPLE 28(15)

4-(3-(N-(2-(N'-cyclobutylamino)acetyl)amino)phenyl)-5,6,7,8-tetrahydrophthalazin-1(2H)-one hydrochloride TLC: Rf 0.40 (methanol:methylene chloride=1:10);
NMR (DMSO-$d_6$): δ 12.92 (s, 1H), 10.81 (s, 1H), 9.29 (m, 2H), 7.69 (s, 1H), 7.63 (d, J=7.8 Hz, 1H), 7.43 (t, J=7.8 Hz, 1H), 7.18 (d, J=7.8 Hz, 1H), 3.85-3.71 (m, 3H), 2.45-2.13 (m, 8H), 1.80-1.61 (m, 6H).

EXAMPLE 28(16)

4-(3-(N-(3-(morpholin-4-yl)propanoyl)amino)phenyl)-5,6,7,8-tetrahydrophthalazin-1(2H)-one hydrochloride TLC: Rf 0.41 (methanol:methylene chloride=1:10);
NMR (DMSO-$d_6$): δ 12.89 (s, 1H), 10.57 (brs, 1H), 10.42 (s, 1H), 7.70 (s, 1H), 7.61 (d, J=7.8 Hz, 1H), 7.38 (t, J=7.8 Hz, 1H), 7.12 (d, J=7.8 Hz, 1H), 3.96 (m, 2H), 3.74 (t, J=11.5 Hz, 2H), 3.42-3.33 (m, 4H), 3.09 (m, 2H), 2.92 (t, J=7.5 Hz, 2H), 2.48-2.34 (m, 4H), 1.69 (m, 2H), 1.60 (m, 2H).

EXAMPLE 28(17)

4-(3-(N-(3-(N'-(2-propynyl)amino)propanoyl)amino)phenyl)-5,6,7,8-tetrahydrophthalazin-1(2H)-one hydrochloride TLC: Rf 0.40 (methanol:methylene chloride=1:10);
NMR (DMSO-$d_6$): δ 12.89 (s, 1H), 10.43 (s, 1H), 9.37 (brs, 2H), 7.72 (s, 1H), 7.61 (d, J=7.8 Hz, 1H), 7.38 (t, J=7.8 Hz, 1H), 7.12 (d, J=7.8 Hz, 1H), 3.93-3.71 (m, 3H), 3.25 (m, 2H), 2.83 (t, J=6.9 Hz, 2H), 2.48-2.34 (m, 4H), 1.69 (m, 2H), 1.59 (m, 2H).

EXAMPLE 28(18)

4-(3-(N-(4-(N'-(2-propynyl)amino)butanoyl)amino)phenyl)-5,6,7,8-tetrahydrophthalazin-1(2H)-one hydrochloride TLC: Rf 0.25 (methanol:methylene chloride=1:10);
NMR (DMSO-$d_6$): δ 12.89 (s, 1H), 10.24 (s, 1H), 9.35 (brs, 2H), 7.70 (s, 1H), 7.62 (d, J=8.1 Hz, 1H), 7.36 (t, J=8.1 Hz, 1H), 7.10 (d, J=8.1 Hz, 1H), 3.91 (d, J=2.7 Hz, 2H), 3.70 (t, J=2.7 Hz, 1H), 3.00 (m, 2H), 2.44 (m, 4H), 2.34 (m, 2H), 1.92 (m, 2H), 1.69 (m, 2H), 1.60 (m, 2H).

EXAMPLE 28(19)

8-(3-(N-(4-(morpholin-4-yl)butanoyl)amino)phenyl)-2,3,4,6-tetrahydropyrido[2,3-d]pyridazin-5(1H)-one dihydrochloride TLC: Rf 0.54 (chloroform:methanol=4:1);
NMR (DMSO-$d_6$): δ 12.34 (brs, 1H), 11.04 (brs, 1H), 10.31 (s, 1H), 7.78-7.64 (m, 2H), 7.39 (dd, J=7.8, 7.8 Hz, 1H), 7.11 (m, 1H), 4.02-3.70 (m, 4H), 3.50-3.32 (m, 2H), 3.24-2.90 (m, 6H), 2.60-2.34 (m, 4H), 2.12-1.90 (m, 2H), 1.82-1.62 (m, 2H).

EXAMPLE 28(20)

4-(2-(N-(2-(pyrrolidin-1-yl)acetyl)amino)ethyl)-5,6,7,8-tetrahydrophthalazin-1(2H)-one TLC: Rf 0.43 (chloroform:methanol=4:1);
NMR (DMSO-$d_6$): δ 12.56 (s, 1H), 7.77 (t, J=5.7 Hz, 1H), 3.42-3.26 (m, 2H), 2.97 (s, 2H), 2.63 (t, J=6.9 Hz, 2H), 2.54-2.28 (m, 8H), 1.76-1.52 (m, 8H).

EXAMPLE 28(21)

4-(N-(2-(N'-cyclobutylamino)ethyl)carbamoylmethyl)-5,6,7,8-tetrahydrophthalazin-1(2H)-one TLC: Rf 0.21 (chloroform:methanol:water=8:2:0.2);
NMR (DMSO-$d_6$): δ 12.57 (br, 1H), 7.97 (t, J=6.0 Hz, 1H), 3.40 (s, 2H), 3.18-3.03 (m, 3H), 2.52-2.45 (m, 2H), 2.44-2.32 (m, 4H), 2.12-2.02 (m, 2H), 1.78-1.56 (m, 8H).

EXAMPLE 28(22)

4-(N-(2-(azepan-1-yl)ethyl)carbamoylmethyl)-5,6,7,8-tetrahydrophthalazin-1(2H)-one Free Form:
TLC: Rf 0.29 (chloroform:methanol:water=8:2:0.2);
NMR (DMSO-$d_6$): δ 12.58 (br, 1H), 7.82 (t, J=6.0 Hz, 1H), 3.39 (s, 2H), 3.10 (q, J=6.0 Hz, 2H), 2.60-2.52 (m, 4H), 2.52-2.45 (m, 2H), 2.44-2.33 (m, 4H), 1.68-1.60 (m, 4H), 1.58-1.46 (m, 8H).

Hydrochloride:
TLC: Rf 0.34 (methylene chloride:methanol:water=8:2:0.2);
NMR (DMSO-$d_6$): δ 12.61 (s, 1H), 10.44 (br, 1H), 8.49 (m, 1H), 3.51-3.42 (m, 2H), 3.47 (s, 2H), 3.42-3.31 (m, 2H), 3.18-3.03 (m, 4H), 2.46-2.34 (m, 4H), 1.88-1.76 (m, 4H), 1.72-1.50 (m, 8H).

EXAMPLE 28(23)

4-(2-(N-(3-(N'-cyclobutylamino)propanoyl)amino)ethyl)-5,6,7,8-tetrahydrophthalazin-1(2H)-one TLC: Rf 0.17 (chloroform:methanol=4:1);
NMR (DMSO-$d_6$): δ 12.55 (brs, 1H), 7.99 (t, J=5.4 Hz, 1H), 4.08 (br, 1H), 3.46-3.20 (m, 2H), 3.09 (m, 1H), 2.68-2.28 (m, 8H), 2.13 (t, J=6.9 Hz, 2H), 2.04 (m, 2H), 1.80-1.40 (m, 8H).

EXAMPLE 28(24)

4-(2-(N-(3-(piperidin-1-yl)propanoyl)amino)ethyl)-5,6,7,8-tetrahydrophthalazin-1(2H)-one TLC: Rf 0.26 (chloroform:methanol=4:1);
NMR (DMSO-$d_6$): δ 12.55 (s, 1H), 8.05 (t, J=5.4 Hz, 1H), 3.42-3.24 (m, 4H), 2.60 (t, J=7.2 Hz, 2H), 2.56-2.22 (m, 8H), 2.18 (t, J=7.2 Hz, 2H), 1.76-1.54 (m, 4H), 1.52-1.24 (m, 6H).

EXAMPLE 28(25)

4-(N-(2-(N'-methyl-N'-isopropylamino)ethyl)carbamoylmethyl)-5,6,7,8-tetrahydrophthalazin-1(2H)-one TLC: Rf 0.25 (chloroform:methanol:water=8:2:0.2);
NMR (DMSO-$d_6$): δ 12.57 (s, 1H), 7.84 (m, 1H), 3.39 (s, 2H), 3.09 (q, J=6.0 Hz, 2H), 2.72 (m, 1H), 2.46-2.30 (m, 6H), 2.10 (s, 3H), 1.66-1.60 (m, 4H), 0.89 (d, J=6.6 Hz, 6H).

EXAMPLE 28(26)

4-(N-(2-(N'-cyclopropylamino)ethyl)carbamoylmethyl)-5,6,7,8-tetrahydrophthalazin-1(2H)-one TLC: Rf 0.43 (chloroform:methanol:water=8:2:0.2);
NMR (DMSO-$d_6$): δ 12.56 (s, 1H), 7.93 (m, 1H), 3.40 (s, 2H), 3.12 (q, J=6.0 Hz, 2H), 2.61 (t, J=6.0 Hz, 2H), 2.44-2.32 (m, 2H), 2.04 (m, 1H), 1.68-1.60 (m, 4H), 0.37-0.30 (m, 2H), 0.20-0.14 (m, 2H).

EXAMPLE 28(27)

4-(N-(3-(piperidin-1-yl)propyl)carbamoylmethyl)-5,6,7,8-tetrahydrophthalazin-1(2H)-one TLC: Rf 0.20 (chloroform:methanol:water=8:2:0.2);
NMR (DMSO-$d_6$): δ 12.70 (s, 1H), 8.00 (m, 1H), 3.38 (s, 2H), 3.04 (q, J=6.3 Hz, 2H), 2.46-2.33 (m, 4H), 2.32-2.16 (m, 6H), 1.68-1.60 (m, 4H), 1.59-1.42 (m, 6H), 1.41-1.30 (m, 2H).

EXAMPLE 28(28)

4-(N-(2-(N'-cyclopentylamino)ethyl)carbamoylmethyl)-5,6,7,8-tetrahydrophthalazin-1(2H)-one hydrobromide TLC: Rf 0.35 (ethyl acetate:acetic acid:water=3:1:1);
NMR (DMSO-$d_6$): δ 12.62 (s, 1H), 8.44 (m, 2H), 8.21 (t, J=6.0 Hz, 1H), 3.46 (m, 1H), 3.46 (s, 2H), 3.38-3.26 (m, 2H), 300-2.92 (m, 2H), 2.45-2.34 (m, 4H), 2.00-1.86 (m, 2H), 1.74-1.60 (m, 6H), 1.60-1.48 (m, 4H).

EXAMPLE 28(29)

4-(N-(3-(N'-cyclobutylamino)propyl)carbamoylmethyl)-5,6,7,8-tetrahydrophthalazin-1(2H)-one hydrobromide TLC: Rf 0.30 (ethyl acetate:acetic acid:water=3:1:1);

NMR (DMSO-$d_6$): δ 12.61 (s, 1H), 8.53 (m, 2H), 8.19 (t, J=6.0 Hz, 1H), 3.65 (quin, J=7.8 Hz, 1H), 3.42 (s, 2H), 3.12 (q, J=6.0 Hz, 2H), 2.80-2.70 (m, 2H), 2.45-2.36 (m, 4H), 2.20-2.00 (m, 4H), 1.84-1.60 (m, 8H).

EXAMPLE 28(30)

4-(N-(4-(N'-cyclobutylamino)butyl)carbamoylmethyl)-5,6,7,8-tetrahydrophthalazin-1(2H)-one hydrobromide TLC: Rf 0.26 (ethyl acetate:acetic acid:water=3:1:1);

NMR (DMSO-$d_6$): δ 12.58 (s, 1H), 8.53 (br, 2H), 8.09 (t, J=6.0 Hz, 1H), 3.64 (quin, J=6.0 Hz, 1H), 3.40 (s, 2H), 3.06, (q, J=6.0 Hz, 2H), 2.82-2.70 (m, 2H), 2.46-2.33 (m, 4H), 2.22-2.02 (m, 4H), 1.84-1.72 (m, 2H), 1.70-1.60 (m, 4H), 1.60-1.38 (m, 4H).

EXAMPLE 28(31)

4-(N-(2-(N'-cyclohexylamino)ethyl)carbamoylmethyl)-5,6,7,8-tetrahydrophthalazin-1(2H)-one hydrobromide TLC: Rf 0.18 (ethyl acetate:acetic acid:water=3:1:1);

NMR (DMSO-$d_6$): δ 12.62 (br, 1H), 8.40-8.20 (m, 2H), 8.22 (m, 1H), 3.45 (s, 2H), 3.30 (m, 1H), 3.03-2.90 (m, 2H), 2.43-2.32 (m, 4H), 2.00-1.90 (m, 2H), 1.78-1.54 (m, 8H), 1.28-1.00 (m, 6H).

EXAMPLE 28(32)

4-(N-(4-(N'-methylamino)butyl)carbamoylmethyl)-5,6,7,8-tetrahydrophthalazin-1(2H)-one hydrobromide TLC: Rf 0.063 (methylene chloride:methanol:saturated aqueous ammonia=8:2:0.2);

NMR (DMSO-$d_6$): δ 12.58(brs, 1H), 8.28-8.00 (br, 2H), 8.10 (m, 1H), 3.40 (s, 2H), 3.05 (q, J=6.0 Hz, 2H), 2.86 (t, J=7.2 Hz, 2H), 2.52 (s, 3H), 2.48-2.32 (m, 4H), 1.70-1.60 (m, 4H), 1.60-1.36 (m, 4H).

EXAMPLE 28(33)

4-(N-(4-(N'-cyclopentylamino)butyl)carbamoylmethyl)-5,6,7,8-tetrahydrophthalazin-1(2H)-one hydrobromide TLC: Rf 0.28 (methylene chloride:methanol:saturated aqueous ammonia=8:2:0.2);

NMR (DMSO-$d_6$): δ 12.58(s 1H), 8.37 (br, 2H), 8.11 (m, 1H), 3.43 (m, 1H), 3.41 (s, 2H), 3.07 (q, J=6.0 Hz, 2H), 2.92-2.83 (m, 2H), 2.46-2.33 (m, 4H), 2.00-1.88 (m, 2H), 1.74-1.40 (m, 14H).

EXAMPLE 28(34)

4-(N-(3-(N'-cyclopentylamino)propyl)carbamoylmethyl)-5,6,7,8-tetrahydrophthalazin-1(2H)-one hydrobromide TLC: Rf 0.56 (methylene chloride:methanol:saturated aqueous ammonia=8:2:0.2);

NMR (DMSO-$d_6$): δ 12.61(s 1H), 8.30-8.00 (br, 2H), 8.22 (m, 1H), 3.43 (s, 2H), 3.43 (m, 1H), 3.14 (q, J=6.6 Hz, 2H), 2.86 (t, J=7.5 Hz, 2H), 2.46-2.34 (m, 4H), 1.96-1.84 (m, 2H), 1.80-1.46 (m, 12H).

EXAMPLE 28(35)

4-(N-(4-(N'-cyclohexylamino)butyl)carbamoylmethyl)-5,6,7,8-tetrahydrophthalazin-1(2H)-one hydrobromide TLC: Rf 0.56 (methylene chloride:methanol:saturated aqueous ammonia=8:2:0.2);

NMR (DMSO-$d_6$): δ 12.58(s 1H), 8.24 (br, 2H), 8.10 (m, 1H), 3.40 (s, 2H), 3.07 (q, J=6.3 Hz, 2H), 3.00-2.84 (m, 3H), 2.46-2.34 (m, 4H), 2.04-1.95 (m, 2H), 1.80-1.40 (m, 11H), 1.28-1.10 (m, 5H).

EXAMPLE 28(36)

4-(N-(3-(N'-cyclopropylamino)propyl)carbamoylmethyl)-5,6,7,8-tetrahydrophthalazin-1(2H)-one TLC: Rf 0.44 (methylene chloride:methanol:saturated aqueous ammonia=8:2:0.2);

NMR (DMSO-$d_6$): δ 12.59(s 1H), 8.09 (t, J=6.0 Hz, 1H), 3.40 (s, 2H), 3.09 (q, J=6.0 Hz, 2H), 2.74 (t, J=5.2 Hz, 2H), 2.46-2.25 (m, 5H), 1.70-1.55 (m, 6H), 0.58-0.50 (m, 2H), 0.50-0.40 (m, 2H).

EXAMPLE 28(37)

4-(N-(4-(N'-cyclopropylamino)butyl)carbamoylmethyl)-5,6,7,8-tetrahydrophthalazin-1(2H)-one TLC: Rf 0.44 (methylene chloride:methanol:saturated aqueous ammonia=8:2:0.2);

NMR (DMSO-$d_6$): δ 12.56(brs 1H), 8.01 (t, J=6.0 Hz, 1H), 3.38 (s, 2H), 3.18-2.98 (m, 2H), 2.60-2.52 (m, 2H), 2.46-2.32 (m, 4H), 2.06 (m, 1H), 1.70-1.60 (m, 4H), 1.44-1.35 (m, 4H), 0.40-0.34 (m, 2H), 0.26-0.18 (m, 2H).

EXAMPLE 28(38)

4-(N-methyl-N-(3-(N'-cyclohexylamino)propyl)carbamoylmethyl)-5,6,7,8-tetrahydrophthalazin-1(2H)-one hydrochloride TLC: Rf 0.20 (methylene chloride:methanol:saturated aqueous ammonia=8:2:0.2);

NMR (DMSO-$d_6$): δ 12.60 (s, 1H), 8.62 and 8.42 (br, 2H), 3.68 (s, 2H), 3.43-3.34 (m, 2H), 3.02 and 2.82 (s, 3H), 3.00-2.78 (m, 3H), 2.42-2.32 (m, 4H), 2.02-1.54 (m, 12H), 1.32-1.17 (m, 4H).

EXAMPLE 28(39)

4-(N-methyl-N-(3-(N'-cyclopentylamino)propyl) carbamoylmethyl)-5,6,7,8-tetrahydrophthalazin-1 (2H)-one hydrochloride TLC: Rf 0.20 (methylene chloride:methanol:saturated aqueous ammonia=8:2:0.2);

NMR (DMSO-$d_6$): δ 12.60 (s, 1H), 8.73 and 8.49 (br, 2H), 3.68 and 3.67 (s, 2H), 3.46-3.36 (m, 3H), 3.01 and 2.82 (s, 3H), 2.98-2.78 (m, 2H), 2.42-2.34 (m, 4H), 1.98-1.76 (m, 4H), 1.70-1.44 (m, 10H).

EXAMPLE 28(40)

4-(N-methyl-N-(3-(N'-cyclobutylamino)propyl)carbamoylmethyl)-5,6,7,8-tetrahydrophthalazin-1(2H)-one hydrochloride TLC: Rf 0.24 (methylene chloride:methanol:water=8:2:0.2);

NMR (DMSO-$d_6$): δ 12.59 (s, 1H), 8.63 (br, 2H), 3.67 and 3.65 (s, 2H), 3.62 (m, 1H), 3.44-3.30 (m, 2H), 3.00 and 2.81 (s, 3H), 2.82-2.67 (m, 2H), 2.41-2.32 (m, 4H), 2.20-2.04 (m, 4H), 1.90-1.70 (m, 4H), 1.70-1.60 (m, 4H).

EXAMPLE 28(41)

4-(N-methyl-N-(3-(N'-cyclopropylamino)propyl) carbamoylmethyl)-5,6,7,8-tetrahydrophthalazin-1 (2H)-one hydrochloride TLC: Rf 0.24 (methylene chloride:methanol:water=8:2:0.2);

NMR (DMSO-$d_6$): δ 12.59 and 12.57 (s, 1H), 8.57 (br, 2H), 3.67 (s, 2H), 3.46-3.30 (m, 2H), 3.01 and 2.81 (s, 3H), 2.95-2.82 (m, 2H), 2.57 (m, 1H), 2.41-2.33 (m, 4H), 1.95-1.75 (m, 2H), 1.70-1.58 (m, 4H), 0.81-0.72 (m, 2H), 0.72-0.64 (m, 2H).

EXAMPLE 28(42)

4-(N-(4-(morpholin-4-yl)butyl)carbamoylmethyl)-5,6,7,8-tetrahydrophthalazin-1(2H)-one Free Form:

TLC: Rf 0.38 (methanol:methylene chloride=1:4);

NMR (DMSO-$d_6$): δ 12.57 (s, 1H), 8.00 (t, J=5.4 Hz, 1H), 3.55 (m, 4H), 3.39 (s, 2H), 3.29-2.20 (m, 12H), 1.63 (brs, 4H), 1.40 (brs, 4H).

Hydrochloride:

TLC: Rf 0.37 (methanol:methylene chloride:saturated aqueous ammonia=1:9:0.1);

NMR (DMSO-$d_6$): δ 12.59 (s, 1H), 10.34 (brs, 1H), 8.13 (t, J=5.4 Hz, 1H), 3.94 (m, 2H), 3.72 (t, J=11.4 Hz, 2H), 3.41 (s, 2H), 3.38 (m, 2H), 3.07 (m, 6H), 2.39 (m, 4H), 1.63-1.40 (m, 8H).

Methanesulfonate:

TLC: Rf 0.34 (methanol:methylene chloride:28% ammonia water=1:9:0.1);

NMR (DMSO-$d_6$): δ 12.58 (s, 1H), 9.54 (brs, 1H), 8.10 (t, J=5.4 Hz, 1H), 4.00-3.94 (m, 2H), 3.69-3.61 (m, 2H), 3.41 (s, 2H), 3.36 (m, 2H), 3.11-2.97 (m, 6H), 2.42-2.33 (m, 4H), 2.34 (s, 3H), 1.63 (m, 6H), 1.48-1.38 (m, 2H).

EXAMPLE 29

4-(3-(N-(5-aminopentanoyl)amino)phenyl)-5,6,7,8-tetrahydrophthalazin-1(2H)-one methanesulfonate Under an atmosphere of hydrogen, a mixture of the compound prepared in Example 26(4) (430 mg) and 10% palladium on carbon (86.0 mg) in methanol (5.0 mL) was stirred at room temperature for 10 hours. The reaction mixture was filtrated through Celite. The filtrate was concentrated. The obtained powder was recrystallized from ethyl acetate to give a free form of the title compound (268 mg). A suspension of the obtained free form (264 mg) and methanesulfonate (74.6 mg) in methanol (3.0 mL) was stirred at room temperature for 1 hour. The reaction mixture was concentrated to give the compound of the present invention (307 mg) having the following physical data.

TLC: Rf 0.28 (methanol:methylene chloride:saturated aqueous ammonia=4:8:0.1);

NMR (CD$_3$OD): δ 7.80 (s, 1H), 7.66 (m, 1H), 7.47 (t, J=7.8 Hz, 1H), 7.22 (m, 1H), 3.01 (brt, J=6.8 Hz, 2H), 2.75 (s, 3H), 2.68 (brt, J=6.0 Hz, 2H), 2.53 (m, 4H), 1.90-1.74 (m, 8H).

EXAMPLE 29(1) TO EXAMPLE 29(6)

By the same procedure as described in Example 29, if necessary, by converting to corresponding salts by conventional method, using the compound prepared in Example 26(6) to 26(8), 26(12), 24(31) or 27(38) instead of the compound prepared in Example 26(4), the following compounds of the present invention were obtained.

EXAMPLE 29(1)

4-(3-N-(5N—(N'-methylamino)pentanoyl)amino) phenyl)-7,8,9,9a-tetrahydro-2H-pyrido[1,2-d][1,2,4] triazin-1(6H)-one methanesulfonate TLC: Rf 0.34 (methanol:methylene chloride:saturated aqueous ammonia=1:4:0.2);

NMR (CD$_3$OD): δ 10.02 (brs, 1H), 7.78 (s, 1H), 7.65 (d, J=7.8 Hz, 1H), 7.45 (t, J=7.8 Hz, 1H), 7.17 (d, J=7.8 Hz, 1H), 4.07 (m, 1H), 3.47 (m, 1H), 3.07 (t, J=6.9 Hz, 2H), 2.91 (m, 1H), 2.75 (s, 6H), 2.53 (t, J=6.6 Hz, 2H), 2.29-1.52 (m, 10H).

EXAMPLE 29(2)

4-(3-(N-(5-(N'-methylamino)pentanoyl)amino)phenyl)-6,7,9,9a-tetrahydro[1,4]thiazino[4,3-d][1,2,4] triazin-1(2H)-one methanesulfonate TLC: Rf 0.26 (methanol:methylene chloride:saturated aqueous ammonia=1:4:0.2);

NMR (CD$_3$OD): δ 8.14 (t, J=1.8 Hz, 1H), 7.78 (m, 1H), 7.64 (t, J=7.8 Hz, 1H), 7.39 (m, 1H), 4.68 (dd, J=11.1, 2.4 Hz, 1H), 4.00 (dt, J=14.1, 3.0 Hz, 1H), 3.53-3.34 (m, 2H), 3.10 (m, 4H), 2.76 (s, 6H), 2.57 (m, 3H), 1.84 (m, 4H).

EXAMPLE 29(3)

4-(3-(N-(5-(N'-methylamino)pentanoyl)amino)phenyl)-2,5,6,7,8,9-hexahydro-1H-cyclohepta[d]pyridazin-1-one methanesulfonate TLC: Rf 0.29 (chloroform:methanol:28% ammonia water=40:10:1);
NMR (DMSO-$d_6$): δ 12.96 (br-s, 1H), 10.05 (s, 1H), 8.22 (br-s, 2H), 7.69 (m, 1H), 7.57 (m, 1H), 7.37 (m, 1H), 7.00 (m, 1H), 2.92-2.78 (m, 4H), 2.58-2.52 (m, 5H), 2.40-2.32 (m, 2H), 2.30 (s, 3H), 1.86-1.76 (m, 2H), 1.66-1.46 (m, 8H).

EXAMPLE 29(4)

4-(3-(N-(5-(N'-methylamino)pentanoyl)amino)phenyl)-6,7-dihydro[1,4]thiazino[4,3-d][1,2,4]triazin-1(2H)-one hydrochloride TLC: Rf 0.34 (chloroform:methanol:water=8:2:0.2);
NMR (DMSO-$d_6$): δ 10.89 (s, 1H), 10.37 (br, 1H), 8.83 (br, 2H), 7.76 (s, 1H), 7.68 (d, J=7.8 Hz, 1H), 7.38 (t, J=7.8 Hz, 1H), 7.08 (d, J=7.8 Hz, 1H), 6.26 (s, 1H), 3.64-3.58 (m, 2H), 3.20-3.14 (m, 2H), 2.94-2.84 (m, 2H), 2.54-2.30 (m, 5H), 1.70-1.60 (m, 4H).

EXAMPLE 29(5)

4-(N-(2-(piperidin-4-yl)ethyl)carbamoylmethyl)-5,6,7,8-tetrahydrophthalazin-1(2H)-one Free Form:
TLC: Rf 0.14 (methanol:methylene chloride:saturated aqueous ammonia=1:4:0.1);
NMR (DMSO-$d_6$): δ 12.54 (brs, 1H), 8.44 (s, 1H), 8.01 (t, J=5.4 Hz, 1H), 3.38 (s, 2H), 3.08-2.26 (m, 12H), 1.63 (brs, 4H), 1.34-1.00 (m, 5H).

Methanesulfonate:
TLC: Rf 0.43 (methylene chloride:methanol:28% ammonia water=6:3:1);
NMR (DMSO-$d_6$): δ 12.58 (brs, 1H), 8.18 (brs, 2H), 8.02 (t, J=5.4 Hz, 1H), 3.38 (s, 2H), 3.22 (m, 2H), 3.08 (m, 2H), 2.76 (m, 2H), 2.46-2.34 (m, 4H), 2.30 (s, 3H), 1.77 (m, 2H), 1.63 (m, 4H), 1.50 (m, 1H), 1.40-1.24 (m, 4H).

EXAMPLE 29(6)

4-(2-(1,4-diazepan-1-yl)ethyl)-5,6,7,8-tetrahydrophthalazin-1(2H)-one

TLC: Rf 0.083 (methylene chloride:methanol=4:1);
NMR (DMSO-$d_6$): δ 12.5 (brs, 1H), 2.80-2.55 (m, 12H), 2.49 (m, 2H), 2.35 (m, 2H), 1.75-1.68 (m, 6H).

EXAMPLE 30

4-(3-(N-(5-(N'-methylamino)pentanoyl)amino)phenyl)-5,6,7,8-tetrahydrophthalazin-1(2H)-one methanesulfonate 4N hydrogen chloride in dioxane (2.50 mL) was added dropwise to a solution of the compound prepared in Example 26 (290 mg) in methanol (3.0 mL) in ice bath, the mixture was stirred at room temperature for 2 hours. The reaction mixture was concentrated. The residue was purified by column chromatography on silica gel (methanol:methylene chloride=1:9→methanol:methylene chloride:saturated aqueous ammonia=2:8:0.1). 1N sodium hydroxide solution (0.34 mL) was added dropwise to a suspension of the obtained solid (134 mg) in methanol (1.0 mL) and the mixture was stirred at room temperature for 30 minutes. A saturated aqueous ammonium chloride solution was added to the reaction mixture, which was extracted with methylene chloride. The extract was washed with brine, dried over anhydrous magnesium sulfate and concentrated. A solution of the obtained solid (64.8 mg) and methanesulfonate (17.6 mg) in methanol (3.0 mL) was stirred at room temperature for 30 minutes. The reaction mixture was concentrated to give the compound of the present invention (82.4 mg) having the following physical data.

TLC: Rf 0.27 (methanol:methylene chloride:saturated aqueous ammonia=2:8:0.5);
NMR (CD$_3$OD): δ 10.00 (brs, 1H), 7.75 (d, J=1.2 Hz, 1H), 7.63 (dd, J=8.1, 1.2 Hz, 1H), 7.45 (t, J=8.1 Hz, 1H), 7.21 (d, J=8.1 Hz, 1H), 3.07 (brt, J=7.2 Hz, 2H), 2.74 (s, 6H), 2.65 (brt, J=6.3 Hz, 2H), 2.52 (m, 4H), 1.82 (m, 8H).

EXAMPLE 30(1) TO EXAMPLE 30(19)

By the same procedure as described in Example 30, if necessary, by converting to corresponding salts by conventional method, using the compound prepared in Example 26(9), 26(10), 26(11), 23, 26(14), 26(15), 23(3), 23(4), 23(9), 23(16), 26(16), 27(7), 23(21), 26(17), 27(14), 26(19), 23(25), 23(33) or 24(48) instead of the compound prepared in Example 26, the following compounds of the present invention were obtained.

EXAMPLE 30(1)

4-(3-(N-(4-(N'-methylamino)butanoyl)amino)phenyl)-6,7,9,9a-tetrahydro[1,4]thiazino[4,3-d][1,2,4]triazin-1(2H)-one methanesulfonate TLC: Rf 0.20 (chloroform:methanol:water=8:2:0.2);
NMR (DMSO-$d_6$): δ 10.56 (s, 1H), 10.17 (s, 1H), 8.45 (br, 2H), 7.71 (s, 1), 7.58 (d, J=7.8 Hz, 1H), 7.36 (t, J=7.8 Hz, 1H), 7.08 (d, J=7.8 Hz, 1H), 4.24 (dd, J=8.4, 4.5 Hz, 1H), 3.56 (m, 1H), 3.09 (m, 1H), 2.98-2.90 (m, 2H), 2.88-2.84 (m, 2H), 2.71 (m, 1H), 2.56 (t, J=6.0 Hz, 3H), 2.44 (t, J=6.0 Hz, 2H), 2.31 (s, 3H), 2.31 (m, 1H), 1.94-1.86 (m, 2H).

EXAMPLE 30(2)

4-(3-(N-(6-(N'-methylamino)hexanoyl)amino)phenyl)-6,7,9,9a-tetrahydro[1,4]thiazino[4,3-d][1,2,4]triazin-1(2H)-one methanesulfonate TLC: Rf 0.17 (chloroform:methanol:water=8:2:0.2);
NMR (DMSO-$d_6$): δ 10.54 (s, 1H), 10.05 (s, 3H), 8.36 (br, 2H), 7.71 (s, 1H), 7.58 (d, J=7.5 Hz, 1H), 7.35 (t, J=7.5 Hz, 1H), 7.06 (d, J=7.5 Hz, 1H), 4.24 (m, 1H), 3.59 (m, 1H), 3.08 (m, 1H), 2.92-2.82 (m, 2H), 2.71 (m, 1H), 2.60-2.40 (m, 3H), 2.31 (m, 1H), 2.293 (s, 3H), 2.289 (s, 3H), 1.68-1.55 (m, 4H), 1.40-1.30 (m, 2H).

EXAMPLE 30(3)

4-(3-(N-(5-(N'-(3-methyl-2-butenyl)amino)pentanoyl)amino)phenyl)-5,6,7,8-tetrahydrophthalazin-1(2H)-one hydrochloride TLC: Rf 0.34 (chloroform:methanol=4:1);
NMR (DMSO-$d_6$): δ 12.88 (s, 1H), 10.24 (s, 1H), 8.84 (s, 2H), 7.73 (s, 1H), 7.64 (m, 1H), 7.35 (dd, J=7.8, 7.8 Hz, 1H), 7.08 (m, 1H), 5.25 (t, J=7.2 Hz, 1H), 3.56-3.40 (m, 2H), 2.98-2.72 (m, 2H), 2.60-2.24 (m, 6H), 1.80-1.50 (m, 14H).

EXAMPLE 30(4)

4-(N-(2-aminoethyl)carbamoylmethyl)-5,6,7,8-tetrahydrophthalazin-1(2H)-one

Free Form:
TLC: Rf 0.19 (methylene chloride:methanol:ammonia water=8:2:0.2);
NMR (DMSO-$d_6$): δ 7.98 (m, 1H), 3.41 (s, 2H), 3.03 (q, J=6.6 Hz, 2H), 2.55 (t, J=6.6 Hz, 2H), 2.46-2.33 (m, 4H), 1.70-1.60 (m, 4H).

Hydrochloride:
TLC: Rf 0.44 (methanol:methylene chloride:saturated aqueous ammonia=1:4:0.2);
NMR (DMSO-$d_6$): δ 12.60 (brs, 1H), 8.42 (t, J=6.0 Hz, 1H), 8.11 (brs, 3H), 3.46 (s, 2H), 3.31 (q, J=6.0 Hz, 2H), 2.84 (q, J=6.0 Hz, 2H), 2.39 (m, 4H), 1.63 (m, 4H).

EXAMPLE 30(5)

4-(3-(N-(azetidin-3-ylcarbonyl)amino)phenyl)-5,6,7,8-tetrahydrophthalazin-1(2H)-one hydrochloride TLC: Rf 0.18 (chloroform:methanol=4:1);
NMR (DMSO-$d_6$): δ 10.43 (s, 1H), 9.10 (brs, 1H), 8.82 (brs, 1H), 7.73 (m, 1H), 7.64 (m, 1H), 7.39 (dd, J=7.8, 7.8 Hz, 1H), 7.14 (m, 1H), 4.20-3.92 (m, 4H), 3.79 (m, 1H), 2.62-2.20 (m, 4H), 1.78-1.50 (m, 4H).

EXAMPLE 30(6)

4-(3-(N-(pyrrolidin-2-ylcarbonyl)amino)phenyl)-5,6,7,8-tetrahydrophthalazin-1(2H)-one hydrochloride TLC: Rf 0.53 (methanol:methylene chloride=1:4);
NMR (DMSO-$d_6$): δ 12.91 (s, 1H), 10.86 (s, 1H), 9.65 (brs, 1H), 8.67 (brs, 1H), 7.71 (s, 1H), 7.64 (d, J=7.8 Hz, 1H), 7.43 (t, J=7.8 Hz, 1H), 7.19 (d, J=7.8 Hz, H), 4.37 (m, 1H), 3.27-2.26 (m, 6H), 1.94 (m, 4H), 1.70-1.59 (m, 4H).

EXAMPLE 30(7)

4-(N-(3-aminopropyl)carbamoylmethyl)-5,6,7,8-tetrahydrophthalazin-1(2H)-one hydrochloride TLC: Rf 0.41 (ethyl acetate:acetic acid:water=3:3:1);
NMR (DMSO-$d_6$): δ 12.59 (s, 1H), 8.23 (br, 1H), 7.88 (br, 3H), 3.42 (s, 2H), 3.11 (q, J=6.6 Hz, 2H), 2.76 (q, J=6.6 Hz, 2H), 2.50-2.32 (m, 4H), 1.76-1.60 (m, 6H).

EXAMPLE 30(8)

4-(N-(2-(N'-methylamino)ethyl)carbamoylmethyl)-5,6,7,8-tetrahydrophthalazin-1(2H)-one hydrochloride TLC: Rf 0.29 (ethyl acetate:acetic acid:water=3:3:1);
NMR (DMSO-$d_6$): δ 12.60(brs, 1H), 8.86 (br, 2H), 8.38 (br, 1H), 3.47 (s, 2H), 3.35 (q, J=6.0 Hz, 2H), 2.94(quin, J=6.0 Hz, 2H), 2.53 (t, J=5.4 Hz, 3H), 2.50-2.34 (m, 4H), 1.70-1.60 (m, 4H).

EXAMPLE 30(9)

4-(1-(N-(2-aminoethyl)carbamoyl)ethyl)-5,6,7,8-tetrahydrophthalazin-1(2H)-one hydrochloride TLC: Rf 0.62 (methanol:methylene chloride:saturated aqueous ammonia=1:4:0.2);
NMR (DMSO-$d_6$): δ 12.62 (s, 1H), 8.25 (t, J=5.4 Hz, 1H), 8.00 (brs, 3H), 3.73 (q, J=6.9 Hz, 1H), 3.26 (m, 2H), 2.83 (m, 2H), 2.48-2.30 (m, 4H), 1.64 (m, 4H), 1.31 (d, J=6.9 Hz, 3H).

EXAMPLE 30(10)

4-(N-(4-aminobutyl)carbamoylmethyl)-5,6,7,8-tetrahydrophthalazin-1(2H)-one hydrochloride TLC: Rf 0.15 (ethyl acetate:acetic acid:water=3:1:1);
NMR (DMSO-$d_6$): δ 12.58 (s, 1H), 8.17 (t, J=6.3 Hz, 1H), 7.95 (br, 3H), 3.41 (s, 2H), 3.05 (q, J=6.3 Hz, 2H), 2.75 (m, 2H), 2.46-2.33 (m, 4H), 1.68-1.60 (m, 4H), 1.60-1.40 (m, 4H).

EXAMPLE 30(11)

4-(2-(N-(2-aminoacetyl)amino)ethyl)-5,6,7,8-tetrahydrophthalazin-1(2H)-one hydrochloride TLC: Rf 0.11 (chloroform:methanol=4:1);
NMR (DMSO-$d_6$): δ 12.58 (brs, 1H), 8.59 (t, J=5.7 Hz, 1H), 8.19 (brs, 3H), 3.56-3.28 (m, 4H), 2.65 (t, J=7.2 Hz, 2H), 2.54-2.28 (m, 4H), 1.76-1.54 (m, 4H).

EXAMPLE 30(12)

4-(2-(piperazin-1-yl)ethyl)-5,6,7,8-tetrahydrophthalazin-1(2H)-one dihydrochloride TLC: Rf 0.15 (chloroform:methanol=9:1);
NMR (CD$_3$OD): δ 3.80-3.50 (m, 10H), 3.14 (t, J=7.5 Hz, 2H), 2.64-2.50 (m, 4H), 1.90-1.74 (m, 4H).

EXAMPLE 30(13)

4-(1-(N-(4-aminobutyl)carbamoyl)ethyl)-5,6,7,8-tetrahydrophthalazin-1(2H)-one hydrochloride TLC: Rf 0.19 (methanol:methylene chloride:saturated aqueous ammonia=1:4:0.1);
NMR (DMSO-$d_6$): δ 12.60 (s, 1H), 8.04 (t, J=5.4 Hz, 1H), 7.83 (brs, 3H), 3.69 (q, J=7.2 Hz, 1H), 3.09 (m, 2H), 2.74 (m, 2H), 2.48-2.25 (m, 4H), 1.64-1.42 (m, 8H), 1.31 (d, J=7.2 Hz, 3H).

EXAMPLE 30(14)

4-(2-(N-(3-aminopropanoyl)amino)ethyl)-5,6,7,8-tetrahydrophthalazin-1(2H)-one hydrochloride TLC: Rf 0.11 (chloroform:methanol=4:1);

NMR (DMSO-$d_6$): δ 12.56 (brs, 1H), 8.24 (t, J=5.7 Hz, 1H), 7.94 (brs, 3H), 3.42-3.24 (m, 2H), 3.04-2.84 (m, 2H), 2.63 (t, J=7.2 Hz, 2H), 2.56-2.28 (m, 6H), 1.76-1.52 (m, 4H).

EXAMPLE 30(15)

4-(2-(N-(2-aminoethyl)amino)ethyl)-5,6,7,8-tetrahydrophthalazin-1(2H)-one dihydrochloride TLC: Rf 0.10 (methylene chloride:methanol:saturated aqueous ammonia=8:2:0.1);

NMR (DMSO-$d_6$): δ 12.69 (s, 1H), 9.63 (brs, 2H), 8.41 (brs, 3H), 3.78-3.06 (m, 6H), 2.94 (t, J=7.5 Hz, 2H), 2.58-2.30 (m, 4H), 1.78-1.54 (m, 4H).

EXAMPLE 30(16)

4-(2-(N-(4-aminobutanoyl)amino)ethyl)-5,6,7,8-tetrahydrophthalazin-1(2H)-one hydrochloride TLC: Rf 0.10 (chloroform:methanol=4:1);

NMR (DMSO-$d_6$): δ 12.56 (brs, 1H), 8.09 (m, 4H), 3.36-3.20 (m, 2H), 2.82-2.66 (m, 2H), 2.61 (t, J=7.2 Hz, 2H), 2.54-2.28 (m, 4H), 2.15 (t, J=7.2 Hz, 2H), 1.84-1.52 (m, 6H).

EXAMPLE 30(17)

4-(N-(5-aminopentyl)carbamoylmethyl)-5,6,7,8-tetrahydrophthalazin-1(2H)-one hydrochloride TLC: Rf 0.34 (chloroform:methanol:water=8:2:0.2);

NMR (DMSO-$d_6$): δ 12.57 (br, 1H), 8.09 (m, 1H), 7.87 (br, 2H), 3.40 (s, 2H), 3.03 (q, J=6.0 Hz, 2H), 2.80-2.66 (m, 2H), 2.46-2.33 (m, 4H), 1.70-1.60 (m, 4H), 1.60-1.49 (m, 2H), 1.48-1.36 (m, 2H), 1.36-1.26 (m, 2H).

EXAMPLE 30(18)

4-(2-(N-(2-aminoethyl)carbamoyl)ethyl)-5,6,7,8-tetrahydrophthalazin-1(2H)-one hydrochloride TLC: Rf 0.18 (chloroform:methanol=4:1);

NMR (DMSO-$d_6$): δ 12.52 (s, 1H), 8.20 (t, J=5.4 Hz, 1H), 8.02 (brs, 3H), 3.36-3.20 (m, 2H), 2.92-2.76 (m, 2H), 2.73 (t, J=7.5 Hz, 2H), 2.54-2.28 (m, 6H), 1.76-1.54 (m, 4H).

EXAMPLE 30(19)

8-(N-(3-aminopropyl)carbamoylmethyl)-2,3,4,6-tetrahydropyrido[2,3-d]pyridazin-5(1H)-one dihydrochloride TLC: Rf 0.25 (methanol:acetic acid=5:1);

NMR (DMSO-$d_6$): δ 12.24 (s, 1H), 8.41 (t, J=5.4 Hz, 1H), 7.94 (brs, 5H), 3.42 (s, 2H), 3.20 (t, J=5.4 Hz, 2H), 3.12 (m, 2H), 2.78 (m, 2H), 2.37 (t, J=6.0 Hz, 2H), 1.69 (m, 4H).

EXAMPLE 31

4-(2-acetylthioethyl)-5,6,7,8-tetrahydrophthalazin-1(2H)-one

To a solution of the compound prepared in Reference example 13 (650 mg) in dimethylformamide (15 mL) were added potassium thioacetate (698 mg) and potassium carbonate (422 mg) and the mixture was stirred at 50° C. for 2 hours. After cooling to room temperature, the reaction mixture was poured in cold water and extracted with ethyl acetate. The extract was washed with water and brine sequentially, dried over anhydrous magnesium sulfate and concentrated to give the compound of the present invention (688 mg) having the following physical data.

TLC: Rf 0.40 (chloroform:methanol=8:1);

NMR (DMSO-$d_6$): δ 12.60 (s, 1H), 3.11 (t, J=7.2 Hz, 2H), 2.75 (t, J=7.2 Hz, 2H), 2.56-2.28 (m, 4H), 2.31 (s, 3H), 1.76-1.54 (m, 4H).

EXAMPLE 31(1)

8-(2-acetylthioethyl)-2,3,4,6-tetrahydropyrido[2,3-d]pyridazin-5(1H)-one

By the same procedure as described in Example 31 using a corresponding derivative instead of the compound prepared in Reference example 13, the compound of the present invention having the following physical data was obtained.

TLC: Rf 0.43 (chloroform:methanol=8:1);

NMR (DMSO-$d_6$): δ 11.82 (s, 1), 6.32 (s, 1H), 3.16 (m, 2H), 3.09 (t, J=7.2 Hz, 2H), 2.66 (t, J=7.2 Hz, 2H), 2.32 (t, J=6.3 Hz, 2H), 2.31 (s, 3H), 1.69 (m, 2H).

EXAMPLE 32

4-(2-benzylthioethyl)-5,6,7,8-tetrahydrophthalazin-1(2H)-one

To a suspension of the compound prepared in Example 31 (100 mg) in methanol (4.0 mL) were added benzyl bromide (0.06 mL) and potassium carbonate (82 mg) and the mixture was stirred at room temperature for 2 hours. The reaction mixture was poured in cold 0.5N hydrochloric acid and extracted with ethyl acetate. The extract was washed with brine, dried over anhydrous magnesium sulfate and concentrated. The residue was purified by column chromatography on silica gel (methylene chloride:methanol=70:1→30:1) to give the compound of the present invention (47 mg) having the following physical data.

TLC: Rf 0.42 (chloroform:methanol=8:1);

NMR (DMSO-$d_6$): δ 12.54 (s, 1H), 7.38-7.16 (m, 5H), 3.77 (s, 2H), 2.80-2.58 (m, 4H), 2.50-2.26 (m, 4H), 1.76-1.52 (m, 4H).

EXAMPLE 32(1) TO EXAMPLE 32(2)

By the same procedure as described in Example 32, if necessary, by converting to corresponding salts by conventional method, using a corresponding derivative instead of benzyl bromide, the following compounds of the present invention were obtained.

EXAMPLE 32(1)

4-(2-(3-(piperidin-1-yl)propylthio)ethyl)-5,6,7,8-tetrahydrophthalazin-1(2H)-one TLC: Rf 0.57 (chloroform:methanol=4:1);
NMR (DMSO-$d_6$): δ 12.56 (s, 1H), 2.78-2.70 (m, 4H), 2.58-2.20 (m, 12H), 1.76-1.56 (m, 6H), 1.54-1.26 (m, 6H).

EXAMPLE 32(2)

4-(2-(2-(piperidin-1-yl)ethylthio)ethyl)-5,6,7,8-tetrahydrophthalazin-1(2H)-one

Free Form:
TLC: Rf 0.28 (chloroform:methanol=8:1);
NMR (DMSO-$d_6$): δ 12.56 (s, 1H), 2.82-2.70 (m, 4H), 2.68-2.56 (m, 2H), 2.54-2.22 (m, 10H), 1.76-1.55 (m, 4H), 1.54-1.26 (m, 6H).

Hydrochloride:
TLC: Rf 0.28 (chloroform:methanol=8:1);
NMR (DMSO-$d_6$): δ 12.61 (s, 1H), 10.22 (brs, 1H), 3.44 (m, 2H), 3.19 (m, 2H), 3.04-2.68 (m, 8H), 2.62-2.28 (m, 4H), 1.90-1.54 (m, 9H), 1.35 (m, 1H).

EXAMPLE 33

4-(2-(2-hydroxyethylthio)ethyl)-5,6,7,8-tetrahydrophthalazin-1(2H)-one

To a solution of 4-(2-(2-t-butyldimethylsilyloxyethylthio)ethyl)-5,6,7,8-tetrahydrophthalazin-1(2H)-one (300 mg; It was prepared by the same procedure as described in Example 32 using 1-t-butyldimethylsilyloxy-2-iodoethane instead of benzyl bromide.) in tetrahydrofuran (4.0 mL) was added tetrabutylammonium fluoride (638 mg) and the mixture was stirred at room temperature overnight. The reaction mixture was poured in a cold saturated aqueous ammonium chloride solution and extracted with ethyl acetate. The extract was washed with brine, dried over magnesium sulfate and concentrated. The residue was washed with t-butyl methyl ether to give the compound of the present invention (191 mg) having the following physical data.

TLC: Rf 0.36 (chloroform:methanol=8:1);
NMR (DMSO-$d_6$): δ 12.56 (s, 1H), 4.77 (t, J=5.4 Hz, 1H), 3.53 (dt, J=5.4, 6.6 Hz, 2H), 2.84-2.72 (m, 4H), 2.59 (t, J=6.6 Hz, 2H), 2.56-2.28 (m, 4H), 1.76-1.54 (m, 4H).

EXAMPLE 33(1) TO EXAMPLE 33(3)

By the same procedure as described in Example 33 using 4-(2-(3-t-butyldimethylsilyloxypropylthio)ethyl)-5,6,7,8-tetrahydrophthalazin-1(2H)-one, 8-(2-(2-t-butyldimethylsilyloxyethylthio)ethyl)-2,3,4,6-tetrahydropyrido[2,3-d]pyridazin-5(1H)-one or 8-(2-(3-t-butyldimethylsilyloxypropylthio)ethyl)-2,3,4,6-tetrahydropyrido[2,3-d]pyridazin-5(1H)-one instead of 4-(2-(2-t-butyldimethylsilyloxyethylthio)ethyl)-5,6,7,8-tetrahydrophthalazin-1(2H)-one, the following compounds of the present invention were obtained.

EXAMPLE 33(1)

4-(2-(3-hydroxypropylthio)ethyl)-5,6,7,8-tetrahydrophthalazin-1(2H)-one

TLC: Rf 0.37 (chloroform:methanol=8:1);
NMR (DMSO-$d_6$): δ 12.56 (s, 1H), 4.46 (t, J=5.1 Hz, 1H), 3.44 (dt, J=5.1, 6.9 Hz, 2H), 2.80-2.68 (m, 4H), 2.56 (t, J=7.2 Hz, 2H), 2.54-2.30 (m, 4H), 1.76-1.54 (m, 6H).

EXAMPLE 33(2)

8-(2-(2-hydroxyethylthio)ethyl)-2,3,4,6-tetrahydropyrido[2,3-d]pyridazin-5(1H)-one TLC: Rf 0.31 (chloroform:methanol=8:1);
NMR (DMSO-$d_6$): δ 11.78 (s, 1H), 6.33 (s, 1H), 4.78 (t, J=5.4 Hz, 1H), 3.53 (dt, J=5.4, 6.6 Hz, 2H), 3.17 (m, 2H), 2.84-2.60 (m, 4H), 2.59 (t, J=6.6 Hz, 2H), 2.32 (t, J=6.3 Hz, 2H), 1.69 (m, 2H).

EXAMPLE 33(3)

8-(2-(3-hydroxypropylthio)ethyl)-2,3,4,6-tetrahydropyrido[2,3-d]pyridazin-5(1H)-one TLC: Rf 0.32 (chloroform:methanol=8:1);
NMR (DMSO-$d_6$): δ 11.77 (s, 1H), 6.33 (s, 1H), 4.46 (t, J=5.1 Hz, 1H), 3.44 (dt, J=5.1, 5.7 Hz, 2H), 3.16 (m, 2H), 2.80-2.60 (m, 4H), 2.55 (t, J=7.2 Hz, 2H), 2.32 (t, J=6.3 Hz, 2H), 1.78-1.50 (m, 4H).

EXAMPLE 34

4-(2-(2-bromoethylthio)ethyl)-5,6,7,8-tetrahydrophthalazin-1(2H)-one

To a solution of the compound prepared in Example 33 (160 mg) in chloroform (5.0 mL) were added triphenylphosphine (248 mg) and carbon tetrabromide (313 mg), and the mixture was stirred at room temperature for 2 hours. Methanol (1.0 mL) was added dropwise to the reaction mixture, which was stirred for 5 minutes and concentrated. The residue was purified by column chromatography on silica gel (methylene chloride:methanol=80:1→50:1) to give a crude compound of the present invention (598 mg) having the following physical data. The obtained compound was used in next reaction without purifying.

TLC: Rf 0.49 (chloroform:methanol=8:1);
NMR (CD$_3$OD): δ 3.55 (t, J=6.3 Hz, 2H), 2.96-2.82 (m, 4H), 2.72 (t, J=6.3 Hz, 2H), 2.64-2.44 (m, 4H), 1.86-1.70 (m, 4H).

EXAMPLE 35

4-(2-(3-chloropropylthio)ethyl)-5,6,7,8-tetrahydrophthalazin-1(2H)-one

To a suspension of the compound prepared in Example 33(1) (110 mg) in methylene chloride (2.1 mL) were added thionyl chloride (0.08 mL) and pyridine (0.01 mL), and the mixture was stirred at room temperature for 1 day. The reaction mixture was poured in cold water and extracted with methylene chloride. The extract was washed with a saturated aqueous sodium hydrogen carbonate solution and brine sequentially, dried over anhydrous magnesium sulfate and concentrated to give the compound of the present invention (109 mg) having the following physical data.

TLC: Rf 0.49 (chloroform:methanol=8:1);
NMR (DMSO-$d_6$): δ 12.57 (s, 1H), 3.70 (t, J=6.3 Hz, 2H), 2.82-2.72 (m, 4H), 2.64 (t, J=6.9 Hz, 2H), 2.54-2.30 (m, 4H), 1.95 (tt, J=6.9, 6.3 Hz, 2H), 1.76-1.54 (m, 4H).

EXAMPLE 36 TO EXAMPLE 36(1)

By the same procedure as described in Example 28, if necessary, by converting to corresponding salts by conventional method, using the compound prepared in Example 34 or 35 instead of the compound prepared in Example 25(1) and cyclopentylamine instead of morpholine, the following compounds of the present invention were obtained.

EXAMPLE 36

4-(2-(2-(N-cyclopentylamino)ethylthio)ethyl)-5,6,7,8-tetrahydrophthalazin-1(2H)-one TLC: Rf 0.36 (chloroform:methanol=4:1);
NMR (DMSO-$d_6$): δ 12.56 (brs, 1H), 3.00 (quint, J=6.3 Hz, 1H), 2.82-2.72 (m, 4H), 2.71-2.28 (m, 8H), 1.80-1.16 (m, 12H).

EXAMPLE 36(1)

4-(2-(3-(N-cyclopentylamino)propylthio)ethyl)-5,6,7,8-tetrahydrophthalazin-1(2H)-one hydrochloride TLC: Rf 0.38 (chloroform:methanol=4:1);
NMR (DMSO-$d_6$): δ 12.59 (s, 1H), 8.99 (brs, 2H), 3.41 (m, 1H), 2.92 (m, 2H), 2.84-2.70 (m, 4H), 2.63 (t, J=7.2 Hz, 2H), 2.58-2.28 (m, 4H), 2.06-1.38 (m, 14H).

EXAMPLE 37

8-(3-(N-(5-(N'-methylamino)pentanoyl)amino)phenyl)-2,3,4,6-tetrahydropyrazino[2,3-d]pyridazin-5(1H)-one methanesulfonate By the same procedure as described in Reference example 1→Example 1→Example 26→Example 29 using furo[3,4-d]pyrazine-5,7-dione instead of 4,5,6,7-tetrahydro-2-benzofuran-1,3-dione, the compound of the present invention having the following physical data was obtained.

TLC: Rf 0.17 (methanol:methylene chloride:saturated aqueous ammonia=1:4:0.2);
NMR (CD$_3$OD): δ 7.81 (s, 1H), 7.69 (d, J=7.8 Hz, 1H), 7.49 (t, J=7.8 Hz, 1H), 7.32 (d, J=7.8 Hz, 1H), 3.50 (m, 2H), 3.39 (m, 2H), 3.08 (m, 2H), 2.75 (s, 3H), 2.74 (s, 3H), 2.53 (m, 2H), 1.81 (m, 4H).

EXAMPLE 38

4-(N-(2-(1H-tetrazol-5-yl)ethyl)carbamoylmethyl)-5,6,7,8-tetrahydrophthalazin-1(2H)-one A mixture of the compound prepared in Example 23(34) (180 mg), trimethyltin azide (285 mg) and toluene (1.5 mL) was refluxed overnight. The reaction mixture was concentrated. The residue was washed with ethyl acetate and hot methanol sequentially to give the compound of the present invention (113 mg) having the following physical data.

TLC: Rf 0.14 (methylene chloride:methanol:saturated aqueous ammonia=8:2:0.2);
NMR (DMSO-$d_6$): δ 12.57 (s, 1H), 8.19 (t, J=6.0 Hz, 1H), 3.44 (q, J=6.0 Hz, 2H), 3.37 (s, 2H), 3.02 (t, J=6.0 Hz, 2H), 2.40-2.24 (m, 4H), 1.67-1.58 (m, 4H).

EXAMPLE 39

6-acetyl-4-phenyl-5,6,7,8-tetrahydropyrido[3,4-d]pyridazin-1(2H)-one

To a suspension of the compound prepared in Example 11(1) (150 mg) in tetrahydrofuran (2.9 mL) was added an aqueous solution (1.1 mL) of potassium carbonate (157 mg) and then thereto was added acetyl chloride (0.05 mL) at 0° C., and the mixture was stirred at room temperature for 4 hours. The reaction mixture was diluted with water and 1N hydrochloric acid was added thereto. The mixture was extracted with ethyl acetate. The extract was washed with brine, dried over anhydrous magnesium sulfate and concentrated. The residue was washed with ether to give the compound of the present invention (131 mg) having the following physical data.

TLC: Rf 0.36 (chloroform:methanol=8:1);
NMR (DMSO-$d_6$): δ 13.08 (s, 1H), 7.60-7.40 (m, 5H), 4.28 (s, 2H), 3.66 (t, J=5.7 Hz, 2H), 2.63 (t, J=5.7 Hz, 2H), 2.04 (s, 3H).

EXAMPLE 39(1)

6-(2-(N,N-dimethylamino)acetyl)-4-phenyl-5,6,7,8-tetrahydropyrido[3,4-d]pyridazin-1(2H)-one hydrochloride By the same procedure as described in Example 39 and then by converting to a corresponding salt by conventional method, using 2-dimethylaminoacetyl chloride instead of acetyl chloride, the compound of the present invention having the following physical data was obtained.

TLC: Rf 0.57 (chloroform:methanol=4:1);
NMR (DMSO-$d_6$): δ 13.17 (s, 1H), 9.75 (brs, 1H), 7.64-7.36 (m, 5H), 4.48-4.30 (m, 3H), 4.21 (m, 1H), 3.96-3.52 (m, 8H), 2.86-2.64 (m, 2H).

EXAMPLE 40

4-(N-(2-carboxyethyl)carbamoylmethyl)-5,6,7,8-tetrahydrophthalazin-1(2H)-one

By the same procedure as described in Reference example 11 using the compound prepared in Example 23(36) instead of the compound prepared in Example 15, the compound of the present invention having the following physical data was obtained.

TLC: Rf 0.26 (methylene chloride:methanol:water=8:2:0.2);
NMR (DMSO-$d_6$): δ 12.57 (s, 1H), 8.15 (m, 1H), 4.11 (m, 1H), 3.39 (s, 2H), 3.23 (q, J=6.0 Hz, 2H), 2.58-2.35 (m, 2H), 2.42-2.32 (m, 4H), 1.66-1.58 (m, 4H).

EXAMPLE 41

4-(N-(2-(4-hydroxyphenyl)ethyl)carbamoylmethyl)-5,6,7,8-tetrahydrophthalazin-1(2H)-one By the same procedure as described in Example 20 using the compound prepared in Example 24(41) instead of the compound prepared in Example 4(4), the compound of the present invention having the following physical data was obtained.

TLC: Rf 0.35 (methanol:methylene chloride=1:10);

NMR (DMSO-d$_6$): δ 12.57 (s, 1H), 9.15 (s, 1H), 8.04 (t, J=5.7 Hz, 1H), 6.96 (d, J=8.4 Hz, 2H), 6.65 (d, J=8.4 Hz, 2H), 3.36 (s, 2H), 3.22 (m, 2H), 2.58 (t, J=7.5 Hz, 2H), 2.33 (m, 4H), 1.61 (brs, 4H).

REFERENCE EXAMPLE 18

3-hydroxy-4,5,6,7-tetrahydro-2-benzofuran-1(3H)-one

To a solution of 3,4,5,6-tetrahydrophthalic acid anhydride (10.0 g) in tetrahydrofuran (50.0 mL) was added sodium borohydride (600 mg) in ice bath. The mixture was stirred at room temperature for 30 minutes and refluxed for 5 hours. After cooling to room temperature, 1N hydrochloric acid (10.0 mL) was added to the reaction mixture, which was concentrated. Water was added to the residue, which was extracted with ethyl acetate. The extract was washed with water and brine sequentially, dried over anhydrous magnesium sulfate and concentrated. The residue was purified by column chromatography on silica gel (ethyl acetate:hexane=1:4) to give the title compound (5.40 g) having the following physical data.

TLC: Rf 0.64 (ethyl acetate:hexane=1:1);

NMR (CDCl$_3$): δ 5.98 (brs, 1H), 4.90-4.50 (m, 1H), 2.52-2.40 (m, 1H), 2.32-2.16 (m, 3H), 1.86-1.60 (m, 4H).

REFERENCE EXAMPLE 19

Tributyl(3-oxo-1,3,4,5,6,7-hexahydro-2-benzofuran-1-yl)phosphonium bromide

A mixed solution of the compound prepared in Reference example 18 (1.54 g), tri-n-butylphosphine (2.02 g) and hydrogen bromide acetic acid solution (47%, 1.20 mL) in acetic acid (0.700 mL) was refluxed for 21 hours. After cooling to room temperature, the reaction mixture was concentrated. The residue was purified by column chromatography on silica gel (methylene chloride:methanol=20:1) to give the title compound (3.56 g) having the following physical data.

TLC: Rf 0.51 (methanol:methylene chloride=1:10).

REFERENCE EXAMPLE 20

3-benzylidene-4,5,6,7-tetrahydro-2-benzofuran-1(3H)-one

To a solution of the compound prepared in Reference example 19 (419 mg) and benzaldehyde (106 mg) in methylene chloride (4.00 mL) was added triethylamine (0.130 mL) and the mixture was stirred at room temperature for 3 hours. Water was added to the reaction mixture, which was extracted with ethyl acetate. The extract was washed with water and brine sequentially, dried over anhydrous magnesium sulfate and concentrated. The residue was purified by column chromatography on silica gel (ethyl acetate:hexane=1:8) to give the title compound (206 mg) having the following physical data.

TLC: Rf 0.83 (hexane:ethyl acetate=2:1).

EXAMPLE 42

4-benzyl-5,6,7,8-tetrahydrophthalazin-1(2H)-one

A solution of the compound prepared in Reference example 20 (206 mg) and hydrazine monohydrate (49.0 μL) in ethanol (4.00 mL) was refluxed for 1 hour. Hydrazine monohydrate (49.0 μL) was added to the reaction mixture, which was refluxed for 1 hour. After cooling the reaction mixture to room temperature, the deposited crystal was collected by filtration. It was washed with ethanol and hexane, and dried under reduced pressure to give the compound of the present invention (152 mg) having the following physical data.

TLC: Rf 0.63 (methylene chloride:methanol=10:1);

NMR (DMSO-d$_6$): δ 12.61 (s, 1H), 7.32-7.24 (m, 2H), 7.23-7.13 (m, 3H), 3.88 (s, 2H), 2.44-2.25 (m, 4H), 1.65-1.54 (m, 4H).

EXAMPLE 43 TO EXAMPLE 43 (6)

By the same procedure as described in Reference example 20→Example 42 using a corresponding derivative instead of benzaldehyde, the following compounds of the present invention were obtained.

EXAMPLE 43

4-(2-phenylethyl)-5,6,7,8-tetrahydrophthalazin-1(2H)-one

TLC: Rf 0.51 (methylene chloride:methanol=10:1);

NMR (DMSO-d$_6$): δ 12.54 (s, 1H), 7.35-7.15 (m, 5H), 2.90-2.82 (m, 2H), 2.81-2.72 (m, 2H), 2.52-2.42 (m, 2H), 2.41-2.32 (m, 2H), 1.70-1.58 (m, 4H).

EXAMPLE 43(1)

4-(pyridin-3-ylmethyl)-5,6,7,8-tetrahydrophthalazin-1(2H)-one

TLC: Rf 0.42 (methylene chloride:methanol=10:1);

NMR (DMSO-d$_6$): δ 12.59 (s, 1H), 8.45-8.39 (m, 2H), 7.56 (m, 1H), 7.31 (dd, J=7.5, 4.8 Hz, 1H), 3.92 (s, 2H), 2.46-2.33 (m, 4H), 1.72-1.56 (m, 4H).

EXAMPLE 43(2)

4-(pyridin-2-ylmethyl)-5,6,7,8-tetrahydrophthalazin-1(2H)-one

TLC: Rf 0.59 (methylene chloride:methanol=10:1);

NMR (DMSO-d$_6$): δ 12.58 (s, 1H), 8.45 (d, J=4.5 Hz, 1H), 7.71 (t, J=7.8 Hz, 1H), 7.28-7.18 (m, 2H), 4.04 (s, 2H), 2.44-2.32 (m, 4H), 1.68-1.56 (m, 4H).

EXAMPLE 43(3)

4-(5-methylfuran-2-ylmethyl)-5,6,7,8-tetrahydrophthalazin-1(2H)-one

TLC: Rf 0.68 (methylene chloride:methanol=10:1);

NMR (DMSO-d$_6$): δ 12.60 (s, 1H), 5.95 (m, 2H), 3.84 (s, 2H), 2.50-2.35 (m, 4H), 2.18 (s, 3H), 1.70-1.58 (m, 4H).

EXAMPLE 43(4)

4-(2-nitrobenzyl)-5,6,7,8-tetrahydrophthalazin-1(2H)-one

TLC: Rf 0.59 (methanol:methylene chloride=1:10);
NMR (DMSO-$d_6$): δ 12.40 (s, 1H), 8.03 (dd, J=7.8, 1.2 Hz, 1H), 7.68 (dt, J=1.2, 7.8 Hz, 1H), 7.53 (m, 1H), 7.46 (d, J=7.8 Hz, 1H), 4.24 (s, 2H), 2.56-2.46 (m, 2H), 2.44-2.35 (m, 2H), 1.78-1.62 (m, 4H).

EXAMPLE 43(5)

4-(3-nitrobenzyl)-5,6,7,8-tetrahydrophthalazin-1(2H)-one

NMR (DMSO-$d_6$): δ 12.61 (s, 1H), 8.15-8.06 (m, 2H), 7.68-7.57 (m, 2H), 4.06 (s, 2H), 2.47-2.34 (m, 4H), 1.70-1.56 (m, 4H).

EXAMPLE 43(6)

4-(4-nitrobenzyl)-5,6,7,8-tetrahydrophthalazin-1(2H)-one

TLC: Rf 0.60 (methanol:methylene chloride=1:10);
NMR (DMSO-$d_6$): δ 12.65 (s, 1H), 8.16 (dt, J=6.9, 1.8 Hz, 2H), 7.46 (dt, J=6.9, 1.8 Hz, 2H), 4.05 (s, 2H), 2.42-2.33 (m, 4H), 1.70-1.55 (m, 4H).

EXAMPLE 44

4-(2-aminobenzyl)-5,6,7,8-tetrahydrophthalazin-1(2H)-one

Under an atmosphere of hydrogen, a mixed solution of the compound prepared in Example 43(4) (145 mg) and 10% palladium on carbon (30.0 mg) in methanol (15.0 mL) was stirred at room temperature for 30 minutes. The reaction mixture was filtrated through Celite. The filtrate was concentrated to give the compound of the present invention (129 mg) having the following physical data.
TLC: Rf 0.42 (methylene chloride:methanol=10:1);
NMR (DMSO-$d_6$): δ 12.57 (s, 1H), 6.91 (dt, J=1.2, 7.8 Hz, 1H), 6.72 (dd, J=7.8, 1.2 Hz, 1H), 6.61 (dd, J=7.8, 1.2 Hz, 1H), 6.46 (dt, J=1.2, 7.8 Hz, 1H), 4.97 (s, 2H), 3.66 (s, 2H), 2.50-2.30 (m, 4H), 1.70-1.57 (m, 4H).

EXAMPLE 44(1) TO EXAMPLE 44(2)

By the same procedure as described in Example 44 using the compound prepared in Example 43(5) or 43(6) instead of the compound prepared in Example 43(4), the following compounds of the present invention were obtained.

EXAMPLE 44(1)

4-(3-aminobenzyl)-5,6,7,8-tetrahydrophthalazin-1(2H)-one

Free Form:
TLC: Rf 0.38 (methylene chloride:methanol=10:1);
NMR (DMSO-$d_6$): δ 12.60 (s, 1H), 6.91 (t, J=8.1 Hz, 1H), 6.37 (d, J=8.1 Hz, 1H), 6.31 (s, 1H), 6.29 (d, J=8.1 Hz, 1H), 5.00 (s, 2H), 3.71 (s, 2H), 2.45-2.30 (m, 4H), 1.70-1.50 (m, 4H).

Methanesulfonate:
TLC: Rf 0.53(methylene chloride:methanol=10:1);
NMR (DMSO-$d_6$): δ 12.67 (s, 1H), 9.60 (br, 3H), 7.41 (t, J=7.8 Hz, 1H), 7.22 (d, J=7.8 Hz, 1H), 7.16 (d, J=7.8 Hz, 1H), 7.06 (s, 1H), 3.93 (s, 2H), 2.43-2.28 (m, 4H), 2.33 (s, 3H), 1.67-1.54 (m, 4H).

EXAMPLE 44(2)

4-(4-aminobenzyl)-5,6,7,8-tetrahydrophthalazin-1(2H)-one

TLC: Rf 0.44 (methylene chloride:methanol=10:1);
NMR (DMSO-$d_6$): δ 12.55 (s, 1H), 6.78 (d, J=8.1 Hz, 2H), 6.47 (d, J=8.1 Hz, 2H), 4.90 (s, 2H), 3.68 (s, 2H), 2.42-2.25 (m, 4H), 1.70-1.50 (m, 4H).

EXAMPLE 45

4-phenyl-2,5,6,7-tetrahydro-1H-cyclopenta[d]pyridazin-1-one

A solution of (4aS,7aR)-4-phenyl-2,4a,5,6,7,7a-hexahydro-1H-cyclopenta[d]pyridazin-1-one (210 mg; It was prepared by the same procedure as described in Example 1 using (1R,2S)-2-benzoylcyclopentanecarboxylic acid instead of the compound prepared in Reference example 1.) and thionyl chloride (0.500 mL) in benzene (3.00 mL) was refluxed for 18 hours. After cooling to room temperature, the reaction mixture was concentrated. The residue was recrystallized from ethyl acetate to give the compound of the present invention (154 mg) having the following physical data.
TLC: Rf 0.21 (methanol:methylene chloride=1:20);
NMR (DMSO-$d_6$): δ 13.02 (s, 1H), 7.62-7.58 (m, 2H), 7.50-7.42 (m, 3H), 2.99 (t, J=7.5 Hz, 2H), 2.76 (t, J=7.5 Hz, 2H), 2.06-1.96 (m, 2H).

REFERENCE EXAMPLE 21

6-phenyl-5H-pyrrolo[3,4-b]pyridine-5,7(6H)-dione

To a solution of 2,3-pyridinedicarboxylic acid anhydride (19.4 g) in tetrahydrofuran (260 mL) was added aniline (11.8 mL) and the mixture was refluxed 2 hours. The reaction mixture was concentrated. Acetic anhydride (65 mL) was added to the reaction mixture, which was refluxed for 1.5 hours. After cooling in ice bath, the reaction mixture was poured in ice water (200 mL) and stirred for 1 hours. The precipitate was collected by filtration. It was washed with water and then washed with ethanol on heating to give the title compound (20.9 g) having the following physical data.
TLC: Rf 0.31 (hexane:ethyl acetate=1:1);
NMR (CDCl$_3$): δ 7.48 (m, 5H) 7.70 (dd, J=7.69, 4.94 Hz, 1H) 8.28 (dd, J=7.69, 1.65 Hz, 1H) 9.06 (dd, J=4.94, 1.65 Hz, 1H).

REFERENCE EXAMPLE 22

7-(3-aminophenyl)-7-hydroxy-6-phenyl-6,7-dihydro-5H-pyrrolo[3,4-b]pyridin-5-one

A solution of 3-(bis(trimethylsilyl)amino)phenylmagnesium chloride in tetrahydrofuran (5.50 mL, 1.0M) was added dropwise to a suspension of the compound prepared in Reference example 21 (1.12 g) in tetrahydrofuran (20 mL) in ice bath and the mixture was stirred for 1 hour. 1N hydrochloric acid (10 mL) was added dropwise to the reaction mixture, which was stirred for 30 minutes. A saturated aqueous sodium hydrogen carbonate solution (10 mL) was added to the reaction mixture, which was extracted with ethyl acetate. The extract was washed with brine, dried over anhydrous sodium sulfate and concentrated. The residue was washed with ethyl acetate on heating to give the title compound (1.35 g) having the following physical data.

TLC: Rf 0.52 (methylene chloride:methanol=9:1);

NMR (DMSO-$d_6$): δ 5.02 (s, 2H) 6.36 (m, 1H) 6.47 (m, 1H) 6.62 (t, J=1.92 Hz, 1H) 6.86 (t, J=7.83 Hz, 1H) 7.14 (m, 1H) 7.28 (m, 2H) 7.54 (m, 4H) 8.20 (dd, J=7.69, 1.65 Hz, 1H) 8.70 (dd, J=4.94, 1.65 Hz, 1H).

REFERENCE EXAMPLE 23

2-(3-aminobenzoyl)nicotinic acid

To the compound prepared in Reference example 22 (3.17 g) was added 6N hydrochloric acid (20 mL) and the mixture was refluxed overnight. The reaction mixture was cooled in ice bath, adjusted to pH 5 with 5N sodium hydroxide solution (24 mL) and concentrated. The residue was azeotroped with ethanol and suspended in ethanol (50 mL) with refluxing. Unnecessary sodium chloride was separated by filtration. The filtrate was concentrated. The residue was washed with isopropanol (15 mL) on heating to give the title compound (2.13 g) having the following physical data.

TLC: Rf 0.49 (methylene chloride:methanol:acetic acid=8:1:1);

NMR (DMSO-$d_6$): δ 6.74 (m, 2H) 6.85 (t, J=2.00 Hz, 1H) 7.09 (t, J=7.87 Hz, 1H) 7.63 (dd, J=7.97, 4.76 Hz, 1H) 8.33 (dd, J=7.97, 1.55 Hz, 1H) 8.77 (dd, J=4.76, 1.55 Hz, 1H).

REFERENCE EXAMPLE 24

8-(3-aminophenyl)pyrido[2,3-d]pyridazin-5(6H)-one

To a suspension of the compound prepared in Reference example 23 (1.94 g) in ethanol (40 mL) was added hydrazine monohydrate (400 mg) and the mixture was refluxed overnight. After cooling the reaction mixture to room temperature, the precipitate was collected by filtration. It was washed with ethanol to give the title compound (1.70 g) having the following physical data.

TLC: Rf 0.54 (methylene chloride:methanol=9:1);

NMR (DMSO-$d_6$): δ 5.14 (s, 2H) 6.64 (m, 1H) 6.94 (m, 1H) 6.99 (m, 1H) 7.09 (t, J=7.69 Hz, 1H) 7.84 (dd, J=8.06, 4.39 Hz, 1H) 8.63 (dd, J=8.06, 1.83 Hz, 1H) 9.12 (dd, J=4.39, 1.83 Hz, 1H) 13.00 (s, 1H).

EXAMPLE 46

8-(3-aminophenyl)-2,3,4,6-tetrahydropyrido[2,3-d]pyridazin-5(1H)-one

To a suspension of the compound prepared in Reference example 24 (1.67 g) and platinum oxide (83 mg) in dimethylformamide (35 mL) was added 6N hydrochloric acid (2.5 mL) and the mixture was stirred 8 hours under an atmosphere of hydrogen. The reaction mixture was filtrated through Celite. The filtrate was concentrated. A saturated aqueous sodium hydrogen carbonate solution was added to the residue, which was extracted with tetrahydrofuran three times. The combined organic layer was washed with brine, dried over anhydrous sodium sulfate and concentrated. The residue was dissolved in methanol (35 mL) on heating. Activated carbon (340 mg) was added to the mixture, which was stirred for 15 minutes. Activated carbon was filtrated through Celite. The filtrate was concentrated. The residue was washed with isopropanol on heating to give the compound of the present invention (1.25 g; free form) having the following physical data. The obtained compound (242 mg) was suspended in methanol (4 mL). A solution of methanesulfonic acid (96 mg) in methanol (1 mL) was added to the mixture, which was stirred. The deposited crystal was collected by filtration. It was washed with methanol to give the compound of the present invention (258 mg; methanesulfonate) having the following physical data.

Free Form:

TLC: Rf 0.40 (methylene chloride:methanol=9:1);

NMR (DMSO-$d_6$): δ 12.00 (s, 1H), 7.07 (m, 1H), 6.64-6.60 (m, 2H), 6.53 (d, J=7.3 Hz, 1H), 5.60 (s, 1H), 5.21 (s, 2H), 3.15 (m, 2H), 2.38 (t, J=6.2 Hz, 2H), 1.71 (m, 2H).

Methanesulfonate:

TLC: Rf 0.40 (methylene chloride:methanol=9:1);

NMR (DMSO-$d_6$): δ 12.28 (s, 1H), 7.53 (m, 1H), 7.40-7.30 (m, 3H) 3.13 (m, 2H), 2.40 (t, J=6.0 Hz, 2H), 2.35 (s, 3H), 1.73 (m, 2H).

EXAMPLE 47 TO EXAMPLE 47(13)

By the same procedure as described in Reference example 21→Reference example 22→Reference example 23→Reference example 24→Example 46, if necessary, by converting to corresponding salts by conventional method, using furo[3,4-b]pyridine-5,7-dione or a corresponding derivative, and a corresponding derivative instead of 3-(bis(trimethylsilyl)amino)phenylmagnesium chloride, the following compounds of the present invention were obtained.

EXAMPLE 47

8-(3-(N,N-dimethylamino)phenyl)-2,3,4,6-tetrahydropyrido[2,3-d]pyridazin-5(1H)-one methanesulfonate TLC: Rf 0.56 (methylene chloride:methanol=9:1);

NMR (DMSO-$d_6$): δ 12.29 (s, 1H), 7.39 (t, J=8.1 Hz, 1H), 7.22-6.78 (m, 3H), 3.15 (m, 2H), 3.01 (s, 6H), 2.41 (t, J=6.0 Hz, 2H), 2.33 (s, 3H), 1.73 (m, 2H).

EXAMPLE 47(1)

8-benzyl-2,3,4,6-tetrahydropyrido[2,3-d]pyridazin-5(1H)-one methanesulfonate

TLC: Rf 0.51 (methanol:methylene chloride=1:10);

NMR (DMSO-$d_6$): δ 12.13 (s, 1H), 7.31-7.16 (m, 5H), 6.22 (brs, 2H), 3.83 (s, 2H), 3.19 (t, J=6.0 Hz, 2H), 2.36 (t, J=6.0 Hz, 2H), 2.32 (s, 3H), 1.73-1.65 (m, 2H).

EXAMPLE 47(2)

8-(3-methoxyphenyl)-2,3,4,6-tetrahydropyrido[2,3-d]pyridazin-5(1H)-one methanesulfonate TLC: Rf 0.50 (methanol:methylene chloride=1:10);

NMR (DMSO-$d_6$): δ 12.27 (s, 1H), 7.38 (t, J=7.8 Hz, 1H), 7.03-6.96 (m, 3H), 6.21 (m, 2H), 3.78 (s, 3H), 3.16-3.13 (m, 2H), 2.41 (t, J=6.0 Hz, 2H), 2.32 (s, 3H), 1.76-1.71 (m, 2H).

EXAMPLE 47(3)

8-(4-aminophenyl)-2,3,4,6-tetrahydropyrido[2,3-d]pyridazin-5(1H)-one methanesulfonate TLC: Rf 0.25 (methylene chloride:methanol=19:1);

NMR (DMSO-$d_6$): δ 12.2 (brs, 1H), 7.42 (d, J=8.1 Hz, 2H), 7.16 (d, J=8.1 Hz, 2H), 3.14 (m, 2H), 2.40 (t, J=6.3 Hz, 2H), 2.33 (s, 3H), 1.73 (m, 2H).

EXAMPLE 47(4)

8-(3-(morpholin-4-ylmethyl)phenyl)-2,3,4,6-tetrahydropyrido[2,3-d]pyridazin-5(1H)-one methanesulfonate TLC: Rf 0.49 (methylene chloride:methanol=9:1);

NMR (DMSO-$d_6$): δ 12.21 (s, 1H), 9.79 (br-s, 1H), 7.80-7.37 (m, 4H), 5.83 (s, 1H), 4.40 (d, J=4.0 Hz, 2H), 3.96 (d, J=12.1 Hz, 2H), 3.62 (t, J=11.7 Hz, 2H), 3.30 (d, J=12.1 Hz, 2H), 3.20-3.06 (m, 4H), 2.40 (t, J=6.0 Hz, 2H), 2.30 (s, 3H), 1.73 (m, 2H).

EXAMPLE 47(5)

8-(4-(N,N-dimethylamino)phenyl)-2,3,4,6-tetrahydropyrido[2,3-d]pyridazin-5(1H)-one methanesulfonate TLC: Rf 0.50 (methylene chloride:methanol=9:1);

NMR (DMSO-$d_6$): δ 12.38 (s, 1H), 7.34 (d, J=8.1 Hz, 2H), 6.95 (m, 2H), 3.15 (m, 2H), 2.99 (s, 6H), 2.42 (m, 2H), 2.34 (s, 3H), 1.73 (m, 2H).

EXAMPLE 47(6)

8-(4-(morpholin-4-ylmethyl)phenyl)-2,3,4,6-tetrahydropyrido[2,3-d]pyridazin-5(1H)-one dimethanesulfonate TLC: Rf 0.51 (methylene chloride:methanol=10:1);

NMR (CD$_3$OD): δ 7.72 (d, J=8.1 Hz, 2H), 7.66 (d, J=8.1 Hz, 2H), 4.46 (s, 2H), 4.11-4.02 (m, 2H), 3.80 (t, J=12.6 Hz, 2H), 3.42 (d, J=12.6 Hz, 2H), 3.40-3.18 (m, 4H), 2.69 (s, 6H), 2.72-2.64 (m, 2H), 2.00-1.89 (m, 2H).

EXAMPLE 47(7)

8-(2-(morpholin-4-ylmethyl)phenyl)-2,3,4,6-tetrahydropyrido[2,3-d]pyridazin-5(1H)-one methanesulfonate TLC: Rf 0.54 (methylene chloride:methanol=10:1);

NMR (DMSO-$d_6$): δ 12.32 (s, 1H), 9.45 (br, 1H), 7.76 (m, 1H), 7.64-7.53 (m, 2H), 7.43 (m, 1H), 5.64 (br, 1H), 4.25 (s, 2H), 3.87 (d, J=12.0 Hz, 2H), 3.67 (t, J=12.0 Hz, 2H), 3.25 (d, J=12.0 Hz, 2H), 3.16-3.00 (m, 4H), 2.42 (t, J=6.0 Hz, 2H), 2.33 (s, 3H), 1.79-1.66 (m, 2H).

EXAMPLE 47(8)

8-(3-(4-ethylpiperazin-1-ylmethyl)phenyl)-2,3,4,6-tetrahydropyrido[2,3-d]pyridazin-5(1H)-one trihydrochloride TLC: Rf 0.42 (methylene chloride:methanol:water=8:2:0.2);

NMR (DMSO-$d_6$): δ 12.40 (br, 1H), 11.99 (br, 1H), 7.77-7.69 (m, 2H), 7.62-7.48 (m, 2H), 6.30-5.30 (br, 3H), 4.45 (s, 2H), 3.80-3.50 (m, 4H), 3.70-3.40 (m, 4H), 3.30-3.00 (m, 4H), 2.42 (t, J=6.3 Hz, 2H), 1.80-1.66 (m, 2H), 1.24 (t, J=7.2 Hz, 3H).

EXAMPLE 47(9)

8-(3-(N,N-dimethylaminomethyl)phenyl)-2,3,4,6-tetrahydropyrido[2,3-d]pyridazin-5(1H)-one methanesulfonate TLC: Rf 0.27 (methylene chloride:methanol:water=8:2:0.2);

NMR (DMSO-$d_6$): δ 12.21 (s, 1H), 9.59 (br, 1H), 7.62-7.52 (m, 4H), 5.82 (s, 1H), 4.35-4.31 (m, 2H), 3.20-3.12 (m, 2H), 2.76 (s, 3H), 2.75 (s, 3H), 2.41 (t, J=6.3 Hz, 2H), 2.30 (s, 3H), 1.81-1.68 (m, 2H).

EXAMPLE 47(10)

8-(4-(N,N-dimethylaminomethyl)phenyl)-2,3,4,6-tetrahydropyrido[2,3-d]pyridazin-5(1H)-one methanesulfonate TLC: Rf 0.82 (methylene chloride:methanol:ammonia water=8:2:0.2);

NMR (DMSO-$d_6$): δ 12.19 (s, 1H), 9.68 (br, 1H), 7.57 (d, J=8.4 Hz, 2H), 7.53 (d, J=8.4 Hz, 2H), 5.76 (s, 1H), 4.34 (s, 2H), 3.18-3.10 (m, 2H), 2.76 (s, 6H), 2.40 (t, J=6.0 Hz, 2H), 2.31 (s, 3H), 1.80-1.68 (m, 2H).

EXAMPLE 47(11)

8-(4-(N,N-diethylaminomethyl)phenyl)-2,3,4,6-tetrahydropyrido[2,3-d]pyridazin-5(1H)-one methanesulfonate TLC: Rf 0.38 (methylene chloride:methanol:ammonia water=8:2:0.2);

NMR (DMSO-$d_6$): δ 12.20 (s, 1H), 9.34 (br, 1H), 7.60 (d, J=8.4 Hz, 2H), 7.54 (d, J=8.4 Hz, 2H), 5.77 (s, 1H), 4.36 (d, J=4.8 Hz, 2H), 3.12-3.02 (m, 6H), 2.40 (t, J=6.0 Hz, 2H), 2.30 (s, 3H), 1.80-1.68 (m, 2H), 1.24 (t, J=7.2 Hz, 6H).

EXAMPLE 47(12)

4-(4-(N,N-dimethylaminomethyl)phenyl)-5,6,7,8-tetrahydrophthalazin-1(2H)-one methanesulfonate TLC: Rf 0.49 (methylene chloride:methanol:water=8:2:0.2);

NMR (DMSO-$d_6$): δ 12.95 (s, 1H), 9.64 (br, 1H), 7.60-7.52 (m, 4H), 4.33 (s, 2H), 2.76 (s, 6H), 2.50-2.40 (m, 2H), 2.40-2.32 (m, 2H), 2.30 (s, 3H), 1.76-1.66 (m, 2H), 1.66-1.55 (m, 2H).

EXAMPLE 47(13)

8-(4-(2-(N,N-dimethylamino)ethyl)phenyl)-2,3,4,6-tetrahydropyrido[2,3-d]pyridazin-5(1H)-one methanesulfonate TLC: Rf 0.50 (methylene chloride:methanol:ammonia water=8:2:0.2);
NMR (DMSO-d$_6$): δ 12.12 (s, 1H), 9.41 (br, 1H), 7.42 (d, J=8.1 Hz, 2H), 7.37 (d, J=8.1 Hz, 2H), 5.70 (s, 1H), 3.35-3.25 (m, 2H), 3.18-3.09 (m, 2H), 3.05-2.96 (m, 2H), 2.83 (s, 6H), 2.39 (t, J=6.3 Hz, 2H), 2.30 (s, 3H), 1.80-1.68 (m, 2H).

REFERENCE EXAMPLE 25

2-(3-aminobenzoyl)nicotinic acid methyl ester

After cooling methanol (5 mL) to −15° C., thionyl chloride (1.3 mL) was added dropwise thereto and the solution was stirred for 15 minutes. To the solution was added the compound prepared in Reference example 23 (1.21 g). The solution was allowed to return to room temperature and then refluxed overnight. The reaction mixture was concentrated. To the residue were added a saturated aqueous sodium hydrogen carbonate solution and ethyl acetate. The organic layer was washed with brine, dried over anhydrous sodium sulfate and concentrated. The residue was recrystallized from isopropanol (5 mL) to give the title compound (815 mg) having the following physical data.
TLC: Rf 0.37 (hexane:ethyl acetate=1:3);
NMR (DMSO-d$_6$): 63.69 (s, 3H) 5.36 (s, 2H) 6.79 (m, 2H) 6.89 (m, 1H) 7.12 (t, J=7.83 Hz, 1H) 7.70 (dd, J=8.04, 4.81 Hz, 1H) 8.39 (dd, J=8.04, 1.65 Hz, 1H) 8.83 (dd, J=4.74, 1.65 Hz, 1H).

REFERENCE EXAMPLE 26

2-(3-(trifluoroacetyl)aminobenzoyl)nicotinic acid methyl ester

To a solution of the compound prepared in Reference example 25 (800 mg) in methylene chloride (15 mL) were added pyridine (505 μL) and trifluoroacetic acid anhydride (529 μL) sequentially in ice bath, and the mixture was stirred for 30 minutes. The reaction mixture was diluted with methylene chloride and washed with 1N hydrochloric acid and water sequentially. The organic layer was dried over anhydrous sodium sulfate and concentrated. The residue was purified by column chromatography on silica gel (hexane:ethyl acetate=1:1) to give the title compound (1.10 g) having the following physical data.
TLC: Rf 0.48 (hexane:ethyl acetate=1:1);
NMR (CDCl$_3$): δ 3.79 (s, 3H) 7.49 (t, J=7.97 Hz, 1H) 7.56 (dd, J=8.11, 4.81 Hz, 1H) 7.63 (m, 1H) 7.99 (m, 2H) 8.28 (s, 1H) 8.39 (dd, J=8.11, 1.65 Hz, 1H) 8.82 (dd, J=4.81, 1.65 Hz, 1H).

REFERENCE EXAMPLE 27

2-(3-(N-methyl-N-(trifluoroacetyl)amino)benzoyl)nicotinic acid methyl ester

To a solution of the compound prepared in Reference example 26 (1.06 g) in dimethylformamide (12 mL) was added sodium hydride (127 mg) in ice bath and the mixture was stirred for 30 minutes. Methyl iodide (224 mL) was added to the reaction mixture, which was stirred at 0° C. for 1 hour and subsequently at room temperature for 6 hours. The reaction mixture was poured in ice water and extracted with a mixed solvent (ethyl acetate:hexane=1:1) twice. The combined organic layer was washed with water and brine sequentially, dried over anhydrous sodium sulfate and concentrated. The residue was recrystallized from a mixed solvent (isopropanol:hexane=1:1) to give the title compound (892 mg) having the following physical data.
TLC: Rf 0.31 (hexane:ethyl acetate=1:1);
NMR (CDCl$_3$): δ 3.37 (s, 3H) 3.76 (s, 3H) 7.55 (m, 3H) 7.71 (s, 1H) 7.87 (d, J=7.69 Hz, 1H) 8.40 (dd, J=7.97, 1.65 Hz, 1H) 8.83 (dd, J=4.94, 1.65 Hz, 1H).

REFERENCE EXAMPLE 28

8-(3-(N-methylamino)phenyl)pyrido[2,3-d]pyridazin-5(6H)-one

To a solution of the compound prepared in Reference example 27 (880 mg) in ethanol (12 mL) was added a solution of hydrazine monohydrate (240 mg) in ethanol (3 mL) and the mixture was refluxed overnight. 1N sodium hydroxide solution (5 mL) was added to the reaction mixture, which was refluxed for 1 hour. The reaction mixture was cooled in ice bath and 1N hydrochloric acid (5 mL) was added thereto. The precipitate was collected by filtration. It was washed with water and then washed with ethanol on heating to give the title compound (581 mg) having the following physical data.
TLC: Rf 0.39 (methylene chloride:methanol=19:1);
NMR (DMSO-d$_6$): δ 2.69 (d, J=5.13 Hz, 3H) 5.73 (q, J=5.13 Hz, 1H) 6.62 (m, 1H) 6.97 (m, 2H) 7.18 (t, J=7.69 Hz, 1H) 7.85 (dd, J=8.06, 4.39 Hz, 1H) 8.64 (dd, J=8.06, 1.83 Hz, 1H) 9.13 (dd, J=4.39, 1.83 Hz, 1H) 13.02 (s, 1H).

EXAMPLE 48

8-(3-(N-methylamino)phenyl)-2,3,4,6-tetrahydropyrido[2,3-d]pyridazin-5(1H)-one methanesulfonate By the same procedure as described in Example 46 using the compound prepared in Reference example 28 instead of the compound prepared in Reference example 24, the compounds of the present invention having the following physical data was obtained.
TLC: Rf 0.49 (methylene chloride:methanol=9:1);
NMR (DMSO-d$_6$): δ 12.31 (s, 1H), 7.36 (t, J=7.9 Hz, 1H), 7.18-6.85 (m, 3H), 3.16 (m, 2H), 2.83 (s, 3H), 2.41 (t, J=6.0 Hz, 2H), 2.34 (s, 3H), 1.73 (m, 2H).

EXAMPLE 49

8-(4-(N-methylamino)phenyl)-2,3,4,6-tetrahydropyrido[2,3-d]pyridazin-5(1H)-one methanesulfonate By the same procedure as described in Reference example 25→Reference example 26→Reference example 27→Reference example 28→Example 46 using a corresponding derivative instead of the compound prepared in Reference example 23, the compounds of the present invention having the following physical data was obtained.
TLC: Rf 0.39 (methanol:methylene chloride=1:9);
NMR (DMSO-d$_6$): δ 12.26 (brs, 1H), 7.27 (d, J=7.8 Hz, 2H), 6.79 (d, J=7.8 Hz, 2H), 5.96 (brs, 3H), 3.16 (m, 2H), 2.76 (s, 3H), 2.41 (m, 2H), 2.32 (s, 3H), 1.72 (m, 2H).

EXAMPLE 50 TO EXAMPLE 50(4)

By the same procedure as described in Reference example 20→Example 42 using a corresponding derivative instead of benzaldehyde, the compounds of the present invention having the following physical data was obtained.

EXAMPLE 50

4-(2-phenoxyethyl)-5,6,7,8-tetrahydrophthalazin-1(2H)-one

TLC: Rf 0.41 (methylene chloride:methanol=19:1);
NMR (DMSO-$d_6$): δ 12.6 (s, 1H), 7.30-7.22 (m, 2H), 6.95-6.90 (m, 3H), 4.26 (t, J=6.9 Hz, 2H), 2.97 (t, J=6.9 Hz, 2H), 2.60-2.35 (m, 4H), 1.66 (m, 4H).

EXAMPLE 50(1)

4-(3-phenoxypropyl)-5,6,7,8-tetrahydrophthalazin-1(2H)-one

TLC: Rf 0.40 (methylene chloride:methanol=19:1);
NMR (DMSO-$d_6$): δ 12.52 (s, 1H), 7.26 (m, 2H), 6.90 (m, 3H), 4.01 (t, J=6.3 Hz, 2H), 2.65 (t, J=7.5 Hz, 2H), 2.55-2.30 (m, 4H), 2.01 (m, 2H), 1.64 (m, 4H).

EXAMPLE 50(2)

4-(4-(3-(N,N-dimethylamino)propoxy)benzyl)-5,6,7,8-tetrahydrophthalazin-1(2H)-one hydrochloride TLC: Rf 0.37 (methylene chloride:methanol:ammonia water=8:2:0.2);
NMR (DMSO-$d_6$): δ 12.60 (s, 1H), 9.32(brs, 1H), 7.08 (d, J=8.4 Hz, 2H), 6.86 (d, J=8.4 Hz, 2H), 3.99 (t, J=6.0 Hz, 2H), 3.81 (s, 21), 3.24-3.16 (m, 2H), 2.79 (s, 6H), 2.40-2.28 (m, 4H), 2.14-2.02 (m, 2H), 1.64-1.54 (m, 4H).

EXAMPLE 50(3)

4-(2-benzyloxyethyl)-5,6,7,8-tetrahydrophthalazin-1(2H)-one

TLC: Rf 0.54 (methylene chloride:methanol=19:1);
NMR (DMSO-$d_6$): δ 12.5 (s, 1H), 7.35-7.22 (m, 5H), 4.47 (s, 2H), 3.69 (t, J=7.2 Hz, 2H), 2.78 (t, J=7.2 Hz, 2H), 2.50-2.36 (m, 4H), 1.63 (m, 4H).

EXAMPLE 50(4)

4-(quinolin-3-ylmethyl)-5,6,7,8-tetrahydrophthalazin-1(2H)-one

TLC: Rf 0.53(methylene chloride:methanol=10:1);
NMR (DMSO-$d_6$): δ 12.60 (s, 1H), 8.79 (d, J=1.8 Hz, 1H), 8.08 (d, J=1.8 Hz, 1H), 7.98 (d, J=8.1 Hz, 1H), 7.92 (dd, J=8.1, 1.5 Hz, 1H), 7.70 (ddd, J=8.1, 6.9, 1.5 Hz, 1H), 7.57 (ddd, J=8.1, 6.9, 1.5 Hz, 1H), 4.12 (s, 2H), 2.54-2.40 (m, 2H), 2.46-2.30 (m, 2H), 1.70-1.55 (m, 4H).

EXAMPLE 51 TO EXAMPLE 51(3)

By the same procedure as described in Example 27, if necessary, by converting to corresponding salts by conventional method, using a corresponding derivative instead of the compound prepared in Reference example 13 and a corresponding derivative instead of benzylamine, the following compounds of the present invention were obtained.

EXAMPLE 51

4-(5-(piperidin-1-yl)pentyl)-5,6,7,8-tetrahydrophthalazin-1(2H)-one hydrochloride TLC: Rf 0.83(methylene chloride:methanol:ammonia water=8:2:0.2);
NMR (DMSO-$d_6$): δ 12.51 (s, 1H), 9.96 (br, 1H), 3.46-3.28 (m, 2H), 3.02-2.84 (m, 2H), 2.95-2.65 (m, 2H), 2.54-2.44 (m, 2H), 2.42-2.32 (m, 2H), 1.84-1.54 (m, 14H), 1.44-1.26 (m, 4H).

EXAMPLE 51 (1)

8-(2-(4-(2-(morpholin-4-yl)ethyl)piperazin-1-yl)ethyl)-2,3,4,6-tetrahydropyrido[2,3,-d]pyridazin-5(1H)-one TLC: Rf 0.15 (methylene chloride:methanol:saturated aqueous ammonia=4:1:0.5%);
NMR (CD$_3$OD): δ 3.69 (m, 4H), 3.33 (m, 2H), 2.78-2.42 (m, 22H), 1.85 (m, 2H).

EXAMPLE 51(2)

8-(2-(4-benzyloxycarbonyl-1,4-diazepan-1-yl)ethyl)-2,3,4,6-tetrahydropyrido[2,3,-d]pyridazin-5(1H)-one methanesulfonate TLC: Rf 0.19 (methylene chloride:methanol=19:1);
NMR (DMSO-$d_6$): δ 11.97 (s, 1H), 9.39 (s, 1H), 7.41-7.30 (m, 5H), 6.38 (brs, 1H), 5.11 (s, 2H), 4.32 (brs, 2H), 3.87 (m, 1H), 3.70-3.40 (m, 7H), 3.30-3.15 (m, 2H), 2.84 (t, J=7.5 Hz, 2H), 2.35 (t, J=6.3 Hz, 2H), 2.31 (s, 3H), 2.07 (m, 2H), 1.72 (m, 2H).

EXAMPLE 51(3)

4-(4-(morpholin-4-yl)butyl)-5,6,7,8-tetrahydrophthalazin-1(2H)-one

Hydrochloride:
TLC: Rf 0.29 (methylene chloride:methanol=10:1);
NMR (300 MHz, CD$_3$OD) 3.10-3.00 (m, 4H), 2.37-2.26 (m, 4H), 2.25-2.16 (m, 2H), 1.85 (t, J=6.9 Hz, 2H), 1.83-1.75 (m, 2H), 1.75-1.67 (m, 2H), 1.08-0.88 (m, 8H).

Methanesulfonate:
TLC: Rf 0.25 (methylene chloride:methanol=10:1);
NMR (DMSO-$d_6$): δ 12.55 (s, 1H), 9.52 (br, 1H), 4.01-3.92 (m, 2H), 3.64 (t, J=11.4 Hz, 2H), 3.45-3.36 (m, 2H), 3.17-2.95 (m, 4H), 2.58-2.43 (m, 4H), 2.43-2.34 (m, 2H), 2.31 (s, 3H), 1.77-1.54 (m, 8H).

EXAMPLE 52 TO EXAMPLE 52(3)

By the same procedure as described in Example 24, if necessary, by converting to corresponding salts by conventional method, using a corresponding ester derivative instead of the compound prepared in Example 15 and a corresponding derivative instead of 2-aminoethanol, the following compounds of the present invention were obtained.

EXAMPLE 52

8-(N-(4-hydroxybutyl)carbamoylmethyl)-2,3,4,6-tetrahydropyrido[2,3,-d]pyridazin-5(1H)-one TLC: Rf 0.54 (methanol:methylene chloride=1:4);

NMR (DMSO-$d_6$): δ 11.84 (s, 1H), 8.06 (t, J=5.7 Hz, 1H), 6.42 (s, 1H), 4.37 (t, J=4.8 Hz, 1H), 3.35 (m, 4H), 3.18 (m, 2H), 3.03 (td, J=6.6, 5.7 Hz, 2H), 2.32 (t, J=6.3 Hz, 2H), 1.69 (m, 2H), 1.41 (m, 4H).

EXAMPLE 52(1)

8-(N-(4-(morpholin-4-yl)butyl)carbamoylmethyl)-2,3,4,6-tetrahydropyrido[2,3,-d]pyridazin-5(1H)-one TLC: Rf 0.22 (methanol:methylene chloride=1:4);

NMR (DMSO-$d_6$): δ 11.84 (s, 1H), 8.06 (t, J=5.4 Hz, 1H), 6.43 (s, 1H), 3.55-3.52 (m, 4H), 3.32-3.31 (m, 2H), 3.18 (brs, 2H), 3.04 (m, 2H), 2.34-2.19 (m, 8H), 1.71-1.68 (m, 2H), 1.40-1.36 (m, 4H).

EXAMPLE 52(2)

8-(N-(2-(azepan-1-yl)ethyl)carbamoylmethyl)-2,3,4,6-tetrahydropyrido[2,3,-d]pyridazin-5(1H)-one methanesulfonate TLC: Rf 0.39 (methanol:methylene chloride:saturated aqueous ammonia=2:8:0.1);

NMR (DMSO-$d_6$): δ 11.90 (s, 1H), 9.13 (brs, 1H), 8.30 (t, J=5.4 Hz, 1H), 6.30 (brs, 1H), 3.45-3.35 (m, 6H), 3.19-3.08 (m, 6H), 2.40-2.29 (m, 2H), 2.33 (s, 3H), 1.80-1.52 (m, 10H).

EXAMPLE 52(3)

4-(N-(6-hydroxyhexyl)carbamoylmethyl)-5,6,7,8-tetrahydrophthalazin-1(2H)-one

TLC: Rf 0.23 (methanol:methylene chloride=1:10);

NMR (DMSO-$d_6$): δ 12.56 (s, 1H), 7.99 (t, J=5.7 Hz, 1H), 4.32 (t, J=5.1 Hz, 1H), 3.38 (s, 2H), 3.37-3.33 (m, 2H), 3.05-2.99 (m, 2H), 2.41-2.36 (m, 4H), 1.63 (m, 4H), 1.40-1.23 (m, 8H).

EXAMPLE 53 TO EXAMPLE 53(1)

By the same procedure as described in Example 34 using a corresponding derivative instead of the compound prepared in Example 33, the following compounds of the present invention were obtained.

EXAMPLE 53

4-(N-(5-bromopentyl)carbamoylmethyl)-5,6,7,8-tetrahydrophthalazin-1(2H)-one

TLC: Rf 0.53(methylene chloride:methanol=10:1);

NMR (DMSO-$d_6$): δ 12.57 (s, 1H), 8.02 (t, J=5.1 Hz, 1H), 3.51 (t, J=6.3 Hz, 2H), 3.39 (s, 2H), 3.04 (q, J=6.3 Hz, 2H), 2.46-2.33 (m, 4H), 1.78(quin, J=6.3 Hz, 2H), 1.70-1.58 (m, 4H), 1.48-1.30 (m, 4H).

EXAMPLE 53(1)

4-(N-(6-bromohexyl)carbamoylmethyl)-5,6,7,8-tetrahydrophthalazin-1(2H)-one

TLC: Rf 0.37 (methanol:methylene chloride=1:10);

NMR (DMSO-$d_6$): δ 12.57 (s, 1H), 7.99 (t, J=5.4 Hz, 1H), 3.51 (t, J=6.6 Hz, 2H), 3.38 (s, 2H), 3.06-3.00 (m, 2H), 2.41-2.36 (m, 4H), 1.82-1.75 (m, 2H), 1.64 (m, 4H), 1.41-1.16 (m, 6H).

EXAMPLE 54 TO EXAMPLE 54(2)

By the same procedure as described in Example 28, if necessary, by converting to corresponding salts by conventional method, using the compound prepared in Example 53, 23(23) or 53(1) instead of the compound prepared in Example 25(1), the following compounds of the present invention were obtained.

EXAMPLE 54

4-(N-(5-(morpholin-4-yl)pentyl)carbamoylmethyl)-5,6,7,8-tetrahydrophthalazin-1(2H)-one TLC: Rf 0.57 (methylene chloride:methanol:water=8:2:0.2);

NMR (DMSO-$d_6$): δ 12.57 (s, 1H), 7.99 (t, J=5.7 Hz, 1H), 3.54 (t, J=4.8 Hz, 4H), 3.38 (s, 2H), 3.02 (q, J=6.9 Hz, 2H), 2.46-2.33 (m, 4H), 2.33-2.25 (m, 4H), 2.21 (t, J=6.9 Hz, 2H), 1.68-1.58 (m, 4H), 1.39(quin, J=6.9 Hz, 4H), 1.31-1.19 (m, 2H).

EXAMPLE 54(1)

4-(N-(2-(azocan-1-yl)ethyl)carbamoylmethyl)-5,6,7,8-tetrahydrophthalazin-1(2H)-one methanesulfonate TLC: Rf 0.67 (methanol:methylene chloride:28% ammonia water=2:8:0.1);

NMR (DMSO-$d_6$): δ 12.63 (s, 1H), 9.37 (brs, 11H), 8.36 (t, J=5.7 Hz, 1H), 3.46 (s, 2H), 3.43-3.34 (m, 4H), 3.16-3.12 (m, 4H), 2.42-2.37 (m, 4H), 2.29 (s, 3H), 1.84-1.49 (m, 14H).

EXAMPLE 54(2)

4-(N-(6-(morpholin-4-yl)hexyl)carbamoylmethyl)-5,6,7,8-tetrahydrophthalazin-1(2H)-one methanesulfonate TLC: Rf 0.22 (methanol:methylene chloride=1:9);

NMR (DMSO-$d_6$): δ 12.58 (s, 1H), 9.48 (brs, 1H), 8.03 (t, J=5.4 Hz, 1H), 3.98-3.94 (m, 2H), 3.67-3.39 (m, 6H), 3.07-3.01 (m, 6H), 2.48-2.36 (m, 7H), 1.63-1.27 (m, 12H).

EXAMPLE 55 TO EXAMPLE 55(2)

By the same procedure as described in Reference example 22→Reference example 24→Example 20→Example 46, if necessary, by converting to corresponding salts by conventional method, using a corresponding derivative instead of 4-(bis(trimethylsilyl)amino)phenylmagnesium bromide, the following compounds of the present invention were obtained.

EXAMPLE 55

8-(3,4-dihydroxyphenyl)-2,3,4,6-tetrahydropyrido[2,3-d]pyridazin-5(1H)-one

TLC: Rf 0.59 (methylene chloride:methanol:water=8:2:0.2);
NMR (DMSO-$d_6$): δ 11.94 (s, 1H), 9.14 (br, 2H), 6.80 (s, 1H), 6.79 (d, J=7.8 Hz, 1H), 6.68 (m, 1H), 5.65 (s, 1H), 3.16-3.08 (m, 2H), 2.37 (t, J=6.0 Hz, 2H), 1.77-1.65 (m, 2H).

EXAMPLE 55(1)

8-(4-hydroxyphenyl)-2,3,4,6-tetrahydropyrido[2,3-d]pyridazin-5(1H)-one methanesulfonate TLC: Rf 0.29 (methanol:methylene chloride=1:10);
NMR (DMSO-$d_6$): δ 12.40 (brs, 1H), 9.20 (brs, 1H), 7.26 (d, J=8.7 Hz, 2H), 6.84 (d, J=8.7 Hz, 2H), 3.16 (t, J=5.1 Hz, 2H), 2.42 (t, J=6.0 Hz, 2H), 2.34 (s, 3H), 1.71 (m, 2H).

EXAMPLE 55(2)

8-(2-hydroxyphenyl)-2,3,4,6-tetrahydropyrido[2,3-d]pyridazin-5(1H)-one

TLC: Rf 0.4 (methylene chloride:methanol=10:1);
NMR (DMSO-$d_6$): δ 12.58 (br, 1H), 9.58 (br, 1H), 7.29 (t, J=7.5 Hz, 1H), 7.12 (d, J=7.5 Hz, 1H), 6.93 (d, J=7.5 Hz, 1H), 6.88 (t, J=7.5 Hz, 1H), 5.96 (br, 1H), 3.23-3.12 (m, 2H), 2.54-2.4 (m, 2H), 1.82-1.64 (m, 2H).

EXAMPLE 56 TO EXAMPLE 56(6)

By the same procedure as described in Example 46, if necessary, by converting to corresponding salts by conventional method, using the compound prepared in Example 43(1), Example 43(2), 23(17), 23(22), 24(11) or 24(16), or 4-(pyridin-4-ylmethyl)-5,6,7,8-tetrahydrophthalazin-1(2H)-one instead of the compound prepared in Reference example 24 and, the following compounds of the present invention were obtained.

EXAMPLE 56

4-(piperidin-3-ylmethyl)-5,6,7,8-tetrahydrophthalazin-1(2H)-one acetate

TLC: Rf 0.21 (methylene chloride:methanol:ammonia water=8:2:0.2);
NMR (DMSO-$d_6$): δ 12.49 (br, 1H), 2.97-2.84 (m, 2H), 2.53-2.42 (m, 5H), 2.41-2.31 (m, 4H), 2.26 (m, 1H), 1.84 (m, 1H), 1.82 (s, 3H), 1.77-1.53 (m, 6H), 1.40 (m, 1H), 1.09 (m, 1H).

EXAMPLE 56(1)

4-(piperidin-4-ylmethyl)-5,6,7,8-tetrahydrophthalazin-1(2H)-one acetate

TLC: Rf 0.16 (methylene chloride:methanol:ammonia water=8:2:0.2);
NMR (DMSO-$d_6$): δ 12.51 (br, 1H), 2.90 (m, 1H), 2.78 (m, 1H), 2.58-2.40 (m, 7H), 2.40-2.32 (m, 2H), 1.86 (s, 3H), 1.74-1.45 (m, 7H), 1.38-1.20 (m, 2H), 1.10 (m, 1H).

EXAMPLE 56(2)

4-(piperidin-2-ylmethyl)-5,6,7,8-tetrahydrophthalazin-1(2H)-one acetate

TLC: Rf 0.58 (methylene chloride:methanol:ammonia water=8:2:0.2);
NMR (DMSO-$d_6$): δ 12.47 (br, 1H), 3.01-2.91 (m, 2H), 2.56-2.42 (m, 6H), 2.41-2.32 (m, 4H), 1.81 (s, 3H), 1.80 (m, 1H), 1.70-1.55 (m, 6H), 1.22-1.07 (m, 2H).

EXAMPLE 56(3)

4-(N-(piperidin-2-yl)carbamoylmethyl)-5,6,7,8-tetrahydrophthalazin-1(2H)-one methanesulfonate TLC: Rf 0.27 (methylene chloride:methanol:water=8:2:0.2);
NMR (DMSO-$d_6$): δ 12.64 (s, 1H), 9.22 (d, J=7.5 Hz, 1H), 8.77 (br, 21), 4.83 (m, 1H), 3.55 (s, 2H), 3.10 (m, 1H), 2.97 (m, 1H), 2.55-2.35 (m, 4H), 2.34 (s, 3H), 1.94-1.50 (m, 10H).

EXAMPLE 56(4)

4-(N-(piperidin-2-ylmethyl)carbamoylmethyl)-5,6,7,8-tetrahydrophthalazin-1(2H)-one methanesulfonate TLC: Rf 0.55 (methylene chloride:methanol:28% ammonia water=15:5:1);
NMR (DMSO-$d_6$): δ 12.62 (s, 1H), 8.50 (m, 1H), 8.30-8.10 (m, 2H), 3.48 (s, 2H), 3.40-3.00 (m, 4H), 2.84 (m, 1H), 2.46-2.34 (m, 4H), 2.32 (s, 3H), 1.82-1.20 (m, 10H).

EXAMPLE 56(5)

4-(N-(2-(piperidin-2-yl)ethyl)carbamoylmethyl)-5,6,7,8-tetrahydrophthalazin-1(2H)-one methanesulfonate TLC: Rf 0.40 (methylene chloride:methanol:28% ammonia water=15:5:1);
NMR (DMSO-$d_6$): δ 12.61 (s, 1H), 8.41 (m, 1H), 8.30-8.16 (m, 2H), 3.42 (s, 2H), 3.30-2.70 (m, 5H), 2.46-2.32 (m, 4H), 2.31 (s, 3H), 1.92-1.20 (m, 12H).

EXAMPLE 56(6)

4-(N-(2-(piperidin-3-yl)ethyl)carbamoylmethyl)-5,6,7,8-tetrahydrophthalazin-1(2H)-one methanesulfonate TLC: Rf 0.28 (methylene chloride:methanol:28% ammonia water=15:5:1);
NMR (DMSO-$d_6$): δ 12.57 (brs, 1H), 8.26 (brs, 2H), 8.06 (t, J=5.5 Hz, 1H), 3.39 (s, 2H), 3.24-3.02 (m, 4H), 2.73 (m, 1H), 2.46-2.32 (m, 4H), 2.30 (s, 3H), 1.80-1.04 (m, 12H).

EXAMPLE 57

8-(3-hydroxyphenyl)-2,3,4,6-tetrahydropyrido[2,3-d]pyridazin-5(1H)-one

By the same procedure as described in Example 20, if necessary, by converting to corresponding salts by conventional method, using the compound prepared in Example 47(2) instead of the compound prepared in Example 4(4), the compounds of the present invention having the following data were obtained.

Free Form:

TLC: Rf 0.33 (methanol:methylene chloride=1:20);

NMR (DMSO-$d_6$): δ 12.06 (s, 1H), 9.60 (s, 1H), 7.25 (t, J=8.1 Hz, 1H), 6.81 (m, 3H), 5.71 (s, 1H), 3.13 (m, 2H), 2.36 (m, 2H), 1.71 (m, 2H).

Sodium Salt:

TLC: Rf 0.43 (methanol:methylene chloride=1:9);

NMR (DMSO-$d_6$): δ 11.85 (brs, 1H), 6.92 (t, J=7.8 Hz, 1H), 6.36 (brs, 2H), 6.17 (brs, 1H), 5.40 (s, 1H), 3.13 (m, 2H), 2.36 (m, 2H), 1.68 (m, 2H).

EXAMPLE 58

8-(N-(2-(piperidin-4-yl)ethyl)carbamoylmethyl)-2,3,4,6-tetrahydropyrido[2,3-d]pyridazin-5(1H)-one A mixed solution of the compound prepared in Example 24(44) (307 mg), 10% palladium on carbon (307 mg) and ammonium formate (236 mg) in methanol (3.00 mL) was refluxed for 30 minutes. After cooling to room temperature, the reaction mixture was filtrated through Celite. The filtrate was concentrated. The residue was washed with a mixed solution of methanol and ethyl acetate and dried under reduced pressure to give the compound of the present invention (187 mg) having the following physical data.

TLC: Rf 0.13 (methanol:methylene chloride:acetic acid=1:4:1);

NMR (DMSO-$d_6$): δ 11.83 (brs, 1H), 8.06 (t, J=5.1 Hz, 1H), 6.44 (s, 1H), 3.18-2.09 (m, 13H), 1.69 (m, 2H), 1.52 (m, 2H), 1.29 (m, 3H), 0.94 (m, 2H).

EXAMPLE 59

8-(pyridin-2-yl)-2,3,4,6-tetrahydropyrido[2,3-d]pyridazin-5(1H)-one (compound A) and 8-(piperidin-2-yl)-2,3,4,6-tetrahydropyrido[2,3-d]pyridazin-5(1H)-one (compound B)

Under an atmosphere of argon, to 8-(pyridin-2-yl)pyrido[2,3-d]pyridazin-5(6H)-one (118 mg; It was prepared by the same procedure as described in Reference example 22→Reference example 23→Reference example 24 using pyridin-2-ylmagnesium bromide instead of 3-(bis(trimethylsilyl)amino)phenylmagnesium chloride.) were added methanol (6 mL), methanesulfonate (51 mg) and platinum oxide (12 mg) sequentially. Under an atmosphere of hydrogen, the reaction mixture was stirred at room temperature for 5.5 hours. The reaction mixture was filtrated through Celite. The filtrate was concentrated. The residue was purified by column chromatography on silica gel (methylene chloride:methanol=20:1>methylene chloride:methanol:water=8:2:0.2) to give free form of the compound A (14 mg) and methanesulfonate of the compound B (77 mg) having the following physical data. The obtained compound A and B were converted to corresponding salts or free form by conventional method to give the compound of the present invention having the following physical data.

Free Form of the Compound A:

TLC: Rf 0.51 (methylene chloride:methanol=10:1).

NMR (DMSO-$d_6$): δ 12.39 (br, 1H), 8.88 (br, 1H), 8.59 (m, 1H), 8.04 (d, J=8.4 Hz, 1H), 7.93 (m, 1H), 7.44 (m, 1H), 3.40-3.25 (m, 2H), 2.43 (t, J=6.3 Hz, 2H), 1.85-1.74 (m, 2H).

Methanesulfonate of the Compound B:

TLC: Rf 0.15 (methylene chloride:methanol:water=8:2:0.2);

NMR (DMSO-$d_6$): δ 12.36 (s, 1H), 8.76 (br, 2H), 6.63 (s, 1H), 4.21 (d, J=9.9 Hz, 1H), 3.30 (m, 1H), 3.28-3.16 (m, 2H), 2.89 (m, 1H), 2.36 (t, J=6.0 Hz, 2H), 2.29 (s, 3H), 2.03 (d, J=12.3 Hz, 1H), 1.84-1.60 (m, 6H), 1.43 (m, 1H).

Free Form of the Compound B:

TLC: Rf 0.14 (methylene chloride:methanol:water=8:2:0.2);

NMR (DMSO-$d_6$): δ 11.74 (s, 1H), 7.36 (s, 1H), 3.54 (dd, J=9.6, 3.9 Hz, 1H), 3.26-3.16 (m, 2H), 2.94 (d, J=12.0 Hz, 1H), 2.65-2.50 (m, 1H), 2.32 (t, J=6.3 Hz, 2H), 1.79 (m, 1H), 1.76-1.26 (m, 7H).

Methanesulfonate of the Compound A:

TLC: Rf 0.50 (methylene chloride:methanol=10:1);

NMR (DMSO-$d_6$): δ 12.63 (br, 1H), 9.45 (br, 2H), 8.60 (d, J=4.5 Hz, 1H), 8.06 (d, J=8.4 Hz, 1H), 7.97 (t, J=8.4 Hz, 1H), 7.48 (m, 1H), 3.40-3.33 (m, 2H), 2.52-2.42 (m, 2H), 2.36 (s, 3H), 1.84-1.73 (m, 2H).

Dimethanesulfonate of the Compound B:

TLC: Rf 0.66 (methylene chloride:methanol:ammonia water=8:2:0.2);

NMR (DMSO-$d_6$): δ 1.45 (m, 1H) 1.72 (m, 6H) 2.04 (d, J=12.82 Hz, 1H) 2.37 (m, 8H) 2.94 (s, 1H) 3.25 (m, 3H) 4.26 (t, J=10.44 Hz, 1H) 7.21 (m, 1H) 8.71 (m, 1H) 8.89 (m, 1H) 12.48 (s, 1H).

EXAMPLE 59(1) TO EXAMPLE 59(3)

By the same procedure as described in Example 59, if necessary, by converting to corresponding salts by conventional method, using 8-(pyridin-3-yl)pyrido[2,3-d]pyridazin-5(6H)-one, 8-(pyridin-4-yl)pyrido[2,3-d]pyridazin-5(6H)-one or 8-(1-benzylpyridin-4-yl)pyrido[2,3-d]pyridazin-5(6H)-one instead of 8-(pyridin-2-yl)pyrido[2,3-d]pyridazin-5(6H)-one, the following compounds of the present invention were obtained.

EXAMPLE 59(1)

8-(pyridin-3-yl)-2,3,4,6-tetrahydropyrido[2,3-d]pyridazin-5(1H)-one methanesulfonate (compound A) and 8-(piperidin-3-yl)-2,3,4,6-tetrahydropyrido[2,3-d]pyridazin-5(1H)-one acetate (compound B)

Compound A:

TLC: Rf 0.66 (methylene chloride:methanol=4:1);

NMR (DMSO-$d_6$): δ 12.46 (s, 1H), 8.92 (s, 1H), 8.86 (d, J=5.1 Hz, 1H), 8.37 (d, J=7.5 Hz, 1H), 7.91 (dd, J=7.5, 5.1 Hz, 1H), 6.20 (brs, 1H), 3.13 (m, 2H), 2.41 (m, 2H), 2.31 (s, 3H), 1.75 (m, 2H).

Compound B:

TLC: Rf 0.12 (methylene chloride:methanol:acetic acid=4:1:2%);

NMR (DMSO-$d_6$): δ 11.75 (s, 1H), 6.48 (s, 1H), 3.18 (m, 2H), 2.98 (m, 2H), 2.71 (m, 1H), 2.44 (m, 2H), 2.32 (m, 2H), 1.86 (s, 3H), 1.83 (m, 1H), 1.74-1.43 (m, 5H).

EXAMPLE 59(2)

8-(pyridin-4-yl)-2,3,4,6-tetrahydropyrido[2,3-d]pyridazin-5(1H)-one methanesulfonate (compound A) and 8-(piperidin-4-yl)-2,3,4,6-tetrahydropyrido[2,3-d]pyridazin-5(1H)-one (compound B)

Compound A:
TLC: Rf 0.28(methylene chloride:methanol=10:1);
NMR (DMSO-$d_6$): δ 12.63 (br, 1H), 8.90 (d, J=6.0 Hz, 2H), 8.00 (d, J=6.0 Hz, 2H), 6.23 (br, 1H), 3.18-3.10 (m, 2H), 2.42 (t, J=6.0 Hz, 2H), 2.31 (s, 3H), 1.82-1.70 (m, 2H).

Free Form of Compound B:
TLC: Rf 0.053 (methylene chloride:methanol:acetic acid=4:1:2%);
NMR (DMSO-$d_6$): δ 11.71 (s, 1H), 6.33 (s, 1H), 3.16 (m, 2H), 2.94 (m, 2H), 2.74-2.38 (m, 3H), 2.32 (m, 2H), 1.75-1.32 (m, 6H).

Dimethanesulfonate of Compound B:
TLC: Rf 0.86 (methylene chloride:methanol:water=8:2:0.2);
NMR (DMSO-$d_6$): δ 11.79 (br, 1H), 8.13 (br, 3H), 6.40 (s, 1H), 3.23-3.15 (m, 2H), 3.15-3.04 (m, 2H), 2.81-2.64 (m, 3H), 2.33 (t, J=6.3 Hz, 2H), 1.82 (s, 6H), 1.80-1.65 (m, 4H), 1.64-1.46 (m, 2H).

EXAMPLE 59(3)

8-(1-cyclohexylmethylpiperidin-4-yl)-2,3,4,6-tetrahydropyrido[2,3-d]pyridazin-5(1H)-one TLC: Rf 0.41 (methylene chloride:methanol:acetic acid=4:1:2%).

EXAMPLE 60 TO EXAMPLE 60(7)

By the same procedure as described in Reference example 2→Reference example 3→Example 3 using thiomorpholin-3-ylcarboxylic acid ethyl ester or a corresponding derivative, and a corresponding derivative instead of 3-nitrobenzoyl chloride, the following compounds of the present invention were obtained.

EXAMPLE 60

4-cyclohexenyl-6,7,9,9a-tetrahydro[1,4]thiazino[4,3-d][1,2,4]triazin-1(2H)-one

TLC: Rf 0.18 (hexane:ethyl acetate=2:1);
NMR (DMSO-$d_6$): δ 10.27 (s, 1H), 5.79 (m, 1H), 4.03 (dd, J=10.3, 3.0 Hz, 1H), 3.82 (dt, J=13.8, 3.0 Hz, 1H), 3.06 (ddd, J=13.8, 11.7, 2.1 Hz, 1H), 2.77 (m, 1H), 2.74-2.58 (m, 2H), 2.42 (m, 1H), 2.10-2.00 (m, 4H), 1.68-1.50 (m, 4H).

EXAMPLE 60(1)

4-(furan-2-yl)-6,7,9,9a-tetrahydro[1,4]thiazino[4,3-d][1,2,4]triazin-1(2H)-one

TLC: Rf 0.37 (hexane:ethyl acetate=1:1);
NMR (DMSO-$d_6$): δ 10.66 (s, 1H) 7.80 (m, 1H), 6.72 (d, J=3.3 Hz, 1H), 6.58 (m, 1H), 4.22 (dd, J=10.2, 3.0 Hz, 1H), 3.73 (dt, J=14.1, 3.0 Hz, 1H), 3.22 (m, 1H), 2.94-2.72 (m, 3H), 2.49 (m, 1H).

EXAMPLE 60(2)

4-(thiophen-2-yl)-6,7,9,9a-tetrahydro[1,4]thiazino[4,3-d][1,2,4]triazin-1(2H)-one TLC: Rf 0.37 (hexane:ethyl acetate=1:1);
NMR (DMSO-$d_6$): δ 10.62 (s, 1H), 7.65 (dd, J=5.1, 1.2 Hz, 1H), 7.30 (dd, J=3.6, 1.2 Hz, 1H), 7.11 (dd, J=5.1, 3.6 Hz, 1H), 4.24 (dd, J=8.1, 3.3 Hz, 1H), 3.96 (dt, J=13.8, 3.3 z, 1H), 3.20 (m, 1H), 2.92-2.76 (m, 3H), 2.49 (m, 1H).

EXAMPLE 60(3)

4-(thiazol-2-yl)-6,7,9,9a-tetrahydro[1,4]thiazino[4,3-d][1,2,4]triazin-1(2H)-one TLC: Rf 0.53 (hexane:ethyl acetate=1:1);
NMR (CDCl$_3$): δ 8.24 (br, 1H), 7.85 (d, J=3.3 Hz, 1H), 7.42 (d, J=3.3 Hz, 1H), 5.15 (m, 1H), 4.20 (dd, J=11.1, 3.0 Hz, 1H), 3.36-3.20 (m, 2H), 3.03-2.83 (m, 2H), 2.41 (m, 1H).

EXAMPLE 60(4)

4-(pyridin-3-yl)-6,7,9,9a-tetrahydro[1,4]thiazino[4,3-d][1,2,4]triazin-1(2H)-one TLC: Rf 0.32 (methylene chloride:methanol=10:1);
NMR (CDCl$_3$): δ 8.70 (dd, J=4.8, 1.8 Hz, 1H), 8.66 (d, J=1.8 Hz, 1H), 8.13 (br, 1H), 7.71 (dt, J=8.1, 1.8 Hz, 1H), 7.39 (dd, J=8.1, 4.8 Hz, 1H), 4.38 (dd, J=11.1, 2.7 Hz, 1H), 3.75 (dt, J=14.1, 2.7 Hz, 1H), 3.21 (ddd, J=14.1, 12.0, 2.7 Hz, 1H), 3.11 (m, 1H), 2.98 (dd, J=14.1, 10.8 Hz, 1H), 2.76 (m, 1H), 2.31 (m, 1H).

EXAMPLE 60(5)

4-(1,3-dioxaindan-5-yl)-6,7,9,9a-tetrahydro[1,4]thiazino[4,3-d][1,2,4]triazin-1(2H)-one TLC: Rf 0.30 (chloroform:methanol=9:1);
NMR (CD$_3$OD): δ 8.10-8.00 (brs, 1H), 6.85-6.83 (in, 2H), 6.82-6.80 (m, 1H), 6.01 (s, 2H), 4.33 (dd, J=10.8, 2.4 Hz, 1H), 3.83 (dt, J=13.5, 2.7 Hz, 1H), 3.20-3.02 (m, 2H), 3.00-2.88 (m, 1H), 2.80-2.68 (m, 1H), 2.32-2.22 (m, 1H).

EXAMPLE 60(6)

4-(pyridin-3-yl)-6,7-dihydro[1,4]thiazino[4,3-d][1,2,4]triazin-1(2H)-one

TLC: Rf 0.36 (methanol:methylene chloride=1:10);
NMR (DMSO-$d_6$): δ 10.99 (s, 1H), 8.66 (m, 2H), 7.90 (dt, J=7.8, 2.1 Hz, 1H), 7.50 (dd, J=7.8, 4.8 Hz, 1H), 6.27 (s, 1H), 3.62 (m, 2H), 3.16 (m, 2H).

EXAMPLE 60(7)

4-(naphthalen-2-yl)-6,7-dihydro[1,4]thiazino[4,3-d][1,2,4]triazin-1(2H)-one

TLC: Rf 0.54 (methylene chloride:methanol=10:1);
NMR (DMSO-$d_6$): δ 10.96 (s, 1H), 8.04-7.95 (m, 4H), 7.62-7.53 (m, 3H), 6.28 (s, 1H), 3.69-3.64 (m, 2H), 3.24-3.16 (m, 2H).

EXAMPLE 61

4-(piperazin-1-yl)-5,6,7,8-tetrahydrophthalazin-1(2H)-one hydrochloride

To a suspension of 4-chloro-5,6,7,8-tetrahydrophthalazin-1(2H)-one (150 mg; CAS Registry No. 89981-21-5; the compound described in *Yakugaku Zassi.*, 82, 302-303 (1962)) in ethylene glycol (1.6 mL) was added piperazine (420 mg) and the mixture was stirred at 200° C. for 7 hours. After cooling to room temperature, the reaction mixture was poured in a cold saturated aqueous sodium hydrogen carbonate solution and extracted with chloroform. The extract was washed brine, dried over anhydrous magnesium sulfate and concentrated. The residue was purified by column chromatography on silica gel (methylene chloride:methanol=20:1→10:1) to give free form of the title compound (64 mg). To a solution of the obtained free form in methanol (2.0 mL) was added 4N hydrogen chloride-ethyl acetate solution (1 mL). The mixture was stirred at room temperature and concentrated. The residue was recrystallized from a mixed solution of methanol and ethyl acetate to give the compound of the present invention (21 mg) having the following physical data.

TLC: Rf 0.46 (methylene chloride:methanol:acetic acid=20:5:2);

NMR (DMSO-$d_6$): δ 12.31 (s, 1H), 8.98 (brs, 2H), 3.24-3.02 (m, 8H), 2.58-2.30 (m, 4H), 1.78-1.50 (m, 4H).

EXAMPLE 62

8-(piperazin-1-yl)-2,3,4,6-tetrahydropyrido[2,3-d]pyridazin-5(1H)-one

By the same procedure as described in Example 60→Example 59 using 8-chloropyrido[2,3-d]pyridazin-5(6H)-one (the compound described in *Chem. Pharm. Bull*, 13(5), 586-593 (1965)) instead of 4-chloro-5,6,7,8-tetrahydrophthalazin-1(2H)-one, the compound of the present invention having the following physical data was obtained.

TLC: Rf 0.18 (methylene chloride:methanol:acetic acid=20:5:2);

NMR (DMSO-$d_6$): δ 11.51 (s, 1H), 6.12 (s, 1H), 3.26-3.04 (m, 8H), 3.02-2.88 (m, 3H), 2.31 (t, J=6.0 Hz, 2H), 1.71 (m, 2H).

FORMULATION EXAMPLE 1

The following components were admixed in conventional method and punched out to obtain 100 tablets each containing 50 mg of active ingredient.

| | |
|---|---|
| 4-(N-(2-aminoethyl)carbamoylmethyl)-5,6,7,8-tetrahydrophthalazin-1(2H)-one | 5.0 g |
| carboxymethyl cellulose calcium (disintegrating agent) | 0.2 g |
| magnesium stearate (lubricating agent) | 0.1 g |
| microcrystalline cellulose | 4.7 g |

FORMULATION EXAMPLE 2

After mixing the following components by a conventional method, the resulting solution was sterilized by a conventional method and 5 ml portions thereof were filled in amples, respectively, and freeze-dried by a conventional method to obtain 100 amples of injection containing each 20 mg of the active ingredient.

| | |
|---|---|
| 4-(N-(2-aminoethyl)carbamoylmethyl)-5,6,7,8-tetrahydrophthalazin-1(2H)-one | 2.0 g |
| mannitol | 20 g |
| distilled water | 1000 mL |

The invention claimed is:

1. A fused pyridazine derivative compound represented by formula (I)

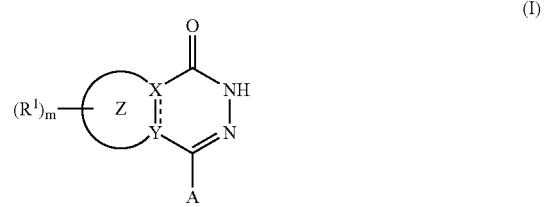

(I)

wherein $R^1$ is
(1) a hydrogen atom, (2) C1-8 alkyl, (3) C1-8 alkoxy, (4) hydroxy, (5) halogen atom, (6) nitro, (7) $NR^2R^3$, (8) C2-8 acyl, (9) C1-8 alkoxy substituted by phenyl or (10) C2-8 acyl substituted by $NR^2R^3$, $R^2$ and $R^3$ are each independently
(1) hydrogen atom or (2) C1-8 alkyl, X and Y are each independently
(1) C or (2) CH, ----- is (1) single bond or (2) double bond

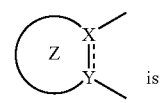 is cyclohexane, cyclohexene, or cyclohexadiene,

A is (1) $A^1$, (2) $A^2$, (3) $A^3$, (4) $A^4$ or (5) $A^5$, $A^1$ is (R⁴)ₙ—⟨phenyl⟩—$D^1$—$D^2$—$D^3$, $A^2$ is —$E^1$—$E^2$—$E^3$—$E^4$, $A^3$ is —$G^1$—(Cyc1)—$G^2$, $A^4$ is ⟨phenyl⟩—$(R^5)_n$, $A^5$ is (Cyc7)—$(R^5)_n$,

381

D¹ is
(1) —NR⁶C(O)—, (2) —NR⁶C(S)—, (3) —NR⁶SO₂—, (4) —CH₂—NR⁶—, (5) —CH₂—O—, (6) —OC(O)—, (7) —CH₂—NR⁶C(O)—, (8) —NR⁶C(O)NR⁷—, (9) —NR⁶C(O)O—, (10) —NR⁶C(S)NR⁷—, (11) —NR⁶— or (12) —NR⁶C(=NR⁷)—,

R⁶ and R⁷ are each independently
(1) a hydrogen atom, (2) C1-8 alkyl, (3) phenyl or (4) C1-8 alkyl substituted by phenyl, D² is
(1) C1-8 alkylene, (2) C2-8 alkenylene, (3) Cyc2, (4) —(C1-4 alkylene)-O—(C1-4 alkylene)-, (5) —(C1-4 alkylene)-S—(C1-4 alkylene)-, (6) —(C1-4 alkylene)-NR⁸—(C1-4 alkylene)-, (7) -(Cyc2)-(C1-8 alkylene)-, (8) —(C1-8 alkylene)-(Cyc2)- or (9) —(C1-4 alkylene)-(Cyc2)-(C1-4 alkylene)-, R⁸ is
(1) a hydrogen atom, (2) C1-8 alkyl, (3) C1-8 alkoxycarbonyl, (4) phenyl or (5) C1-8 alkyl substituted by phenyl, D³ is
(1) a hydrogen atom, (2) —NR⁹R¹⁰, (3) Cyc3, (4) —OR¹¹, (5) COOR¹², (6) CONR¹³R¹⁴, (7) cyano, (8) a halogen atom, (9) —C(=CR¹⁵)NR¹⁶R¹⁷ or (10) —NR¹⁸C(=NR¹⁹)NR²⁰R²¹, R⁹ and R¹³ are each independently
(1) a hydrogen atom, (2) C1-8 alkyl, (3) C2-8 alkenyl, (4) C2-8 alkynyl, (5) Cyc3, (6) C1-8 alkoxy, (7) C2-8 alkenyloxy, (8) C2-8 alkynyloxy or (9) C1-8 alkyl substituted by Cyc3, C1-8 alkoxy, C1-8 alkylthio, cyano, hydroxy or 1 to 3 halogen atoms, R¹⁰ and R¹⁴ are each independently
(1) a hydrogen atom, (2) C1-8 alkyl, (3) C2-8 alkenyl, (4) C2-8 alkynyl, (5) C1-8 alkoxycarbonyl, (6) C2-8 acyl, (7) C3-8 cycloalkyl, (8) C1-8 alkoxycarbonyl substituted by Cyc4 or 1 to 3 halogen atoms, or (9) C1-8 alkyl substituted by C1-8 alkoxy, R¹¹ and R¹² are each independently
(1) a hydrogen atom or (2) C1-8 alkyl, R¹⁵, R¹⁶, R¹⁷, R¹⁸, R¹⁹, R²⁰ and R²¹ are each independently
(1) a hydrogen atom, (2) C1-8 alkyl, (3) C1-8 alkoxycarbonyl, (4) phenyl or (5) C1-8 alkyl substituted by phenyl, R⁴ is
(1) a hydrogen atom, (2) C1-8 alkyl, (3) C1-8 alkoxy, (4) hydroxy, (5) halogen atom, (6) nitro or (7) NR²²R²³, R²² and R²³ are each independently
(1) a hydrogen atom or (2) C1-8 alkyl, E¹ is
C1-4 alkylene, E² is
(1) —C(O)NR²⁴—, (2) —NR²⁴C(O)—, (3) —NR²⁴—, (4) —C(O)O— or (5) —S—, R²⁴ is
(1) a hydrogen atom, (2) C1-8 alkyl or (3) C1-8 alkyl substituted by phenyl, E³ is
(1) bond or (2) C1-8 alkylene, E⁴ is
(1) C1-8 alkyl, (2) C2-8 alkenyl, (3) C2-8 alkynyl, (4) cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, pentalene, azulene, perhy-

382 droazulene, perhydropentalene, indene, perhydroindene, indan, naphthalene, teterahydronaphthalene, perhydronaphthalene, pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzoftiran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine, tetrahydrothiaine, dihydrothiepine, tetrahydrothiepine, perhydrothiepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofiiran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydroplithalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane or benzodithiane, which may be substituted by 1 to 3 substituents selected from (i) C1-8 alkyl, (ii) C2-8 alkenyl, (iii) C1-8 alkoxy, (iv) a halogen atom, (v) trihalomethyl, (vi) trihalomethoxy, (vii) C1-8 alkoxycarbonyl, (viii) oxo, (ix) C1-8 alkyl substituted by C1-8 alkoxy or phenyl, (x) hydroxy and (xi) $NR^{29}R^{30}$, (5) $NR^{25}R^{26}$, (6) $OR^{27}$, (7) $SR^{27}$, (8) $COOR^{27}$, (9) C1-8 alkyl substituted by two of $OR^{25}$, (10) C1-8 alkyl substituted by 1 to 3 halogen atoms, (11) cyano or (12) C2-8 acyl, $R^{25}$ is (1) a hydrogen atom, (2) C1-8 alkyl, (3) C2-8 alkenyl, (4) C2-8 alkynyl, (5) Cyc5 or (6) C1-8 alkyl substituted by Cyc5 or $OR^{28}$, $R^{26}$ is (1) a hydrogen atom, (2) C1-8 alkyl, (3) C1-8 alkoxycarbonyl, (4) phenyl or (5) C1-8 alkyl substituted by phenyl, $R^{27}$ is (1) a hydrogen atom, (2) C1-8 alkyl, (3) Cyc5, or (4) C1-8 alkyl substituted by Cyc5, $R^{28}$ is (1) a hydrogen atom or (2) C1-8 alkyl, $G^1$ is C1-8 alkylene, Cyc1 is (1) cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, benzene, pentalene, azulene, perhydroazulene, perhydropentalene, indene, perhydroindene, indan, naphthalene, teterahydronaphthalene or perhydronaphthalene, or (2) pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydroftiran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothjaine, tetrahydrothiaine, dihydrothiepine, tetrahydrothiepine, perhydrothiepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofiiran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane or benzodithiane, $G^2$ is (1) a hydrogen atom, (2) C1-8 alkyl, (3) C1-8 alkoxycarbonyl, (4) C2-8 acyl, (5) cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, pentalene, azulene, perhydroazulene, perhydropentalene, indene, perhydroindene, indan, naphthalene, teterahydronaphthalene, perhydronaphthalene, pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine, tetrahydrothiaine, dihydrothiepine, tetrahydrothiepine, perhydrothiepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane or benzodithiane, which may be substituted by 1 to 3 substituents selected from (i) C1-8 alkyl, (ii) C2-8 alkenyl, (iii) C1-8 alkoxy, (iv) halogen atom, (v) trihalomethyl, (vi) trihalomethoxy, (vii) C1-8 alkoxycarbonyl, (viii) oxo, (ix) C1-8 alkyl substituted by C1-8 alkoxy or phenyl, (x) hydroxy and (xi) $NR^{29}R^{30}$, (6) C1-8 alkyl or C2-8 alkenyl substituted by 1 to 2 substituents selected from Cyc6, hydroxy and C1-8 alkoxy, (7) C1-8 alkoxycarbonyl substituted by Cyc6, (8) —C(O)-Cyc6, (9) nitro, (10) $NR^{41}R^{42}$, (11) C1-8 alkoxy or (12) C1-8 alkyl substituted by $NR^{41}R^{42}$, $R^{41}$ and $R^{42}$ are each independently (1) a hydrogen atom or (2) C1-8 alkyl, $R^5$ is (1) a hydrogen atom, (2) C1-8 alkyl, (3) C1-8 alkoxy, (4) hydroxy, (5) nitro, (6) $NR^{29}R^{30}$, (7) C1-C8 alkyl substituted by $NR^{29}R^{30}$, (8) $NHSO_2OH$, (9) amidino, (10) cyano, (11) halogen atom, (12) Cyc8 or (13) C1-8 alkyl substited by Cyc8, $R^{29}$ and $R^{30}$ are each independently (1) a hydrogen atom or (2) C1-8 alkyl, Cyc2, Cyc3, Cyc4, Cyc5, Cyc6 and Cyc8 are each independently (1) cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, benzene, pentalene, azulene, perhydroazulene, perhydropentalene, indene, perhydroindene, indan, naphthalene, teterahydronaphthalene or perhydronaphthalene, or (2) pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, plithalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiaine, tetrahydrothiaine, dihydrothiepine, tetrahydrothiepine, perhydrothiepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzoffiran, dihydroisobenzofuran, perhydroisobenzofiiran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaplithyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobeuzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane or benzodithiane, Cyc7 is (1) cyclopropane, cyclobutane, cyclopentane, cyclohexane, cycloheptane, cyclooctane, cyclononane, cyclodecane, cyclopropene, cyclobutene, cyclopentene, cyclohexene, cycloheptene, cyclooctene, cyclononene, cyclodecene, cyclopentadiene, cyclohexadiene, cycloheptadiene, cyclooctadiene, pentalene, azulene, perhydroazulene, perhydropentalene, indene, perhydroindene, indan, naphthalene, teterahydronaphthalene or perhydronaphthalene, or (2) pyrrole, imidazole, triazole, tetrazole, pyrazole, pyridine, pyrazine, pyrimidine, pyridazine, azepine, diazepine, furan, pyran, oxepine, thiophene, thiaine, thiepine, oxazole, isoxazole, thiazole, isothiazole, flirazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thuirane, thietane, dihydrothiophene, tetrahydrothiophene, dihydrothiaine, tetrahydrothiaine, dihydrothiepine, tetrahydrothiepine, perhydrothiepine, dihydrooxazole, tetrahydrooxazole, dihydroisoxazole, tetrahydroisoxazole, dihydrothiazole, tetrahydrothiazole, dihydroisothiazole, tetrahydroisothiazole, dihydrofurazan, tetrahydrofurazan, dihydrooxadiazole, tetrahydrooxadiazole, dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole, dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindan, benzodioxane, chroman, benzodithiolane or benzodithiane, Cyc2, Cyc3, Cyc4, Cyc5, Cyc6 and Cyc8 are optionally substituted by 1 to 3 substituents selected from (1) C1-8 alkyl, (2) C2-8 alkenyl, (3) C1-8 alkoxy, (4) halogen atom, (5) trihalomethyl, (6) trihalomethoxy, (7) C1-8 alkoxycarbonyl, (8) oxo, (9) C1-8 alkyl substituted by C1-8 alkoxy or phenyl, (10) hydroxy and (11) $NR^{29}R^{30}$;

m and n are each independently 1 or 2, wherein (i) when A is $A^1$ or $A^2$, then

(ii) when A is $A^4$ and

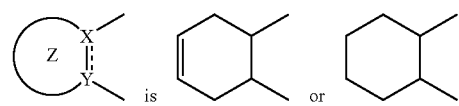

then $R^5$ is not hydroxy or C1-8 alkoxy, (iii) when A is $A^5$, then

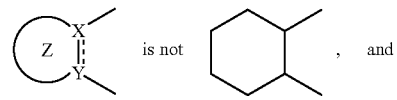

(iv) following compounds of (1) to (11) are excepted;

(1) 4-(3-chloro-4-methoxyphenyl)-4a,5,8,8a-tetrahydrophthalazin-1(2H)-one, (2) 4-(3,4-dimethoxyphenyl)-5,6,7,8-tetrahydrophthalazin-1(2H)-one, (3) 4-phenyl-6,7,8,8a-tetrahydropyrrolo[1,2-d][1,2,4]triazin-1(2H)-one, (4) 4-phenyl-5,6,7,8-tetrahydrophthalazin-1(2H)-one, (5) 4-(4-methylphenyl)-5,6,7,8-tetrahydrophthalazin-1(2H)-one, (6) 4-(4-fluorophenyl)-5,6,7,8-tetrahydrophthalazin-1(2H)-one, (7) 4-(4-chlorophenyl)-5,6,7,8-tetrahydrophthalazin-1(2H)-one, (8) 4-(4-bromophenyl)-5,6,7,8-tetrahydrophthalazin-1(2H)-one, (9) 4-(pyridin-4-ylmethyl)-5,6,7,8-tetrahydrophthalazin-1(2H)-one,

(10) 4-t-butoxycarbonylmethyl-5,6,7,8-tetrahydrophthalazin-1(2H)-one,

(11) 4-ethoxycarbonylmethyl-5,6,7,8-tetrahydrophthalazin-1(2H)-one, or a pharmaceutically acceptable salt thereof.

2. The compound represented by formula (I) according to claim 1, wherein A is $A^1$, or a pharmaceutically acceptable salt thereof.

3. The compound represented by formula (I) according to claim 1, wherein A is $A^2$, or a pharmaceutically acceptable salt thereof.

4. The compound represented by formula (I) or the pharmaceutically acceptable salt thereof according to claim 1, wherein A is $A^3$, or a pharmaceutically acceptable salt thereof.

5. The compound represented by formula (I) according to claim 1, wherein A is $A^4$ or $A^5$, or a pharmaceutically acceptable salt thereof.

6. The compound represented by formula (I) according to claim 1, wherein

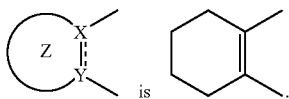

or a pharmaceutically acceptable salt thereof.

7. A pharmaceutical composition, comprising, as an active ingredient, the compound represented by formula (I) according to claim 1 or a pharmaceutically acceptable salt thereof, and a pharmaceutically acceptable carrier or diluent.

8. A method for treating ischemic diseases, inflammatory bowel disease, multiple sclerosis, arthritis, lung injury, glaucoma, shock, head trauma, spinal cord injury, renal failure or hyperalgesia, comprising administrating, as an active ingredient, an effective amount of the compound represented by formula (I) according to claim 1 or a pharmaceutically acceptable salt thereof to a patient in need thereof.

9. The method according to claim 8 wherein the method is for treating an isehemic disease, and the isehemic disease is cerebral infarction.

10. A compound selected from the group consisting of:
4-(N-(3-(morpholin-4-yl)propyl)carbamoylmethyl)-5,6,7,8-tetrahydrophthalazin-1(2H)-one,
4-(3-(N-(5-(N',N'-dimethylamino)pentanoyl)amino)phenyl)-5,6,7,8-tetrahydrophthalazin-1(2H)-one,
4-(2-(morpholin-4-yl)ethyl)-5,6,7,8-tetrahydrophthalazin-1(2H)-one,
4-(2-(4-methyl-1,4-diazepan-1-yl)ethyl)-5,6,7,8-tetrahydrophthalazin-1(2H)-one,
4-(2-(N-(4-fluorobenzyl)amino)ethyl)-5,6,7,8-tetrahydrophthalazin-1(2H)-one,
4-(2-(4-isopropylpiperazin-1-yl)ethyl)-5,6,7,8-tetrahydrophthalazin-1(2H)-one,
4-(3-(N-(5-(morpholin-4-yl)pentanoyl)amino)phenyl)-5,6,7,8-tetrahydrophthalazin-1(2H)-one,
4-(3-(N-(5-(N'-cyclopropylamino)pentanoyl)amino)phenyl)-5,6,7,8-tetrahydrophthalazin-1(2H)-one,
4-(N-(2-(azepan-1-yl)ethyl)carbamoylmethyl)-5,6,7,8-tetrahydrophthalazin-1(2H)-one,
4-(N-(4-(N'-cyclohexylamino)butyl)carbamoylmethyl)-5,6,7,8-tetrahydrophthalazin-1(2H)-one,
4-(N-(4-(N'-cyclopropylamino)butyl)carbamoylmethyl)-5,6,7,8-tetrahydrophthalazin-1(2H)-one,
4-(N-(4-(morpholin-4-yl)butyl)carbamoylmethyl)-5,6,7,8-tetrahydrophthalazin-1(2H)-one,
4-(3-(N-(5-(N'-methylamino)pentanoyl)amino)phenyl)-5,6,7,8-tetrahydrophthalazin-1(2H)-one,
4-(N-(2-aminoethyl)carbamoylmethyl)-5,6,7,8-tetrahydrophthalazin-1(2H)-one
4-(pyridin-3-ylmethyl)-5,6,7,8-tetrahydrophthalazin-1(2H)-one,
4-(5-(piperidin-1-yl)pentyl)-5,6,7,8-tetrahydrophthalazin-1(2H)-one and
4-(N-(5-(morpholin-4-yl)pentyl)carbamoylmethyl)-5,6,7,8-tetrahydrophthalazin-1(2H)-one.

11. A compound of 4-(N-(4-(morpholin-4-yl)butyl)carbamoylmethyl)-5,6,7,8-tetrahydrophthalazin-1(2H)-one or a pharmaceutically acceptable salt thereof.

12. The compound according to claim 11, which is 4-(N-(4-(morpholin-4-yl)butyl)carbamoylmethyl)-5,6,7,8-tetrahydrophthalazin-1(2H)-one.

* * * * *